United States Patent
Ren et al.

(10) Patent No.: US 9,738,644 B2
(45) Date of Patent: Aug. 22, 2017

(54) CHEMICAL COMPOUNDS, COMPOSITIONS AND METHODS FOR KINASE MODULATION

(71) Applicant: Infinity Pharmaceuticals, Inc., Cambridge, MA (US)

(72) Inventors: Pingda Ren, San Diego, CA (US); Yi Liu, San Diego, CA (US); Liansheng Li, San Diego, CA (US); Katrina Chan, Fremont, CA (US); Alfredo C. Castro, Woburn, MA (US); Catherine A. Evans, Somerville, MA (US)

(73) Assignee: Infinity Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 14/869,637

(22) Filed: Sep. 29, 2015

(65) Prior Publication Data

US 2016/0016957 A1 Jan. 21, 2016

Related U.S. Application Data

(62) Division of application No. 14/085,660, filed on Nov. 20, 2013, now Pat. No. 9,181,221, which is a division of application No. 13/112,611, filed on May 20, 2011, now Pat. No. 8,604,032.

(60) Provisional application No. 61/347,370, filed on May 21, 2010.

(51) Int. Cl.

| | |
|---|---|
| *A01N 43/64* | (2006.01) |
| *A61K 31/53* | (2006.01) |
| *A01N 43/66* | (2006.01) |
| *A01N 43/90* | (2006.01) |
| *A61K 31/52* | (2006.01) |
| *A61K 31/519* | (2006.01) |
| *A01N 43/54* | (2006.01) |
| *A61K 31/505* | (2006.01) |
| *C07D 473/34* | (2006.01) |
| *A61K 31/47* | (2006.01) |
| *C07D 401/14* | (2006.01) |
| *C07D 473/16* | (2006.01) |
| *C07D 473/32* | (2006.01) |
| *C07D 487/04* | (2006.01) |

(52) U.S. Cl.
CPC ............ *C07D 473/34* (2013.01); *A61K 31/47* (2013.01); *A61K 31/52* (2013.01); *C07D 401/14* (2013.01); *C07D 473/16* (2013.01); *C07D 473/32* (2013.01); *C07D 487/04* (2013.01)

(58) Field of Classification Search
None
See application file for complete search history.

(56) References Cited

U.S. PATENT DOCUMENTS

| | | |
|---|---|---|
| 4,547,508 A | 10/1985 | Konz et al. |
| 4,656,159 A | 4/1987 | McPherson et al. |
| 4,704,381 A | 11/1987 | Schaumann et al. |
| 4,795,627 A | 1/1989 | Fisher et al. |
| 5,240,941 A | 8/1993 | Bruneau |
| 5,294,612 A | 3/1994 | Bacon et al. |
| 5,310,731 A | 5/1994 | Olsson et al. |
| 5,364,862 A | 11/1994 | Spada et al. |
| 5,420,419 A | 5/1995 | Wood |
| 5,428,125 A | 6/1995 | Hefner, Jr. et al. |
| 5,442,039 A | 8/1995 | Hefner, Jr. et al. |
| 5,446,040 A | 8/1995 | Walter |
| 5,504,103 A | 4/1996 | Bonjouklian et al. |
| 5,506,347 A | 4/1996 | Erion et al. |
| 5,525,604 A | 6/1996 | Lee et al. |
| 5,561,134 A | 10/1996 | Spada et al. |
| 5,563,257 A | 10/1996 | Zilch et al. |
| 5,593,997 A | 1/1997 | Dow et al. |
| 5,646,128 A | 7/1997 | Firestein et al. |
| 5,652,366 A | 7/1997 | Spada et al. |
| 5,654,307 A | 8/1997 | Bridges et al. |
| 5,665,721 A | 9/1997 | Bhagwat et al. |
| 5,674,998 A | 10/1997 | Boyer et al. |
| 5,686,455 A | 11/1997 | Adams et al. |
| 5,736,554 A | 4/1998 | Spada et al. |
| 5,747,235 A | 5/1998 | Farid et al. |
| 5,756,711 A | 5/1998 | Zilch et al. |
| 5,763,596 A | 6/1998 | Boyer et al. |
| 5,763,597 A | 6/1998 | Ugarkar et al. |
| 5,763,885 A | 6/1998 | Murphy et al. |
| 5,795,977 A | 8/1998 | Ugarkar et al. |

(Continued)

FOREIGN PATENT DOCUMENTS

| | | |
|---|---|---|
| CA | 1338379 C | 6/1996 |
| CN | 101602768 A | 12/2009 |

(Continued)

OTHER PUBLICATIONS

Abdel-Mohsen, "Synthesis, Reactions and Antimicrobial Activity of 2-Amino-4-(8-quinolino1-5-yl)-1-(p-toly1)-pyrrole-3-carbonitrile," *Bull. Korean Chem. Soc.* 26(5):719-728 (2005).

(Continued)

*Primary Examiner* — Jeffrey H Murray

(74) *Attorney, Agent, or Firm* — Jones Day

(57) ABSTRACT

Substituted isoquinolinone compounds and pharmaceutical compositions that modulate kinase activity, including PI3 kinase activity, and compounds, pharmaceutical compositions, and methods of treatment of diseases and conditions associated with kinase activity, including PI3 kinase activity, are described herein.

30 Claims, No Drawings

(56) References Cited

U.S. PATENT DOCUMENTS

| | | |
|---|---|---|
| 5,811,454 A | 9/1998 | Springer |
| 5,824,492 A | 10/1998 | Hiles et al. |
| 5,858,753 A | 1/1999 | Chantry et al. |
| 5,914,488 A | 6/1999 | Sone |
| 5,919,808 A | 7/1999 | Petrie et al. |
| 5,922,753 A | 7/1999 | Petrie et al. |
| 5,948,776 A | 9/1999 | Petrie et al. |
| 5,965,573 A | 10/1999 | Petrie et al. |
| 5,977,061 A | 11/1999 | Holy et al. |
| 5,981,533 A | 11/1999 | Traxler et al. |
| 5,985,589 A | 11/1999 | Chantry et al. |
| 5,990,169 A | 11/1999 | Petrie et al. |
| 5,994,358 A | 11/1999 | Petrie et al. |
| 6,001,839 A | 12/1999 | Calderwood et al. |
| 6,057,305 A | 5/2000 | Holy et al. |
| 6,063,930 A | 5/2000 | Dinsmore et al. |
| 6,084,095 A | 7/2000 | Bridges et al. |
| 6,093,737 A | 7/2000 | Anthony et al. |
| 6,127,121 A | 10/2000 | Meyer, Jr. et al. |
| 6,150,352 A | 11/2000 | Goulet et al. |
| 6,153,631 A | 11/2000 | Petrie et al. |
| 6,191,170 B1 | 2/2001 | Medina |
| 6,251,901 B1 | 6/2001 | Petrie et al. |
| 6,265,410 B1 | 7/2001 | Bridges et al. |
| 6,268,370 B1 | 7/2001 | Adams et al. |
| 6,312,894 B1 | 11/2001 | Hedgpeth et al. |
| 6,323,201 B1 | 11/2001 | Carson et al. |
| 6,342,514 B1 | 1/2002 | Petrie et al. |
| 6,350,741 B1 | 2/2002 | Golec et al. |
| 6,383,790 B1 | 5/2002 | Shokat |
| 6,384,039 B1 | 5/2002 | Fossa |
| 6,387,894 B1 | 5/2002 | Fossa |
| 6,390,821 B1 | 5/2002 | Shokat |
| 6,455,534 B2 | 9/2002 | Bridges et al. |
| 6,472,153 B1 | 10/2002 | Dempcy et al. |
| 6,482,623 B1 | 11/2002 | Vanhaesebroeck et al. |
| 6,485,906 B2 | 11/2002 | Meyer, Jr. et al. |
| 6,492,346 B1 | 12/2002 | Hedgpeth et al. |
| 6,506,769 B2 | 1/2003 | Snow et al. |
| 6,518,277 B1 | 2/2003 | Sadhu et al. |
| 6,521,417 B1 | 2/2003 | Shokat |
| 6,521,620 B1 | 2/2003 | Bridges et al. |
| 6,531,491 B1 | 3/2003 | Kania et al. |
| 6,534,524 B1 | 3/2003 | Kania et al. |
| 6,545,005 B1 | 4/2003 | Baxter et al. |
| 6,552,192 B1 | 4/2003 | Hanus et al. |
| 6,562,819 B2 | 5/2003 | Carson et al. |
| 6,583,161 B1 | 6/2003 | Medina |
| 6,586,441 B2 | 7/2003 | Borroni et al. |
| 6,613,798 B1 | 9/2003 | Porter et al. |
| 6,630,495 B1 | 10/2003 | Cooke et al. |
| 6,632,789 B1 | 10/2003 | June |
| 6,645,989 B2 | 11/2003 | Adams et al. |
| 6,649,631 B1 | 11/2003 | Orme et al. |
| 6,653,296 B1 | 11/2003 | Holy et al. |
| 6,653,306 B1 | 11/2003 | Alexander et al. |
| 6,660,744 B1 | 12/2003 | Hirst et al. |
| 6,660,845 B1 | 12/2003 | Gall et al. |
| 6,664,269 B2 | 12/2003 | Martin et al. |
| 6,667,300 B2 | 12/2003 | Sadhu et al. |
| 6,690,583 B1 | 2/2004 | Bergstedt et al. |
| 6,710,058 B2 | 3/2004 | Jacobson et al. |
| 6,713,484 B2 | 3/2004 | Bridges et al. |
| 6,720,344 B2 | 4/2004 | Kerwin et al. |
| 6,734,187 B1 | 5/2004 | Tanaka et al. |
| 6,770,639 B2 | 8/2004 | Snow et al. |
| 6,777,425 B2 | 8/2004 | Burli et al. |
| 6,777,439 B2 | 8/2004 | Durden |
| 6,790,844 B2 | 9/2004 | Ueno et al. |
| 6,800,620 B2 | 10/2004 | Sadhu et al. |
| 6,849,420 B2 | 2/2005 | Vanhaesebroeck et al. |
| 6,849,713 B2 | 2/2005 | Zhang et al. |
| 6,852,727 B2 | 2/2005 | Goulet et al. |
| 6,906,103 B2 | 6/2005 | Zhang et al. |
| 6,916,949 B2 | 7/2005 | Springer et al. |
| 6,919,332 B2 | 7/2005 | Noe et al. |
| 6,921,763 B2 | 7/2005 | Hirst et al. |
| 6,949,535 B2 | 9/2005 | Sadhu et al. |
| 7,026,461 B1 | 4/2006 | Shokat |
| 7,041,676 B2 | 5/2006 | McDonald et al. |
| 7,049,116 B2 | 5/2006 | Shokat |
| 7,049,312 B1 | 5/2006 | Rafferty et al. |
| 7,064,218 B2 | 6/2006 | Dyatkina et al. |
| 7,071,355 B2 | 7/2006 | Leban et al. |
| 7,087,614 B2 | 8/2006 | Guo et al. |
| 7,115,627 B2 | 10/2006 | Pinto et al. |
| 7,115,653 B2 | 10/2006 | Baxter et al. |
| 7,144,903 B2 | 12/2006 | Collins et al. |
| 7,157,487 B2 | 1/2007 | Nakayama et al. |
| 7,166,293 B2 | 1/2007 | Teng et al. |
| 7,173,028 B2 | 2/2007 | Dahmann et al. |
| 7,208,601 B2 | 4/2007 | Mjalli et al. |
| 7,217,794 B2 | 5/2007 | Abdel-Meguid et al. |
| 7,235,585 B2 | 6/2007 | Springer et al. |
| 7,244,741 B2 | 7/2007 | Simon et al. |
| 7,247,736 B2 | 7/2007 | Leban et al. |
| 7,262,204 B2 | 8/2007 | Collins et al. |
| 7,265,111 B2 | 9/2007 | Bigot et al. |
| 7,265,131 B2 | 9/2007 | Johnson et al. |
| 7,273,868 B2 | 9/2007 | Yamada et al. |
| 7,329,765 B2 | 2/2008 | Burli et al. |
| 7,332,497 B2 | 2/2008 | Hirst et al. |
| 7,338,959 B2 | 3/2008 | Chamberlain et al. |
| 7,348,427 B2 | 3/2008 | Burli et al. |
| 7,365,094 B2 | 4/2008 | Leban et al. |
| 7,384,967 B2 | 6/2008 | Polisetti et al. |
| 7,396,836 B2 | 7/2008 | Harada et al. |
| 7,414,036 B2 | 8/2008 | Sevillano et al. |
| 7,429,596 B2 | 9/2008 | Tanaka et al. |
| 7,439,254 B2 | 10/2008 | Bergnes |
| 7,449,456 B2 | 11/2008 | Nagashima et al. |
| 7,449,477 B2 | 11/2008 | Barda et al. |
| 7,459,462 B2 | 12/2008 | Simon et al. |
| 7,459,472 B2 | 12/2008 | Mjalli et al. |
| 7,470,721 B2 | 12/2008 | Durden |
| 7,501,538 B2 | 3/2009 | Mjalli et al. |
| 7,514,445 B2 | 4/2009 | Freyne et al. |
| 7,517,889 B2 | 4/2009 | Harris et al. |
| 7,534,797 B2 | 5/2009 | Arnold et al. |
| 7,541,373 B2 | 6/2009 | Polisetti et al. |
| 7,569,571 B2 | 8/2009 | Dong et al. |
| 7,572,913 B2 | 8/2009 | McKerracher et al. |
| 7,579,348 B2 | 8/2009 | Wang et al. |
| 7,585,868 B2 | 9/2009 | Knight et al. |
| 7,608,594 B2 | 10/2009 | Blagg et al. |
| 7,615,552 B2 | 11/2009 | Ono et al. |
| 7,622,451 B2 | 11/2009 | Blagg et al. |
| 7,678,803 B2 | 3/2010 | Huang et al. |
| 7,700,607 B2 | 4/2010 | Hu et al. |
| 7,700,620 B2 | 4/2010 | Sutton et al. |
| 7,705,018 B2 | 4/2010 | Chen et al. |
| 7,728,008 B2 | 6/2010 | Qiao et al. |
| 7,745,485 B2 | 6/2010 | Durden |
| 7,932,260 B2 | 4/2011 | Fowler et al. |
| 7,989,458 B2 | 8/2011 | Leblanc et al. |
| 8,053,603 B2 | 11/2011 | Shao et al. |
| 8,106,146 B2 | 1/2012 | Benz et al. |
| 8,173,639 B2 | 5/2012 | Simonsen et al. |
| 8,193,182 B2 | 6/2012 | Ren et al. |
| 8,399,483 B2 | 3/2013 | Allen et al. |
| 8,415,365 B2 | 4/2013 | Li et al. |
| 8,420,667 B2 | 4/2013 | Khanzhin et al. |
| 8,461,147 B2 | 6/2013 | Sapountzis et al. |
| 8,604,032 B2 | 12/2013 | Ren et al. |
| 8,785,456 B2* | 7/2014 | Ren .................. C07D 487/04 514/263.22 |
| 8,785,470 B2 | 7/2014 | Ren et al. |
| 8,828,998 B2* | 9/2014 | Palombella ............ A61K 31/00 424/133.1 |
| 9,115,141 B2* | 8/2015 | Castro ................ C07D 401/14 |
| 9,181,221 B2* | 11/2015 | Ren ..................... A61K 31/47 |
| 2001/0019829 A1 | 9/2001 | Nelson et al. |
| 2001/0027197 A1 | 10/2001 | Bridges et al. |
| 2002/0016460 A1 | 2/2002 | Snow et al. |

(56) References Cited

U.S. PATENT DOCUMENTS

| | | |
|---|---|---|
| 2002/0016976 A1 | 2/2002 | Shokat |
| 2002/0037856 A1 | 3/2002 | Zhang et al. |
| 2002/0102590 A1 | 8/2002 | Taing et al. |
| 2002/0127625 A1 | 9/2002 | Oxelius |
| 2002/0146690 A1 | 10/2002 | Meyer et al. |
| 2002/0147160 A1 | 10/2002 | Bhat et al. |
| 2002/0156081 A1 | 10/2002 | Hirst et al. |
| 2002/0161014 A1 | 10/2002 | Sadhu et al. |
| 2002/0173524 A1 | 11/2002 | Collins et al. |
| 2003/0001141 A1 | 1/2003 | Sun et al. |
| 2003/0008896 A1 | 1/2003 | Martin et al. |
| 2003/0018022 A1 | 1/2003 | Collins et al. |
| 2003/0022344 A1 | 1/2003 | Williams et al. |
| 2003/0064997 A1 | 4/2003 | Adams et al. |
| 2003/0073218 A1 | 4/2003 | Shokat |
| 2003/0083268 A1 | 5/2003 | Burli et al. |
| 2003/0113765 A1 | 6/2003 | Dempcy et al. |
| 2003/0119479 A1 | 6/2003 | Arima et al. |
| 2003/0119791 A1 | 6/2003 | Kerwin et al. |
| 2003/0139427 A1 | 7/2003 | Castelhano et al. |
| 2003/0143602 A1 | 7/2003 | Meyer et al. |
| 2003/0166929 A1 | 9/2003 | Snow et al. |
| 2003/0180924 A1 | 9/2003 | DeSimone |
| 2003/0186987 A1 | 10/2003 | Bridges et al. |
| 2003/0187001 A1 | 10/2003 | Calderwood et al. |
| 2003/0195211 A1 | 10/2003 | Sadhu et al. |
| 2003/0199516 A1 | 10/2003 | Moser et al. |
| 2003/0208800 A1 | 11/2003 | Eby et al. |
| 2003/0212113 A1 | 11/2003 | Dyatkina et al. |
| 2003/0232849 A1 | 12/2003 | Noe et al. |
| 2003/0235822 A1 | 12/2003 | Lokhov et al. |
| 2004/0039035 A1 | 2/2004 | Collins et al. |
| 2004/0043959 A1 | 3/2004 | Bloom et al. |
| 2004/0043983 A1 | 3/2004 | Li |
| 2004/0067901 A1 | 4/2004 | Bhat et al. |
| 2004/0067915 A1 | 4/2004 | McMahon et al. |
| 2004/0072766 A1 | 4/2004 | June |
| 2004/0072788 A1 | 4/2004 | Bhat et al. |
| 2004/0102423 A1 | 5/2004 | McLaughlan et al. |
| 2004/0102437 A1 | 5/2004 | Takami et al. |
| 2004/0110717 A1 | 6/2004 | Carroll et al. |
| 2004/0110945 A1 | 6/2004 | Nakayama et al. |
| 2004/0116689 A1 | 6/2004 | Gall et al. |
| 2004/0122235 A1 | 6/2004 | Polisetti et al. |
| 2004/0127434 A1 | 7/2004 | Bigot et al. |
| 2004/0176458 A1 | 9/2004 | Leban et al. |
| 2004/0176601 A1 | 9/2004 | Goulet et al. |
| 2004/0192758 A1 | 9/2004 | Leban et al. |
| 2004/0266780 A1 | 12/2004 | Sadhu et al. |
| 2005/0004149 A1 | 1/2005 | Harada et al. |
| 2005/0043239 A1 | 2/2005 | Douangpanya et al. |
| 2005/0049310 A1 | 3/2005 | Mjalli et al. |
| 2005/0054614 A1 | 3/2005 | Diacovo et al. |
| 2005/0059713 A1 | 3/2005 | Mjalli et al. |
| 2005/0085472 A1 | 4/2005 | Tanaka et al. |
| 2005/0101551 A1 | 5/2005 | Sevillano et al. |
| 2005/0124637 A1 | 6/2005 | Cheng et al. |
| 2005/0143317 A1 | 6/2005 | Abdel-Meguid et al. |
| 2005/0153997 A1 | 7/2005 | Simon et al. |
| 2005/0171148 A1 | 8/2005 | Mjalli et al. |
| 2005/0182045 A1 | 8/2005 | Nagase et al. |
| 2005/0187418 A1 | 8/2005 | Small et al. |
| 2005/0197340 A1 | 9/2005 | Arora et al. |
| 2005/0214310 A1 | 9/2005 | Toki et al. |
| 2005/0215579 A1 | 9/2005 | Simon et al. |
| 2005/0239809 A1 | 10/2005 | Watts et al. |
| 2005/0250770 A1 | 11/2005 | Ono et al. |
| 2005/0256066 A1 | 11/2005 | Abel et al. |
| 2005/0261317 A1 | 11/2005 | Sadhu et al. |
| 2005/0272751 A1 | 12/2005 | McKerracher et al. |
| 2006/0019988 A1 | 1/2006 | McDonald et al. |
| 2006/0069034 A1 | 3/2006 | Burli et al. |
| 2006/0079538 A1 | 4/2006 | Hallahan et al. |
| 2006/0106038 A1 | 5/2006 | Bouscary et al. |
| 2006/0116326 A1 | 6/2006 | Burli et al. |
| 2006/0135790 A1 | 6/2006 | Hyett et al. |
| 2006/0156485 A1 | 7/2006 | Lim |
| 2006/0183783 A1 | 8/2006 | Polisetti et al. |
| 2006/0199776 A1 | 9/2006 | Blagg et al. |
| 2006/0205694 A1 | 9/2006 | Alonso et al. |
| 2006/0235031 A1 | 10/2006 | Arnold et al. |
| 2006/0276470 A1 | 12/2006 | Jackson et al. |
| 2006/0287295 A1 | 12/2006 | Barlaam et al. |
| 2006/0293274 A1 | 12/2006 | Wu |
| 2007/0015773 A1 | 1/2007 | Bergeron et al. |
| 2007/0017915 A1 | 1/2007 | Weder et al. |
| 2007/0027193 A1 | 2/2007 | Leban et al. |
| 2007/0032640 A1 | 2/2007 | Varghese et al. |
| 2007/0054915 A1 | 3/2007 | Arora et al. |
| 2007/0072897 A1 | 3/2007 | Mahaney et al. |
| 2007/0099871 A1 | 5/2007 | Davis et al. |
| 2007/0142405 A1 | 6/2007 | Dong et al. |
| 2007/0179151 A1 | 8/2007 | Chen et al. |
| 2007/0224672 A1 | 9/2007 | Leban et al. |
| 2007/0249598 A1 | 10/2007 | Wang et al. |
| 2007/0270452 A1 | 11/2007 | Blagg et al. |
| 2008/0032960 A1 | 2/2008 | Knight et al. |
| 2008/0058521 A1 | 3/2008 | Krishnan et al. |
| 2008/0070935 A1 | 3/2008 | Huang et al. |
| 2008/0119454 A1 | 5/2008 | Polisetti et al. |
| 2008/0119455 A1 | 5/2008 | Polisetti et al. |
| 2008/0119461 A1 | 5/2008 | Sin et al. |
| 2008/0200465 A1 | 8/2008 | Burli et al. |
| 2008/0249090 A1 | 10/2008 | Hu et al. |
| 2008/0261956 A1 | 10/2008 | Choi et al. |
| 2008/0287469 A1 | 11/2008 | Diacovo et al. |
| 2008/0292626 A1 | 11/2008 | Wang et al. |
| 2008/0293674 A1 | 11/2008 | Schwarz et al. |
| 2008/0306053 A1 | 12/2008 | Tachdjian et al. |
| 2008/0306093 A1 | 12/2008 | Servant et al. |
| 2008/0306099 A1 | 12/2008 | Li et al. |
| 2008/0312180 A1 | 12/2008 | Liang et al. |
| 2008/0318942 A1 | 12/2008 | Simon et al. |
| 2009/0023729 A1 | 1/2009 | Nakamura et al. |
| 2009/0030023 A1 | 1/2009 | Harada et al. |
| 2009/0053192 A1 | 2/2009 | Millan et al. |
| 2009/0088452 A1 | 4/2009 | Coleman et al. |
| 2009/0099214 A1 | 4/2009 | Fairhurst et al. |
| 2009/0105233 A1 | 4/2009 | Chua et al. |
| 2009/0118283 A1 | 5/2009 | Defert et al. |
| 2009/0124638 A1 | 5/2009 | Shokat et al. |
| 2009/0124654 A1 | 5/2009 | Mjalli et al. |
| 2009/0137581 A1 | 5/2009 | Chen et al. |
| 2009/0143402 A1 | 6/2009 | Simonsen et al. |
| 2009/0163481 A1 | 6/2009 | Murphy et al. |
| 2009/0163709 A1 | 6/2009 | Blagg |
| 2009/0170879 A1 | 7/2009 | Szucova et al. |
| 2009/0181920 A1 | 7/2009 | Watkins et al. |
| 2009/0181988 A1 | 7/2009 | Tanaka et al. |
| 2009/0187014 A1 | 7/2009 | Blagg |
| 2009/0203689 A1 | 8/2009 | Dhalla et al. |
| 2009/0209539 A1 | 8/2009 | Leblanc et al. |
| 2009/0232768 A1 | 9/2009 | Birkus et al. |
| 2009/0247513 A1 | 10/2009 | Burli et al. |
| 2009/0253694 A1 | 10/2009 | Ono et al. |
| 2009/0264409 A1 | 10/2009 | Dong et al. |
| 2009/0264423 A2 | 10/2009 | Chua et al. |
| 2009/0270426 A1 | 10/2009 | Knight et al. |
| 2009/0270567 A1 | 10/2009 | Small et al. |
| 2009/0312319 A1 | 12/2009 | Ren et al. |
| 2009/0312406 A1 | 12/2009 | Hsieh et al. |
| 2009/0318411 A1 | 12/2009 | Castanedo et al. |
| 2009/0325967 A1 | 12/2009 | Fairhurst et al. |
| 2010/0009963 A1 | 1/2010 | Knight et al. |
| 2010/0022585 A1 | 1/2010 | deLong et al. |
| 2010/0028280 A1 | 2/2010 | Philippe et al. |
| 2010/0029658 A1 | 2/2010 | Gavish et al. |
| 2010/0029693 A1 | 2/2010 | Douangpanya et al. |
| 2010/0048540 A1 | 2/2010 | Boyle et al. |
| 2010/0048882 A1 | 2/2010 | Blagg et al. |
| 2010/0056494 A1 | 3/2010 | Winzeler et al. |
| 2010/0105630 A1 | 4/2010 | Blagg |
| 2010/0163070 A1 | 7/2010 | Malle et al. |
| 2010/0168153 A1 | 7/2010 | Stowasser et al. |

(56) References Cited

U.S. PATENT DOCUMENTS

| | | |
|---|---|---|
| 2010/0179167 A1 | 7/2010 | Xu et al. |
| 2010/0190749 A1 | 7/2010 | Ren et al. |
| 2010/0280067 A1 | 11/2010 | Sarma et al. |
| 2010/0305099 A1 | 12/2010 | Sapountzis et al. |
| 2010/0324074 A1 | 12/2010 | Zhang |
| 2010/0331306 A1 | 12/2010 | Bui et al. |
| 2011/0009378 A1 | 1/2011 | Lange et al. |
| 2011/0046165 A1 | 2/2011 | Ren et al. |
| 2011/0105508 A1 | 5/2011 | Allen et al. |
| 2011/0124641 A1 | 5/2011 | Ren et al. |
| 2011/0130306 A1 | 6/2011 | Chang |
| 2011/0130420 A1 | 6/2011 | Khanzhin et al. |
| 2011/0135655 A1 | 6/2011 | Katsikis et al. |
| 2011/0144134 A1 | 6/2011 | Shokat et al. |
| 2011/0172228 A1 | 7/2011 | Ren et al. |
| 2011/0172335 A1 | 7/2011 | Deshpande |
| 2011/0224223 A1 | 9/2011 | Shokat et al. |
| 2011/0251182 A1 | 10/2011 | Sun et al. |
| 2011/0269779 A1 | 11/2011 | Wilson et al. |
| 2011/0281866 A1 | 11/2011 | Ren et al. |
| 2011/0301144 A1 | 12/2011 | Knight et al. |
| 2012/0059000 A1 | 3/2012 | Ren et al. |
| 2012/0065154 A1 | 3/2012 | Tanaka et al. |
| 2012/0077815 A1 | 3/2012 | Allen et al. |
| 2012/0122838 A1 | 5/2012 | Ren et al. |
| 2012/0149701 A1 | 6/2012 | Ren et al. |
| 2012/0184568 A1 | 7/2012 | Ren et al. |
| 2012/0202784 A1 | 8/2012 | Aronov et al. |
| 2012/0220575 A1 | 8/2012 | Chang et al. |
| 2012/0245169 A1 | 9/2012 | Ren et al. |
| 2012/0329776 A1 | 12/2012 | Ren et al. |
| 2013/0029982 A1 | 1/2013 | Castro et al. |
| 2013/0029984 A1 | 1/2013 | Castro et al. |
| 2013/0053362 A1 | 2/2013 | Castro et al. |
| 2014/0275135 A1 | 9/2014 | Genov et al. |
| 2014/0288048 A1 | 9/2014 | Castro et al. |

FOREIGN PATENT DOCUMENTS

| | | |
|---|---|---|
| DE | 2139107 A1 | 2/1973 |
| EP | 0530149 A1 | 3/1993 |
| EP | 0640599 A1 | 3/1995 |
| EP | 773023 A1 | 5/1997 |
| EP | 1020445 B1 | 8/2008 |
| EP | 2433636 A1 | 3/2012 |
| GB | 812366 A | 4/1959 |
| GB | 937725 A | 9/1963 |
| JP | 61-109797 A | 5/1986 |
| JP | 05-256693 A | 10/1993 |
| JP | 08295667 A | 11/1996 |
| JP | 09143163 A | 6/1997 |
| JP | 10206995 A | 8/1998 |
| JP | 2000072773 A | 3/2000 |
| JP | 2002131859 A | 5/2002 |
| JP | 2003073357 A | 3/2003 |
| JP | 2004161716 A | 6/2004 |
| JP | 4834699 | 12/2011 |
| JP | 4846769 | 12/2011 |
| WO | WO 83/01446 A1 | 4/1983 |
| WO | WO 91/17161 A1 | 11/1991 |
| WO | WO 92/14733 A1 | 9/1992 |
| WO | WO 93/16091 A1 | 8/1993 |
| WO | WO 93/16092 A1 | 8/1993 |
| WO | WO 93/18035 A1 | 9/1993 |
| WO | WO 93/19767 A1 | 10/1993 |
| WO | WO 93/22443 A1 | 11/1993 |
| WO | WO 94/13677 A1 | 6/1994 |
| WO | WO 94/17803 A1 | 8/1994 |
| WO | WO 94/19340 A1 | 9/1994 |
| WO | WO 94/20490 A1 | 9/1994 |
| WO | WO 94/29436 A1 | 12/1994 |
| WO | WO 95/01975 A1 | 1/1995 |
| WO | WO 95/07278 A1 | 3/1995 |
| WO | WO 95/10628 A2 | 4/1995 |
| WO | WO 95/12588 A1 | 5/1995 |
| WO | WO 95/29673 A1 | 11/1995 |
| WO | WO 95/32984 A1 | 12/1995 |
| WO | WO 95/10628 A3 | 9/1996 |
| WO | WO 96/40706 A1 | 12/1996 |
| WO | WO 97/28133 A1 | 8/1997 |
| WO | WO 97/28161 A1 | 8/1997 |
| WO | WO 98/41525 A1 | 9/1998 |
| WO | WO 98/52611 A1 | 11/1998 |
| WO | WO 98/57952 A1 | 12/1998 |
| WO | WO 00/17202 A1 | 3/2000 |
| WO | WO 01/02369 A2 | 1/2001 |
| WO | WO 01/16114 A2 | 3/2001 |
| WO | WO 01/19829 A2 | 3/2001 |
| WO | WO 01/25238 A2 | 4/2001 |
| WO | WO 01/31063 A1 | 5/2001 |
| WO | WO 01/38584 A2 | 5/2001 |
| WO | WO 01/16114 A3 | 8/2001 |
| WO | WO 01/55140 A1 | 8/2001 |
| WO | WO 01/55143 A1 | 8/2001 |
| WO | WO 01/56988 A1 | 8/2001 |
| WO | WO 01/19829 A3 | 9/2001 |
| WO | WO 01/25238 A3 | 10/2001 |
| WO | WO 01/38584 A3 | 10/2001 |
| WO | WO 01/81346 A2 | 11/2001 |
| WO | WO 02/06192 A1 | 1/2002 |
| WO | WO 01/81346 A3 | 3/2002 |
| WO | WO 01/02369 A3 | 4/2002 |
| WO | WO 02/30944 A2 | 4/2002 |
| WO | WO 02/57425 A2 | 7/2002 |
| WO | WO 02/076986 A1 | 10/2002 |
| WO | WO 02/080926 A1 | 10/2002 |
| WO | WO 02/083143 A1 | 10/2002 |
| WO | WO 02/088025 A1 | 11/2002 |
| WO | WO 02/090334 A1 | 11/2002 |
| WO | WO 02/30944 A3 | 1/2003 |
| WO | WO 03/000187 A2 | 1/2003 |
| WO | WO 03/016275 A1 | 2/2003 |
| WO | WO 03/020880 A2 | 3/2003 |
| WO | WO 03/024969 A1 | 3/2003 |
| WO | WO 03/028341 A2 | 4/2003 |
| WO | WO 03/035075 A1 | 5/2003 |
| WO | WO 03/059884 A1 | 7/2003 |
| WO | WO 03/020880 A3 | 10/2003 |
| WO | WO 03/082341 A1 | 10/2003 |
| WO | WO 03/106426 A1 | 12/2003 |
| WO | WO 2004/006906 A2 | 1/2004 |
| WO | WO 2004/006906 A3 | 3/2004 |
| WO | WO 2004/018058 A2 | 3/2004 |
| WO | WO 2004/031177 A1 | 4/2004 |
| WO | WO 2004/039774 A2 | 5/2004 |
| WO | WO 2004/018058 A3 | 7/2004 |
| WO | WO 2004/039774 A3 | 7/2004 |
| WO | WO 2004/058717 A1 | 7/2004 |
| WO | WO 03/000187 A3 | 8/2004 |
| WO | WO 2004/087053 A2 | 10/2004 |
| WO | WO 2004/111014 A1 | 12/2004 |
| WO | WO 2005/002585 A1 | 1/2005 |
| WO | WO 2005/007085 A2 | 1/2005 |
| WO | WO 2005/012323 A2 | 2/2005 |
| WO | WO 2005/016348 A1 | 2/2005 |
| WO | WO 2005/016349 A1 | 2/2005 |
| WO | WO 2005/016528 A2 | 2/2005 |
| WO | WO 2005/021533 A1 | 3/2005 |
| WO | WO 02/57425 A3 | 4/2005 |
| WO | WO 2005/012323 A3 | 5/2005 |
| WO | WO 2005/016528 A3 | 5/2005 |
| WO | WO 2005/044181 A2 | 5/2005 |
| WO | WO 2005/047289 A1 | 5/2005 |
| WO | WO 2005/061460 A1 | 7/2005 |
| WO | WO 2005/063258 A1 | 7/2005 |
| WO | WO 2005/067901 A2 | 7/2005 |
| WO | WO 2005/074603 A2 | 8/2005 |
| WO | WO 2005/007085 A3 | 9/2005 |
| WO | WO 2005/097800 A1 | 10/2005 |
| WO | WO 2005/105760 A1 | 11/2005 |
| WO | WO 2005/067901 A3 | 12/2005 |
| WO | WO 2005/112935 A1 | 12/2005 |
| WO | WO 2005/113556 A1 | 12/2005 |
| WO | WO 2005/117889 A1 | 12/2005 |

(56) References Cited

FOREIGN PATENT DOCUMENTS

| | | |
|---|---|---|
| WO | WO 2005/120511 A1 | 12/2005 |
| WO | WO 2005/044181 A3 | 3/2006 |
| WO | WO 2006/030032 A1 | 3/2006 |
| WO | WO 2006/038865 A1 | 4/2006 |
| WO | WO 2006/050501 A2 | 5/2006 |
| WO | WO 2006/050946 A1 | 5/2006 |
| WO | WO 2006/068760 A2 | 6/2006 |
| WO | WO 2004/087053 A3 | 8/2006 |
| WO | WO 2006/089106 A2 | 8/2006 |
| WO | WO 2006/108107 A1 | 10/2006 |
| WO | WO 2006/112666 A1 | 10/2006 |
| WO | WO 2005/074603 A3 | 11/2006 |
| WO | WO 2006/114064 A2 | 11/2006 |
| WO | WO 2006/114065 A2 | 11/2006 |
| WO | WO 2006/068760 A3 | 12/2006 |
| WO | WO 2006/089106 A3 | 12/2006 |
| WO | WO 2007/002293 A2 | 1/2007 |
| WO | WO 2007/006547 A1 | 1/2007 |
| WO | WO 2007/020046 A1 | 2/2007 |
| WO | WO 2007/002293 A3 | 3/2007 |
| WO | WO 2007/025090 A2 | 3/2007 |
| WO | WO 2006/050501 A3 | 5/2007 |
| WO | WO 2007/061737 A2 | 5/2007 |
| WO | WO 2006/114064 A3 | 6/2007 |
| WO | WO 2006/114065 A3 | 6/2007 |
| WO | WO 2007/025090 A3 | 6/2007 |
| WO | WO 2007/075554 A2 | 7/2007 |
| WO | WO 2007/079164 A2 | 7/2007 |
| WO | WO 2007/079164 A3 | 9/2007 |
| WO | WO 2007/103308 A2 | 9/2007 |
| WO | WO 2007/112005 A2 | 10/2007 |
| WO | WO 2007/114926 A2 | 10/2007 |
| WO | WO 2007/121453 A2 | 10/2007 |
| WO | WO 2007/121920 A2 | 11/2007 |
| WO | WO 2007/121924 A2 | 11/2007 |
| WO | WO 2007/124854 A1 | 11/2007 |
| WO | WO 2007/125310 A2 | 11/2007 |
| WO | WO 2007/125315 A2 | 11/2007 |
| WO | WO 2007/126841 A2 | 11/2007 |
| WO | WO 2007/134828 A1 | 11/2007 |
| WO | WO 2007/135380 A2 | 11/2007 |
| WO | WO 2007/135398 A1 | 11/2007 |
| WO | WO 2007/061737 A3 | 12/2007 |
| WO | WO 2007/125315 A3 | 12/2007 |
| WO | WO 2007/121920 A3 | 1/2008 |
| WO | WO 2008/001236 A2 | 1/2008 |
| WO | WO 2008/012326 A1 | 1/2008 |
| WO | WO 2007/103308 A3 | 2/2008 |
| WO | WO 2007/112005 A3 | 2/2008 |
| WO | WO 2007/125310 A3 | 3/2008 |
| WO | WO 2008/025755 A1 | 3/2008 |
| WO | WO 2008/039882 A1 | 4/2008 |
| WO | WO 2008/047821 A1 | 4/2008 |
| WO | WO 2008/063625 A2 | 5/2008 |
| WO | WO 2008/064018 A1 | 5/2008 |
| WO | WO 2008/070507 A2 | 6/2008 |
| WO | WO 2007/121453 A3 | 7/2008 |
| WO | WO 2008/079028 A1 | 7/2008 |
| WO | WO 2008/082487 A2 | 7/2008 |
| WO | WO 2008/094737 A2 | 8/2008 |
| WO | WO 2007/121924 A3 | 9/2008 |
| WO | WO 2008/112715 A2 | 9/2008 |
| WO | WO 2007/114926 A3 | 10/2008 |
| WO | WO 2008/118454 A2 | 10/2008 |
| WO | WO 2008/118455 A1 | 10/2008 |
| WO | WO 2008/118468 A1 | 10/2008 |
| WO | WO 2008/125014 A1 | 10/2008 |
| WO | WO 2008/125207 A1 | 10/2008 |
| WO | WO 2008/127226 A2 | 10/2008 |
| WO | WO 2007/126841 A3 | 11/2008 |
| WO | WO 2008/112715 A3 | 11/2008 |
| WO | WO 2008/118454 A3 | 11/2008 |
| WO | WO 2008/136457 A1 | 11/2008 |
| WO | WO 2008/082487 A3 | 12/2008 |
| WO | WO 2008/127226 A3 | 12/2008 |
| WO | WO 2009/000412 A1 | 12/2008 |
| WO | WO 2009/004621 A1 | 1/2009 |
| WO | WO 2009/010925 A2 | 1/2009 |
| WO | WO 2009/023718 A2 | 2/2009 |
| WO | WO 2008/094737 A3 | 3/2009 |
| WO | WO 2009/029617 A1 | 3/2009 |
| WO | WO 2009/023718 A3 | 4/2009 |
| WO | WO 2009/044707 A1 | 4/2009 |
| WO | WO 2009/050506 A2 | 4/2009 |
| WO | WO 2009/064802 A2 | 5/2009 |
| WO | WO 2009/010925 A3 | 7/2009 |
| WO | WO 2009/064802 A3 | 7/2009 |
| WO | WO 2009/088986 A1 | 7/2009 |
| WO | WO 2009/088990 A1 | 7/2009 |
| WO | WO 2009/100406 A2 | 8/2009 |
| WO | WO 2009/103022 A1 | 8/2009 |
| WO | WO 2009/117157 A1 | 9/2009 |
| WO | WO 2009/117985 A1 | 10/2009 |
| WO | WO 2009/050506 A3 | 11/2009 |
| WO | WO 2009/100406 A3 | 11/2009 |
| WO | WO 2010/006086 A2 | 1/2010 |
| WO | WO 2010/009207 A1 | 1/2010 |
| WO | WO 2010/019210 A2 | 2/2010 |
| WO | WO 2010/024430 A1 | 3/2010 |
| WO | WO 2010/036380 A1 | 4/2010 |
| WO | WO 2010/039534 A2 | 4/2010 |
| WO | WO 2010/019210 A3 | 5/2010 |
| WO | WO 2010/065923 A2 | 6/2010 |
| WO | WO 2010/070032 A1 | 6/2010 |
| WO | WO 2010/039534 A3 | 8/2010 |
| WO | WO 2010/092340 A1 | 8/2010 |
| WO | WO 2010/101949 A1 | 9/2010 |
| WO | WO 2010/106436 A2 | 9/2010 |
| WO | WO 2010/119050 A1 | 10/2010 |
| WO | WO 2010/129816 A2 | 11/2010 |
| WO | WO 2010/133836 A1 | 11/2010 |
| WO | WO 2011/008302 A1 | 1/2011 |
| WO | WO 2011/017296 A1 | 2/2011 |
| WO | WO 2011/045353 A1 | 4/2011 |
| WO | WO 2010/151735 A2 | 5/2011 |
| WO | WO 2011/058108 A1 | 5/2011 |
| WO | WO 2011/058109 A1 | 5/2011 |
| WO | WO 2011/058110 A1 | 5/2011 |
| WO | WO 2011/058113 A1 | 5/2011 |
| WO | WO 2011/075628 A1 | 6/2011 |
| WO | WO 2011/133722 A2 | 10/2011 |
| WO | WO 2011/144742 A1 | 11/2011 |
| WO | WO 2011/146882 A1 | 11/2011 |
| WO | WO 2012/003271 A1 | 1/2012 |
| WO | WO 2012/003274 A1 | 1/2012 |
| WO | WO 2012/032334 A1 | 3/2012 |
| WO | WO 2012/061696 A1 | 5/2012 |
| WO | WO 2012/064973 A2 | 5/2012 |
| WO | WO 2012/097000 A1 | 7/2012 |
| WO | WO 2013/012915 A1 | 1/2013 |
| WO | WO 2013/032591 A1 | 3/2013 |
| WO | WO 2013/116562 A1 | 8/2013 |
| WO | WO 2014/100767 A1 | 6/2014 |
| WO | WO 2014/151386 A1 | 9/2014 |
| WO | WO 2014/201409 A1 | 12/2014 |
| WO | WO 2015/010641 A1 | 1/2015 |

OTHER PUBLICATIONS

Abe et al., "T cell receptor-mediated recognition of self-ligand induces signaling in immature thymocytes before negative selection," *J. Exp. Med.* 176(2):459-468 (1992).

Abrahamian et al., "Immunological and Clinical Profile of Adult Patients with Selective Immunoglobulin Subclass deficiency: response to intravenous immunoglobulin therapy," *Clin. Exp. Immunol.* 159(3):344-350 (2010).

Abraham, T., "Thermally induced intramolecular cycloaddition reaction of N-phenyl-2-phenylethynlbenzamide potential cure reaction for thermosetting polymers," *J. Polym. Sci. Polym. Chem. Ed.* 20(7):1953-1957 (1982).

Ames et al., "Heterocyclic Syntheses from o-Halogeno-acids. Part II. Thienopyridinones and Thienopyranones from

(56) References Cited

OTHER PUBLICATIONS

"3-Bromothiophen-2- and 4-Bromothiophen-3-carboxylic Acids," *J.C.S. Perkin I* 1390-1395 (1975).
Anderson et al., "Paradoxical inhibition of T-cell function in response to CTLA-4 blockade; heterogeneity within the human T-cell population," *Nat. Med.* 6(2):211-214 (2000).
Andrews et al., "Effects of the 11β-hydroxysteroid dehydrogenase inhibitor carbenoxolone on insulin sensitive in men with type 2 diabetes," *J. Clin. Endocrinol. Metab.* 88(1):285-291 (2003).
Arcaro et al., "Wortmannin is a potent phosphatidylinositol 3-kinase inhibitor: the role of phosphatidylinositol 3,4,5-triphosphate in neutrophil responses," *Biochem. J.*, 296(Pt 2):297-301 (1993).
Arnold et al., "Pyrrolo[2,3-d]pyrimidines containing an extended 5-substituent as potent and selective inhibitors of Ick I," *Bioorg. Med. Chem. Lett.* 10(19):2167-2170 (2000).
Augustine et al., "Interleukin 2- and polyomavirus middle T antigen-induced modification of phosphatidylinositol 3-kinase activity in activated T lymphocytes," *Mol. Cell. Biol.* 11(9):4431-4440 (1991).
Baggiolini et al., "Inhibition of the phagocytosis-induced respiratory burst by the fungal metabolite wortmannin and some analogues," *Exp. Cell. Res.* 169(2): 408-418 (1987).
Ballell et al. "New Thiopyrazolo[3,4-d] pyrimidine derivatives as anti-mycobacterial agents," *Bioorg. Med. Chem. Lett.* 17(6):1736-1740 (2007).
Banker et al., Modern Pharmaceutics, pp. 451, 596, 3$^{rd}$ ed, Marcel Dekker, New York (1996).
Bansal et al., "The Molecular Biology of Endometrial Cancers and the Implications for Pathogenesis, Classification, and Targeted Therapies," *Cancer Control* 16(1):8-13 (2009).
Barber et al., "PI3Kgamma inhibition blocks glomerulonephritis and extends lifespan in a mouse model of systemic lupus," *Nat. Med.* 11(9):933-935 (2005). (Epub Aug. 28, 2005).
Barf et al., "Arylsulfonamidothiazoles as a new class of potential antidiabetic drugs. Discovery of potent and selective inhibitors of the 11β-hydroxysteroid dehydrogenase Type 1," *J. Med. Chem.* 45(18):3813-3815 (2002).
Barnes et al., "Efficacy and Safety of Inhaled Corticosteroids in Asthma—Report of a Workshop Held in Eze, France Oct. 1992," *Am. Rev. Respir. Dis.* 148:S1-S26 (1993).
Bartholomeusz et al., "Targeting the PI3K Signaling Pathway in Cancer Therapy," *Expert Opin. Ther. Targets* 16(1):121-130 (2012).
BASOTEST®, Test Kit for the Quantitative Determination of the Degranulation of Basophilic Granulocytes in Heparinized Human Whole Blood, version 04/02, pp. 1-10, [www.biocarta.com/TDS/10-0500.pdf], Retrieved from the Internet Nov. 29, 2011.
Beeram et al., "Akt-induced endocrine therapy resistance is reversed by inhibition of mTOR signaling," *Ann Oncol.* 18(8):1323-1328 (2007).
Bell et al., "Glucokinase mutations insulin secretion, and diabetes mellitus", *Annu. Rev. Physiol.* 58:171-186 (1996).
Berndt et al., "The p110δ crystal structure uncovers mechanisms for selectivity and potency of novel PI3K inhibitors," *Nat. Chem. Biol.* 6(2):117-124 (2010).
Bhat et al., "Pyrazolopyrimidine nucleosides. 12. Synthesis and biological activity of certain pyrazolo [3,4-d]pyrimidine nucleosides related to adenosine," *J. Med. Chem.* 24(10):1165-1172 (1981).
Bhatt et al., "Dual inhibition of PI3K and mTOR inhibits autocrine and paracrine proliferative loops in PI3K/Akt/mTOR-addicted lymphomas," *Blood* 115(22):4455-4463 (2010).
Bi et al., "Proliferative defect and embryonic lethality in mice homozygous for a deletion in the p110α subunit of phosphoinositide 3-kinase," *J. Biol. Chem.* 274:10963-10968 (1999).
Billottet et al., "A selective inhibitor of the p110δ isoform of PI 3-kinase inhibits AML cell proliferation and survival and increases the cytotoxic effects of VP16," *Oncogene* 25:6648-6659 (2006).
Billottet et al., "Inhibition of Class 1 Phosphoinositide 3-Kinase Activity Impairs Proliferation and Triggers Apoptosis in Acute Promyelocytic Leukemia without Affecting Atra-Induced Differentiation," *Cancer Res.* 69(3):1027-1036 (2009).
Bishop et al., "Generation of monospecific nanomolar tyrosine kinase inhibitors via a chemical genetic approach," *J. Am. Chem. Soc.* 121(4):627-631 (1999).
Blunden et al., "Mycotoxins in food," *Med. Lab. Sci.* 48(4):271-282 (1991).
Bochner et al., "Immunological aspects of allergic asthma," *Annu. Rev. Immunol.* 12:295-335 (1994).
Bohren et al., "Expression, crystallization and preliminary crystallographic analysis of human carbonyl reductase," *J. Mol. Biol.* 224:659-664 (1994).
Bone et al., "Phosphoinositide 3-kinase signalling regulates early development and developmental haemopoiesis," *J. Cell. Sci.* 120(Pt 10):1752-1762 (2007).
Bowers et al., "A platelet biomarker for assessing phosphoinositide 3-kinase inhibition during cancer chemotherapy," *Mol. Cancer Ther.* 6(9):2600-2607 (2007).
Brzezianska et al., "A Minireview: The Role of MAPK/ERK and PI3K/Akt Pathways in Thyroid Follicular Cell-Derived Neoplasm," *Front. Biosci.* 16:422-439 (2011).
Buitenhuis et al., "The role of the PI3k-PKB signaling module in regulation of hematopoiesis," *Cell Cycle* 8(4):560-566 (2009).
Burger et al., "High-level expression of the T-cell chemokines CCL3 and CCL4 by chronic lymphocytic leukemia B cells in nurselike cell cocultures and after BCR stimulation," *Blood* 113(13):3050-3058 (2009).
Burger et al., "Phosphoinositide 3'-kinase delta: turning off BCR signaling in Chronic Lymphocytic Leukemia," *Oncotarget* 2(10):737-738 (2011).
Burger, "Inhibiting B-Cell Receptor Signaling Pathways in Chronic Lymphocytic Leukemia," *Curr. Mematol. Malig. Rep.* 7:26-33 (2012).
Byrd et al., "Translating PI3K-Delta Inhibitors to the Clinic in Chronic Lymphocytic Leukemia: The Story of CAL-101 (GS1101)," *ASCO Program Proceedings*, pp. 691-694 (2012).
Campora et al., "Binuclear complexes of nickel bridged by hydrocarbon ligands. Isocyanide insertion chemistry and amide formation by intramolecular coupling of acyl and imidoyl functionalities," *Organometallics* 11(1):11-13 (1992).
Campora et al., "Isocyanide insertion chemistry. Synthesis and structural characterization of bridging imidoyl complexes of nickel and amide formation by intramolecular coupling of acyl and imidoyl functionalities," *Organometallics* 12(10):4025-4031 (1993).
Camps et al., "Blockade of PI3Kγ suppresses joint inflammation and damage in mouse models of rheumatoid arthritis," *Nat. Med.* 11(9):936-943 (2005).
Chaisuparat et al., "Dual inhibition of PI3Kα and mTOR as an alternative treatment for Kaposi's Sarcoma," *Cancer Res.* 68:8361-8368 (2008).
Chang et al., "The Bruton tyrosine kinase inhibitor PCI-32765 ameliorates autoimmune arthritis by inhibition of multiple effector cells," *Arthritis Research & Therapy* 13:R115 (2011).
Chappelow et al., "Neovascular age-related macular degeneration: potential therapies," *Drugs* 68(8):1029-1036 (2008).
Chapuis et al., "Dual Inhibition of PI3K and mTORC1/2 Signaling by NVP-BEZ235 as a New Therapeutic Strategy for Acute Myeloid Leukemia," *Clin. Cancer Res.* 16(22):5424-5435 (2010).
Chawla et. al., "Challenges in Polymorphism of Pharmaceuticals," *Current Research & Information on Pharmaceutical Science* 5(1):9-12 (2004).
Chen et al., "Characterization of Structurally Distinct, Isoform-Selective Phosphoinositide 3'-Kinase Inhibitors in Combination with Radiation in the Treatment of Glioblastoma," *Mol. Cancer Ther.* 7(4):841-850 (2008).
Cheson et al., "Bendamustine: Rebirth of an Old Drug," *J. Clin. Oncol.* 27(9):1492-1501 (2009).
Chiarini et al., "Activity of the Novel Dual Phosphatidylinositol 3-Kinase/Mammalian Target of Rapamycin Inhibitor NVP-BEZ235 against T-Cell Acute Lymphoblastic Leukemia," *Cancer Res.* 70(20):8097-8107 (2010).

(56) References Cited

OTHER PUBLICATIONS

Chiarini et al., "Dual Inhibition of Class IA Phosphatidylinositol 3-Kinase and Mammalian Target of Rapamycin as a New Therapeutic Option for T-Cell Acute Lymphoblastic Leukemia," *Cancer Res.* 69(8): 3520-3528 (2009).
Cho et al., "A novel synthesis of benzo[c]phenanthridine skeleton and biological evaluation of isoquinoline derivatives," *Chem. Pharm. Bull.(Tokyo)* 47(6):900-902 (1999).
Clayton et al., "A crucial role for the p110delta subunit of phosphatidylinositol 3-kinase in B cell development and activation," *J. Exp. Med.* 196:753-763 (2002).
Closse et al., "2,3-dihydrobenzofuran-2-ones: a new class of highly potent antiinflammatory agents," *J. Med. Chem.* 24:1465-1471 (1981).
Courtney et al., "The PI3K Pathway As Drug Target in Human Cancer," *J. Clin. Oncol.* 28(6):1075-1083 (2010).
Cox et al., "Human colorectal cancer cells efficiently conjugate the cyclopentenone prostaglandin, prostaglandin $J_2$, to glutathione," *Biochem. Biophys. Acta.* 1584:37-45 (2002).
Cushing et al., "PI3Kδ and PI3Kγ as Targets for Autoimmune and Inflammatory Diseases," *J. Med. Chem.* 55:8559-8581 (2012).
Dai et al., "Distinct Roles of Phosphoinositide-3 Kinase and Phospholipase Cγ2 in B-Cell Receptor-Mediated Signal Transduction," *Mol. Cell. Biol.* 26(1):88-99 (2006).
Davids et al., "Decreased mitochondrial apoptotic priming underlies stroma-mediated treatment resistance in chronic lymphocytic leukemia," *Blood* 120(17):3501-3509 (2012).
Davies et al., "The Human T3 γ Chain is Phosphorylated at Serine 126 in Response to T Lymphocyte Activation," *J. Biol. Chem.* 262(23):10918-10921 (1987).
Davis et al., "The preparation of substituted 1(2H)-isoquinolinones from dilithiated 2-methyl-N-arylbenzamides, 2-methyl-N-(arylmethyl)-benzamides, or 2-methylbenzoic acid, 2, 2-dimethylhydrazide," *Synthetic Commun.* 27(17):2961-2969 (1997).
Davis et al., "Chronic active B-cell-receptor signaling in diffuse large B-cell lymphoma," *Nature* 463:88-92 (2010).
De Weers et al., "The Bruton's tyrosine kinase gene is expressed throughout B cell differentiation, from early precursor B cell stages preceding immunoglobulin gene rearrangement up to mature B cell stages," *Eur. J. Immunol.* 23:3109-3114 (1993).
Diederich et al., "In search for specific inhibitors of human 11β-hydroxysteroid-dehydrogenases (11βHSDs): chenodeoxycholic acid selectively inhibits 11β-HSD-I," *Eur. J. Endocrinol.* 142(2):200-207 (2000).
Dijksman et al., "271.1: 2-dihydro-2-thianaphthalene derivatives. Part I. Preparation and reactions of 1 : 2-dihydro-1-keto-2-thianaphthalenes," *J. Chem. Soc.* 1213-1218 (1951).
Ding et al., "A combinatorial scaffold approach toward kinase-directed heterocycle libraries," *J. Am. Chem. Soc.* 124(8):1594-1596 (2002).
Ding et al., "A concise and traceless linker strategy toward combinatorial libraries of 2,6,9-substituted purines," *J. Org. Chem.* 66(24):8273-8276 (2001).
Ding et al., "Resin-capture and release strategy toward combinatorial libraries of 2,6,9-substituted purines," *J. Comb. Chem.* 4(2):183-186 (2002).
Donati, G., "Emerging therapies for neovascular age-related macular degeneration: state of the art," *Ophthalmologica* 221(6):366-377 (2007).
European Examination Report for EP Application No. 07873406.8 dated Sep. 14, 2011.
European Search Report for EP Application No. 05857011.0 dated Feb. 4, 2011.
European Search Report for EP Application No. 09700784.3 dated Oct. 28, 2011.
European Search Report and Search Opinion for EP Application No. 09700424.6 dated Oct. 26, 2011.
European Search Report for EP Application No. 07873406.8 dated Mar. 1, 2010.
European Search Report for EP Application No. 07754845.1 dated Sep. 20, 2011.
Examination Report for GB Application No. GB 0819947.3 dated Oct. 27, 2010.
Extended European Search Report for EP Application No. 09816603.6 dated Mar. 19, 2012.
Extended European Search Report from European Application No. 09700784.3 dated Oct. 28, 2011.
Fajans et al., "Maturity onset diabetes of the young (MODY)," *Diabet. Med.* 13(9 Suppl 6):590-595 (1996).
Feinstein et al., "Regulation of the action of hydrocotisone in airway epithelial cells by 11b-hydroxysteroid dehydrogenase," *Am. J. Respir. Cell. Mol. Biol.* 21(3):403-408 (1999).
Feldman et al., "Active-Site Inhibitors of mTOR Target Rapamycin-Resistant Outputs of mTORC1 and mTORC2," *PLoS Biol.* 7(2):371-383 (2009).
Fingl et al., "Chapter 1—General Principles," The Pharmacological Basis of Therapeutics, 5th edition, Goodman and Gilman editors, MacMillan Publishings Co., Inc., New York, pp. 1-46, (1975).
Flinn et al., "Preliminary Evidence of Clinical Activity in a Phase I Study of CAL-101, a Selective Inhibitor of the p110δ Isoform of Phosphatidylinositol 3-Kinase (PI3K), in Patients with Select Hematologic Malignancies," *J. Clin. Oncol.* 27(15s) (Suppl: Abstr 3543) (2009).
Forrest et al., "Carbonyl Reductase," *Chem. Biol. Interact.* 129(1-2): 21-40 (2000).
Forrest et al., "Induction of a human carbonyl reductase gene located on chromosome 21," *Biochem. Biophys. Acta.* 1048(2-3):149-155 (1990).
Franzen, "The Suzuki, the Heck, and the Stille reaction—three versatile methods for the introduction of new C-C bonds on solid support," *Can. J. Chem.* 78:957-962 (2000).
Funder et al., "Mineralocorticoid action: target tissue specificity is enzyme, not receptor, mediated," *Science* 242:583-585 (1998).
Fung-Leung, W. P., "Phosphoinositide 3-kinase delta (PI3Kδ) in leukocyte signaling and function," *Cell Signal* 23:603-608 (2011).
Furukawa, T., "Molecular Targeting Therapy for Pancreatic Cancer: Current Knowledge and Perspectives from Bench to Bedside," *J. Gastroenterol.* 43(12):905-911 (2008).
Garber et al., "Diversity of gene expression in adenocarcinoma of the lung," *Proc. Natl. Acad. Sci. U.S.A.* 98(24):13784-13789 (2001).
Gillespie et al., "Antagonists of the human adenosine $A_{2A}$ receptor. Part 3: Design and synthesis of pyrazolo [3,4-d]pyrimidines, pyrrolo [2,3-d]pyrimidines and 6-arylpurines," *Bioorg. Med. Chem. Lett.* 18(9):2924-2929 (2008).
Gonzalez et al., "Protection against daunorubicin cytotoxicity by expression of a cloned human carbonyl reductase cDNA in K562 leukemia cells," *Cancer Res.* 55(20):4646-4650 (1995).
Graber et al., "The protein tyrosine kinase inhibitor herbimycin A, but not genistein, specifically inhibits signal transduction by the T cell antigen receptor," *Int. Immunol.* 4(1):1201-1210 (1992).
Graupera et al., "Angiogenesis selectively requires the p110α isoform of PI3K to control endothelial cell migration," *Nature* 453(7195):662-666 (2008).
Gunther et al., "Acute pathological effects on rats of orally administered wortmannin-containing preparations and purified wortmannin from Fusarium oxysporum," *Food Chem. Toxicol.* 27(3):173-179 (1989).
Gunther et al., "Immunosuppressive effects of dietary wortmannin on rats and mice," *Immunopharmacol. Immunotoxicol.* 11(4):559-570 (1989).
Haase et al., "Detection of viral nucleic acids by in situ hybridization," *Methods in Virology* 7:189-226 (1984).
Haluska et al., "The RTK/RAS/BRAF/PI3K Pathways in Melanoma: Biology, Small Molecule Inhibitors, and Potential Applications," *Semin. Oncol.* 34(6):546-554 (2007).
Hanefeld et al., "One-pot synthesis of tetrasubstituted pyrazoles proof of regiochemistry," *J. Chem. Soc. Perkin* 1 1545-1552 (1996).
Harada et al., "Novel role of phosphatidylinositol 3-kinase in CD28-mediated costimulation," *J. Biol. Chem.* 276(12):9003-9008 (2001).

(56) References Cited

OTHER PUBLICATIONS

Harding et al., "CD28-mediated signalling co-stimulates murine T cells and prevents induction of anergy in T-cell clones," *Nature* 356(6370):607-609 (1992).
Hasselblom et al., "High immunohistochemical expression of p-AKT predicts inferior survival in patients with diffuse large B-cell lymphoma treated with immunochemotherapy," *Brit. J. Haematol.* 149:560-568 (2010).
Haylock-Jacobs et al., "PI3Kδ drives the pathogenesis of experimental autoimmune encephalomyelitis by inhibiting effector T cell apoptosis and promoting Th17 differentiation," *J. Autoimmun.* 36:278-287 (2011).
Hellwinkel et al., "Heterocyclensynthesen mit MF/Al2O3-basensystemen; 2-arylbenzofurane and 2,3-diarylisochinolin-1(2H)-one," *Synthesis* 1995(9):1135-1141 (1995).
Herishanu et al., "The lymph node microenvironment promotes B-cell receptor signaling, NF-κB activation, and tumor proliferation in chronic lymphocytic leukemia," *Blood* 117(2):563-574 (2011).
Herman et al., "Phosphatidylinositol 3-kinase-δ inhibitor CAL-101 shows promising preclinical activity in chronic lymphocytic leukemia by antagonizing intrinsic and extrinsic cellular survival signals," *Blood* 116(12):2078-2088 (2010).
Herman et al., "The role of phosphatidylinositol 3-kinase-δ in the immunomodulatory effects of lenalidomide in chronic lymphocytic leukemia," *Blood* 117(16):4323-4327 (2011).
Herrera et al., "The dual PI3K/mTOR inhibitor BEZ235 is effective in lung cancer cell lines," *Anticancer Res.* 31:849-854 (2011).
Hickey et al., "BCR-ABL Regulates Phosphatidylinositol 3-Kinase-p110γ Transcription and Activation and is Required for Proliferation and Drug Resistance," *J. Biol. Chem.* 281(5):2441-2450 (2006).
Hirsch et al., "CALming Down T Cell Acute Leukemia," *Cancer Cell* 21:449-450 (2012).
Hirsch et al., "Central Role for G Protein-Coupled Phosphoinositide 3-Kinase γ in Inflammation," *Science* 287:1049-1053 (2000).
Hoellenriegel and Burger, "Phosphoinositide 3'-kinase delta: turning off BCR signaling in Chronic Lymphocytic Leukemia," *Oncotarget* 2(10):737-738 (2011).
Hoellenriegel et al., "The phosphoinositide 3'-kinase delta inhibitor, CAL-101, inhibits B-cell receptor signaling and chemokine networks in chronic lymphocytic leukemia," *Blood* 118(13):3603-3612 (2011).
Hoellenriegel et al., "Phosphoinositide 3'-kinase (PI3K) Delta Inhibition with CAL-101 Blocks B-cell Receptor (BCR) Signaling and the Prosurvival Actions of Nurse-Like Cells (NLC) in Chronic Lymphocytic Leukemia (CLL)," (ASH Annual Meeting 2010).
Honigberg et al., "The Bruton tyrosine kinase inhibitor PCI-32765 blocks B-Cell activation and is efficacious in models of autoimmune disease and B-cell malignancy," *PNAS* 107(29):13075-13080 (2010).
Ikeda et al., "PI3K/p110δ is a novel therapeutic target in multiple myeloma," *Blood* 116(9):1460-1468 (2010).
International Preliminary Report on Patentability and Written Opinion for PCT/US2005/042524 dated May 22, 2007.
International Preliminary Report on Patentability and Written Opinion for PCT/US2007/008355 dated Nov. 4, 2008.
International Preliminary Report on Patentability and Written Opinion for PCT/US2007/008395 dated Oct. 8, 2008.
International Preliminary Report on Patentability and Written Opinion for PCT/US2009/049969 dated Jan. 11, 2011.
International Preliminary Report on Patentability and Written Opinion for PCT/US2009/060985 dated Apr. 19, 2011.
International Preliminary Report on Patentability for PCT/US2009/000038 dated Jul. 6, 2010.
International Preliminary Report on Patentability for PCT/US2009/005380 dated Apr. 7, 2011.
International Preliminary Report on Patentability for PCT/US2010/002020 dated Jan. 26, 2012.
International Preliminary Report on Patentability for PCT/US2009/000042 dated Jul. 6, 2010.
International Search Report & Written Opinion for PCT/US2011/060212 dated Jun. 1, 2012.
International Search Report & Written Opinion issued after Submission of Request for Additional Search for PCT/US2011/060212 dated Jul. 6, 2012.
International Search Report and Written Opinion for PCT/US2009/005380 dated Nov. 20, 2009.
International Search Report and Written Opinion for PCT/US2009/049969 dated Mar. 15, 2010.
International Search Report and Written Opinion for PCT/US2010/033939, dated Nov. 5, 2010.
International Search Report and Written Opinion for PCT/US2012/047190 dated Oct. 2, 2012.
International Search Report and Written Opinion for PCT/US2012/020831 dated May 2, 2012.
International Search Report for PCT/US2011/037412 dated Aug. 22, 2011.
International Search Report for PCT/US1995/005213 dated Aug. 21, 1995.
International Search Report for PCT/US2007/008395 (4 pages) dated Aug. 27, 2008.
International Search Report for PCT/US2009/000038 dated Mar. 11, 2009.
International Search Report for PCT/US2009/000042 dated Mar. 23, 2009.
International Search Report for PCT/US2005/042524 (7 pages) dated Oct. 2, 2006.
International Search Report for PCT/US2007/008355 dated Sep. 25, 2008.
International Search Report for PCT/US2009/060985 dated Jun. 28, 2010.
International Search Report for PCT/US2010/002020 dated Nov. 2, 2010.
Ishiyama et al., "A stoichiometric aromatic C—H borylation catalyzed by iridium(I)/2,2'-bipyridine complexes at room temperature," *Angew. Chem. Int. Ed. Engl.* 41(16):3056-3058 (2002).
Ishiyama et al., "Mild iridium-catalyzed borylation of arenes. High turnover numbers, room temperature reactions, and isolation of a potential intermediate," *J. Am. Chem. Soc.* 124(3):390-391 (2002).
Jackson et al., "PI 3-kinase p110β: a new target for antithrombotic therapy," *Nat. Med.* 11:507-514 (2005).
Jimeno et al., "Phase I Trial of PX-866, a Novel Phosphoinositide-3-Kinase (PI-3K) Inhibitor," *J. Clin. Oncol.* 27:15s (Suppl; Abstract 3542) (2009).
Johnson et al., "Accessory cell-derived signals required for T cell activation," *Immunol. Res.* 48-64 (1993).
Jou et al., "Essential, nonredundant role for the phosphoinositide 3-kinase p110delta in signaling by the B-cell receptor complex," *Mol. Cell. Biol.* 22:8580-8591 (2002).
June et al., "Evidence for the involvement of three distinct signals in the induction of IL-2 gene expression in human T lymphocytes," *J. Immunol.* 143(1):153-161 (1989).
June et al., "Inhibition of tyrosine phosphorylation prevents T-cell receptor mediated signal transduction," *Proc. Natl. Acad. Sci. U.S.A.* 87:7722-7726 (1990).
June et al., "Role of CD28 receptor in T-cell activation," *Immunol Today* 11(6):211-216 (1990).
June, C.H., "Signaling transduction in T cells," *Curr. Opin. Immunol.* 3(3):287-293 (1991).
Kajita et al., "Nickel-catalyzed decarbonylative addition of phthalimides to alkynes," *J. Am. Chem. Soc.* 130(19):6058-6059 (2008).
Kallberg et al., "Short-chain dehydrogenase/reductase (SDR) relationships: a large family with eight clusters common to human, animal, and plant genomes," *Protein Sci.* 11(3):636-641 (2002).
Kallberg et al., "Short-Chain Dehydrogenases/Reductases (SDRs)—Coenzyme-Based Functional Assignments in Completed Genomes," *Eur. J. Biochem.* 269(18):4409-4417 (2002).
Kang et al., "Oncogenic transformation induced by the p110β, -γ, and δ isoforms of class I phosphoinositide 3-kinase," *PNAS* 103(5):1289-1294 (2006).
Karpeiskii et al., "Pyridoxal-5'-Derivatives of Nucleobases," *Bioorganicheskaya Khimiya* 11(8): 1097-1104 (1985).

(56) References Cited

OTHER PUBLICATIONS

Khwaja, A., "PI3K as a Target for Therapy in Haematological Malignancies," *Curr. Top. Microbiol. Immunol.* 347:169-188 (2010).

Kim et al., "Activation and Function of the mTORC1 Pathway in Mast Cells," *J. Immunol.* 180(7):4586-4595 (2008).

Knight et al., "A Pharmacological Map of the PI3-K Family Defines a Role for p110α in Insulin Signaling," *Cell* 125(4):733-747 (2006).

Kong, D. and Yamori, T., "Advances in Development of Phosphatidylinositol 3-Kinase Inhibitors," *Curr. Med. Chem.* 16:2839-2854 (2009).

Kost et al., "Recyclization of 3-Alkyl- and 1,3-Dialkylisoquinolinium Salts to Naphthylamines," *Chemistry of Heterocyclic Compounds* 16(9): 965-970 (1981).

Kraybill et al., "Inhibitor scaffolds as new allele specific kinase substrates," *J. Am. Chem. Soc.* 124(41):12118-12128 (2002).

Kreutzberger et al. "5-Substituierte 4-Aminopyrimidine durch Aminomethinylierung von Acetonitrilen," *Liebigs Ann. Chem.* 537-544 (1977).

Kulkarni et al., "PI3Kbeta plays a critical role in neutrophil activation by immune complexes," *Sci. Signal* 2011, vol. 4, ra23.

Kumar et al., "Keten Dithioacetals. Part 11. Reaction of 3-Cyano-4-Methylthio-2(1H)-pyridones with Hydrazine and Guanidine: Synthesis of Novel Substituted and Fused Pyrazolo[4,3-c]pyridone and Pyrido[4,3-d]pyrimidine derivatives," *J. Chem. Soc. Perkin 1* 8:857-862 (1978).

Kundu et al., "Palladium-catalysed heteroannualation with terminal alkynes; a highly regio-and stereoselective synthesis of (Z)-3-aryl(alykl)idene isoindolin-1-ones," *Tetrahedron* 56(27):4777-4792 (2000).

Kurtova et al., "Diverse marrow stromal cells protect CLL cells from spontaneous and drug-induced apoptosis: development of a reliable and reproducible system to assess stromal cell adhesion-mediated drug resistance," *Blood* 114(20): 4441-4450 (2009).

Kwok et al., "The anti-inflammatory natural product parthenolide from the medicinal herb Feverfew directly binds to and inhibits IκB kinase," *Chem. Biol.* 8(8):759-766 (2001).

Lannutti et al., "Cal-101 a p110δ selective phosphatidylinositol-3-kinase inhibitor for the treatment of B-cell malignancies, inhibits PI3K signaling and cellular viability," *Blood* 117(2):591-594 (2011).

Larabi et al., "Crystal Structure and Mechanism of Activation of TANK-Binding Kinase 1," *Cell Reports* 3:734-746 (2013).

Ledbetter et al., "CD28 ligation in T-cell activation: evidence for two signal transduction pathways," *Blood* 75(7):1531-1539 (1990).

Ledbetter et al., "Crosslinking of surface antigens causes mobilization of intracellular ionized calcium in T lymphocytes," *Proc. Natl. Acad. Sci. U. S. A.* 84(5):1384-1388 (1987).

Lee et al., "All roads lead to mTOR: integrating inflammation and tumor angiogenesis," *Cell Cycle* 6(24):3011-3014 (2007).

Lee et al., "The CD28 signal transduction pathway in T cell activation", Advances in Cell Regulation of Cell Growth, vol. 2, pp. 141-160, New York: Raven Press, Ltd. (1991).

Ley et al., "The T cell receptor/CD3 complex and CD2 stimulate the tyrosine phosphorylation of indistinguishable patterns of polypeptides in the human T leukemic cell line Jurkat," *Eur. J. Immunol.* 21(9):2203-2209 (1991).

Li et al., "Roles of PLC-beta2 and -beta3 and PI3Kgamma in chemoattractant-mediated signal transduction," *Science* 287(5455):1046-1049 (2000).

Liu et al., "Costimulation of T-cell growth," *Curr. Opin. Immunol.* 4(3):265-270 (1992).

Lu et al., "CD28-induced T cell activation. Evidence for a protein-tyrosine kinase signal transduction pathway," *J. Immunol.* 149(1):24-29 (1992).

Majumder et al., "mTOR inhibition reverses Akt-dependent prostate intraepithelial neoplasia through regulation of apoptotic and HIF-1-dependent pathways," *Nat. Med.* 10(6):594-601 (2004).

Markman et al., "Status of PI3K inhibition and biomarker development in cancer therapeutics," *Ann. Oncol.* 21(4):683-691 (2010).

Martelli et al., "The emerging role of the phosphatidylinositol 3-kinase/Akt/mammalian target of rapamycin signaling network in normal myelopoiesis and leukemogenesis," *Biochim. Biophys. Acta.* 803:991-1002 (2010).

Martinez et al., "The Molecular Signature of Mantle Cell Lymphoma Reveals Multiple Signals Favoring Cell Survival," *Cancer Res.* 63:8226-8232 (2003).

Martin-Sanchez et al., "PI3K Inhibition as a Potential Therapeutic Strategy in Peripheral T-Cell Lymphomas," *Blood (Ash Annual Meeting Abstracts)* 118: Abstract 3493 (2011).

Mattes et al., "DNA sequence selectivity of guanine-N7 alkylation by nitrogen mustards," *Nucleic Acids Res.* 14(7):2971-2987 (1986).

Maxwell et al., "Attenuation of phosphoinositide 3-kinase δ signaling restrains autoimmune disease," *J. Autoimmun* 38:381-391 (2012).

Mayer et al., "Small molecule inhibitor of mitotic spindle bipolarity identified in a phenotype-based screen," *Science* 286(5441):971-974 (1999).

Mazzoletti and Broggini, "PI3K/AKT/mTOR inhibitors in ovarian cancer," Curr. Med. Chem. 17(36):4433-4447 (2010).

Meadows, S.A., et al., "CAL-101, a Potent Selective Inhibitor of the p110δ Isoform of Phosphatidylinositol 3-Kinase, Attenuates Pathway Signaling, Induces Apoptosis, and Overcomes Signals From the Microenvironment in Cellular Models of Hodgkin Lymphoma," Blood (ASH Annual Meeting Abstracts), 116:Abstract 3926 (2010).

Mellinghoff et al., "TORward AKTually useful mouse models," *Nat. Med.* 10(6):579-580 (2004).

Merida et al., "IL-2 binding activates a tyrosine-phosphorylated phosphatidylinositol-3-kinase," *J. Immunol.* 147(7): 2202-2207 (1991).

Miyaura et al., "Palladium-catalyzed cross-coupling reactions of organoboron compounds," *Chem. Rev.* 95(7):2457-2483 (1995).

Modi et al., "Isoquinolones; part IV-synthesis of methyl, 3-formyl & other 3-substituted N-arylisoquinolones." *Indian J Chem.* 18B:304-306 (1979).

Moon et al., "A novel microtubule destabilizing entity from orthogonal synthesis of triazine library and zebrafish embryo screening," *J. Am. Chem. Soc.* 124(39):11608-11609 (2002).

Mosmann et al., "The expanding universe of T-cell subsets: Th1, Th2 and more," *Immunology Today* 17(3):138-146 (1996).

Nakanishi et al., "Cloning and sequence analysis of a cDNA encoding tetrameric carbonyl reductase of pig lung," *Biochem. Biophys. Res. Commun.* (3):1311-1316 (1993).

Nemazanyi et al., "3-Amino-4-aryl-1(2H)-isoquinolones," *Chemistry of Heterocyclic Compounds* 27(3):307-308 (1991).

Newman et al., "Solid state analysis of the active pharmaceutical ingredient in drug products," *Drug Discov. Today* 8(19):898-905 (2003).

Nisitani et al., "Posttranscriptional regulation of Bruton's tyrosine kinase expression in antigen receptor-stimulated splenic B cells," *PNAS* 97(6):2737-2742 (2000).

Niswender et al., "Protein engineering of protein kinase a catalytic subunits results in the acquisition of novel inhibitor sensitivity," *J. Biol. Chem.* 277(32):28916-28922 (2002).

Nobel et al., "Purification of full-length recombinant human and rat type 1 11β-hydroxysteroid dehydrogenases with retained oxidoreductase activities," *Protein Expr. Purif.* 26(3):349-356 (2002).

Norman, "Selective PI3K-delta Inhibitors, A Review of the Patent Literature," Expert Opinion on Therapeutic Patents, 21(11): 1773-1790 (2011).

Nunes et al., "Signalling through CD28 T-cell activation pathway involves an inositol phospholipid-specific phospholipase C activity," *Biochem. J.* 293(Pt 3):835-842 (1993).

Oda et al., "PIK3CA cooperates with other phosphatidylinositol 3'-kinase pathway mutations to effect oncogenic transformation," *Cancer Res.* 68(19):8127-8136 (2008).

Office Action dated Dec. 13, 2012 for U.S. Appl. No. 13/112,611.

Okada et al., "Essential role of phosphatidylinositol 3-kinase in insulin-induced glucose transport and antilipolysis in rat adipocytes. Studies with a selective inhibitor wortmannin," *J. Biol. Chem.* 269(5):3568-3573 (1994).

(56) References Cited

OTHER PUBLICATIONS

Okada et al., "Blockage of chemotactic peptide-induced stimulation of neutrophils by wortmannin as a result of selective inhibition of phosphatidylinositol 3-kinase," *J. Biol. Chem.* 269(5):3563-3567 (1994).
Oppermann et al., "Forms and functions of human SDR enzymes," *Chem. Biol. Interact.* 130-132(1-3):699-705 (2001).
O'Shea et al., "Activation of human peripheral blood T lymphocytes by pharmacological induction of protein-tyrosine phosphorylation," *Proc. Natl. Acad. Sci. U. S. A.* 89(21):10306-10310 (1992).
Ozaki et al., "Studies on 4(1H)-quinazolinones. IV. Convenient synthesis of 12-methyl-6H-isoquino [2,1-a] quinazolin-6-one and 6-methyl-13H-quinazolino [3,4-a] quinazolin-13-one," *Chem. Pharm. Bull.* 32(6):2160-2164 (1984).
Ozol et al., "Autoxidative transformations of 2-substituted 3-alkyl-4-hydroxy-1-oxo-1, 2-dihydroisoquinolines," *Chemistry of Heterocyclic Compounds* 14(6):644-648 (1978).
Patel et al., "Immunopathological aspects of age-related macular degeneration," *Semin. Immunopathol.* 30(2):97-110 (2008).
Pérez-Blas et al., "Impaired T cell signal transduction through CD28 in a patient with idiopathic thrombocytopenia," *Clin. Exp. Immunol.* 85(3):424-428 (1991).
Persson, "Glucocorticoids for asthma—early contributions," *Pulm. Pharmacol.* 2(3):163-166 (1989).
Petrie et al., "Novel biotinylated adenylate analogue derived from pyrazolo[3,4-d]pyrimidine for labeling DNA probes," *Bioconjug. Chem.* 2(6):441-446 (1991).
Pighi et al., "Phospho-proteomic analysis of mantle cell lymphoma cells suggests a pro-survival role of B-cell receptor signaling," *Cell Oncol. (Dordr)* 34(2):141-153 (2011).
Polak et al., "The PI3K/PKB signaling module as key regulator of hematopoiesis: implications for therapeutic strategies in leukemia," *Blood* 119(4):911-923 (2012).
Porta and Figlin, "Phosphatidylinositol-3-kinase/Akt signaling pathway and kidney cancer, and the therapeutic potential of phosphatidylinositol-3-kinase/Akt inhibitors," *J. Urol.* 182(6):2569-2577 (2009).
Prasad et al., "Phosphatidylinositol (PI) 3-kinase and PI 4-kinase binding to the CD4-p56$^{lck}$ complex: the p56$^{lck}$ SH3 domain binds to PI 3-kinase but not PI 4-kinase," *Mol. Cell. Biol.* 13(12): 7708-7717 (1993).
Prasad et al., "Src-homology 3 domain of protein kinase p59$^{fyn}$ mediates binding to phosphatidylinositol 3-kinase in T cells," *Proc. Natl. Acad. Sci. U. S. A.* 90(15): 7366-7370 (1993).
Prasad et al., "T-cell antigen CD28 interacts with the lipid kinase phosphatidylinositol 3-kinase by a cytoplasmic Tyr(P)-Met-Xaa-Met motif," *Proc. Natl. Acad. Sci. U. S. A.* 91(7): 2834-2838 (1994).
Pudlo et al., "Synthesis, antiproliferative, and antiviral activity of certain 4-substituted and 4,5 disubstituted 7[1,3-dihydroxy-2-propoxy)methyl]pyrrolo [2,3-d]pyrimidines," *J. Med. Chem.* 33(7):1984-1992 (1990).
Puri and Gold, "Selective inhibitors of phosphoinositide 3-kinase delta: modulators of B-cell function with potential for treating autoimmune inflammatory disease and B-cell malignancies," *Front. Immunol.* 3:256 (2012).
Quiroga et al., "B-cell antigen receptor signaling enhances chronic lymphocytic leukemia cell migration and survival: specific targeting with a novel spleen tyrosine kinase inhibitor, R406," *Blood* 114(5):1029-1037 (2009).
Reif et al., "Divergent regulation of phosphatidylinositol 3-kinase P85α and P85β isoforms upon T cell activation," *J. Biol. Chem.* 268(15):10780-10788 (1993).
Report of the Expert Committee on the Diagnosis and Classification of Diabetes Mellitus, *Diabetes Care* 2(Suppl. 1):S5-S19 (1992).
Rizzatti et al., "Gene expression profiling of mantle cell lymphoma cells reveals aberrant expression of genes from the PI3K-AKT, WNT and TGFβ signaling pathways," *Brit. J. Haematol.* 130:516-526 (2005).
Robertson, "Eicosanoids and human disease", Harrison's Principles of Internal Medicine, Isselbacher K.J. et al. (eds.), vol. 1, pp. 431-435, McGraw-Hill, New York City (1994).
Roller et al., "Blockade of Phosphatidylinositol 3-Kinase (PI3K)δ or PI3Kγ Reduces IL-17 and Ameliorates Imiquimod-Induced Psoriasis-like Dermatitis," *J. Immunol.* 189:4612-4620 (2012).
Romero et al., "Cloning and expression of the bovine 11b-hydroxysteroid dehydrogenase type-2," *J. Steroid Biochem. Mol. Biol.* 72(5):231-237 (2000).
Rommel et al., "PI3Kδ and PI3Kγ: partners in crime in inflammation in rheumatoid arthritis and beyond?" *Nat. Rev. Immunol.* 7:191-201 (2007).
Rott et al., "Recent developments in the use of biologics in psoriasis and autoimmune disorders. The role of autoantibodies," *BMJ* 330(7493):716-720 (2005).
Rudelius et al., "Constitutive activation of Akt contributes to the pathogenesis and survival of mantle cell lymphoma," *Blood* 108(5):1668-1676 (2006).
Saif and Chu, "Biology of colorectal cancer," *Cancer J.* 16(3):196-201 (2010).
Salmena et al., "Tenets of PTEN Tumor Suppression," *Cell* 133(3):403-414 (2008).
Sarker et al., "Targeting the PI3K/AKT pathway for the treatment of prostate cancer," *Clin. Cancer Res.* 15(15):4799-4805 (2009).
Sasaki et al., "Function of PI3Kγ in Thymocyte Development, T Cell Activation, and Neutrophil Migration," *Science* 287:1040-1046 (2000).
Schwartz et al., "Quercetin inhibition of the induction and function of cytotoxic T lymphocytes," *Immunopharmacology* 4(2):125-138 (1982).
Schwartz, "A cell culture model for T lymphocyte clonal anergy," *Science* 248(4961):1349-1356 (1990).
Shapiro et al., "Phase I Dose-Escalation Study of XL147, a PI3K Inhibitor Administered Orally to Patients with Solid Tumors," *J. Clin. Oncol.* 27:146x (Suppl Abstr 3500) (2009).
Shibasaki et al., "Different properties of monomer and heterodimer forms of phosphatidylinositol 3-kinases," *Biochem. J.* 289 (Pt 1):227-231 (1993).
Sinclair et al., "Phosphatidylinositol-3 Kinase Delta (PI3Kδ) Inhibitor AMG 319 is a Potent, Selective and Orally Bioavailable Small Molecule Inhibitor That Suppresses PI3K-Mediated Signaling and Viability in Neoplastic B Cells," *Blood (Ash Annual Meeting Abstracts)* 118:Abstract 4964 (2011).
Singer et al., "Optimization of in situ hybridization using isotopic and non-isotopic detection methods," *Biotechniques* 4(3):230-250 (1986).
Smith et al., "Expression of Bruton's Agammaglobulinemia Tyrosine Kinase Gene, BTK, is Selectively Down-Regulated in T Lymphocytes and Plasma Cells," *J. Immunol.* 152:557-565 (1994).
Soldan et al., "Induction of daunorubicin carbonyl reducing enzymes by daunorubicin in sensitive and resistant pancreas carcinoma cells," *Biochem. Pharmacol.* 51(2):117-123 (1996).
Soond et al., "PI3K p110δ regulates T-cell cytokine production during primary and secondary immune responses in mice and humans," *Blood* 115(11):2203-2213 (2010).
Srinivasan et al., "PI3 Kinase Signals BCR-Dependent Mature B Cell Survival," *Cell* 139:573-586 (2009).
Stanoeva et al., "Homophthalic anhydrides and their application to the synthesis of heterocyclic compounds (review)," *Chemistry of Heterocyclic Compounds* 20(12):1305-1315 (1984).
Subramaniam et al., "Targeting Nonclassical Oncogenes for Therapy in T-ALL," *Cancer Cell* 21:459-472 (2012).
Sujobert et al., "Essential role for the p110δ isoform in phosphoinositide 3-kinase activation and cell proliferation in acute myeloid leukemia," *Blood* 106(3):1063-1066 (2005).
Supplementary European Examination Report EP Application No. 07754845.1 dated Sep. 20, 2011.
Supplementary European Search Report for EP Application No. 07754845 (4 pages) dated Feb. 24, 2010.
Supplementary European Search Report for EP Application No. 10800175.1 dated Nov. 7, 2012.
Sykes et al., "Treatment of severe autoimmune disease by stem-cell transplantation," *Nature* 35(7042):620-627 (2005).

(56) References Cited

OTHER PUBLICATIONS

Takeuchi et al., "Synergistic Augmentation of Rapamycin-Induced Autophagy in Malignant Glioma Cells by Phosphatidylinositol 3-Kinase/Protein Kinase B Inhibitors," *Cancer Res.* 65(8):3336-3346 (2005).
Tanaka et al., "An unbiased cell morphology-based screen for new, biologically active small molecules," *PLoS Biol.* 3(5):0764-0776 (2005).
Thompson et al., "Identification of distinct populations of PI-3 kinase activity following T-cell activation," *Oncogene* 7(4):719-725 (1992).
Torbett et al., "A chemical screen in diverse breast cancer cell lines reveals genetic enhancers and suppressors of sensitivity to PI3K isoform-selective inhibition," *Biochem. J.* 415(1):97-110 (2008).
Truitt et al., "Stimulation of CD28 triggers an association between CD28 and phosphatidylinositol 3-kinase in Jurkat T cells," *J. Exp. Med.* 179(3):1071-1076 (1994).
Tyukavkina et al., Bioorganicheskaya Khimiya, Moskva, DROFA, pp. 83-85 (2004).
Uddin et al., "Role of phosphatidylinositol 3'-kinase/AKT pathway in diffuse large B-cell lymphoma survival," *Blood* 108(13):4178-4186 (2006).
Ugarkar et al., "Adenosine kinase inhibitors. 2. Synthesis, enzyme inhibition, and antiseizure activity of diaryltubercidin analogues," *J. Med. Chem.* 43(15):2894-2905 (2000).
Vandenberghe et al., "Antibody and B7/BB1-mediated ligation of the CD28 receptor induces tyrosine phosphorylation in human T cells," *J. Exp. Med.* 175(4):951-960 (1992).
Vanhaesebroeck et al., "PI3K: from the bench to the clinic and back," *Curr. Top. Microbiol. Immunol.* 347:1-19 (2010).
Vara et al., "PI3K/Akt Signalling Pathway and Cancer," *Cancer Treat. Rev.* 30(2):193-204 (2004).
Vasilevsky et al., "Study of the Heterocyclization of vic-Substituted Hydrazides of Acetylenylpyrazolecalboxylic Acids into N-Amino Pyrazolopyridinones," *Journal of Heterocyclic Chemistry* 39(6):1229-1233 (2002).
Vasilevsky et al., "Unexpected results in the heterocyclization of 5-acetylenylpyrazole-4-carboxylic acid hydrazides under the influence of CuCl: formation of a diazepinone and dehydrodimerization into the corresponding bis(pyrazolo [4,3-d] [1,2] diazepinone)," *Tetrahedron Lett.* 46(26):4457-4459 (2005).
Vippagunta et al., "Crystalline Solids," *Adv. Drug Deliv. Rev.* 48(1):3-26 (2001).
Vitali et al., "Immunotherapy in rheumatoid arthritis: a review," *Int. J. Artif. Organs* 16 Suppl. 5:196-200 (1993).
Vlahos et al., "A specific inhibitor of phosphatidylinositol 3-kinase, 2-(4-morpholinyl)-8-phenyl-4H-1-benzopyran-4-one (LY294002)," *J. Biol. Chem.* 269(7):5241-5248 (1994).
Vogt et al., "Phosphatidylinositol 3-kinase the oncoprotein," *Curr. Top. Microbiol. Immunol.* 347:79-104 (2010).
Vogt et al., "Phosphoinositide 3-kinase from viral oncoprotein to drug target," *Virology* 344(1):131-138 (2006).
Wagner et al., "A First-in-Human Phase I Study to Evaluate the Pan-PI3K Inhibitor GDC-0941 Administered QD or BID in Patients with Advanced Solid Tumors," *J. Clin. Oncol.* 27:146s (Suppl, Abstr 3501) (2009).
Wahlstrom et al., "Aberrant MAPK and PI3K Signaling Contribute to Chemotherapy Resistance in T Cell Acute Lymphobalstic Leukemia by Altering the Balance of Apoptosis Mediators," *Blood (Ash Annual Meeting Abstracts)* 118: Abstract 3490 (2011).
Ward et al., "Inhibition of CD28-mediated T cell costimulation by the phosphoinositide 3-kinase inhibitor wortmannin," *Eur. J. Immunol.* 25(2):526-532 (1995).
Ward et al., "Ligation of CD28 receptor by B7 induces formation of D-3 phosphoinositides in T lymphocytes independently of T cell receptor/CD3 activation," *Eur. J. Immunol.* 23(10):2572-2577 (1993).
Ward et al., "Regulation of D-3 phosphoinositides during T cell activation via the T cell antigen receptor/CD3 complex and CD2 antigens," *Eur. J. Immunol.* 22(1):45-49 (1992).
Ward et al., "Regulation of phosphoinositide kinases in T cells. Evidence that phosphatidylinositol 3-kinase is not a substrate for T cell antigen receptor-regulated tyrosine kinases," *J. Biol. Chem.* 267(33):23862-23869 (1992).
Ward et al., "Therapeutic potential of phosphoinositide 3-kinase inhibitors," *Chem. Biol.* 10(3):207-213 (2003).
White et al., "11β-Hydroxysteroid Dehyrdogenase and the Syndrome of Apparent Mineralocorticoid Excess," *Endocr. Rev.* 18(1):135-156 (1997).
Widler et al., "7-alkyl- and 7-Cycloalkyl-5-aryl-pyrrolo[2,3-d]pyrimidines- potent inhibitors of the tyrosine kinase c-Src," *Bioorg. Med. Chem. Lett.* 11(6):849-852 (2001).
Wiesinger et al., "Antiinflammatory activity of the new mould metabolite 11-desacetoxy- wortmannin and of some of its derivatives," *Experientia* 30(2):135-136 (1974).
Wolff, Burger's Medicinal Chemistry, $5^{th}$ ed, Part 1, pp. 975-977, John Wiley & Sons (1995).
Woscholski et al., "A comparison of demethoxyviridin and wortmannin as inhibitors of phosphatidylinositol 3-kinase," *FEBS Lett.* 342(2):109-114 (1994).
Wu et al., "Decreased immunological responses by wortmannin-containing rice culture of Fusarium oxysporum and by purified wortmannin in avian species," *Immunopharmacol. Immunotoxicol.* 14(4):913-923 (1992).
Wu et al., "Wortmannin (a mycotoxin) inhibited immune responses in chickens," *Poultry Sci.* Vo. 71, Suppl 1, pp. 13 (1992).
Yaguchi et al., "Antitumor activity of ZSTK474, a new phosphatidylinositol 3-kinase inhibitor," *J. Natl. Cancer Inst.* 98(8):545-556 (2006).
Yang et al., "A novel activation pathway for mature thymocytes. Costimulation of CD2 (T,p50) and CD28 (T,p44) induces autocrine interleukin 2/interleukin 2 receptor-mediated cell proliferation," *J. Exp. Med.* 168(4):1457-1468 (1988).
Yano et al., "Inhibition of histamine secretion by wortmannin through the blockade of phosphatidylinositol 3-kinase in RBL-2H3 cells," *J. Biol. Chem.* 268(34):25846-25856 (1993).
Yoshida et al., "Quercetin arrests human leukemic T-cells in late G1 phase of the cell cycle," *Cancer Res.* 52(23):6676-6681 (1992).
Zhao and Vogt, "Class I PI3K in oncogenic cellular transformation," *Oncogene* 27(41):5486-5496 (2008).
Gadhachanda et al., "4-Aminopyrimidines as novel HIV-1 inhibitors," *Bioorg. Med. Chem. Lett.* 17(1):260-265 (2007). (Epub Oct. 10, 2006).
Hackam et al., "Translation of Research Evidence from Animals to Humans," *JAMA* 296(14):1731-1732 (2006).
Jordan et al., "Tamoxifen: A Most Unlikely Pioneering Medicine," *Nature Reviews: Drug Discovery*, 2:205-213 (2003).
Koeberle et al., "Pirinixic acid derivatives as novel dual inhibitors of microsomal prostaglandin E2 synthase-1 and 5-lipoxygenase," J. Med. Chem. 51(24):8068-8076 (2008).
Popescu et al., "Quinoline-based derivatives of pirinixic acid as dual PPAR alpha/gamma agonists," Arch. Pharm. (Weinheim) 340(7):367-371 (2007).
Waltenberger et al., "Pharmacophore modeling and virtual screening for novel acidic inhibitors of microsomal prostaglandin $E_2$ synthase-1 (mPGES-1)," J. Med. Chem. 54(9):3163-3174 (2011). (Epub Apr. 20, 2011).
Werz et al., "Novel and potent inhibitors of 5-lipoxygenase product synthesis based on the structure of pirinixic acid," J. Med. Chem. 51(17):5449-5453 (2008). (Epub Aug. 19, 2008).
Doukas et al., "Aerosolized Phosphoinositide 3-Kinase γ/δ InhibitorTG1 00-115 [3-[2,4-Diamino-6-(3-hydroxyphenyl)pteridin-7 -yl]phenol] as a Therapeutic Candidate for Asthma and Chronic Obstructive Pulmonary Disease", Journal of Pharmacology and Experimental Therapeutics, vol. 328, No. 3, Dec. 4, 2008, pp. 758-765.
Adeyeye, M. ed., Preformulation in Solid Dosage Form Development (Informa Healthcare, 2008) Chapter 2.3, pp. 63-80.
Bastin et al., "Salt Selection and Optimisation Procedures for Pharmaceutical New Chemical Entities", Organic Process Research & Development 2000, 4, pp. 427-435.
Gould et al., "Salt selection for basic drugs", International J. of Therapeutics 33, pp. 201-213 & 217 (1986).

(56) References Cited

OTHER PUBLICATIONS

Liu, R. ed., Water-insoluble drug formulation (CRC Press, 2008), Chapter 15, pp. 417-435.
Morris et al., "An integrated approach to the selection of optimal salt form for a new drug candidate", International Journal of Pharmaceutics, vol. 105, Issue 3, May 9, 1994, pp. 209-217.
Serajuddin, "Salt formation to improve drug solubility", Advanced Drug Delivery Reviews, 59 (2007) 603-616.
Stahl et al., eds., Handbook of pharmaceutical salts. Properties, selection and use. (Wiley-VCH 2008), pp. 265-327.
Swarbrick et al., eds., Encyclopedia of Pharmaceutical Technology 13 (Marcel Dekker, NY 1996), pp. 453-499.
U.S. Appl. No. 13/552,460, filed Jul. 18, 2012, U.S. Pat. No. 8,969,363, Ward, Paul V., Heterocyclic Compounds and Uses Thereof.
U.S. Appl. No. 13/552,473, filed Jul. 18, 2012, U.S. Pat. No. 9,056,877, Masha, Oluwafemi L., Heterocyclic Compounds and Uses Thereof.
U.S. Appl. No. 13/841,265, filed Mar. 15, 2013, U.S. Pat. No. 8,940,742, Pagano, Alexander R., Heterocyclic Compounds and Uses Thereof.
U.S. Appl. No. 13/839,912, filed Mar. 15, 2013, 2014-0120060, Matos Negron, Taina Del Mar, Treatment of Rheumatoid Arthritis and Asthma Using PI3 Kinase Inhibitors.
U.S. Appl. No. 13/840,822, filed Mar. 15, 2013, 2014-0120083, Matos Negron, Taina Del Mar, Treatment of Cancers Using PI3 Kinase Isoform Modulators.
U.S. Appl. No. 12/811,695, filed Nov. 11, 2010, U.S. Pat. No. 8,703,777, Moore, Susanna, Substituted Bicyclic Compounds and Methods of Use Thereof.
U.S. Appl. No. 12/503,776, filed Jul. 15, 2009, U.S. Pat. No. 8,193,182, Berch, Mark L., Substituted Isoquinolin-1(2H)-Ones, and Methods of Use Thereof.
U.S. Appl. No. 13/403,394, filed Feb. 23, 2012, U.S. Pat. No. 8,785,456, Daniel, Laura M., Certain Chemical Entities, Compositions and Methods.
U.S. Appl. No. 13/350,444, filed Jan. 13, 2012, U.S. Pat. No. 8,569,323, Daniel, Laura M., Substituted Isoquinolin-1(2H)-One Compounds, Compositions, and Methods Thereof.
U.S. Appl. No. 13/121,157, filed Aug. 2, 2011, U.S. Pat. No. 8,703,778, Murray, Jeffrey H., Heterocyclic Kinase Inhibitors.
U.S. Appl. No. 13/289,540, filed Nov. 4, 2011, U.S. Pat. No. 8,785,454, Daniel, Laura M., Heterocyclic Compounds and Uses Thereof.
U.S. Appl. No. 13/293,828, filed Nov. 10, 2011, U.S. Pat. No. 8,901,133, Shameem, Golam M., Heterocyclic Compounds and Uses Thereof.
U.S. Appl. No. 13/347,423, filed Jan. 10, 2012, U.S. Pat. No. 8,809,349, Neagu, Irina, Processes for Preparing Isoquinolinones and Solid Forms of Isoquinolinones.
U.S. Appl. No. 13/837,195, filed Mar. 15, 2013, U.S. Pat. No. 8,828,998, Henley III, Raymond J., Treatment of Lupus, Fibrotic Conditions, and Inflammatory Myopathies and Other Disorders Using PI3 Kinase Inhibitors.
U.S. Appl. No. 14/222,488, filed Mar. 21, 2014, 2014-0206684, Moore, Susanna, Certain Chemical Entities, Compositions and Methods.
U.S. Appl. No. 14/085,660, filed Nov. 20, 2013, U.S. Pat. No. 9,181,221, Murray, Jeffrey H., Chemical Compounds, Compositions and Methods for Kinase Modulation.
U.S. Appl. No. 14/099,831, filed Dec. 6, 2013, U.S. Pat. No. 9,115,141, Willis, Douglas M., Heterocyclic Compounds and Uses Thereof.
U.S. Appl. No. 14/776,604, filed Sep. 14, 2015, 2016-0024051, Sackey, Ebenezer O., Salts and Solid Forms of Isoquinolinones and Composition Comprising and Methods of Using the Same.
U.S. Appl. No. 13/971,793, filed Aug. 20, 2013, U.S. Pat. No. 9,206,182, Daniel, Laura M., Certain Chemical Entities, Compositions and Methods.
U.S. Appl. No. 15/026,947, filed Apr. 1, 2016, 2016-0222016, Unassigned, Heterocyclic Compounds and Uses Thereof.
U.S. Appl. No. 14/506,429, filed Oct. 3, 2014, U.S. Pat. No. 9,359,365, Bernhardt, Emily A., Heterocyclic Compounds and Uses Thereof.
U.S. Appl. No. 14/222,500, filed Mar. 21, 2014, U.S. Pat. No. 9,296,742, Murray, Jeffrey H., Heterocyclic Kinase Inhibitors.
U.S. Appl. No. 14/292,475, filed May 30, 2014, 2014-0377258, Reddig, Peter J., Treatment of Cancers Using PI3 Kinase Isoform Modulators.
U.S. Appl. No. 15/030,701, filed Apr. 20, 2016, Unpublished, Unassigned, Heterocyclic Compounds and Uses Thereof.
U.S. Appl. No. 14/296,953, filed Jun. 5, 2014, U.S. Pat. No. 9,216,982, Daniel, Laura M., Certain Chemical Entities, Compositions and Methods.
U.S. Appl. No. 14/302,340, filed Jun. 11, 2014, U.S. Pat. No. 9,315,505, Daniel, Laura M., Heterocyclic Compounds and Uses Thereof.
U.S. Appl. No. 14/327,499, filed Jul. 9, 2014, U.S. Pat. No. 9,290,497, Neagu, Irina, Processes for Preparing Isoquinolinones and Solid Forms of Isoquinolinones.
U.S. Appl. No. 14/439,965, filed Apr. 30, 2015, 2015-0283142, Pihonak, Sarah, Treatment of Cancers Using PI3 Kinase Isoform Modulators.
U.S. Appl. No. 14/448,998, filed Jul. 31, 2014, 2014-0343057, Henley III, Raymond J., Treatment of Lupus, Fibrotic Conditions, and Inflammatory Myopathies and Other Disorders Using PI3 Kinase Inhibitors.
U.S. Appl. No. 15/512,262, filed Oct. 10, 2014, U.S. Pat. No. 9,388,183, Shameem, Golam M., Heterocyclic Compounds and Uses Thereof.
U.S. Appl. No. 14/573,961, filed Dec. 17, 2014, U.S. Pat. No. 9,255,108, Pagano, Alexander R., Heterocyclic Compounds and Uses Thereof.
U.S. Appl. No. 15/059,962, filed Mar. 3, 2016, U.S. Pat. No. 2016-0185800, Moore, Susanna, Certain Chemical Entities, Compositions and Methods.
U.S. Appl. No. 14/661,656, filed Mar. 18, 2015, 2015-0290207, Jean-Louis, Samira JM, Heterocyclic Compounds and Uses Thereof.
U.S. Appl. No. 14/592,628, filed Jan. 8, 2015, 2015-0126506, Ward, Paul V., Heterocyclic Compounds and Uses Thereof.
U.S. Appl. No. 14/687,714, filed Apr. 15, 2015, 2015-0320754, Pihonak, Sarah, Combination Therapies.
U.S. Appl. No. 14/687,768, filed Apr. 15, 2015, 2015-0320755, Schmitt, Michael J, Combination Therapies.
U.S. Appl. No. 14/695,699, filed Apr. 24, 2015, 2015-0225410, Bernhardt, Emily A., Heterocyclic Compounds and Uses Thereof.
U.S. Appl. No. 14/710,336, filed May 12, 2015, 2015-0246932, Murray, Jeffrey H., Heterocyclic Compounds and Uses Thereof.
U.S. Appl. No. 15/051,529, filed Feb. 23, 2016, Unpublished, Unassigned, Processes for Preparing Isoquinolinones and Solid Forms of Isoquinolinones.
U.S. Appl. No. 14/874,328, filed Oct. 2, 2015, 2016-0122365, Murray, Jeffrey H., Heterocyclic Compounds and Uses Thereof.
U.S. Appl. No. 14/876,589, filed Oct. 6, 2015, 2016-0022692, Shafer, Shulamith H., Treatment of Rheumatoid Arthritis and Asthma Using PI3 Kinase Inhibitors.
U.S. Appl. No. 14/884,612, filed Oct. 15, 2015, 2016-0031886, Daniel, Laura M., Certain Chemical Entities, Compositions and Methods.
U.S. Appl. No. 14/894,854, filed Nov. 30, 2015, 2016-0113932, Unassigned, Treatment of Cancers Using PI3 Kinase Isoform Modulators, Published.
U.S. Appl. No. 14/938,647, filed Nov. 11, 2015, 2016-0158239, Daniel, Laura M., Certain Chemical Entities, Compositions and Methods.
U.S. Appl. No. 14/971,954, filed Dec. 16, 2015, 2016-0207940, Pagano, Alexander R., Heterocyclic Compounds and Uses Thereof.
U.S. Appl. No. 15/016,117, filed Feb. 4, 2016, 2016-0152619, Neagu, Irina, Processes for Preparing Isoquinolinones and Solid Forms of Isoquinolinones.

(56) References Cited

OTHER PUBLICATIONS

U.S. Appl. No. 15/050,029, filed Feb. 22, 2016, 2016-0168157, Unassigned, Heterocyclic Kinase Inhibitors.
U.S. Appl. No. 15/179,570, filed Jun. 10, 2016, Unpublished, Unassigned, Heterocyclic Compounds and Uses Thereof.

* cited by examiner

CHEMICAL COMPOUNDS, COMPOSITIONS AND METHODS FOR KINASE MODULATION

CLAIM OF PRIORITY

This application is a divisional application of U.S. application Ser. No. 14/085,660, filed Nov. 20, 2013, which is a divisional application of U.S. application Ser. No. 13/112,611, filed May 20, 2011, now U.S. Pat. No. 8,604,032, which claims priority from U.S. Provisional Application No. 61/347,370, filed May 21, 2010, all of which are incorporated herein by reference in their entireties.

BACKGROUND

The activity of cells can be regulated by external signals that stimulate or inhibit intracellular events. The process by which stimulatory or inhibitory signals are transmitted into and within a cell to elicit an intracellular response is referred to as signal transduction. Over the past decades, cascades of signal transduction events have been elucidated and found to play a central role in a variety of biological responses. Defects in various components of signal transduction pathways have been found to account for a vast number of diseases, including numerous forms of cancer, inflammatory disorders, metabolic disorders, vascular and neuronal diseases (Gaestel et al. *Current Medicinal Chemistry* (2007) 14:2214-2234).

Kinases represent a class of important signaling molecules. Kinases can generally be classified into protein kinases and lipid kinases, and certain kinases exhibit dual specificities. Protein kinases are enzymes that phosphorylate other proteins and/or themselves (i.e., autophosphorylation). Protein kinases can be generally classified into three major groups based upon their substrate utilization: tyrosine kinases which predominantly phosphorylate substrates on tyrosine residues (e.g., erb2, PDGF receptor, EGF receptor, VEGF receptor, src, abl), serine/threonine kinases which predominantly phosphorylate substrates on serine and/or threonine residues (e.g., mTorC1, mTorC2, ATM, ATR, DNA-PK, Akt), and dual-specificity kinases which phosphorylate substrates on tyrosine, serine and/or threonine residues.

Lipid kinases are enzymes that catalyze the phosphorylation of lipids. These enzymes, and the resulting phosphorylated lipids and lipid-derived biologically active organic molecules, play a role in many different physiological processes, including cell proliferation, migration, adhesion, and differentiation. Certain lipid kinases are membrane associated and they catalyze the phosphorylation of lipids contained in or associated with cell membranes. Examples of such enzymes include phosphoinositide(s) kinases (e.g., PI3-kinases, PI4-Kinases), diacylglycerol kinases, and sphingosine kinases.

The phosphoinositide 3-kinases (PI3Ks) signaling pathway is one of the most highly mutated systems in human cancers. PI3K signaling is also a key factor in many other diseases in humans. PI3K signaling is involved in many disease states including allergic contact dermatitis, rheumatoid arthritis, osteoarthritis, inflammatory bowel diseases, chronic obstructive pulmonary disorder, psoriasis, multiple sclerosis, asthma, disorders related to diabetic complications, and inflammatory complications of the cardiovascular system such as acute coronary syndrome.

PI3Ks are members of a unique and conserved family of intracellular lipid kinases that phosphorylate the 3'—OH group on phosphatidylinositols or phosphoinositides. The PI3K family comprises 15 kinases with distinct substrate specificities, expression patterns, and modes of regulation. The class I PI3Ks (p110α, p110β, p110δ, and p110γ) are typically activated by tyrosine kinases or G-protein coupled receptors to generate PIP3, which engages downstream effectors such as those in the Akt/PDK1 pathway, mTOR, the Tec family kinases, and the Rho family GTPases. The class II and III PI3Ks play a key role in intracellular trafficking through the synthesis of PI(3)P and PI(3,4)P2. The PI3Ks are protein kinases that control cell growth (mTORC1) or monitor genomic integrity (ATM, ATR, DNA-PK, and hSmg-1).

The delta (δ) isoform of class I PI3K has been implicated, in particular, in a number of diseases and biological processes. PI3K δ is expressed primarily in hematopoietic cells including leukocytes such as T-cells, dendritic cells, neutrophils, mast cells, B-cells, and macrophages. PI3K δ is integrally involved in mammalian immune system functions such as T-cell function, B-cell activation, mast cell activation, dendritic cell function, and neutrophil activity. Due to its integral role in immune system function, PI3K δ is also involved in a number of diseases related to undesirable immune response such as allergic reactions, inflammatory diseases, inflammation mediated angiogenesis, rheumatoid arthritis, and auto-immune diseases such as lupus, asthma, emphysema and other respiratory diseases. Other class I PI3K involved in immune system function includes PI3K γ, which plays a role in leukocyte signaling and has been implicated in inflammation, rheumatoid arthritis, and auto-immune diseases such as lupus.

Unlike PI3K δ, the beta (β) isoform of class I PI3K appears to be ubiquitously expressed. PI3K β has been implicated primarily in various types of cancer including PTEN-negative cancer (Edgar et al. *Cancer Research* (2010) 70(3):1164-1172), and HER2-overexpressing cancer such as breast cancer and ovarian cancer.

SUMMARY

As such, there remains a need for PI3K inhibitors capable of selectively inhibiting certain isoform(s) of class I PI3K without substantially affecting the activity of the remaining isoforms of the same class. In particular, inhibitors capable of selectively inhibiting PI3K δ and/or PI3K γ, but without substantially affecting the activity of PI3K β, would reduce one or more possible side effects associated with unnecessary down-regulation of PI3K β activity in a subject. Such inhibitors would be effective in ameliorating disease conditions mediated primarily by PI3K δ/γ. The present disclosure addresses this need and provides related advantages as well.

In one aspect, provided herein is a compound of Formula I:

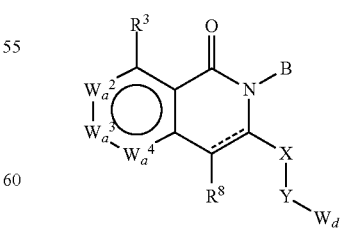

Formula I or pharmaceutically acceptable forms thereof, wherein,
$W_a^2$ is $CR^5$ or N; $W_a^3$ is $CR^6$ or N; $W_a^4$ is $CR^7$ or N; wherein no more than two adjacent ring atoms selected from $W_a^2$, $W_a^3$, and $W_a^4$ are heteroatoms;

B is hydrogen, alkyl, amino, heteroalkyl, or a moiety of formula II:

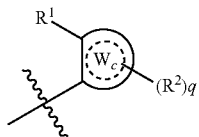

Formula II wherein $W_c$ is aryl, heteroaryl, heterocycloalkyl, or cycloalkyl, and q is an integer of 0, 1, 2, 3, or 4;

X is absent or —$(CH(R^9))_z$—, and z is an integer of 1, 2, 3, or 4;

Y is absent, —O—, —S—, —S(=O)—, —S(=O)$_2$—, —C(=O)—, —C(=O)(CHR$^9$)$_z$—, —N(R$^9$)—, N(R$^9$)—C(=O)—, —N(R$^9$)—C(=O)NH—, or —N(R$^9$)C(R$^9$)$_2$—, and z is an integer of 1, 2, 3, or 4;

$R^1$ is hydrogen, alkyl, alkenyl, alkynyl, alkoxy, amido, alkoxycarbonyl, sulfonamido, halo, cyano, or nitro; each $R^2$ is independently alkyl, alkenyl, alkynyl, cycloalkyl, heterocycloalkyl, aryl, heteroaryl, arylalkyl, heteroarylalkyl, alkoxy, amido, amino, acyl, acyloxy, alkoxycarbonyl, sulfonamido, halo, cyano, hydroxy, nitro, phosphate, urea, or carbonate;

$R^3$ is cycloalkyl, cycloalkylalkyl, aryl, heteroaryl, heterocyclyl, aralkyl, heteroaralkyl, heterocyclylalkyl, alkenyl, or alkynyl, or $R^3$ is a heteroatom selected from N, S, and O, wherein the heteroatom has a covalent bond either directly or through a $C_1$-$C_6$ alkyl group to an aryl, heteroaryl or heterocyclyl, or $R^3$ and $R^5$ are taken together with the carbons to which they are attached form a 5- or 6-membered ring; wherein each of the above substituents can be substituted with 0, 1, 2, or 3 $R^{13}$;

$R^5$, $R^6$, $R^7$, and $R^8$ are independently hydrogen, halo, cyano, alkyl or amino;

each $R^9$ is independently hydrogen, alkyl, or heterocycloalkyl;

$W_d$ is

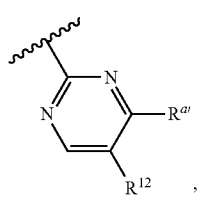 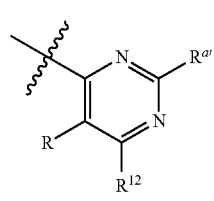

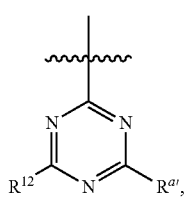 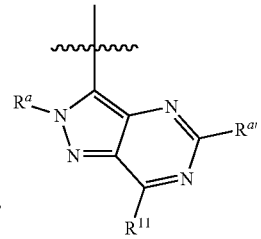

-continued

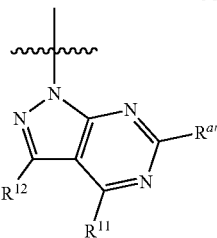

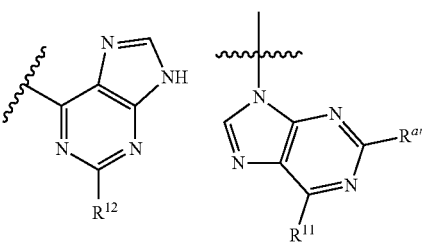

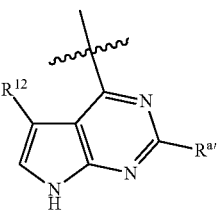 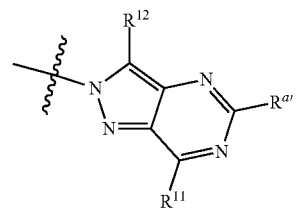

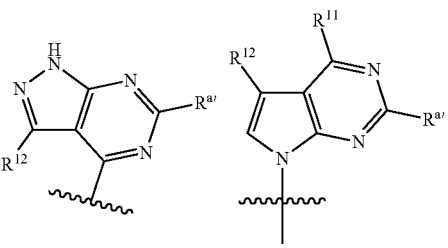

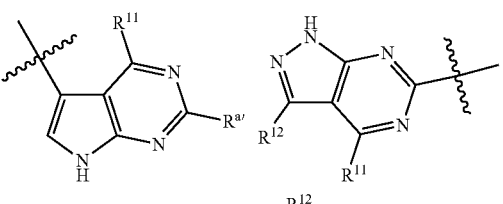

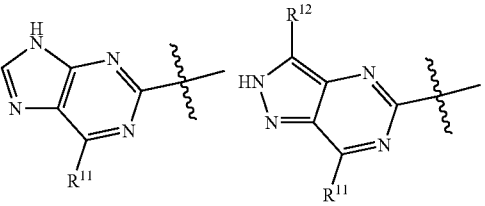

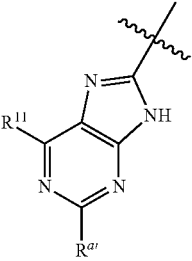 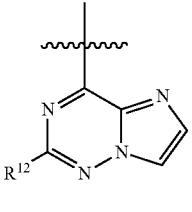

-continued

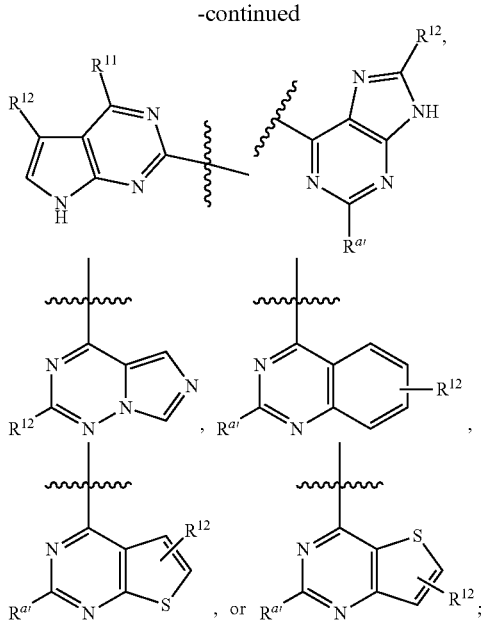

R[11] is hydrogen, alkyl, halo, amino, amido, hydroxy, alkoxy, phosphate, urea, or carbonate;

R[12] is hydrogen, alkyl, haloalkyl, alkynyl, alkenyl, halo, —C(O)NH$_2$, aryl, heteroaryl, nonaromatic heterocyclyl, or cycloalkyl, R[a'] is hydrogen, alkyl, —NH$_2$, cyano, or halogen; and each R[13] is independently hydrogen, C$_1$-C$_6$ alkyl, C$_1$-C$_6$ alkoxy, or halogen.

In certain embodiments, compounds are provided of the following Formula Ib:

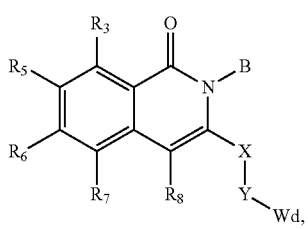

Formula (Ib)

or pharmaceutically acceptable forms thereof, wherein

B is hydrogen, alkyl, amino, heteroalkyl, or a moiety of Formula II:

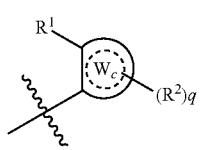

Formula II wherein W$_c$ is aryl, heteroaryl, heterocycloalkyl, or cycloalkyl;

q is an integer of 0, 1, 2, 3, or 4;

X is absent or —(CH(R[9]))$_z$—, and z is an integer of 1, 2, 3, or 4;

Y is absent, —O—, —S—, —S(=O)—, —S(=O)$_2$—, —C(=O)—, —C(=O)(CHR[9])$_z$—, —N(R[9])—, N(R[9])—C(=O)—, —N(R[9])—C(=O)NH—, or —N(R[9])C(R[9])$_2$—, and z is an integer of 1, 2, 3, or 4;

R[1] is hydrogen, alkyl, alkenyl, alkynyl, alkoxy, amido, alkoxycarbonyl, sulfonamido, halo, cyano, or nitro;

each R[2] is independently alkyl, alkenyl, alkynyl, cycloalkyl, heterocycloalkyl, aryl, heteroaryl, arylalkyl, heteroarylalkyl, alkoxy, amido, amino, acyl, acyloxy, alkoxycarbonyl, sulfonamido, halo, cyano, hydroxy, nitro, phosphate, urea, or carbonate;

R[3] is cycloalkyl, cycloalkylalkyl, aryl, heteroaryl, heterocyclyl, aralkyl, heteroaralkyl, heterocyclylalkyl, alkenyl, or alkynyl, or R[3] is a heteroatom selected from N, S, and O, wherein the heteroatom has a covalent bond either directly or through a C$_1$-C$_6$ alkyl group to an aryl, heteroaryl or heterocyclyl, or R[3] and R[5] are taken together with the carbons to which they are attached form a 5- or 6-membered ring; wherein each of the above substituents can be substituted with 0, 1, 2, or 3 R[13];

R[5], R[6], R[7], and R[8] are independently hydrogen, halo, cyano, alkyl or amino;

each R[9] is independently hydrogen, alkyl, or heterocycloalkyl;

W$_d$ is

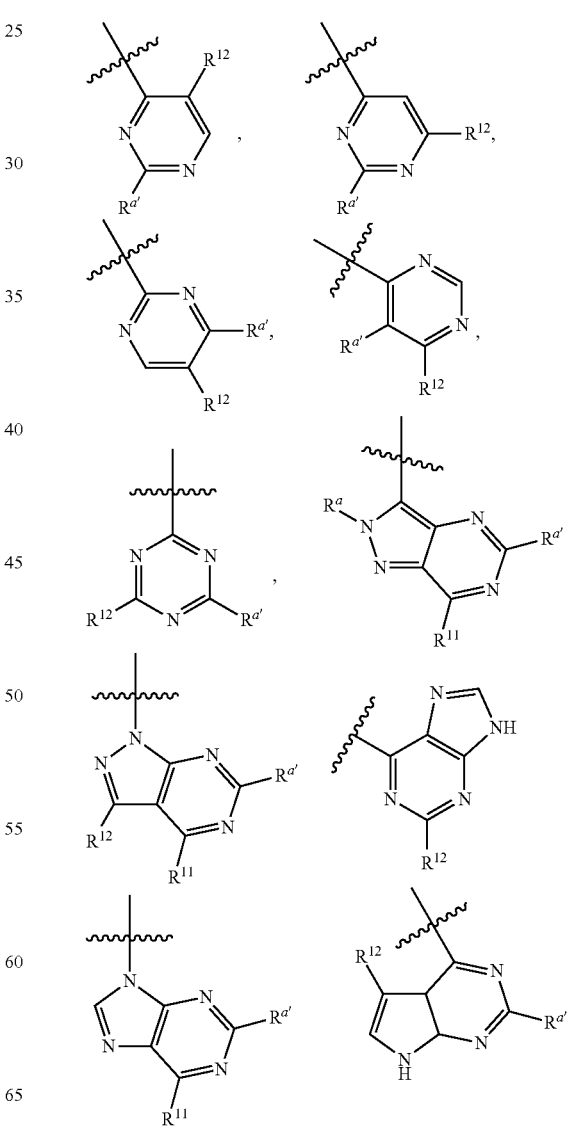

-continued

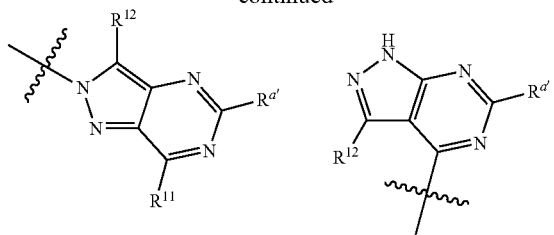

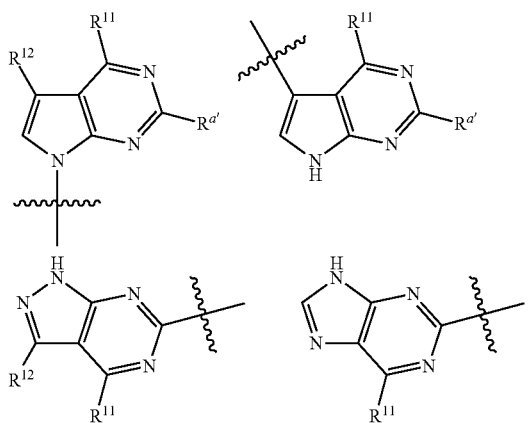

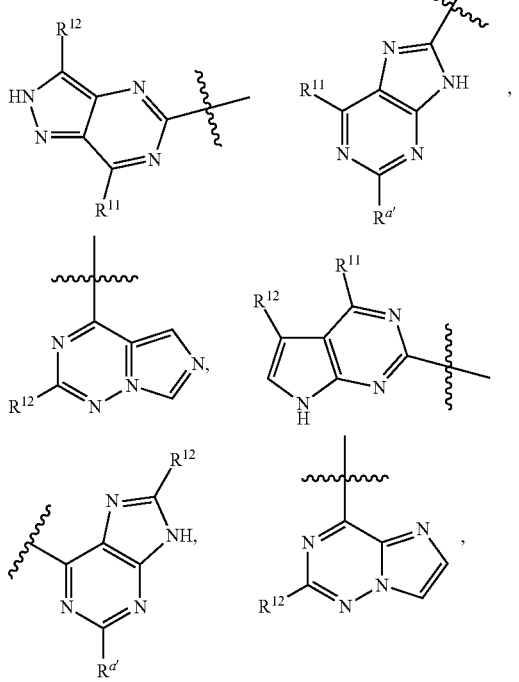

-continued

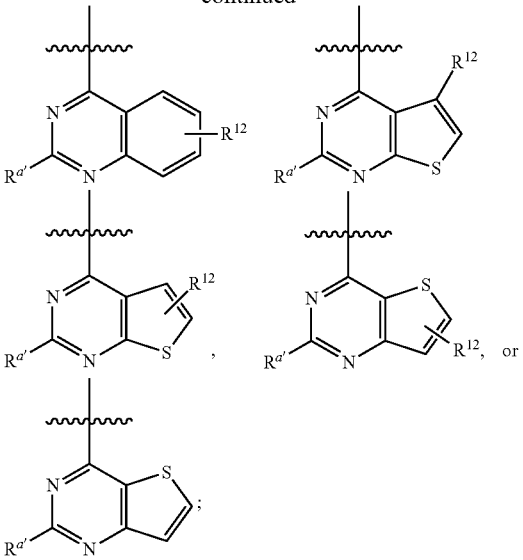

$R^{11}$ is hydrogen, alkyl, halo, amino, amido, hydroxy, alkoxy, phosphate, urea, or carbonate;

$R^{12}$ is hydrogen, alkyl, haloalkyl, alkynyl, alkenyl, halo, —C(O)NH$_2$, aryl, heteroaryl, nonaromatic heterocyclyl, or cycloalkyl, $R^{a'}$ is hydrogen, alkyl, —NH$_2$, cyano or halogen; and each $R^{13}$ is independently hydrogen, $C_1$-$C_6$ alkyl, $C_1$-$C_6$ alkoxy or halogen.

In certain embodiments, $R^3$ is selected from a 5-membered heteroaryl; 5-membered nonaromatic heterocycle; 6-membered aryl; 6-membered heteroaryl; 6-membered nonaromatic heterocycle; fused 5/6-bicyclic heteroaryl; fused 5/6-bicyclic nonaromatic heterocycle; $C_1$-$C_6$ alkyl group substituted with a 5-membered heteroaryl, a 5-membered nonaromatic heterocycle, a 6-membered aryl or heteroaryl, a 6-membered nonaromatic heterocycle, a fused 5/6-bicyclic heteroaryl, or a fused 5/6-bicyclic nonaromatic heterocycle. In some embodiments, $R^3$ is a heteroatom selected from N, S, and O, wherein the heteroatom has a covalent bond either directly or through a $C_1$-$C_6$ alkyl group to a 5-membered heteroaryl, a 5-membered nonaromatic heterocycle, a 6-membered aryl or heteroaryl, a 6-membered nonaromatic heterocycle, a fused 5/6-bicyclic heteroaryl, or a fused 5/6-bicyclic nonaromatic heterocycle. In some embodiments, $R^3$ is a $C_1$-$C_6$ alkyl group substituted with a fused polycyclic group, wherein the polycyclic group has greater than two rings and is carbocyclic or heterocyclic; $C_1$-$C_6$ alkyl group substituted with a bridged cycloalkyl or bridged heterocyclic group. In some embodiments, $R^3$ is $C_1$-$C_6$ alkyl group substituted with a spirocyclic cycloalkyl or spirocyclic heterocyclic group. In some embodiments, $R^3$ is a branched $C_4$-$C_{12}$ alkyl group, wherein said branched alkyl group contains at least one terminal t-butyl group.

In some embodiments, $R^3$ is a 5-membered heteroaryl. In some embodiments, $R^3$ is a 5-membered nonaromatic heterocycle. In some embodiments, $R^3$ is a 6-membered aryl. In some embodiments, $R^3$ is a 6-membered heteroaryl. In some embodiments, $R^3$ is a 6-membered nonaromatic heterocycle. In some embodiments, $R^3$ is a fused 5/6-bicyclic heteroaryl. In some embodiments, $R^3$ is a fused 5/6-bicyclic nonaromatic heterocycle. In some embodiments, $R^3$ is a 5-membered heteroaralkyl. In some embodiments, $R^3$ is a 5-membered nonaromatic heterocyclylalkyl. In some embodiments, $R^3$ is a 6-membered araralkyl. In some embodiments, $R^3$ is a 6-membered heteroaralkyl. In some embodiments, $R^3$ is a 6-membered nonaromatic heterocyclylalkyl. In some embodiments, $R^3$ is a fused 5/6-bicyclic heteroaralkyl. In some embodiments, $R^3$ is a fused 5/6-bicyclic nonaromatic heterocyclylalkyl.

In certain embodiments, $R^3$ is a heteroatom selected from N, S, and O, wherein the heteroatom has a covalent bond either directly or through a $C_1$-$C_6$ alkyl group to an aryl, heteroaryl or heterocyclyl. In some embodiments, $R^3$ is N, wherein the N has a covalent bond either directly or through a $C_1$-$C_6$ alkyl group to an aryl, heteroaryl or heterocyclyl. In some embodiments, $R^3$ is N, wherein the N has a covalent bond directly to an aryl, heteroaryl or heterocyclyl. In some embodiments, $R^3$ is N, wherein N has a covalent bond directly to a heterocyclyl. In some embodiments, the heterocyclyl is 4-tetrahydro-2H-pyran. In some embodiments, $R^3$ is

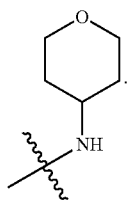 [SMILES: *NC1CCOCC1]

In certain embodiments, $R^3$ is

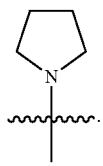

In some embodiments, $R^3$ is

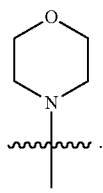

In some embodiments, $R^3$ is

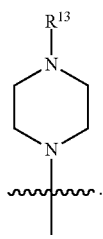

In some embodiments, $R^{13}$ is $C_{1-6}$ alkyl (e.g., methyl).

In certain embodiments, $R^3$ is

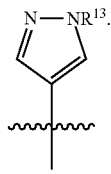

In some embodiments, $R^{13}$ is H. In some embodiments, $R^{13}$ is $C_{1-6}$ alkyl (e.g., methyl).

In certain embodiments, $R^3$ is

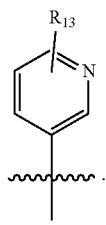

In some embodiments, $R^3$ is

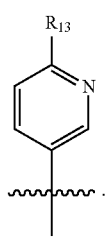

In some embodiments, $R^{13}$ is H. In some embodiments, $R^{13}$ is $C_{1-6}$ alkyl (e.g., methyl).

In certain embodiments, $R^3$ is

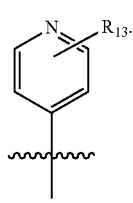

In some embodiments, $R^3$ is

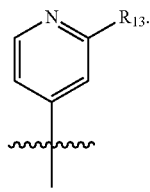

In some embodiments, $R^{13}$ is H. In some embodiments, $R^{13}$ is $C_{1-6}$ alkyl (e.g., methyl).

In certain embodiments, $R^3$ is

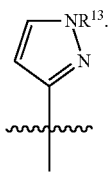

In some embodiments, $R^{13}$ is H.

In certain embodiments, $R^3$ is

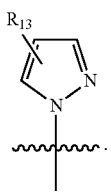

In some embodiments, $R^3$ is

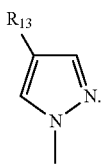

In some embodiments, $R^{13}$ is $C_{1-6}$ alkyl (e.g., methyl). In some embodiments $R^{13}$ is H.

In certain embodiments, $R^3$ is

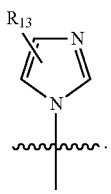

In some embodiments, $R^3$ is

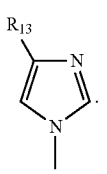

In some embodiments, $R^{13}$ is H. In some embodiments, $R^{13}$ is $C_{1-6}$ alkyl (e.g., methyl).

In certain embodiments, $R^3$ is

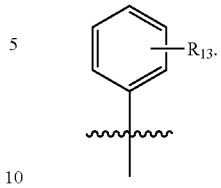

In some embodiments, $R^3$ is

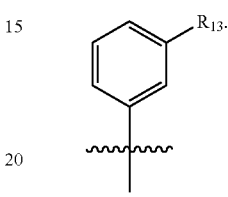

In some embodiments, $R^{13}$ is H. In some embodiments, $R^{13}$ is halogen (e.g., fluoro).

In certain embodiments, $R^3$ is

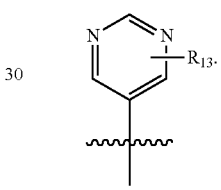

In some embodiments, $R^3$ is

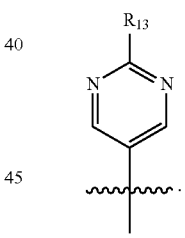

In some embodiments, $R^{13}$ is H. In some embodiments, $R^{13}$ is alkoxy (e.g., methoxy).

In certain embodiments, $R^3$ and $R^5$ taken together with the carbons to which they are attached can form a 5- or 6-membered ring which can be substituted with 0, 1, 2, or 3 $R^{13}$ groups.

In certain embodiments, B is hydrogen. In certain embodiments, a compound is provided of the previous formula wherein B is a moiety of Formula II:

Formula II

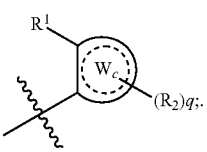

In some embodiments, $W_c$ is aryl or heteroaryl. In some embodiments, $W_c$ is 6-membered aryl (e.g., phenyl). In some embodiments, q is 0. In some embodiments, $R^1$ is hydrogen. In some embodiments, q is 1. In some embodiments, $R^2$ is halo (e.g., fluoro).

In some embodiments, $W_c$ is cycloalkyl (e.g., cyclopropyl). In some embodiments, q is 0. In some embodiments, $R^1$ is hydrogen.

In certain embodiments, Y is absent. In some embodiments, X is —(CH($R^9$))$_z$—. In some embodiments, z is 1. In some embodiments, $R^9$ is independently hydrogen. In some embodiments, $R^9$ is independently alkyl (e.g., methyl).

In certain embodiments, $W_d$ is

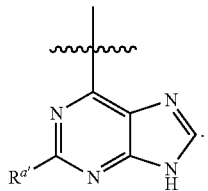

In some embodiments, $R^{a'}$ is hydrogen. In some embodiments, $R^{a'}$ is —NH$_2$.

In some embodiments, $W_d$ is

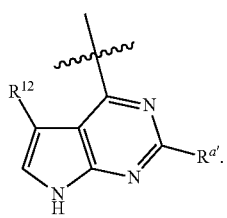

In some embodiments, $R^{12}$ is halogen (e.g., fluoro). In some embodiments, $R^{12}$ is cyano. In some embodiments, $R^{12}$ is —C(O)NH$_2$. In some embodiments, $R^{a'}$ is hydrogen.

In some embodiments, $W_d$ is

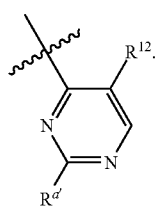

In some embodiments, $R^{a'}$ is —NH$_2$. In some embodiments, $R^{12}$ is halo (e.g., fluoro or iodo). In some embodiments, $R^{12}$ is cyano. In some embodiments, $R^{12}$ is haloalkyl (e.g., trifluoromethyl).

In certain embodiments, $W_d$ is

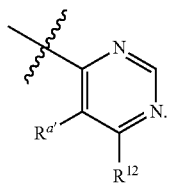

In some embodiments, $R^{a'}$ is cyano. In some embodiments, $R^{12}$ is —NH$_2$.

In some embodiments, $W_d$ is

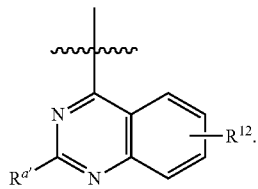

In some embodiments, $W_d$ is

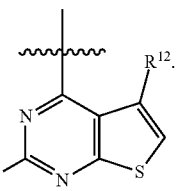

In certain embodiments, $R^3$ is

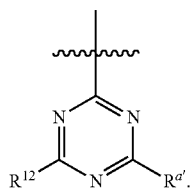

In some embodiments, $R^{a'}$ is —NH$_2$. In some embodiments, $R^{12}$ is hydrogen.

In certain embodiments, $R^6$ is hydrogen. In some embodiments, $R^7$ is hydrogen. In some embodiments, $R^8$ is hydrogen. In some embodiments, $R^6$, $R^7$ and $R^8$ are hydrogen.

In certain aspects, a compound is provided of formulae I or Ib wherein B is a moiety of Formula II:

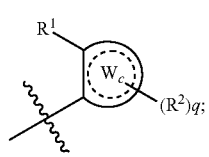

Formula II wherein $W_c$ is aryl, heteroaryl, heterocycloalkyl, or cycloalkyl; q is an integer of 0 or 1; $R^1$ is hydrogen, alkyl, or halo; $R^2$ is alkyl or halo; and $R^3$ is a 5-membered heteroaryl, 6-membered heteroaryl, or fused 5/6-bicyclic heteroaryl group.

In certain aspects, a compound is provided of formulae I or Ib wherein B is a moiety of formula:

Formula II

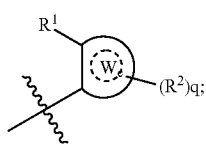

wherein $W_c$ is aryl or cycloalkyl. In various embodiments, $R^3$ contains one or two nitrogen atoms, with the proviso that non-nitrogen heteroatoms can be excluded. In various embodiments, $R^3$ is a substituted or unsubstituted group selected from phenyl, pyridine, pyrazole, piperazine, imidazole and pyrrolidine. For example, the $R^3$ group can be substituted with a $C_1$-$C_6$ alkyl group or a halogen.

In some embodiments of the compound of Formula I, Y is absent and $W_d$ is:

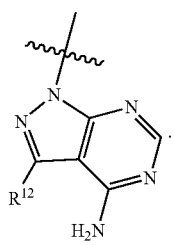

In other embodiments, Y is present and $W_d$ is:

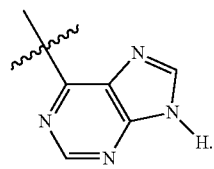

In some embodiments, a compound is provided wherein the compound has a structure of Formula IV-A:

Formula IV-A

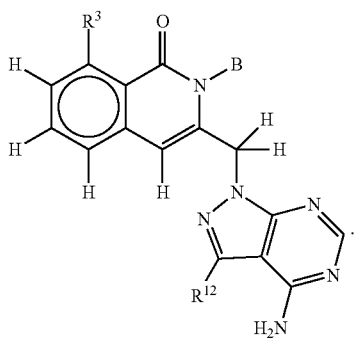

In certain embodiments, $R^{12}$ is monocyclic heteroaryl, bicyclic heteroaryl, or nonaromatic heterocyclyl. For example, $R^{12}$ can be a substituted benzoxazole. In certain embodiments, $R^3$ is a substituted or unsubstituted group selected from pyridine, pyrazole, piperazine, and pyrrolidine. The $R^3$ group can be substituted with a $C_1$-$C_6$ alkyl group or a halogen.

In some embodiments, a compound of any of the above formulae is provided wherein X is $-(CH(R^9))_z-$, wherein $R^9$ is methyl and z=1; and $W_d$ is

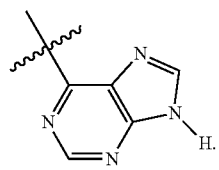

Accordingly, in some embodiments, the compound has one stereocenter, wherein said stereocenter can be in an (S)-stereochemical configuration or an (R)-stereochemical configuration. In some embodiments, a compound is provided wherein the compound has a structure of Formula V-A2:

Formula V-A2

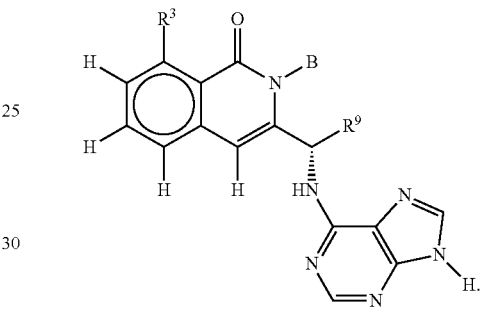

In certain embodiments, a compound described herein (e.g., a compound of Formula V-A2) is present in a racemic mixture (e.g., less than about 10% enantiomeric excess of either the R or S stereoisomer). In some embodiments, a compound described herein (e.g., a compound of Formula V-A2) is present in an enantiomeric excess of the R stereoisomer (e.g., about 10%, 50%, 75%, 85%, 90%, 95%, 97%, 99% or greater). In some embodiments, a compound described herein (e.g., a compound of Formula V-A2) is present in an enantiomeric excess of the S stereoisomer (e.g., about 10%, 50%, 75%, 85%, 90%, 95%, 97%, 99% or greater).

In certain embodiments, $R^3$ is phenyl, pyridine, pyrazole, piperazine, imidazole or pyrrolidine, substituted with 0, 1, 2, or 3 occurrences of $R^{13}$. In some embodiments, $R^{13}$ is $C_1$-$C_6$ alkyl (e.g., methyl). In some embodiments, $R^{13}$ is halogen (e.g., fluoro).

In some embodiments, a compound is provided wherein $R^3$ is selected from a 5-membered heteroaryl selected from pyrrole, a furan, a thiazole, a triazole, a tetrazole and a thiophene group; a 5-membered nonaromatic heterocycle selected from pyrrolidine, a tetrahydrofuran, and a tetrahydrothiophene group; a 6-membered heteroaryl selected from pyridine, pyrazine, pyrimidine, and pyridazine; a 6-membered nonaromatic heterocycle selected from piperidine, tetrahydropyran, and thiane; and a fused 5/6-bicyclic heteroaryl selected from indole, isoindole, benzofuran, isobenzofuran, benzothiophene, benzothiazole, benzimidazole, indazole, benzoxazole, benzisoxazole, and purine; each of which can be substituted with 0, 1, 2, or 3 occurrences of $R^{13}$. In certain embodiments, $R^3$ is selected from pyridine, pyrazole, piperazine, and pyrrolidine; each of which can be substituted with 0, 1, 2, or 3 occurrences of $R^{13}$. In some embodiments, $R^3$ can be substituted with $R^{13}$, which is $C_1$-$C_6$ alkyl (e.g., methyl) or a halogen (e.g., fluoro). In some embodiments, a compound is provided wherein $R^3$ is selected from

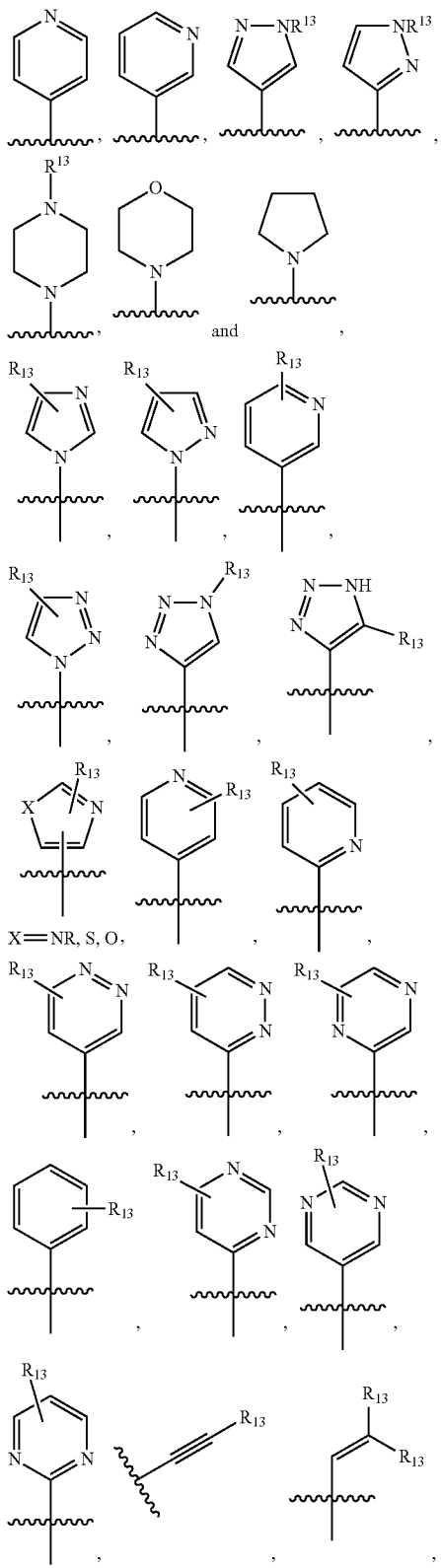

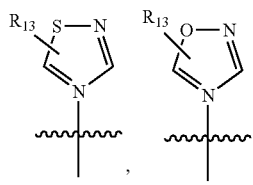

wherein $R^{13}$ is H $C_1$-$C_6$ alkyl (e.g., methyl) or halo (e.g., fluoro). In some embodiments, $R^{13}$ is $C_1$-$C_6$ alkyl (e.g., methyl). In some embodiments, $R^{13}$ is halo (e.g., fluoro).

In some embodiments, $R^3$ is selected from:

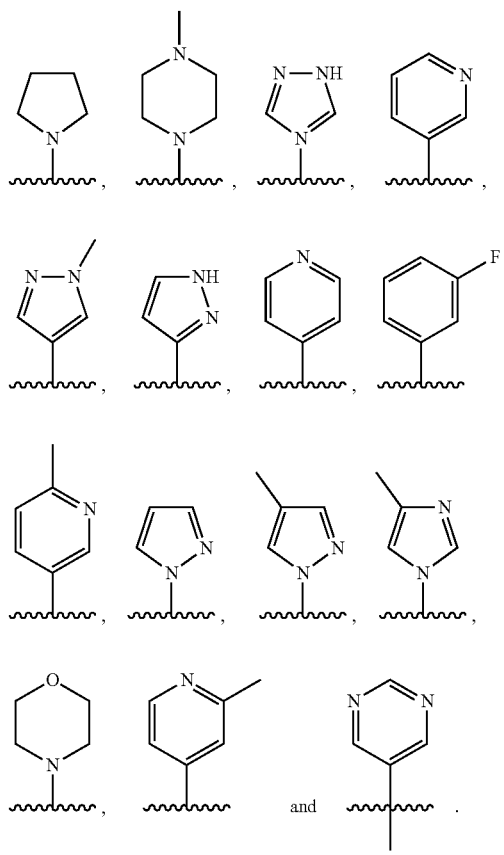

In certain embodiments, B is a moiety of Formula II:

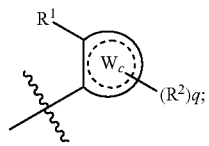

Formula II wherein $W_c$ is aryl or cycloalkyl. In certain embodiments, $W_d$ is selected from

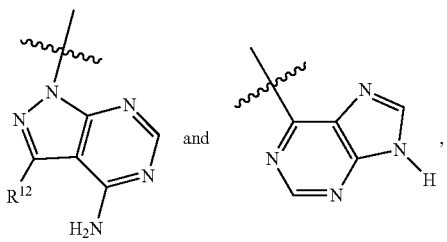

wherein $R^3$ can be selected from pyridine, pyrazole, piperazine, and pyrrolidine; each of which can be substituted with 0, 1, 2, or 3 occurrences of $R^{13}$;
B can be a moiety of Formula II:

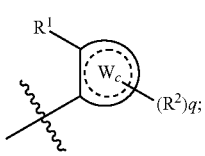

Formula II wherein $W_c$ is aryl or cycloalkyl; and
$W_d$ is selected from

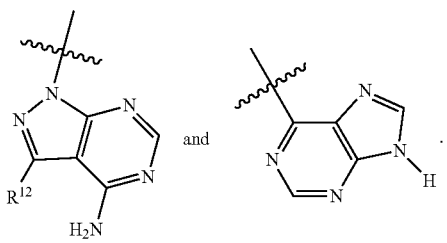

In certain embodiments, $R^{13}$ is $C_1$-$C_6$ alkyl (e.g., methyl) or a halogen (e.g., fluoro).

In certain embodiments, a compound as disclosed herein selectively modulates phosphatidyl inositol-3 kinase (PI3 kinase) delta isoform. In certain embodiments, the compound selectively inhibits the delta isoform over the beta isoform. By way of non-limiting example, the ratio of selectivity can be greater than a factor of about 10, greater than a factor of about 50, greater than a factor of about 100, greater than a factor of about 200, greater than a factor of about 400, greater than a factor of about 600, greater than a factor of about 800, greater than a factor of about 1000, greater than a factor of about 1500, greater than a factor of about 2000, greater than a factor of about 5000, greater than a factor of about 10,000, or greater than a factor of about 20,000, where selectivity can be measured by $IC_{50}$, among other means. In certain embodiments, the PI3 kinase delta isoform $IC_{50}$ activity of a compound as disclosed herein can be less than about 1000 nM, less than about 100 nM, less than about 10 nM, or less than about 1 nM.

In certain embodiments, provided herein is a composition (e.g., a pharmaceutical composition) comprising a compound as described herein and a pharmaceutically acceptable excipient. In some embodiments, provided herein is a method of inhibiting a phosphatidyl inositol-3 kinase (PI3 kinase), comprising contacting the PI3 kinase with an effective amount of a compound or pharmaceutical composition as described herein. In certain embodiments, a method is provided for inhibiting a phosphatidyl inositol-3 kinase (PI3 kinase) wherein said PI3 kinase is present in a cell. The inhibition can take place in a subject suffering from a disorder selected from cancer, bone disorder, inflammatory disease, immune disease, nervous system disease, metabolic disease, respiratory disease, thrombosis, and cardiac disease. In certain embodiments, a second therapeutic agent is administered to the subject.

In certain embodiments, a method is provided of selectively inhibiting a phosphatidyl inositol-3 kinase (PI3 kinase) delta isoform over PI3 kinase beta isoform wherein the inhibition takes place in a cell. Non-limiting examples of the methods disclosed herein can comprise contacting PI3 kinase delta isoform with an effective amount of a compound or pharmaceutical composition as disclosed herein. In an embodiment, such contact can occur in a cell.

In certain embodiments, a method is provided of selectively inhibiting a phosphatidyl inositol-3 kinase (PI3 kinase) delta isoform over PI3 kinase beta isoform wherein the inhibition takes place in a subject suffering from a disorder selected from cancer, bone disorder, inflammatory disease, immune disease, nervous system disease, metabolic disease, respiratory disease, thrombosis, and cardiac disease, said method comprising administering an effective amount of a compound or pharmaceutical composition to said subject. In certain embodiments, provided herein is a method of treating a subject suffering from a disorder associated with phosphatidyl inositol-3 kinase (PI3 kinase), said method comprising selectively modulating the phosphatidyl inositol-3 kinase (PI3 kinase) delta isoform over PI3 kinase beta isoform by administering an amount of a compound or pharmaceutical composition to said subject, wherein said amount is sufficient for selective modulation of PI3 kinase delta isoform over PI3 kinase beta isoform.

INCORPORATION BY REFERENCE

All publications, patents, and patent applications mentioned in this specification are herein incorporated by reference to the same extent as if each individual publication, patent, or patent application was specifically and individually indicated to be incorporated by reference. In case of conflict, the present application, including any definitions herein, will control.

DETAILED DESCRIPTION

While specific embodiments of the present disclosure have been discussed, the specification is illustrative and not restrictive. Many variations of this disclosure will become apparent to those skilled in the art upon review of this specification. The full scope of the disclosure should be determined by reference to the claims, along with their full scope of equivalents, and the specification, along with such variations.

When ranges are used herein for physical properties, such as molecular weight, or chemical properties, such as chemical formulae, all combinations and subcombinations of ranges and specific embodiments therein are intended to be included. Unless otherwise indicated, all numbers expressing quantities of ingredients, reaction conditions, and so forth used in the specification and claims are to be understood as being modified in all instances by the term "about." The term "about" when referring to a number or a numerical range means that the number or numerical range referred to is an approximation within experimental variability (or within statistical experimental error), and thus the number or numerical range can vary from, for example, but not limited to, between 0.1% and 15% of the stated number or numerical range. Accordingly, unless indicated to the contrary, the numerical parameters set forth in this specification and attached claims are approximations that can vary depending upon the desired properties sought to be obtained by the present disclosure.

Unless defined otherwise, all technical and scientific terms used herein have the same meaning as is commonly understood by one of skill in the art to which this specification pertains.

As used in the specification and claims, the singular form "a", "an" and "the" includes plural references unless the context clearly dictates otherwise.

As used herein, "agent" or "biologically active agent" refers to a biological, pharmaceutical, or chemical compound or other moiety. Non-limiting examples include simple or complex organic or inorganic molecules, a peptide, a protein, an oligonucleotide, an antibody, an antibody derivative, an antibody fragment, a vitamin, a vitamin derivative, a carbohydrate, a toxin, or a chemotherapeutic compound, and metabolites thereof. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like. A skilled artisan can readily recognize that there is no limit as to the structural nature of the agents of this disclosure.

The term "agonist" as used herein refers to a compound or agent having the ability to initiate or enhance a biological function of a target protein or polypeptide, such as increasing the activity or expression of the target protein or polypeptide. Accordingly, the term "agonist" is defined in the context of the biological role of the target protein or polypeptide. While some agonists herein specifically interact with (e.g., bind to) the target, compounds and/or agents that initiate or enhance a biological activity of the target protein or polypeptide by interacting with other members of the signal transduction pathway of which the target polypeptide is a member are also specifically included within this definition.

The terms "antagonist" and "inhibitor" are used interchangeably, and they refer to a compound or agent having the ability to inhibit a biological function of a target protein or polypeptide, such as by inhibiting the activity or expression of the target protein or polypeptide. Accordingly, the terms "antagonist" and "inhibitors" are defined in the context of the biological role of the target protein or polypeptide. While some antagonists herein specifically interact with (e.g., bind to) the target, compounds that inhibit a biological activity of the target protein or polypeptide by interacting with other members of the signal transduction pathway of which the target protein or polypeptide is a member are also specifically included within this definition. Non-limiting examples of biological activity inhibited by an antagonist include those associated with the development, growth, or spread of a tumor, or an undesired immune response as manifested in autoimmune disease.

An "anti-cancer agent", "anti-tumor agent" or "chemotherapeutic agent" refers to any agent useful in the treatment of a neoplastic condition. One class of anti-cancer agents comprises chemotherapeutic agents. "Chemotherapy" means the administration of one or more chemotherapeutic drugs and/or other agents to a cancer patient by various methods, including intravenous, oral, intramuscular, intraperitoneal, intravesical, subcutaneous, transdermal, buccal, or inhalation or in the form of a suppository.

The term "cell proliferation" refers to a phenomenon by which the cell number has changed as a result of division. This term also encompasses cell growth by which the cell morphology has changed (e.g., increased in size) consistent with a proliferative signal.

The term "co-administration," "administered in combination with," and their grammatical equivalents, as used herein, encompasses administration of two or more agents to subject so that both agents and/or their metabolites are present in the subject at the same time. Co-administration includes simultaneous administration in separate compositions, administration at different times in separate compositions, or administration in a composition in which both agents are present.

The term "effective amount" or "therapeutically effective amount" refers to that amount of a compound or pharmaceutical composition described herein that is sufficient to effect the intended application including, but not limited to, disease treatment, as illustrated below. The therapeutically effective amount can vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of platelet adhesion and/or cell migration. The specific dose will vary depending on the particular compounds chosen, the dosing regimen to be followed, whether it is administered in combination with other agents, timing of administration, the tissue to which it is administered, and the physical delivery system in which it is carried.

As used herein, the terms "treatment", "treating", "palliating" and "ameliorating" are used interchangeably herein. These terms refer to an approach for obtaining beneficial or desired results including, but not limited to, therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient can still be afflicted with the underlying disorder. For prophylactic benefit, the pharmaceutical compositions can be administered to a patient at risk of developing a particular disease, or to a patient reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

In certain embodiments, the pharmaceutically acceptable form thereof is a pharmaceutically acceptable salt. As used herein, the term "pharmaceutically acceptable salt" refers to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in *J Pharmaceutical Sciences* (1977) 66:1-19. Pharmaceutically acceptable salts of the compounds provided herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In some embodiments, organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Salts derived from appropriate bases include alkali metal, alkaline earth metal, ammonium and $N+(C_{1-4}alkyl)^4$-salts. Representative alkali or alkaline earth metal salts include sodium, lithium, potassium, calcium, magnesium, iron, zinc, copper, manganese, aluminum, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Organic bases from which salts can be derived include, for example, primary, secondary, and tertiary amines, substituted amines including naturally occurring substituted amines, cyclic amines, basic ion exchange resins, and the like, such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

In certain embodiments, the pharmaceutically acceptable form thereof is a prodrug. As used herein, the term "prodrug" refers to compounds that are transformed in vivo to yield a disclosed compound or a pharmaceutically acceptable form of the compound. A prodrug can be inactive when administered to a subject, but is converted in vivo to an active compound, for example, by hydrolysis (e.g., hydrolysis in blood). In certain cases, a prodrug has improved physical and/or delivery properties over the parent compound. Prodrugs are typically designed to enhance pharmaceutically and/or pharmacokinetically based properties associated with the parent compound. The prodrug compound often offers advantages of solubility, tissue compatibility or delayed release in a mammalian organism (see, e.g., Bundgard, H., *Design of Prodrugs* (1985), pp. 7-9, 21-24 (Elsevier, Amsterdam). A discussion of prodrugs is provided in Higuchi, T., et al., "Pro-drugs as Novel Delivery Systems," *A.C.S. Symposium Series*, Vol. 14, and in *Bioreversible Carriers in Drug Design*, ed. Edward B. Roche, American Pharmaceutical Association and Pergamon Press, 1987, both of which are incorporated in full by reference herein. Exemplary advantages of a prodrug can include, but are not limited to, its physical properties, such as enhanced water solubility for parenteral administration at physiological pH compared to the parent compound, or it enhances absorption from the digestive tract, or it can enhance drug stability for long-term storage.

The term "prodrug" is also meant to include any covalently bonded carriers, which release the active compound in vivo when such prodrug is administered to a subject. Prodrugs of an active compound, as described herein, can be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like.

For example, if a disclosed compound or a pharmaceutically acceptable form of the compound contains a carboxylic acid functional group, a prodrug can comprise an ester formed by the replacement of the hydrogen atom of the acid group with a group such as $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$alkyl.

Similarly, if a disclosed compound or a pharmaceutically acceptable form of the compound contains an alcohol functional group, a prodrug can be formed by the replacement of the hydrogen atom of the alcohol group with a group such as $(C_1-C_6)$alkanoyloxymethyl, 1-(($C_1-C_6$)alkanoyloxy)ethyl, 1-methyl-1-(($C_1-C_6$)alkanoyloxy)ethyl$(C_1-C_6)$ alkoxycarbonyloxymethyl, N—$(C_1-C_6)$alkoxycarbonylaminomethyl, succinoyl, $(C_1-C_6)$alkanoyl, α-amino$(C_1-C_4)$alkanoyl, arylacyl and α-aminoacyl, or α-aminoacyl-α-aminoacyl, where each -aminoacyl group is independently selected from the naturally occurring L-amino acids, $P(O)(OH)_2$, —$P(O)(O(C_1-C_6)alkyl)_2$ or glycosyl (the radical resulting from the removal of a hydroxyl group of the hemiacetal form of a carbohydrate).

If a disclosed compound or a pharmaceutically acceptable form of the compound incorporates an amine functional group, a prodrug can be formed by the replacement of a hydrogen atom in the amine group with a group such as R-carbonyl, RO-carbonyl, NRR'-carbonyl where R and R' are each independently $(C_1-C_{10})$alkyl, $(C_3-C_7)$cycloalkyl, benzyl, or R-carbonyl is a natural α-aminoacyl or natural α-aminoacyl-natural α-aminoacyl, —C(OH)C(O)OY$^1$ wherein Y$^1$ is H, $(C_1-C_6)$alkyl or benzyl, —C(OY$^2$)Y$^3$ wherein Y$^2$ is $(C_1-C_4)$alkyl and Y$^3$ is $(C_1-C_6)$alkyl, carboxy ($C_1$-$C_6$)alkyl, amino($C_1$-$C_4$)alkyl or mono-N— or di-N,N—($C_1$-$C_6$)alkylaminoalkyl, —C($Y^4$)$Y^5$ wherein $Y^4$ is H or methyl and $Y^5$ is mono-N— or di-N,N—(C1-C6)alkylamino, morpholino, piperidin-1-yl or pyrrolidin-1-yl.

In certain embodiments, the pharmaceutically acceptable form thereof is a tautomer. As used herein, the term "tautomer" includes two or more interconvertible compounds resulting from at least one formal migration of a hydrogen atom and at least one change in valency (e.g., a single bond to a double bond, a triple bond to a single bond, or vice versa). "Tautomerization" includes prototropic or proton-shift tautomerization, which is considered a subset of acid-base chemistry. "Prototropic tautomerization" or "proton-shift tautomerization" involves the migration of a proton accompanied by changes in bond order. The exact ratio of the tautomers depends on several factors, including temperature, solvent, and pH. Where tautomerization is possible (e.g., in solution), a chemical equilibrium of tautomers can be reached. Tautomerizations (i.e., the reaction providing a tautomeric pair) can be catalyzed by acid or base, or can occur without the action or presence of an external agent. Exemplary tautomerizations include, but are not limited to, keto-to-enol; amide-to-imide; lactam-to-lactim; enamine-to-imine; and enamine-to-(a different) enamine tautomerizations. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

In certain embodiments, the pharmaceutically acceptable form thereof is an isomer. "Isomers" are different compounds that have the same molecular formula. "Stereoisomers" are isomers that differ only in the way the atoms are arranged in space. As used herein, the term "isomer" includes any and all geometric isomers and stereoisomers. For example, "isomers" include cis- and trans-isomers, E- and Z-isomers, R- and S-enantiomers, diastereomers, (d)-isomers, (l)-isomers, racemic mixtures thereof, and other mixtures thereof, as falling within the scope of this disclosure. "Enantiomers" are a pair of stereoisomers that are non-superimposable mirror images of each other. A mixture of a pair of enantiomers in any proportion can be known as a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer, the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry, as (R)- or (S)-. The present chemical entities, pharmaceutical compositions and methods are meant to include all such possible isomers, including racemic mixtures, optically pure forms and intermediate mixtures. Optically active (R)- and (S)-isomers can be prepared, for example, using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

The "enantiomeric excess" or "% enantiomeric excess" of a composition can be calculated using the equation shown below. In the example shown below, a composition contains 90% of one enantiomer, e.g., the S enantiomer, and 10% of the other enantiomer, e.g., the R enantiomer.

$$ee=(90-10)/100=80\%.$$

Thus, a composition containing 90% of one enantiomer and 10% of the other enantiomer is said to have an enantiomeric excess of 80%. Some of the compositions described herein contain an enantiomeric excess of at least about 50%, 75%, 90%, 95%, or 99% of Compound 1 (the S-enantiomer). In other words, the compositions contain an enantiomeric excess of the S enantiomer over the R enantiomer.

For instance, an isomer/enantiomer can, in some embodiments, be provided substantially free of the corresponding enantiomer, and can also be referred to as "optically enriched." "Optically-enriched," as used herein, means that the compound is made up of a significantly greater proportion of one enantiomer. In certain embodiments, the compound provided herein is made up of at least about 90% by weight of one enantiomer. In other embodiments the compound is made up of at least about 95%, 98%, or 99% by weight of one enantiomer. Enantiomers can be isolated from racemic mixtures by any method known to those skilled in the art, including chiral high pressure liquid chromatography (HPLC), the formation and crystallization of chiral salts, or prepared by asymmetric syntheses. See, for example, *Enantiomers, Racemates and Resolutions* (Jacques, Ed., Wiley Interscience, New York, 1981); Wilen et al., *Tetrahedron* 33:2725 (1977); *Stereochemistry of Carbon Compounds* (E. L. Eliel, Ed., McGraw-Hill, N Y, 1962); and *Tables of Resolving Agents and Optical Resolutions* p. 268 (E. L. Eliel, Ed., Univ. of Notre Dame Press, Notre Dame, Ind. 1972).

"Pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions as disclosed herein is contemplated. Supplementary active ingredients can also be incorporated into the pharmaceutical compositions.

"Signal transduction" is a process during which stimulatory or inhibitory signals are transmitted into and within a cell to elicit an intracellular response. A modulator of a signal transduction pathway refers to a compound which modulates the activity of one or more cellular proteins mapped to the same specific signal transduction pathway. A modulator can augment (agonist) or suppress (antagonist) the activity of a signaling molecule.

The term "selective inhibition" or "selectively inhibit" as applied to a biologically active agent refers to the agent's ability to selectively reduce the target signaling activity as compared to off-target signaling activity, via direct or interact interaction with the target. For example, a compound that selectively inhibits one isoform of PI3K over another isoform of PI3K has an activity of at least 2× against a first isoform relative to the compound's activity against the second isoform (e.g., at least 3×, 5×, 10×, 20×, 50×, or 100×).

The term "B-ALL" as used herein refers to B-cell Acute Lymphoblastic Leukemia.

"Subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, and/or turkeys.

"Radiation therapy" means exposing a patient, using routine methods and compositions known to the practitioner, to radiation emitters such as, but not limited to, alpha-particle emitting radionuclides (e.g., actinium and thorium radionuclides), low linear energy transfer (LET) radiation emitters (i.e., beta emitters), conversion electron emitters (e.g., strontium-89 and samarium-153-EDTMP, or high-energy radiation, including without limitation x-rays, gamma rays, and neutrons.

The term "in vivo" refers to an event that takes place in a subject's body.

The term "in vitro" refers to an event that takes places outside of a subject's body. For example, an in vitro assay encompasses any assay conducted outside of a subject. In vitro assays encompass cell-based assays in which cells, alive or dead, are employed. In vitro assays also encompass a cell-free assay in which no intact cells are employed.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this disclosure.

The disclosure also embraces isotopically labeled compounds which are identical to those recited herein, except that one or more atoms are replaced by an atom having an atomic mass or mass number different from the atomic mass or mass number usually found in nature. Examples of isotopes that can be incorporated into disclosed compounds include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Certain isotopically-labeled disclosed compounds (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes can allow for ease of preparation and detectability. Further, substitution with heavier isotopes such as deuterium (i.e., $^{2}H$) can afford certain therapeutic advantages resulting from greater metabolic stability (e.g., increased in vivo half-life or reduced dosage requirements). Isotopically labeled disclosed compounds can generally be prepared by substituting an isotopically labeled reagent for a non-isotopically labeled reagent. In some embodiments, provided herein are compounds that can also contain unnatural proportions of atomic isotopes at one or more of atoms that constitute such compounds. All isotopic variations of the compounds as disclosed herein, whether radioactive or not, are encompassed within the scope of the present disclosure.

The following abbreviations and terms have the indicated meanings throughout: PI3K=Phosphoinositide 3-kinase; PI=phosphatidylinositol; PDK=Phosphoinositide Dependent Kinase; DNA-PK=Deoxyribose Nucleic Acid Dependent Protein Kinase; PTEN=Phosphatase and Tensin homolog deleted on chromosome Ten; PIKK=Phosphoinositide Kinase Like Kinase; AIDS=Acquired Immuno Deficiency Syndrome; HW=Human Immunodeficiency Virus; MeI=Methyl Iodide; $POCl_3$=Phosphorous Oxychloride; KCNS=Potassium Isothiocyanate; TLC=Thin Layer Chromatography; MeOH=Methanol; and $CHCl_3$=Chloroform.

"Alkyl" refers to a straight or branched hydrocarbon chain radical consisting solely of carbon and hydrogen atoms, containing no unsaturation, having from one to ten carbon atoms (e.g., $C_1$-$C_{10}$ alkyl). Whenever it appears herein, a numerical range such as "1 to 10" refers to each integer in the given range; e.g., "1 to 10 carbon atoms" means that the alkyl group can consist of 1 carbon atom, 2 carbon atoms, 3 carbon atoms, etc., up to and including 10 carbon atoms, although the present definition also covers the occurrence of the term "alkyl" where no numerical range is designated. In some embodiments, it is a $C_1$-$C_6$ alkyl group. Typical alkyl groups include, but are in no way limited to, methyl, ethyl, propyl, isopropyl, n-butyl, iso-butyl, sec-butyl isobutyl, tertiary butyl, pentyl, isopentyl, neopentyl, hexyl, septyl, octyl, nonyl, decyl, and the like. The alkyl is attached to the rest of the molecule by a single bond, for example, methyl (Me), ethyl (Et), n-propyl, 1-methylethyl (iso-propyl), n-butyl, n-pentyl, 1,1-dimethylethyl (t-butyl), 3-methylhexyl, 2-methylhexyl, and the like. Unless stated otherwise specifically in the specification, an alkyl group is optionally substituted by one or more of substituents which independently include: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, $SR^a$, —OC(O)—$R^a$, —$N(R^a)_2$, —C(O)$R^a$, —C(O)O$R^a$, —OC(O)N$(R^a)_2$, —C(O)N$(R^a)_2$, —N($R^a$)C(O)OR', —N($R^a$)C(O)$R^a$, —N($R^a$)C(O)N$(R^a)_2$, N($R^a$)C(N$R^a$)N$(R^a)_2$, —N($R^a$)S(O)$_t R^a$ (where t is 1 or 2), —S(O)$_t$O$R^a$ (where t is 1 or 2), —S(O)$_t$N$(R^a)_2$ (where t is 1 or 2), or PO$_3(R^a)_2$ where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkylaryl" refers to an -(alkyl)aryl radical where aryl and alkyl are as disclosed herein and which are optionally substituted by one or more of the substituents described as suitable substituents for aryl and alkyl respectively. The "alkylaryl" is bonded to the parent molecular structure through the alkyl group.

"Alkylheteroaryl" refers to an -(alkyl)heteroaryl radical where heteroaryl and alkyl are as disclosed herein and which are optionally substituted by one or more of the substituents described as suitable substituents for aryl and alkyl respectively. The "alkylheteroaryl" is bonded to the parent molecular structure through the alkyl group.

"Alkylheterocycloalkyl" refers to an -(alkyl) heterocycyl radical where alkyl and heterocycloalkyl are as disclosed herein and which are optionally substituted by one or more of the substituents described as suitable substituents for heterocycloalkyl and alkyl respectively. The "alkylheterocycloalkyl" is bonded to the parent molecular structure through the alkyl group.

"Alkenyl" refers to a straight or branched hydrocarbon chain radical group consisting solely of carbon and hydrogen atoms, containing at least one double bond, and having from two to ten carbon atoms (i.e., $C_2$-$C_{10}$ alkenyl). Whenever it appears herein, a numerical range such as "2 to 10" refers to each integer in the given range; e.g., "2 to 10 carbon atoms" means that the alkenyl group can consist of 2 carbon atoms, 3 carbon atoms, etc., up to and including 10 carbon atoms. In certain embodiments, an alkenyl comprises two to eight carbon atoms. In other embodiments, an alkenyl comprises two to five carbon atoms (e.g., $C_2$-$C_5$ alkenyl). The alkenyl is attached to the parent molecular structure by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more substituents which independently include: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, $OR^a$, —$SR^a$, —OC(O)—$R^a$, —$N(R^a)_2$, —$C(O)R^a$, —$C(O)OR^a$, —$OC(O)N(R^a)_2$, —$C(O)N(R^a)_2$, —$N(R^a)^C(O)OR^a$, —$N(R^a)^C(O)R^a$, —$N(R^a)^C(O)N(R^a)_2$, $N(R^a)^C(N-R^a)^N(R^a)_2$, —$N(R^a)^S(O)_tR_a$ (where t is 1 or 2), —$S(O)_tO_R{}^a$ (where t is 1 or 2), —$S(O)_tN(R^a)^2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkenyl-cycloalkyl" refers to an -(alkenyl)cycloalkyl radical where alkenyl and cyclo alkyl are as disclosed herein and which are optionally substituted by one or more of the substituents described as suitable substituents for alkenyl and cycloalkyl respectively. The "alkenyl-cycloalkyl" is bonded to the parent molecular structure through the alkenyl group.

"Alkynyl" refers to a straight or branched hydrocarbon chain radical group consisting solely of carbon and hydrogen atoms, containing at least one triple bond, having from two to ten carbon atoms (i.e., $C_2$-$C_{10}$ alkynyl). Whenever it appears herein, a numerical range such as "2 to 10" refers to each integer in the given range; e.g., "2 to 10 carbon atoms" means that the alkynyl group can consist of 2 carbon atoms, 3 carbon atoms, etc., up to and including 10 carbon atoms. In certain embodiments, an alkynyl comprises two to eight carbon atoms. In other embodiments, an alkynyl has two to five carbon atoms (e.g., $C_2$-$C_5$ alkynyl). The alkynyl is attached to the parent molecular structure by a single bond, for example, ethynyl, propynyl, butynyl, pentynyl, hexynyl, and the like. Unless stated otherwise specifically in the specification, an alkynyl group is optionally substituted by one or more substituents which independently include: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkynyl-cycloalkyl" refers to refers to an -(alkynyl)cycloalkyl radical where alkynyl and cycloalkyl are as disclosed herein and which are optionally substituted by one or more of the substituents described as suitable substituents for alkynyl and cycloalkyl respectively. The "alkynyl-cycloalkyl" is bonded to the parent molecular structure through the alkenyl group.

"Carboxaldehyde" refers to a —(C=O)H radical.

"Carboxyl" refers to a —(C=O)OH radical.

"Cyano" refers to a —CN radical.

"Cycloalkyl" refers to a monocyclic or polycyclic radical that contains only carbon and hydrogen, and can be saturated, or partially unsaturated. Cycloalkyl groups include groups having from 3 to 10 ring atoms (i.e., $C_3$-$C_{10}$ cycloalkyl). Whenever it appears herein, a numerical range such as "3 to 10" refers to each integer in the given range; e.g., "3 to 10 carbon atoms" means that the cycloalkyl group can consist of 3 carbon atoms, 4 carbon atoms, 5 carbon atoms, etc., up to and including 10 carbon atoms. In some embodiments, it is a $C_3$-$C_8$ cycloalkyl radical. In some embodiments, it is a $C_3$-$C_5$ cycloalkyl radical. Illustrative examples of cycloalkyl groups include, but are not limited to the following moieties: cyclopropyl, cyclobutyl, cyclopentyl, cyclopentenyl, cyclohexyl, cyclohexenyl, cycloseptyl, cyclooctyl, cyclononyl, cyclodecyl, norbornyl, and the like. The term "cycloalkyl" also includes bridged and spiro-fused cyclic structures containing no heteroatoms. The term also includes monocyclic or fused-ring polycyclic (i.e., rings which share adjacent pairs of ring atoms) groups. Unless stated otherwise specifically in the specification, a cycloalkyl group is optionally substituted by one or more substituents which independently include: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(N-R^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Cycloalkyl-alkenyl" refers to a -(cycloalkyl)alkenyl radical where cycloalkyl and heterocycloalkyl are as disclosed herein and which are optionally substituted by one or more of the substituents described as suitable substituents for heterocycloalkyl and cycloalkyl respectively. The "cycloalkyl-alkenyl" is bonded to the parent molecular structure through the cycloalkyl group.

"Cycloalkyl-heterocycloalkyl" refers to a -(cycloalkyl)heterocycyl radical where cycloalkyl and heterocycloalkyl are as disclosed herein and which are optionally substituted by one or more of the substituents described as suitable substituents for heterocycloalkyl and cycloalkyl respectively. The "cycloalkyl-heterocycloalkyl" is bonded to the parent molecular structure through the cycloalkyl group.

"Cycloalkyl-heteroaryl" refers to a -(cycloalkyl) heteroaryl radical where cycloalkyl and heterocycloalkyl are as disclosed herein and which are optionally substituted by one or more of the substituents described as suitable substituents for heterocycloalkyl and cycloalkyl respectively. The "cycloalkyl-heteroaryl" is bonded to the parent molecular structure through the cycloalkyl group.

The term "alkoxy" refers to the group —O-alkyl, including from 1 to 10 carbon atoms of a straight, branched, cyclic configuration and combinations thereof, attached to the parent molecular structure through an oxygen. Examples include methoxy, ethoxy, propoxy, isopropoxy, cyclopropyloxy, cyclohexyloxy and the like. "Lower alkoxy" refers to alkoxy groups containing one to six carbons. In some embodiments, $C_1$-$C_4$ alkyl is an alkyl group which encompasses both straight and branched chain alkyls of from 1 to 4 carbon atoms.

The term "substituted alkoxy" refers to alkoxy wherein the alkyl constituent is substituted (i.e., —O-(substituted alkyl)). Unless stated otherwise specifically in the specification, the alkyl moiety of an alkoxy group is optionally substituted by one or more substituents which independently include: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "alkoxycarbonyl" refers to a group of the formula (alkoxy)(C=O)— attached to the parent molecular structure through the carbonyl carbon wherein the alkoxy group has the indicated number of carbon atoms. Thus a C$_1$-C$_6$ alkoxycarbonyl group is an alkoxy group having from 1 to 6 carbon atoms attached through its oxygen to a carbonyl linker. "Lower alkoxycarbonyl" refers to an alkoxycarbonyl group wherein the alkyl portion of the alkoxy group is a lower alkyl group. In some embodiments, C$_1$-C$_4$ alkoxy, is an alkoxy group which encompasses both straight and branched chain alkoxy groups of from 1 to 4 carbon atoms.

The term "substituted alkoxycarbonyl" refers to the group (substituted alkyl)-O—C(O)— wherein the group is attached to the parent molecular structure through the carbonyl functionality. Unless stated otherwise specifically in the specification, the alkyl moiety of an alkoxycarbonyl group is optionally substituted by one or more substituents which independently include: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Acyl" refers to R—C(O)— groups such as (alkyl)-C(O)—, (aryl)-C(O)—, (heteroaryl)-C(O)—, (heteroalkyl)-C(O)—, and (heterocycloalkyl)-C(O)—, wherein the group is attached to the parent molecular structure through the carbonyl functionality. In some embodiments, it is a C$_1$-C$_{10}$ acyl radical which refers to the total number of chain or ring atoms of the alkyl, aryl, heteroaryl or heterocycloalkyl portion of the alkyl group plus the carbonyl carbon of acyl, i.e., a C$_4$-acyl has three other ring or chain atoms plus carbonyl. If the R radical is heteroaryl or heterocycloalkyl, the hetero ring or chain atoms contribute to the total number of chain or ring atoms. Unless stated otherwise specifically in the specification, the "R" of an acyloxy group is optionally substituted by one or more substituents which independently include: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Acyloxy" refers to a R(C=O)O— radical wherein "R" is alkyl, aryl, heteroaryl, heteroalkyl, or heterocycloalkyl, which are as described herein. In some embodiments, it is a C$_1$-C$_4$ acyloxy radical which refers to the total number of chain or ring atoms of the alkyl, aryl, heteroaryl or heterocycloalkyl portion of the acyloxy group plus the carbonyl carbon of acyl, i.e., a C$_4$-acyloxy has three other ring or chain atoms plus carbonyl. If the R radical is heteroaryl or heterocycloalkyl, the hetero ring or chain atoms contribute to the total number of chain or ring atoms. Unless stated otherwise specifically in the specification, the "R" of an acyloxy group is optionally substituted by one or more substituents which independently include: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Amino" or "amine" refers to a —N(R$^a$)$_2$ radical group, where each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, unless stated otherwise specifically in the specification. When a —N(R$^a$)$_2$ group has two R$^a$ other than hydrogen, they can be combined with the nitrogen atom to form a 4-, 5-, 6-, or 7-membered ring. For example, —N(R$^a$)$_2$ is meant to include, but not be limited to, 1-pyrrolidinyl and 4-morpholinyl. Unless stated otherwise specifically in the specification, an amino group is optionally substituted by one or more substituents which independently include: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl and each of these moieties can be optionally substituted as defined herein.

The term "substituted amino" also refers to N-oxides of the groups —N$^+$(H)(R$^a$)O$^-$, and —N$^+$(R$^a$)(R$^a$)O$^-$, R$^a$ as described above, where the N-oxide is bonded to the parent molecular structure through the N atom. N-oxides can be prepared by treatment of the corresponding amino group with, for example, hydrogen peroxide or m-chloroperoxybenzoic acid. The person skilled in the art is familiar with reaction conditions for carrying out the N-oxidation.

"Amide" or "amido" refers to a chemical moiety with formula —C(O)N(R)$_2$ or —NRC(O)R, where R is selected from hydrogen, alkyl, cycloalkyl, aryl, heteroaryl (bonded through a ring carbon) and heteroalicyclic (bonded through a ring carbon), each of which moiety can itself be optionally substituted. In some embodiments it is a $C_1$-$C_4$ amido or amide radical, which includes the amide carbonyl in the total number of carbons in the radical. The $R_2$ of —N(R)$_2$ of the amide can optionally be taken together with the nitrogen to which it is attached to form a 4-, 5-, 6-, or 7-membered ring. Unless stated otherwise specifically in the specification, an amido group is optionally substituted independently by one or more of the substituents as described herein for alkyl, cycloalkyl, aryl, heteroaryl, or heterocycloalkyl. An amide can be an amino acid or a peptide molecule attached to a compound of Formula (I), thereby forming a prodrug. Any amine, hydroxy, or carboxyl side chain on the compounds described herein can be transformed into an amide group. The procedures and specific groups to make such amides are known to those of skill in the art and can readily be found in reference sources such as Greene and Wuts, *Protective Groups in Organic Synthesis*, 3rd Ed., John Wiley & Sons, New York, N. Y., 1999, which is incorporated herein by reference in its entirety.

"Aromatic" or "aryl" refers to a radical with six to ten ring atoms (e.g., $C_6$-$C_{10}$ aromatic or $C_6$-$C_{10}$ aryl) which has at least one ring having a conjugated pi electron system which is carbocyclic (e.g., phenyl, fluorenyl, and naphthyl). Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 10" refers to each integer in the given range; e.g., "6 to 10 ring atoms" means that the aryl group can consist of 6 ring atoms, 7 ring atoms, etc., up to and including 10 ring atoms. The term includes monocyclic or fused-ring polycyclic (i.e., rings which share adjacent pairs of ring atoms) groups. Unless stated otherwise specifically in the specification, an aryl moiety can be optionally substituted by one or more substituents which are independently: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Aralkyl" or "arylalkyl" refers to an (aryl)alkyl-radical where aryl and alkyl are as disclosed herein and which are optionally substituted by one or more of the substituents described as suitable substituents for aryl and alkyl respectively. The "aralkyl/arylalkyl" is bonded to the parent molecular structure through the alkyl group.

As used herein, a "covalent bond" or "direct bond" refers to a single bond joining two groups.

"Ester" refers to a chemical radical of formula —COOR, where R is selected from alkyl, cycloalkyl, aryl, heteroaryl (bonded through a ring carbon) and heteroalicyclic (bonded through a ring carbon). Any amine, hydroxy, or carboxyl side chain on the compounds described herein can be esterified. The procedures and specific groups to make such esters are known to those of skill in the art and can readily be found in reference sources such as Greene and Wuts, *Protective Groups in Organic Synthesis*, 3rd Ed., John Wiley & Sons, New York, N. Y., 1999, which is incorporated herein by reference in its entirety. Unless stated otherwise specifically in the specification, an ester group can be optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical can be optionally substituted as defined above for an alkyl group.

"Halo", "halide", or, alternatively, "halogen" means fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

"Heteroalkyl" "heteroalkenyl" and "heteroalkynyl" include optionally substituted alkyl, alkenyl and alkynyl radicals and which have one or more skeletal chain atoms selected from an atom other than carbon, e.g., oxygen, nitrogen, sulfur, phosphorus or combinations thereof. A numerical range can be given, e.g., $C_1$-$C_4$ heteroalkyl which refers to the chain length in total, which in this example is 4 atoms long. For example, a —CH$_2$OCH$_2$CH$_3$ radical is referred to as a "$C_4$" heteroalkyl, which includes the heteroatom center in the atom chain length description. Connection to the rest of the parent molecular structure can be through either a heteroatom or a carbon in the heteroalkyl chain. A heteroalkyl group can be substituted with one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Heteroalkylaryl" refers to an -(heteroalkyl)aryl radical where heteroalkyl and aryl are as disclosed herein and which are optionally substituted by one or more of the substituents described as suitable substituents for heteroalkyl and aryl respectively. The "heteroalkylaryl" is bonded to the parent molecular structure through a carbon atom of the heteroalkyl group.

"Heteroalkylheteroaryl" refers to an -(heteroalkyl)heteroaryl radical where heteroalkyl and heteroaryl are as disclosed herein and which are optionally substituted by one or more of the substituents described as suitable substituents for heteroalkyl and heteroaryl respectively. The "heteroalkylheteroaryl" is bonded to the parent molecular structure through a carbon atom of the heteroalkyl group.

"Heteroalkylheterocycloalkyl" refers to an -(heteroalkyl)heterocycloalkyl radical where heteroalkyl and heteroaryl are as disclosed herein and which are optionally substituted by one or more of the substituents described as suitable substituents for heteroalkyl and heterocycloalkyl respectively. The "heteroalkylheterocycloalkyl" is bonded to the parent molecular structure through a carbon atom of the heteroalkyl group.

"Heteroalkylcycloalkyl" refers to an -(heteroalkyl)cycloalkyl radical where heteroalkyl and cycloalkyl are as disclosed herein and which are optionally substituted by one or more of the substituents described as suitable substituents for heteroalkyl and cycloalkyl respectively. The "heteroalkylcycloalkyl" is bonded to the parent molecular structure through a carbon atom of the heteroalkyl group.

"Heteroaryl" or, alternatively, "heteroaromatic" refers to a 5- to 18-membered aromatic radical (e.g., $C_5$-$C_{13}$ heteroaryl) that includes one or more ring heteroatoms selected from nitrogen, oxygen and sulfur, and which can be a monocyclic, bicyclic, tricyclic or tetracyclic ring system. Whenever it appears herein, a numerical range such as "5 to 18" refers to each integer in the given range; e.g., "5 to 18 ring atoms" means that the heteroaryl group can consist of 5 ring atoms, 6 ring atoms, etc., up to and including 18 ring atoms. Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. An N-containing "heteroaromatic" or "heteroaryl" moiety refers to an aromatic group in which at least one of the skeletal atoms of the ring is a nitrogen atom. The polycyclic heteroaryl group can be fused or non-fused. The heteroatom(s) in the heteroaryl radical is optionally oxidized. One or more nitrogen atoms, if present, are optionally quaternized. The heteroaryl is attached to the parent molecular structure through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl(benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pridinyl, and thiophenyl (i.e., thienyl). Unless stated otherwise specifically in the specification, a heteroaryl moiety is optionally substituted by one or more substituents which are independently: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —$OR^a$, $SR^a$, —$OC(O)$—$R^a$, —$N(R^a)_2$, —$C(O)R^a$, —$C(O)OR^a$, —$C(O)N(R^a)_2$, —$N(R^a)C(O)OR^a$, —$N(R^a)C(O)R^a$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

Substituted heteroaryl also includes ring systems substituted with one or more oxide (—O—) substituents, such as pyridinyl N-oxides.

"Heterocyclyl" refers to any 3- to 18-membered aromatic radical monocyclic or polycyclic moiety comprising at least one heteroatom selected from nitrogen, oxygen and sulfur. As used herein, heterocyclyl moieties can be aromatic or nonaromatic. A heterocyclyl group can be a monocyclic, bicyclic, tricyclic or tetracyclic ring system. Whenever it appears herein, a numerical range such as "3 to 18" refers to each integer in the given range; e.g., "5 to 18 ring atoms" means that the heterocyclyl group can consist of 5 ring atoms, 6 ring atoms, etc., up to and including 18 ring atoms. Bivalent radicals derived from univalent heterocyclyl radicals whose names end in "-yl" by removal of one hydrogen atom from the atom with the free valence are named by adding "-idene" to the name of the corresponding univalent radical, e.g., a piperidine group with two points of attachment is a piperidylidene. An N-containing heterocyclyl moiety refers to an non-aromatic group in which at least one of the skeletal atoms of the ring is a nitrogen atom. The polycyclic heterocyclyl group can be fused or non-fused. The heteroatom(s) in the heterocyclyl radical is optionally oxidized. One or more nitrogen atoms, if present, are optionally quaternized. The heteroaryl is attached to the parent molecular structure through any atom of the ring(s). Unless stated otherwise, heterocyclyl moieties are optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —$OR^a$, —$SR^a$, —$OC(O)$—$R^a$, —$N(R^a)_2$, —$C(O)R^a$, —$C(O)OR^a$, —$C(O)N(R^a)_2$, —$N(R^a)C(O)OR^a$, —$N(R^a)C(O)R^a$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heteroaryl or heteroarylalkyl.

"Heteroarylalkyl" refers to an -(heteroaryl)alkyl radical where heteroaryl and alkyl are as disclosed herein and which are optionally substituted by one or more of the substituents described as suitable substituents for heteroaryl and alkyl respectively. The "heteroarylalkyl" is bonded to the parent molecular structure through any atom atom of the heteroaryl group.

"Heterocycloalkyl" refers to a stable 3- to 18-membered non-aromatic ring radical that comprises two to twelve carbon atoms and from one to six heteroatoms selected from nitrogen, oxygen and sulfur. Whenever it appears herein, a numerical range such as "3 to 18" refers to each integer in the given range; e.g., "3 to 18 ring atoms" means that the heterocycloalkyl group can consist of 3 ring atoms, 4 ring atoms, etc., up to and including 18 ring atoms. In some embodiments, it is a $C_5$-$C_{10}$ heterocycloalkyl. In some embodiments, it is a $C_4$-$C_{10}$ heterocycloalkyl. In some embodiments, it is a $C_3$-$C_{10}$ heterocycloalkyl. Unless stated otherwise specifically in the specification, the heterocycloalkyl radical is a monocyclic, bicyclic, tricyclic or tetracyclic ring system, which can include fused or bridged ring systems. The heteroatoms in the heterocycloalkyl radical can be optionally oxidized. One or more nitrogen atoms, if present, are optionally quaternized. The heterocycloalkyl radical is partially or fully saturated. The heterocycloalkyl can be attached to the parent molecular group through any atom of the ring(s). Examples of such heterocycloalkyl radicals include, but are not limited to, dioxolanyl, thienyl [1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocycloalkyl moiety is optionally substituted by one or more substituents which independently include: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —$OR^a$, —$SR^a$, —OC(O)—$R^a$, —$N(R^a)_2$, —C(O)$R^a$, —C(O)O$R^a$, —C(O)N($R^a$)$_2$, —N($R^a$)C(O)O$R^a$, —N($R^a$)C(O)$R^a$, —N($R^a$)S(O)$_t R^a$ (where t is 1 or 2), —S(O)$_t$O$R^a$ (where t is 1 or 2), —S(O)$_t$N($R^a$)$_2$ (where t is 1 or 2), or PO$_3$($R^a$)$_2$, where each $R^a$ is independently hydrogen, alkyl, fluoroalkyl, carbocyclyl, carbocyclylalkyl, aryl, aralkyl, heterocycloalkyl, heteroaryl or heteroarylalkyl.

"Heterocycloalkyl" also includes bicyclic ring systems wherein one non-aromatic ring, such as a ring having 3 to 7 ring atoms, contains at least 2 carbon atoms in addition to 1-3 heteroatoms independently selected from oxygen, sulfur, and nitrogen, as well as combinations comprising at least one of the foregoing heteroatoms; and the other ring, usually having 3 to 7 ring atoms, optionally contains 1-3 heteroatoms independently selected from oxygen, sulfur, and nitrogen and is not aromatic.

"Moiety" refers to a specific segment or functional group of a molecule. Chemical moieties are often recognized chemical entities embedded in or appended to a molecule.

"Nitro" refers to the —$NO_2$ radical.

"Oxa" refers to the —O— radical.

"Oxo" refers to the =O radical.

A "leaving group or atom" is any group or atom that will, under the reaction conditions, cleave from the starting material, thus promoting reaction at a specified site. Suitable non-limiting examples of such groups unless otherwise specified include halogen atoms, mesyloxy, p-nitrobenzensulphonyloxy and tosyloxy groups.

"Protecting group" has the meaning conventionally associated with it in organic synthesis, i.e., a group that selectively blocks one or more reactive sites in a multifunctional compound such that a chemical reaction can be carried out selectively on another unprotected reactive site and such that the group can readily be removed after the selective reaction is complete. A variety of protecting groups are disclosed, for example, in T. H. Greene and P. G. M. Wuts, *Protective Groups in Organic Synthesis*, Third Edition, John Wiley & Sons, New York (1999). For example, a hydroxy protected form is where at least one of the hydroxy groups present in a compound is protected with a hydroxy protecting group. Likewise, amines and other reactive groups can similarly be protected.

"Substituted" means that the referenced group can be substituted with one or more additional group(s) individually and independently selected from acyl, alkyl, alkylaryl, cycloalkyl, aralkyl, aryl, carbohydrate, carbonate, heteroaryl, heterocycloalkyl, hydroxy, alkoxy, aryloxy, mercapto, alkylthio, arylthio, cyano, halo, carbonyl, ester, thiocarbonyl, isocyanato, thiocyanato, isothiocyanato, nitro, oxo, perhaloalkyl, perfluoroalkyl, phosphate, silyl, sulfonyl, sulfonyl, sulfonamidyl, sulfoxyl, sulfonate, urea, and amino, including mono- and di-substituted amino groups, and the protected derivatives thereof. Di-substituted amino groups encompass those which form a ring together with the nitrogen of the amino group, such as for instance, morpholino. The substituents themselves can be substituted, for example, a cycloalkyl substituent can have a halide substituted at one or more ring carbons, and the like. The protecting groups that can form the protective derivatives of the above substituents are known to those of skill in the art and can be found in references such as Greene and Wuts, above.

"Sulfanyl" refers to the groups: —S— (optionally substituted alkyl), —S— (optionally substituted aryl), —S— (optionally substituted heteroaryl), and —S— (optionally substituted heterocycloalkyl).

"Sulfinyl" refers to the groups: —S(O)—H, —S(O)— (optionally substituted alkyl), —S(O)— (optionally substituted amino), —S(O)— (optionally substituted aryl), —S(O)— (optionally substituted heteroaryl), and —S(O)— (optionally substituted heterocycloalkyl).

"Sulfonyl" refers to the groups: —S(O$_2$)—H, —S(O$_2$)— (optionally substituted alkyl), —S(O$_2$)— (optionally substituted amino), —S(O$_2$)— (optionally substituted aryl), —S(O$_2$)— (optionally substituted heteroaryl), and —S(O$_2$)— (optionally substituted heterocycloalkyl).

"Sulfonamidyl" or "sulfonamido" refers to a —S(=O)$_2$—NRR or —N(R)—S(=O)$_2$— radical, where each R is selected independently from hydrogen, alkyl, cycloalkyl, aryl, heteroaryl (bonded through a ring carbon) and heterocycloalkyl (bonded through a ring carbon). The R groups in —NRR of the —S(=O)$_2$—NRR radical can be taken together with the nitrogen to which it is attached to form a 4-, 5-, 6-, or 7-membered ring. In some embodiments, it is a $C_1$-$C_{10}$ sulfonamido, wherein each R in sulfonamido contains 1 carbon, 2 carbons, 3 carbons, or 4 carbons total. A sulfonamido group is optionally substituted by one or more of the substituents described for alkyl, cycloalkyl, aryl, and heteroaryl respectively "Sulfoxyl" refers to a —S(=O)$_2$OH radical.

"Sulfonate" refers to a —S(=O)$_2$—OR radical, where R is selected from alkyl, cycloalkyl, aryl, heteroaryl (bonded through a ring carbon) and heteroalicyclic (bonded through a ring carbon). A sulfonate group is optionally substituted on R by one or more of the substituents described for alkyl, cycloalkyl, aryl, and heteroaryl respectively.

Where substituent groups are specified by their conventional chemical formulae, written from left to right, they equally encompass the chemically identical substituents that would result from writing the structure from right to left, e.g., —CH$_2$O— is equivalent to —OCH$_2$—.

In one aspect, provided herein is a compound of Formula I:

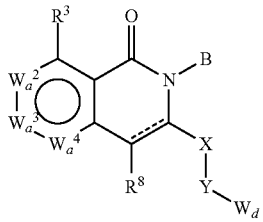

Formula I or pharmaceutically acceptable forms thereof, wherein, $W_a^2$ is CR$^5$ or N; $W_a^3$ is CR$^6$ or N; $W_a^4$ is CR$^7$ or N; wherein no more than two adjacent ring atoms selected from $W_a^2$, $W_a^3$, and $W_a^4$ are heteroatoms;

B is hydrogen, alkyl, amino, heteroalkyl, or a moiety of formula II:

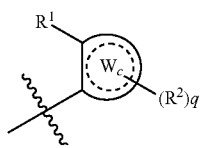

Formula II wherein $W_c$ is aryl, heteroaryl, heterocycloalkyl, or cycloalkyl, and q is an integer of 0, 1, 2, 3, or 4;

X is absent or —(CH(R$^9$))$_z$—, and z is an integer of 1, 2, 3, or 4;

Y is absent, —O—, —S—, —S(=O)—, —S(=O)$_2$, —C(=O)—, —C(=O)(CHR$^9$)$_z$—, —N(R$^9$)—, N(R$^9$)—C(=O)—, —N(R$^9$)—C(=O)NH—, or —N(R$^9$)C(R$^9$)$_2$—, and z is an integer of 1, 2, 3, or 4;

R$^1$ is hydrogen, alkyl, alkenyl, alkynyl, alkoxy, amido, alkoxycarbonyl, sulfonamido, halo, cyano, or nitro; each R$^2$ is independently alkyl, alkenyl, alkynyl, cycloalkyl, heterocycloalkyl, aryl, heteroaryl, arylalkyl, heteroarylalkyl, alkoxy, amido, amino, acyl, acyloxy, alkoxycarbonyl, sulfonamido, halo, cyano, hydroxy, nitro, phosphate, urea, or carbonate;

R$^3$ is cycloalkyl, cycloalkylalkyl, aryl, heteroaryl, heterocyclyl, aralkyl, heteroaralkyl, heterocyclylalkyl, alkenyl, or alkynyl, or R$^3$ is a heteroatom selected from N, S, and O, wherein the heteroatom has a covalent bond either directly or through a C$_1$-C$_6$ alkyl group to an aryl, heteroaryl or heterocyclyl, or R$^3$ and R$^5$ are taken together with the carbons to which they are attached form a 5- or 6-membered ring; wherein each of the above substituents can be substituted with 0, 1, 2, or 3 R$^{13}$;

R$^5$, R$^6$, R$^7$, and R$^8$ are independently hydrogen, halo, cyano, alkyl or amino;

each R$^9$ is independently hydrogen, alkyl, or heterocycloalkyl;

$W_d$ is

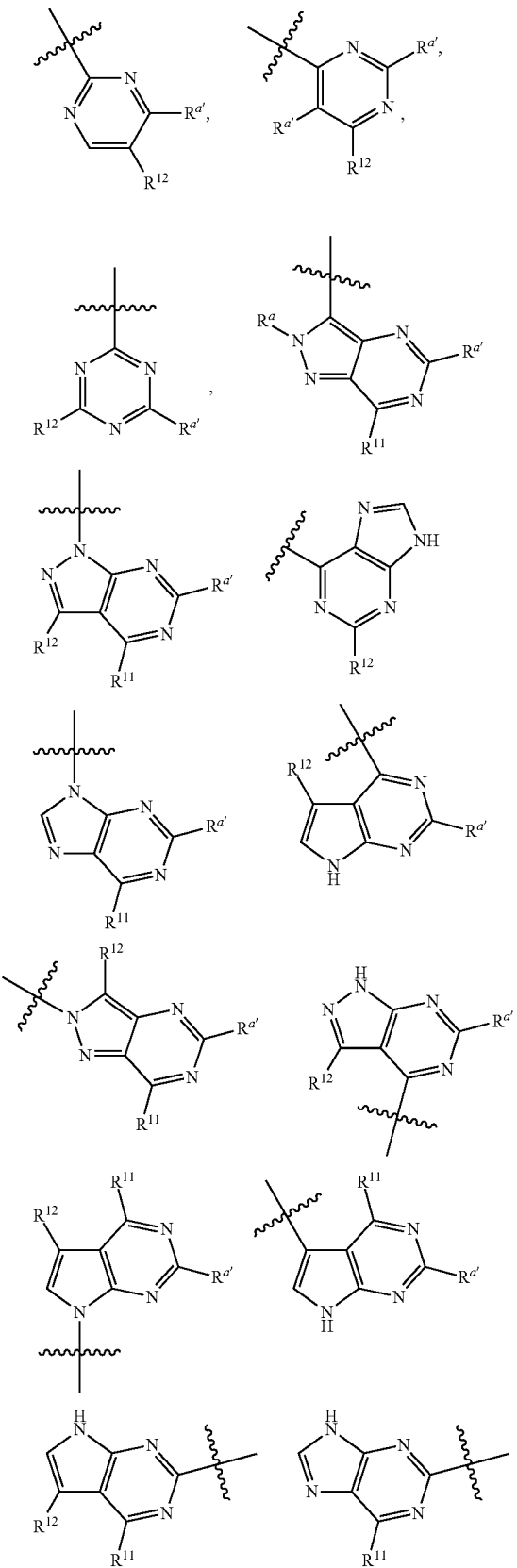

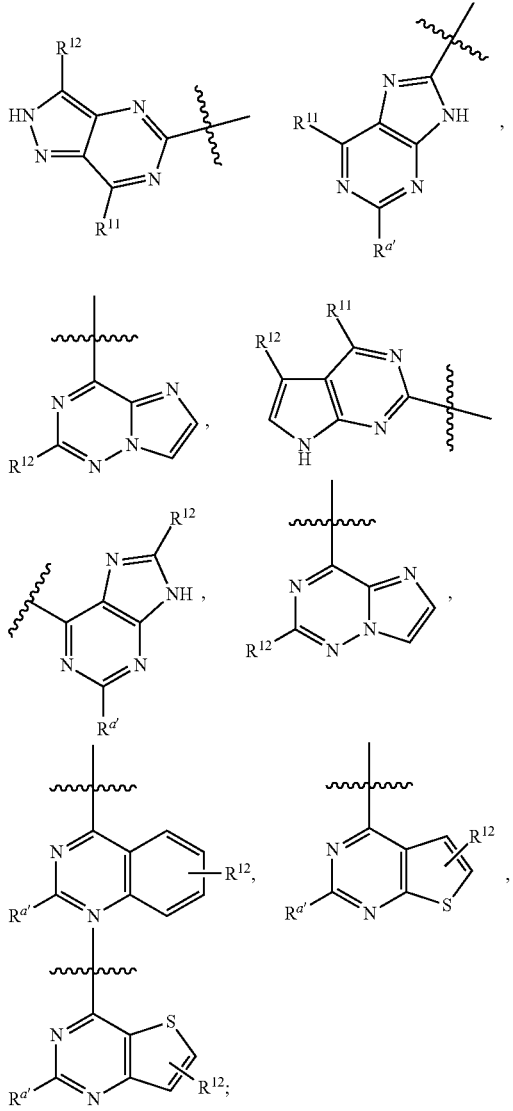

R[11] is hydrogen, alkyl, halo, amino, amido, hydroxy, alkoxy, phosphate, urea, or carbonate;

R[12] is hydrogen, alkyl, haloalkyl, alkynyl, alkenyl, halo, —C(O)NH$_2$, aryl, heteroaryl, nonaromatic heterocyclyl, or cycloalkyl, R[a'] is hydrogen, alkyl, —NH$_2$, cyano, or halogen; and each R[13] is independently hydrogen, $C_1$-$C_6$ alkyl, $C_1$-$C_6$ alkoxy, or halogen.

In some embodiments, $W_a^2$ is CR[5] or N; $W_a^3$ is CR[6] or N; $W_a^4$ is CR[7] or N wherein no more than two adjacent ring atoms selected from $W_a^2$, $W_a^3$, and $W_a^4$ are heteroatoms; B is hydrogen, alkyl, amino, heteroalkyl, or a moiety of the following formula:

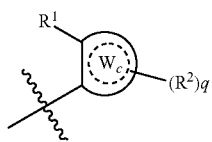

wherein $W_c$ is aryl, heteroaryl, heterocycloalkyl, or cycloalkyl, and q is an integer of 0, 1, 2, 3, or 4; X is absent or —(CH(R[9]))$_z$—, and z is an integer of 1, 2, 3, or 4; and Y is absent, —O—, —S—, —S(=O)—, —S(=O)$_2$, —C(=O)—, —C(=O)(CHR[9])—, —N(R[9])—, N(R[9])—C(=O)—, —N(R[9])—C(=O)NH—, or —N(R[9])C(R[9])$_2$, and z is an integer of 1, 2, 3, or 4. In some embodiments, R[1] is hydrogen, alkyl, alkenyl, alkynyl, alkoxy, amido, alkoxycarbonyl, sulfonamido, halo, cyano, or nitro; each R[2] is independently alkyl, alkenyl, alkynyl, cycloalkyl, heterocycloalkyl, aryl, heteroaryl, arylalkyl, heteroarylalkyl, alkoxy, amido, amino, acyl, acyloxy, alkoxycarbonyl, sulfonamido, halo, cyano, hydroxy, nitro, phosphate, urea, or carbonate; and R[3] is cycloalkyl, cycloalkylalkyl, aryl, heteroaryl, heterocyclyl, aralkyl, heteroaralkyl, heterocyclylalkyl, alkenyl, or alkynyl, or R[3] is a heteroatom selected from N, S, and O, wherein the heteroatom has a covalent bond either directly or through a $C_1$-$C_6$ alkyl group to an aryl, heteroaryl or heterocyclyl, or R[3] and R[5] are taken together with the carbons to which they are attached form a 5- or 6-membered ring; wherein each of the above substituents can be substituted with 0, 1, 2, or 3 R[13]. In some embodiments, R[5], R[6], R[7], and R[8] are independently hydrogen, halo, cyano, alkyl or amino; and each R[9] is independently hydrogen, alkyl, or heterocycloalkyl;

$W_d$ is

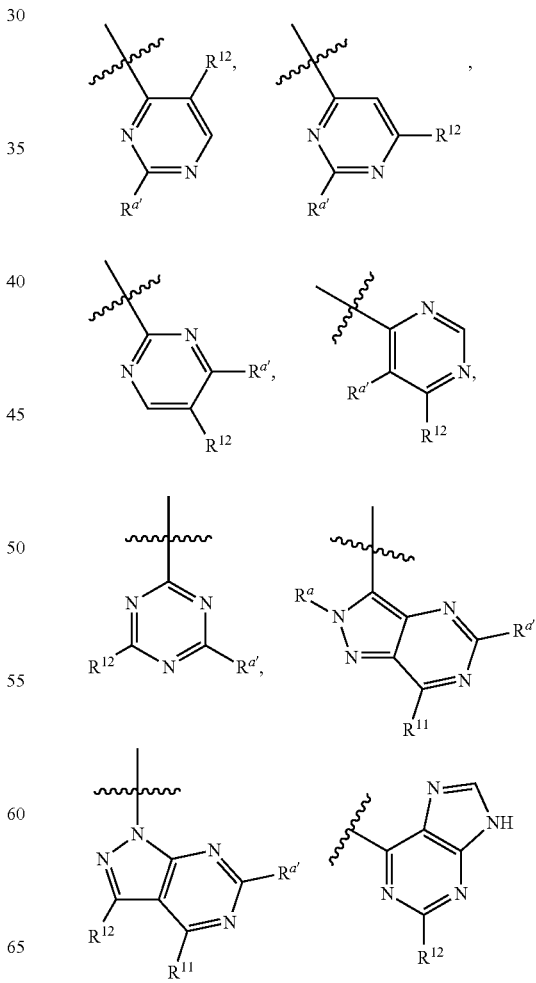

-continued

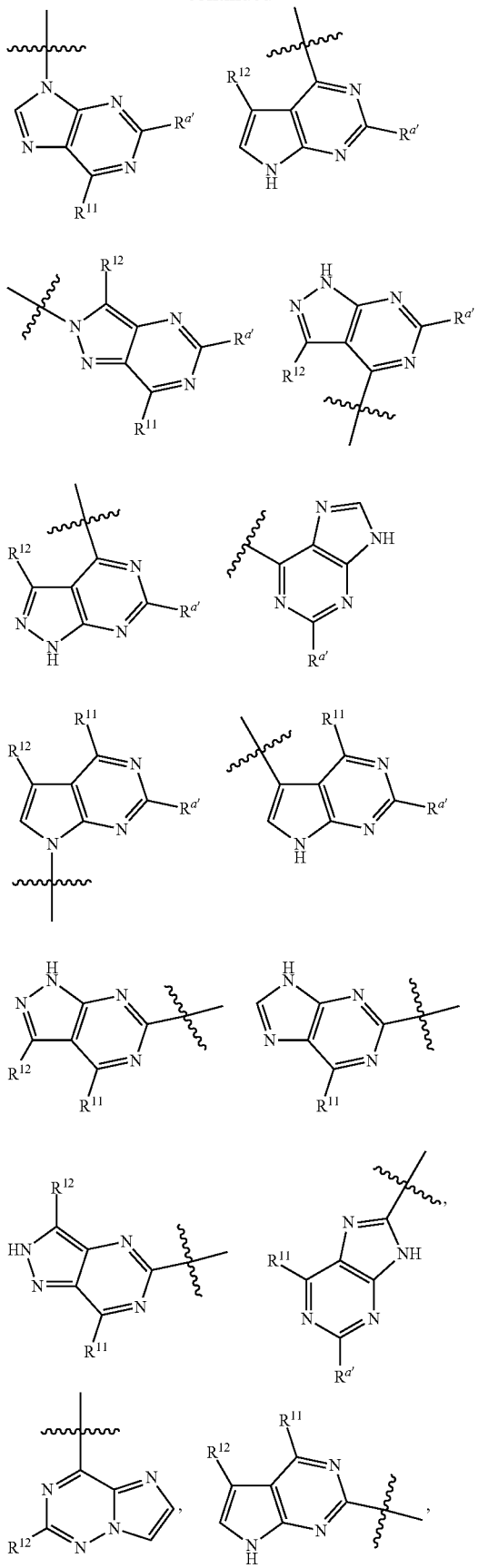

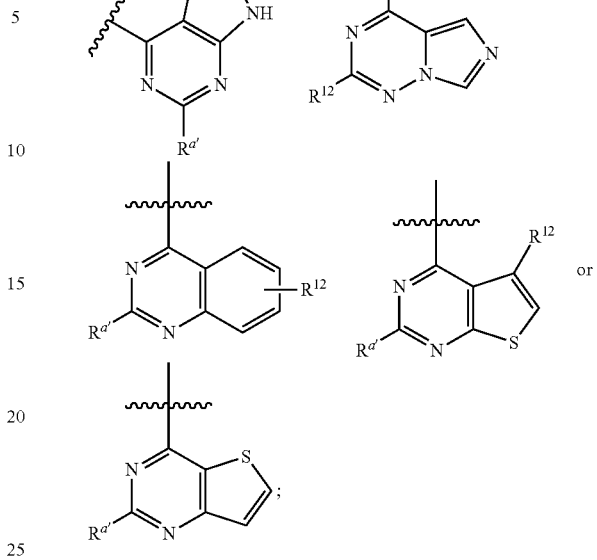

R[11] is hydrogen, alkyl, halo, amino, amido, hydroxy, alkoxy, phosphate, urea, or carbonate; R[12] is hydrogen, alkyl, haloalkyl, alkynyl, alkenyl, halo, —C(O)NH$_2$, aryl, heteroaryl, nonaromatic heterocyclyl, or cycloalkyl; R[a'] is hydrogen, alkyl, —NH$_2$, cyano, or halogen; and each R[13] is independently hydrogen, $C_1$-$C_6$ alkyl, $C_1$-$C_6$ alkoxy, or halogen.

In another aspect, provided herein are compounds of Formula Ib:

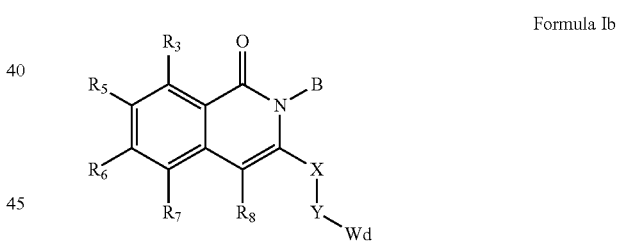

Formula Ib or pharmaceutically acceptable forms thereof, wherein
B is hydrogen, alkyl, amino, heteroalkyl, or a moiety of Formula II:

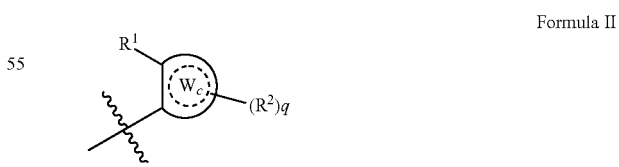

Formula II wherein $W_c$ is aryl, heteroaryl, heterocycloalkyl, or cycloalkyl;
q is an integer of 0, 1, 2, 3, or 4;
X is absent or —(CH($R^9$))$_z$—, and z is an integer of 1, 2, 3, or 4;
Y is absent, —O—, —S—, —S(=O)—, —S(=O)$_2$, —C(=O)—, —C(=O)(CHR$^9$)$_z$—, —N(R$^9$)—, N(R$^9$)—

C(=O)—, —N(R⁹)—C(=O)NH—, or —N(R⁹)C(R⁹)₂—, and z is an integer of 1, 2, 3, or 4;

R¹ is hydrogen, alkyl, alkenyl, alkynyl, alkoxy, amido, alkoxycarbonyl, sulfonamido, halo, cyano, or nitro;

each R² is independently alkyl, alkenyl, alkynyl, cycloalkyl, heterocycloalkyl, aryl, heteroaryl, arylalkyl, heteroarylalkyl, alkoxy, amido, amino, acyl, acyloxy, alkoxycarbonyl, sulfonamido, halo, cyano, hydroxy, nitro, phosphate, urea, or carbonate;

R³ is cycloalkyl, cycloalkylalkyl, aryl, heteroaryl, heterocyclyl, aralkyl, heteroaralkyl, heterocyclylalkyl, alkenyl, or alkynyl, or R³ is a heteroatom selected from N, S, and O, wherein the heteroatom has a covalent bond either directly or through a C₁-C₆ alkyl group to an aryl, heteroaryl or heterocyclyl, or R³ and R⁵ are taken together with the carbons to which they are attached form a 5- or 6-membered ring; wherein each of the above substituents can be substituted with 0, 1, 2, or 3 R¹³;

R⁵, R⁶, R⁷, and R⁸ are independently hydrogen, halo, cyano, alkyl or amino;

each R⁹ is independently hydrogen, alkyl, or heterocycloalkyl;

W_d is

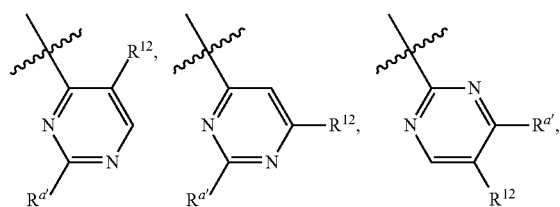

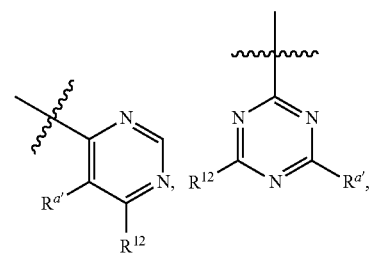

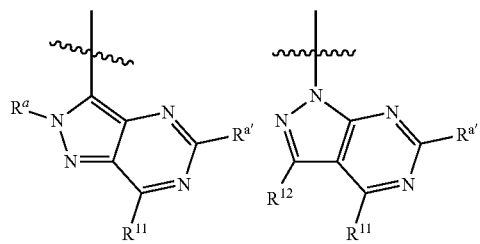

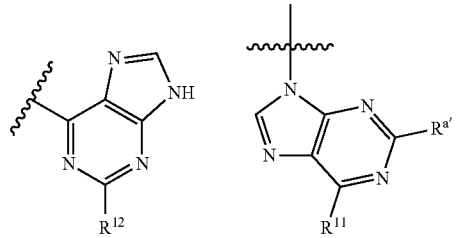

-continued

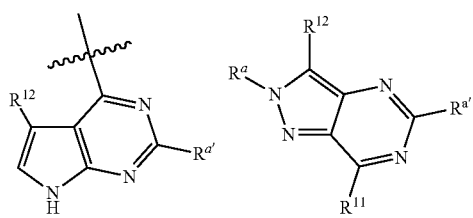

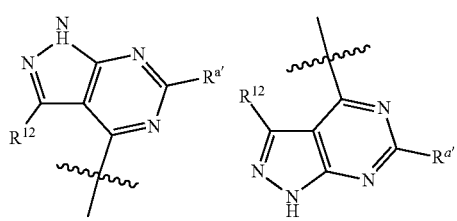

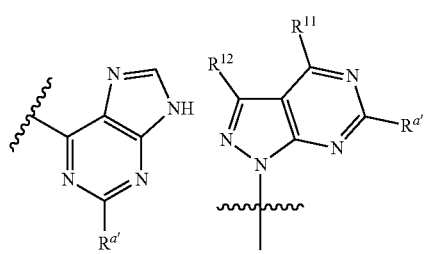

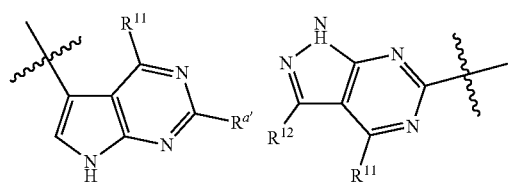

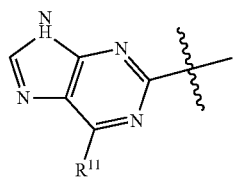

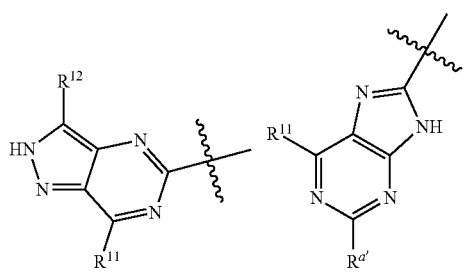

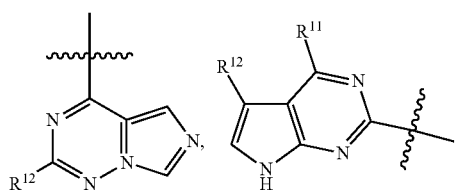

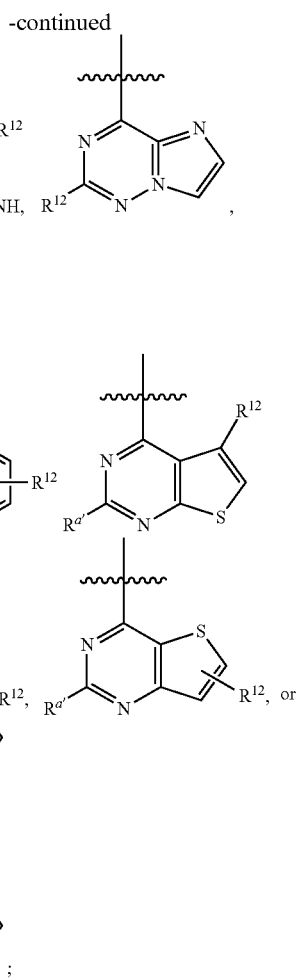

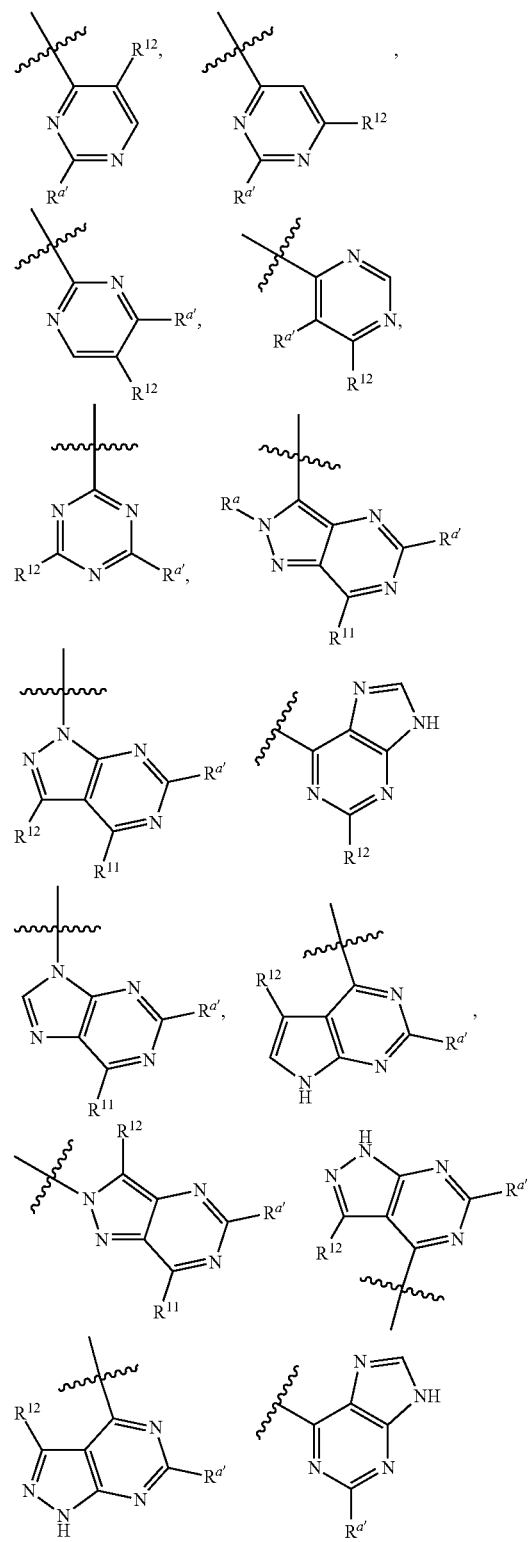

R[11] is hydrogen, alkyl, halo, amino, amido, hydroxy, alkoxy, phosphate, urea, or carbonate;

R[12] is hydrogen, alkyl, haloalkyl, alkynyl, alkenyl, halo, —C(O)NH$_2$, aryl, heteroaryl, nonaromatic heterocyclyl, or cycloalkyl, R[a'] is hydrogen, alkyl, —NH$_2$, cyano or halogen; and each R[13] is independently hydrogen, C$_1$-C$_6$ alkyl, C$_1$-C$_6$ alkoxy or halogen.

In some embodiments of Formula II, W$_c$ is aryl, heteroaryl, heterocycloalkyl, or cycloalkyl; q is an integer of 0, 1, 2, 3, or 4; X is absent or —(CH(R$^9$))$_z$—, and z is an integer of 1, 2, 3, or 4; Y is absent, —O—, —S—, —S(=O)—, —S(=O)$_2$—, —C(=O)—, —C(=O)(CHR$^9$)$_z$—, —N(R$^9$)—, N(R$^9$)—C(=O)—, —N(R$^9$)—C(=O)NH—, or —N(R$^9$)C(R$^9$)$_2$—, and z is an integer of 1, 2, 3, or 4. In some embodiments, R[1] is hydrogen, alkyl, alkenyl, alkynyl, alkoxy, amido, alkoxycarbonyl, sulfonamido, halo, cyano, or nitro; each R[2] is independently alkyl, alkenyl, alkynyl, cycloalkyl, heterocycloalkyl, aryl, heteroaryl, arylalkyl, heteroarylalkyl, alkoxy, amido, amino, acyl, acyloxy alkoxycarbonyl, sulfonamido, halo, cyano, hydroxy, nitro, phosphate, urea, or carbonate; R[3] is cycloalkyl, cycloalkylalkyl, aryl, heteroaryl, heterocyclyl, aralkyl, heteroaralkyl, heterocyclylalkyl, alkenyl, or alkynyl, or R[3] is a heteroatom selected from N, S, and O, wherein the heteroatom has a covalent bond either directly or through a C$_1$-C$_6$ alkyl group to an aryl, heteroaryl or heterocyclyl or R[3] and R[5] are taken together with the carbons to which they are attached form a 5- or 6-membered ring; wherein each of the above substituents can be substituted with 0, 1, 2, or 3 R[13]; R[5], R[6], R[7], and R[8] are independently hydrogen, halo, cyano, alkyl or amino; and each R[9] is independently hydrogen, alkyl, or heterocycloalkyl.

In some embodiments, W$_d$ is

-continued

[chemical structures]

$R^{11}$ is hydrogen, alkyl, halo, amino, amido, hydroxy, alkoxy, phosphate, urea, or carbonate; $R^{12}$ is H, alkyl, alkynyl, alkenyl, halo, aryl, heteroaryl, nonaromatic heterocyclyl, or cycloalkyl; $R^{a'}$ is hydrogen, alkyl, —$NH_2$, cyano or halogen; and each $R^{13}$ is independently hydrogen, $C_1$-$C_6$ alkyl, $C_1$-$C_6$ alkoxy or halogen.

In certain embodiments, $R^3$ is selected from a 5-membered heteroaryl; a 5-membered nonaromatic heterocycle; a 6-membered aryl; a 6-membered heteroaryl; a 6-membered nonaromatic heterocycle; a fused 5/6-bicyclic heteroaryl; a fused 5/6-bicyclic nonaromatic heterocycle; a $C_1$-$C_6$ alkyl group substituted with a 5-membered heteroaryl, a 5-membered nonaromatic heterocycle, a 6-membered aryl or heteroaryl, a 6-membered nonaromatic heterocycle, a fused 5/6-bicyclic heteroaryl, or a fused 5/6-bicyclic nonaromatic heterocycle. In some embodiments, $R^3$ is a heteroatom selected from N, S, and O, wherein the heteroatom has a covalent bond either directly or through a $C_1$-$C_6$ alkyl group to a 5-membered heteroaryl, a 5-membered nonaromatic heterocycle, a 6-membered aryl or heteroaryl, a 6-membered nonaromatic heterocycle, a fused 5/6-bicyclic heteroaryl, or a fused 5/6-bicyclic nonaromatic heterocycle. In some embodiments, $R^3$ is a $C_1$-$C_6$ alkyl group substituted with a fused polycyclic group, wherein the polycyclic group has greater than two rings and is carbocyclic or heterocyclic; $C_1$-$C_6$ alkyl group substituted with a bridged cycloalkyl or bridged heterocyclic group. In some embodiments, $R^3$ is a $C_1$-$C_6$ alkyl group substituted with a spirocyclic cycloalkyl or spirocyclic heterocyclic group. In some embodiments, $R^3$ is a branched $C_4$-$C_{12}$ alkyl group, wherein said branched alkyl group contains at least one terminal t-butyl group. In compounds of Formula I-B, $W_a^2$ is $CR^5$ or N; $W_a^3$ is $CR^6$ or N; $W_a^4$ is $CR^7$ or N wherein no more than two adjacent ring atoms selected from $W_a^2$, $W_a^3$, and $W_a^4$ are heteroatoms; and B is hydrogen, alkyl, amino, heteroalkyl, cycloalkyl, heterocycloalkyl, or a moiety of Formula II:

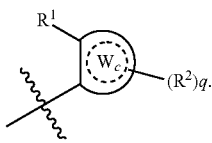

Formula II

In some embodiments of the compounds of Formula II, $W_c$ is aryl, heteroaryl, heterocycloalkyl, or cycloalkyl, and q is an integer of 0, 1, 2, 3, or 4. In some embodiments, X is absent or is —$(CH(R^9))_z$—, and each instance of z is independently an integer of 1, 2, 3, or 4. In some embodiments, Y is absent, —O—, —S—, —S(=O)—, —S(=O)$_2$—, —N($R^9$)—, —C(=O)—(CHR$^9$)$_z$—, —C(=O)—, —N($R^9$)—C(=O)—, or —N($R^9$)—C(=O)NH—, —N($R^9$)C($R^9$)$_2$—, or —C(=O)—(CHR$^9$)$_z$—; wherein when $W_b^5$ is N, no more than one of X or Y is absent. In some embodiments, $R^1$ is hydrogen, alkyl, heteroalkyl, alkenyl, alkynyl, cycloalkyl, heterocycloalkyl, aryl, arylalkyl, heteroaryl, heteroarylalkyl, alkoxy, amido, amino, acyl, acyloxy, alkoxycarbonyl, sulfonamido, halo, cyano, hydroxy, nitro, phosphate, urea, or carbonate. In some embodiments, each $R^2$ is independently alkyl, heteroalkyl, alkenyl, alkynyl, cycloalkyl, heterocycloalkyl, aryl, arylalkyl, heteroaryl, heteroarylalkyl, alkoxy, amido, amino, acyl, acyloxy, alkoxycarbonyl, sulfonamido, halo, cyano, hydroxy, nitro, phosphate, urea, or carbonate. In some embodiments, $R^3$ is cycloalkyl, cycloalkylalkyl, aryl, heteroaryl, heterocyclyl, aralkyl, heteroaralkyl, heterocyclylalkyl, alkenyl, or alkynyl, or $R^3$ is a heteroatom selected from N, S, and O, wherein the heteroatom has a covalent bond either directly or through a $C_1$-$C_6$ alkyl group to an aryl, heteroaryl or heterocyclyl or $R^3$ and $R^5$ are taken together with the carbons to which they are attached form a 5- or 6-membered ring; wherein each of the above substituents can be substituted with 0, 1, 2, or 3 $R^{13}$. In certain embodiments, $R^3$ is selected from a 5-membered heteroaryl; a 5-membered nonaromatic heterocycle; a 6-membered aryl; a 6-membered heteroaryl; a 6-membered nonaromatic heterocycle; a fused 5/6-bicyclic heteroaryl; a fused 5/6-bicyclic nonaromatic heterocycle; a $C_1$-$C_6$ alkyl group substituted with a 5-membered heteroaryl, a 5-membered nonaromatic heterocycle, a 6-membered aryl or heteroaryl, a 6-membered nonaromatic heterocycle, a fused 5/6-bicyclic heteroaryl, or a fused 5/6-bicyclic nonaromatic heterocycle. In some embodiments, $R^3$ is a heteroatom selected from N, S, and O, wherein the heteroatom has a covalent bond either directly or through a $C_1$-$C_6$ alkyl group to a 5-membered heteroaryl, a 5-membered nonaromatic heterocycle, a 6-membered aryl or heteroaryl, a 6-membered nonaromatic heterocycle, a fused 5/6-bicyclic heteroaryl, or a fused 5/6-bicyclic nonaromatic heterocycle. In some embodiments, $R^3$ is a $C_1$-$C_6$ alkyl group substituted with a fused polycyclic group, wherein the polycyclic group has greater than two rings and is carbocyclic or heterocyclic; $C_1$-$C_6$ alkyl group substituted with a bridged cycloalkyl or bridged heterocyclic group. In some embodiments, $R^3$ is a $C_1$-$C_6$ alkyl group substituted with a spirocyclic cycloalkyl or spirocyclic heterocyclic group. In some embodiments, $R^3$ is a branched $C_4$-$C_{12}$ alkyl group, wherein said branched alkyl group contains at least one terminal t-butyl group.

In another aspect, provided herein are compounds of Formula I-C:

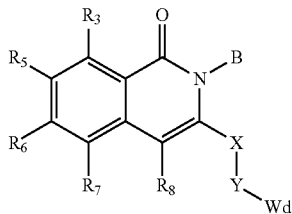

Formula IC or pharmaceutically acceptable forms thereof, wherein
B is alkyl, amino, heteroalkyl, cycloalkyl, heterocycloalkyl, or a moiety of Formula II:

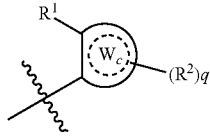

Formula II

In some embodiments of Formula II, $W_c$ is aryl, heteroaryl, heterocycloalkyl, or cycloalkyl, and q is an integer of 0, 1, 2, 3, or 4; X is absent or —(CH($R^9$))$_z$—, and z is an integer of 1, 2, 3, or 4; Y is absent, —O—, —S—, —S(=O)—, —S(=O)$_2$, —C(=O)—, —C(=O)(CHR$^9$)$_z$—, —N(R$^9$)—, N(R$^9$)—C(=O)—, —N(R$^9$)—C(=O)NH—, or —N(R$^9$)C(R$^9$)$_2$—, and z is an integer of 1, 2, 3, or 4. In some embodiments, $R^1$ is hydrogen, alkyl, alkenyl, alkynyl, alkoxy, amido, alkoxycarbonyl, sulfonamido, halo, cyano, or nitro; each $R^2$ is independently alkyl, alkenyl, alkynyl, cycloalkyl, heterocycloalkyl, aryl, heteroaryl, arylalkyl, heteroarylalkyl, alkoxy, amido, amino, acyl, acyloxy, alkoxycarbonyl, sulfonamido, halo, cyano, hydroxy, nitro, phosphate, urea, or carbonate; $R^3$ is alkyl, alkenyl, or alkynyl; 5-membered heteroaryl; a 5-membered nonaromatic heterocycle; a 6-membered aryl; a 6-membered heteroaryl; a 6-membered nonaromatic heterocycle; a fused 5/6-bicyclic heteroaryl; a fused 5/6-bicyclic nonaromatic heterocycle; a $C_1$-$C_6$ alkyl group substituted with a 5-membered heteroaryl, a 5-membered nonaromatic heterocycle, a 6-membered aryl or heteroaryl, a 6-membered nonaromatic heterocycle, a fused 5/6-bicyclic heteroaryl, or a fused 5/6-bicyclic nonaromatic heterocycle. In some embodiments, $R^3$ is a heteroatom selected from N, S, and O, wherein the heteroatom has a covalent bond either directly or through a $C_1$-$C_6$ alkyl group to a 5-membered heteroaryl, a 5-membered nonaromatic heterocycle, a 6-membered aryl or heteroaryl, a 6-membered nonaromatic heterocycle, a fused 5/6-bicyclic heteroaryl, or a fused 5/6-bicyclic nonaromatic heterocycle. In some embodiments, $R^3$ is a $C_1$-$C_6$ alkyl group substituted with a fused polycyclic group, wherein the polycyclic group has greater than two rings and is carbocyclic or heterocyclic; $C_1$-$C_6$ alkyl group substituted with a bridged cycloalkyl or bridged heterocyclic group. In some embodiments, $R^3$ is a $C_1$-$C_6$ alkyl group substituted with a spirocyclic cycloalkyl or spirocyclic heterocyclic group. In some embodiments, $R^3$ is a branched $C_4$-$C_{12}$ alkyl group, wherein said branched alkyl group contains at least one terminal t-butyl group; $R^5$, $R^6$, $R^7$, and $R^8$ are independently hydrogen, halo, cyano, alkyl or amino group; and each $R^9$ is independently hydrogen, alkyl, or heterocycloalkyl. In some embodiments, $R^{11}$ is hydrogen, alkyl, halo, amino, amido, hydroxy, alkoxy, phosphate, urea, or carbonate; $R^{12}$ is H, alkyl, alkynyl, alkenyl, halo, aryl, heteroaryl, nonaromatic heterocyclyl, or cycloalkyl; $R^{a'}$ is hydrogen, alkyl, —NH$_2$, cyano or halogen; and each $R^{13}$ is independently hydrogen, $C_1$-$C_6$ alkyl, $C_1$-$C_6$ alkoxy or halogen. In certain embodiments, $R^3$ and $R^5$ taken together with the carbons to which they are attached can form a 5- or 6-membered ring. In some embodiments of compounds of Formula I-C, $R^3$ is $C_2$-$C_{10}$ alkyl, alkenyl or alkynyl, unsubstituted or substituted with alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$ where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

In some embodiments, the compound of Formula I is a compound having a structure of Formula IV:

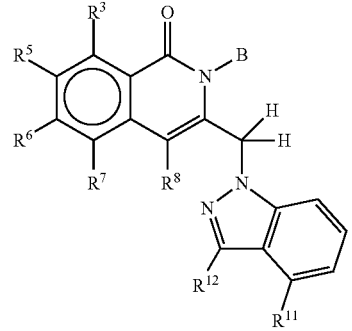

Formula IV or pharmaceutically acceptable forms thereof.

In some embodiments of the compound of Formula IV, $R^{11}$ is H, alkyl, halo, amino, amido, hydroxy, or alkoxy, and $R^{12}$ is H, alkyl, alkynyl, alkenyl, halo, aryl, heteroaryl, heterocycloalkyl, or cycloalkyl. In another embodiment, $R^{11}$ is amino and $R^{12}$ is alkyl, alkenyl, heteroaryl, aryl, or heterocycloalkyl. In some embodiments, $R^{11}$ is amino and and $R^{12}$ is cyano, amino, carboxylic acid, alkoxycarbonyl, or amido.

The disclosure also provides compounds of Formula I having a structure of any of Formulae V, V-A, V-A1, V-A2, V-B, VI, VI-A, VII-A, VII-A1, VII-A2, VIII-A, VIII-A1, VIII-A2, IX-A, IX-A1, IX-A2, X-A, X-A1, X-A2, XI-A, XI-A1, XI-A2, XII-A, XII-A1, XII-A2, XIII-A, XIII-A1, XIII-A2, XIV-A, XIV-A1, XIV-A2, XV-A, XV-A1, XV-A2, XVI-A, XVI-A1, XVI-A2, XVII-A, XVII-A1, XVII-A2, XVIII-A, XVIII-A1, XVIII-A2, XIX-A, XIX-A2, XIX-A3, XX-A, XX-A2, XX-A3, XXI-A, XXI-A2, XXI-A3, XXII-A, XXII-A2 and XXII-A3:

Formula V

Formula V-A

Formula V-A1

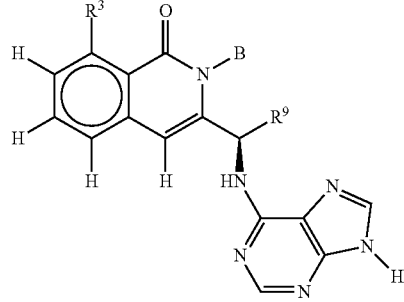

Formula V-A2

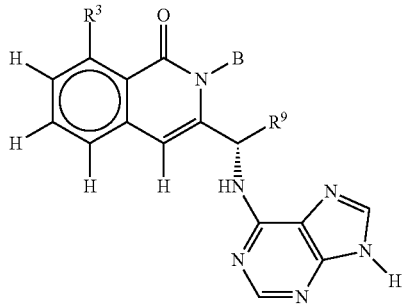

Formula V-B

Formula VI

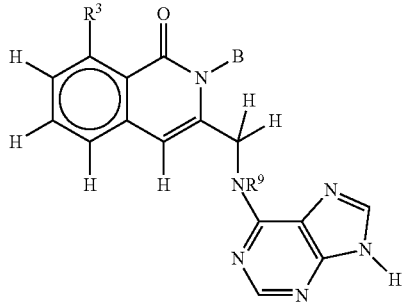

Formula VI-A

Formula VII-A

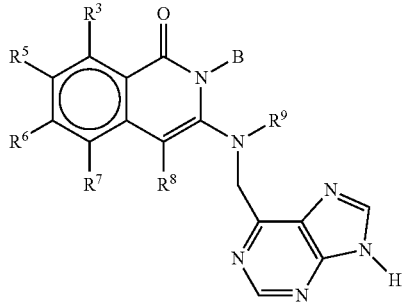

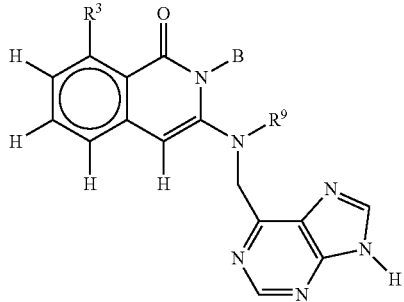

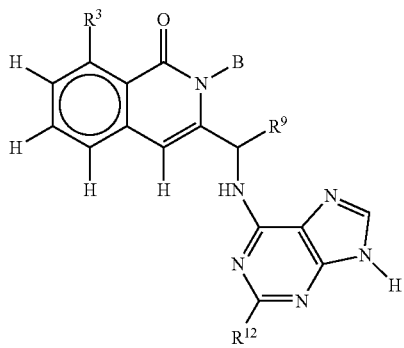

Formula VII-A1
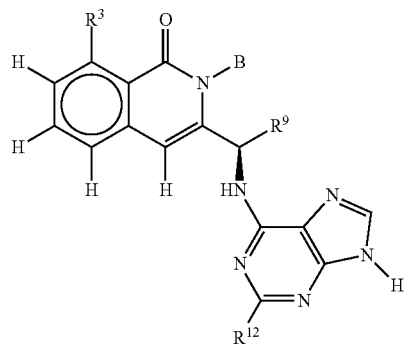
Formula VII-A2
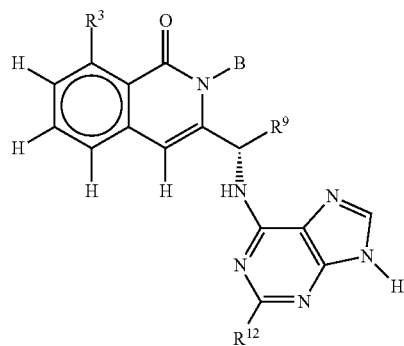
Formula VIII-A
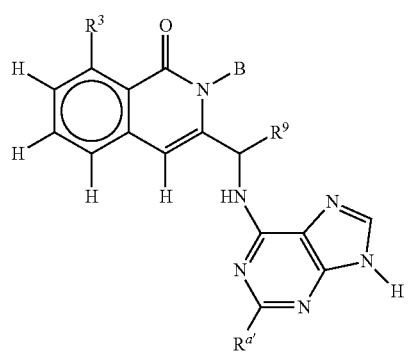
Formula VIII-A1
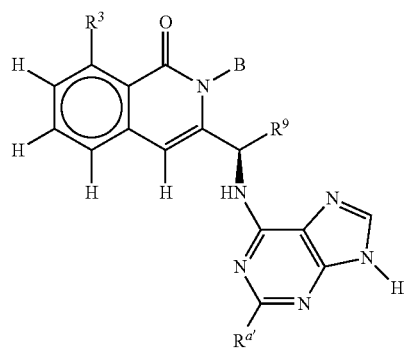
Formula VIII-A2
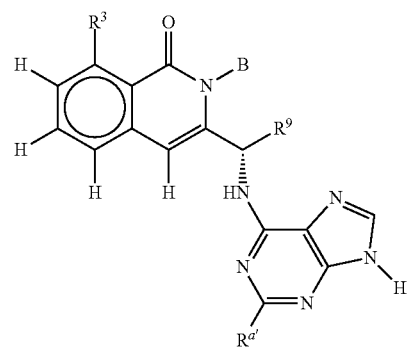
Formula IX-A
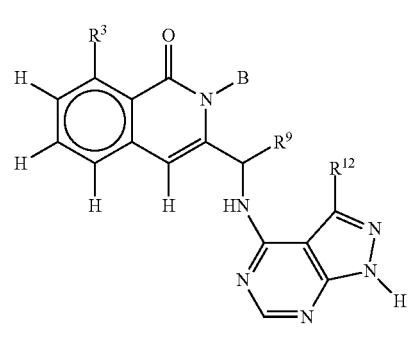
Formula IX-A1
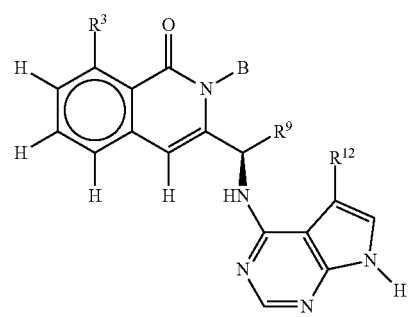
Formula IX-A2
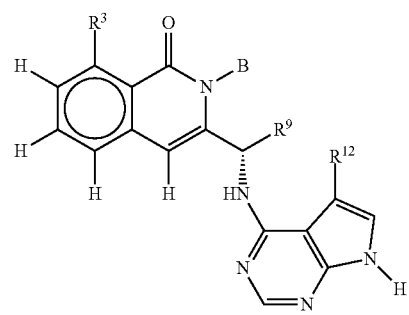

Formula X-A
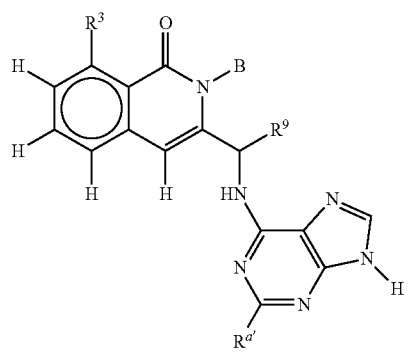
Formula X-A1
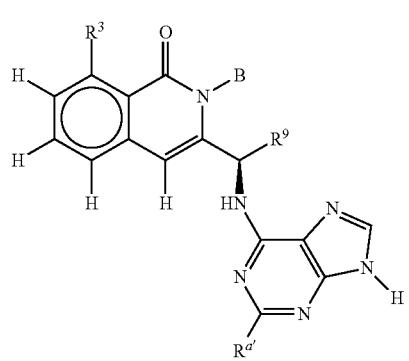
Formula X-A2
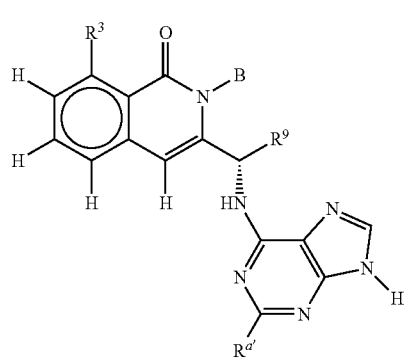
Formula XI-A
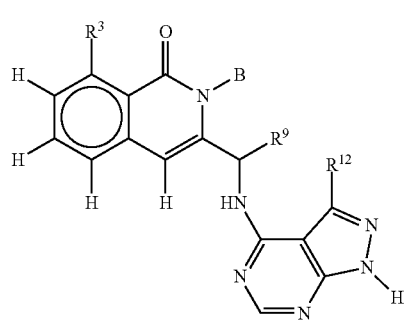
Formula XI-A1
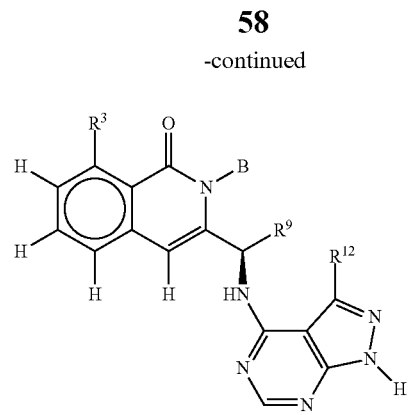
Formula XI-A2
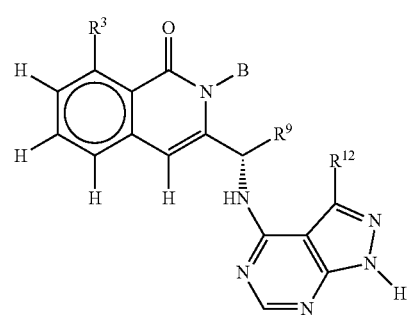
Formula XII-A
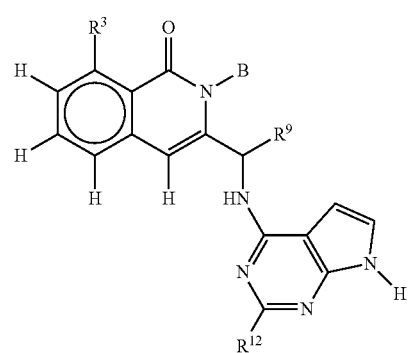
Formula XII-A1
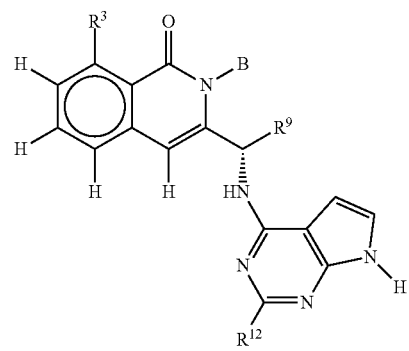

Formula XII-A2
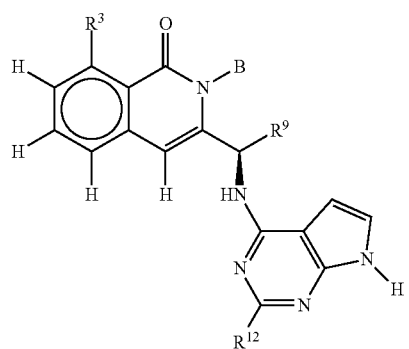
Formula XIII-A
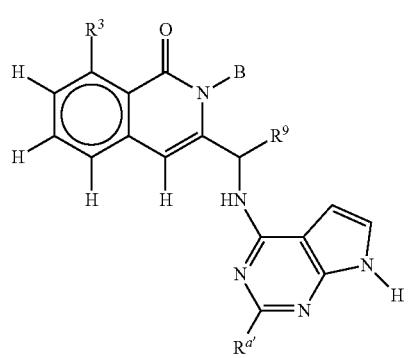
Formula XIII-A1
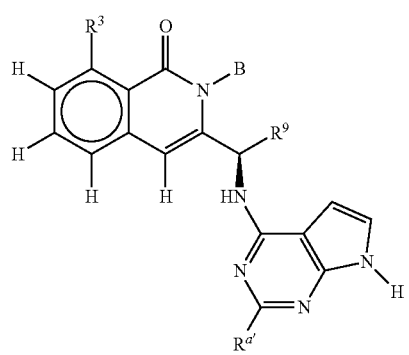
Formula XIII-A2
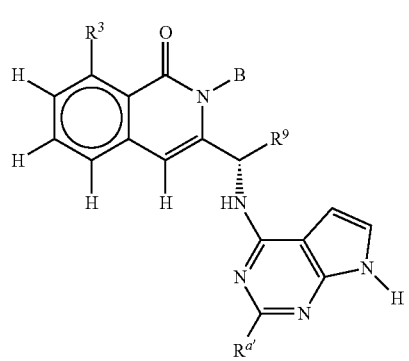
Formula XIV-A
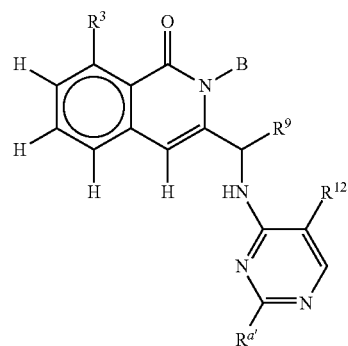
Formula XIV-A1
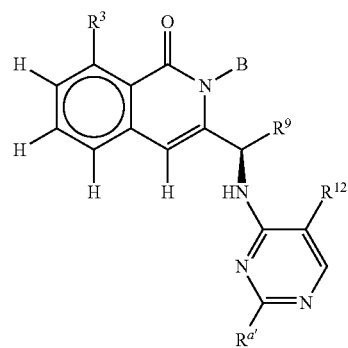
Formula XIV-A2
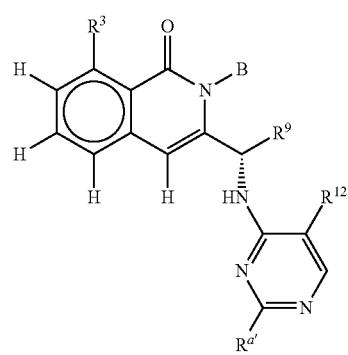
Formula XV-A
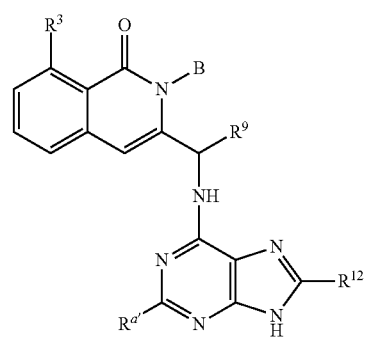

Formula XV-A1
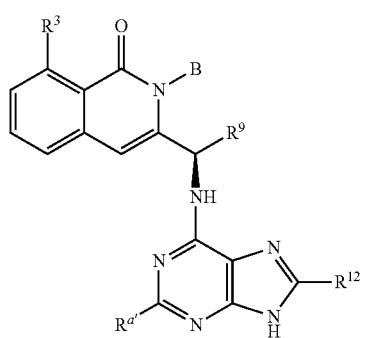
Formula XVI-A2
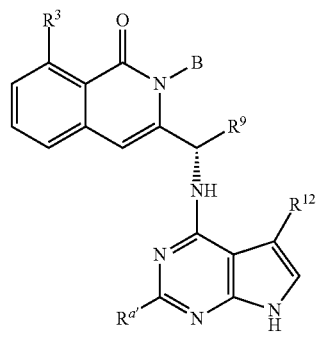
Formula XV-A2
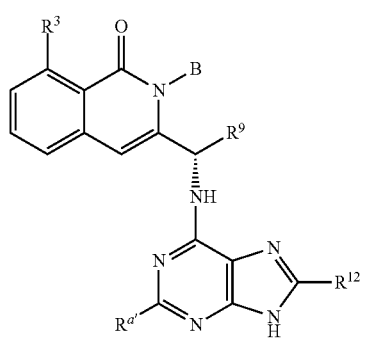
Formula XVII-A
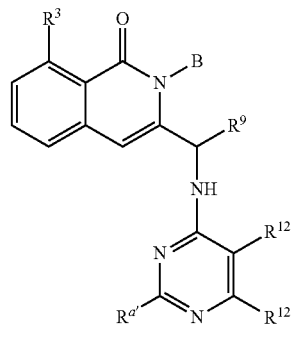
Formula XVI-A
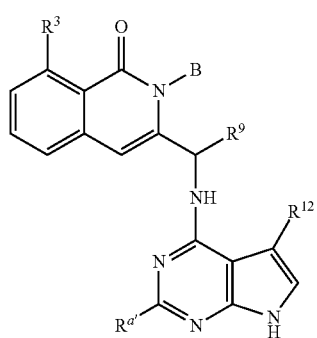
Formula XVII-A1
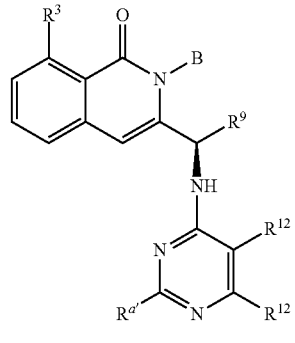
Formula XVI-A1
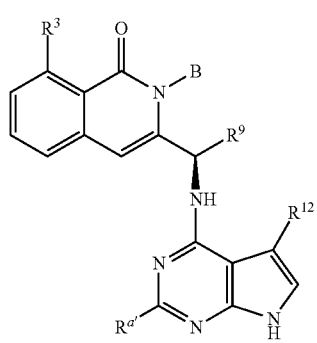
Formula XVII-A2
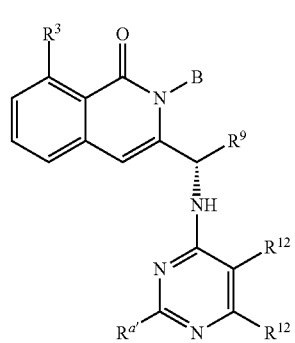

-continued
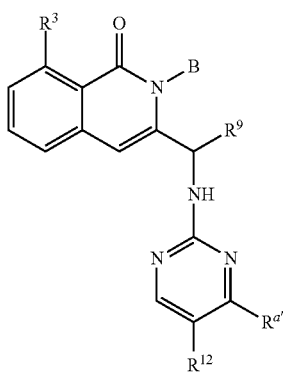
Formula XVIII-A
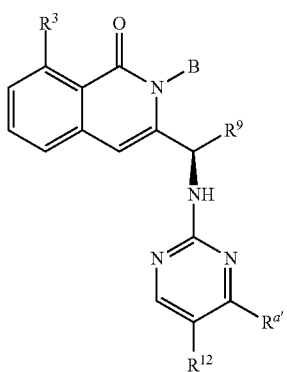
Formula XVIII-A1
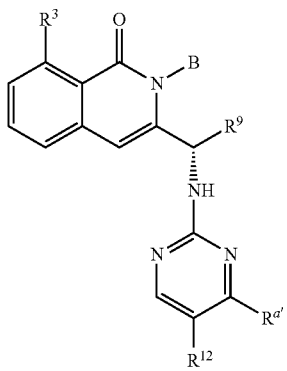
Formula XVIII-A2
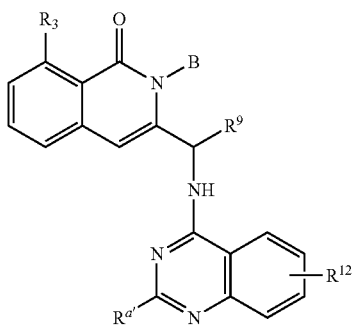
Formula XIX-A
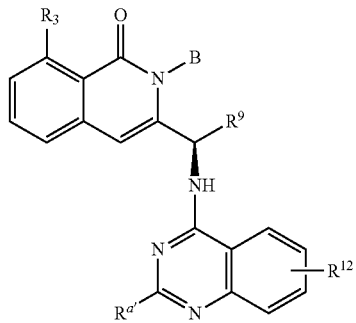
Formula XIX-A2
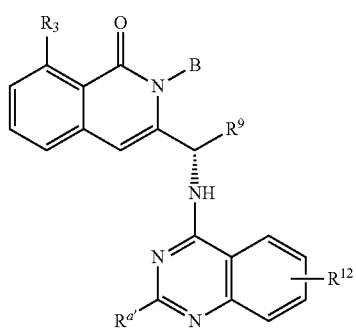
Formula XIX-A3
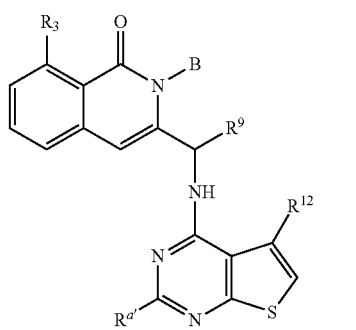
Formula XX-A
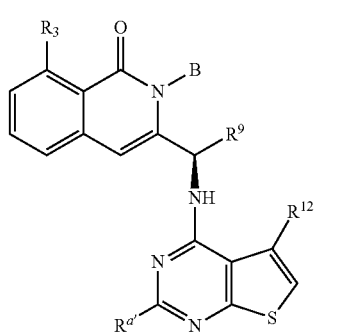
Formula XX-A2
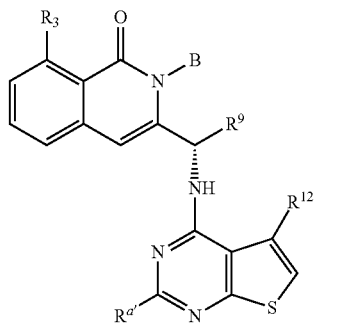
Formula XX-A3

Formula XXI-A

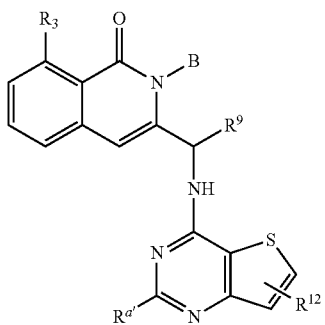

Formula XXI-A2

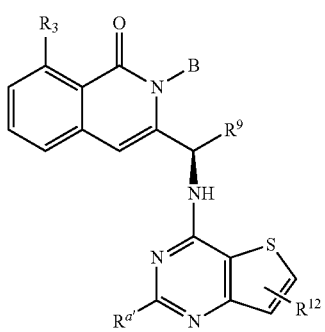

Formula XXI-A3

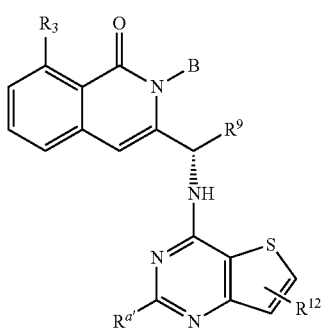

Formula XXII-A

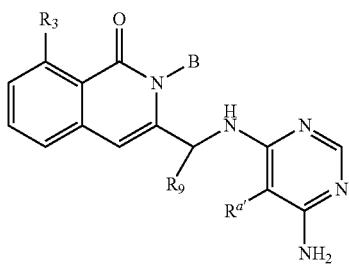

Formula XXII-A2

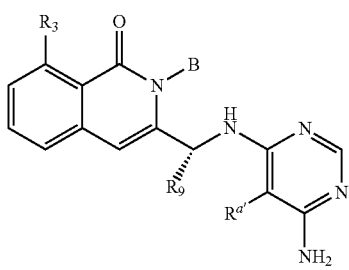

Formula XXII-A3

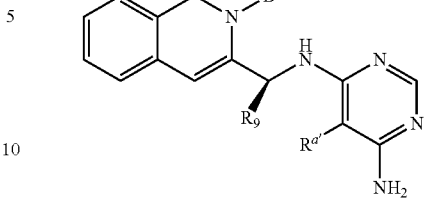

Any of the disclosed elements and their substituents for the compounds of Formula I can be used in any combination.

In some embodiments, B is unsubstituted or substituted alkyl, including but not limited to —(CH$_2$)$_2$—NR$^a$R$^a$, wherein each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl, or NR$^a$R$^a$ are combined together to form a cyclic moiety, which includes but is not limited to piperidinyl, piperazinyl, and morpholinyl. In some embodiments, B is unsubstituted or substituted amino. In some embodiments, B is unsubstituted or substituted heteroalkyl.

In some embodiments, B is a moiety of Formula II:

Formula II

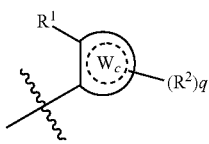

and wherein W$_c$ is selected from unsubstituted or substituted aryl, substituted phenyl, unsubstituted or substituted heteroaryl including, but not limited to, pyridin-2-yl, pyridin-3-yl, pyridin-4-yl, pyrimidin-4-yl, pyrimidin-2-yl, pyrimidin-5-yl, or pyrazin-2-yl, unsubstituted or substituted monocyclic heteroaryl, unsubstituted or substituted bicyclic heteroaryl, a heteroaryl comprising two heteroatoms as ring atoms, unsubstituted or substituted heteroaryl comprising a nitrogen ring atom, a heteroaryl comprising two nitrogen ring atoms, a heteroaryl comprising a nitrogen and a sulfur as ring atoms, unsubstituted or substituted heterocycloalkyl including, but not limited to, morpholinyl, tetrahydropyranyl, piperazinyl, and piperidinyl, or unsubstituted or substituted cycloalkyl including, but not limited, and cyclopentyl and cyclohexyl.

In some embodiments, B is one of the following moieties:

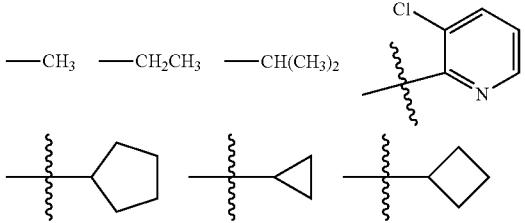

-continued
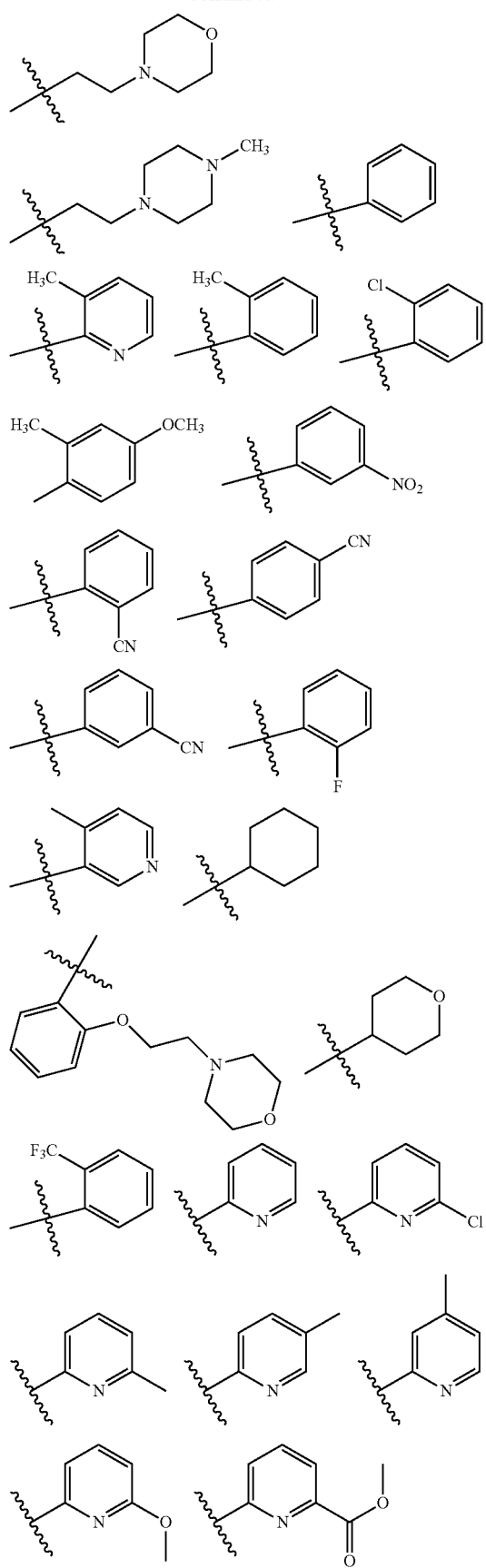
-continued
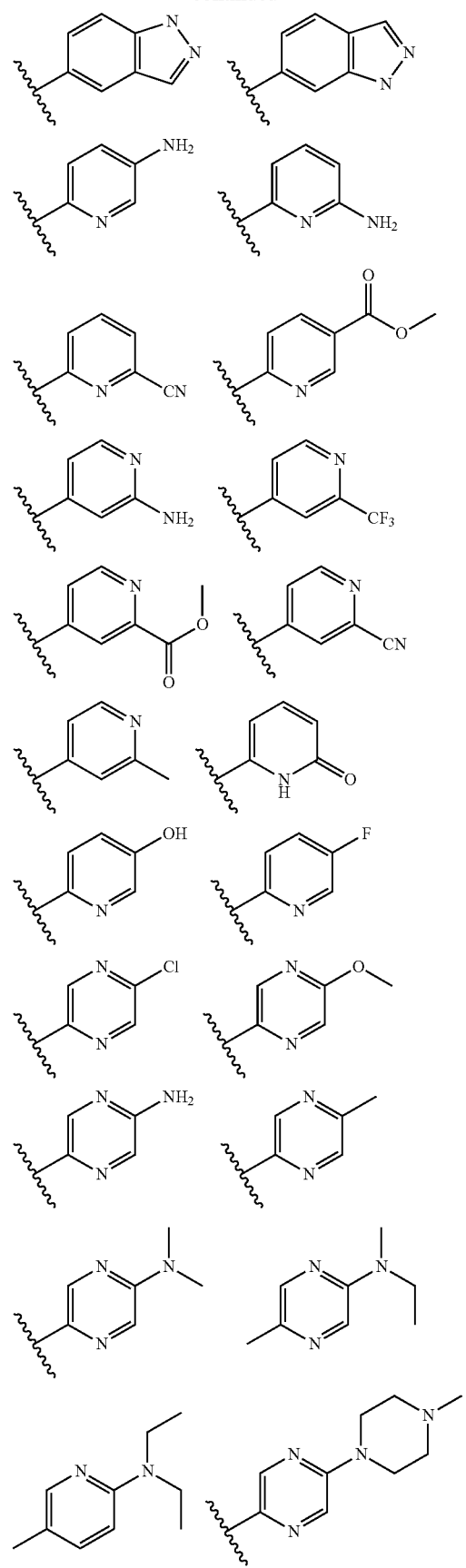

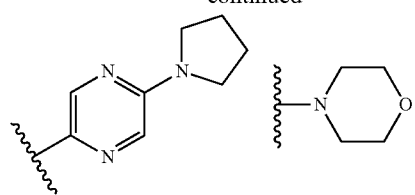
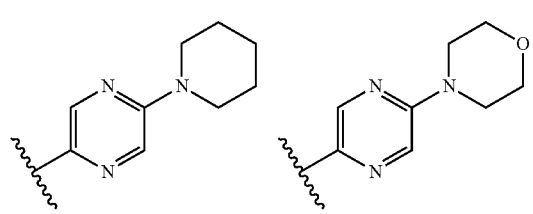
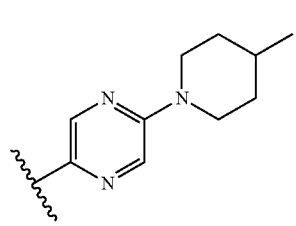
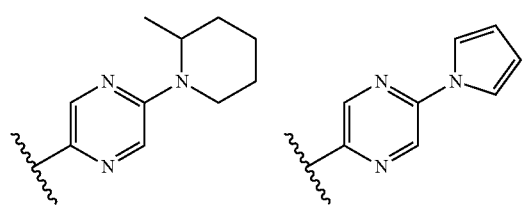
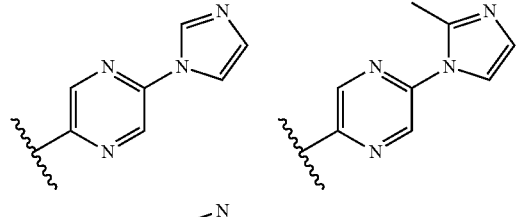
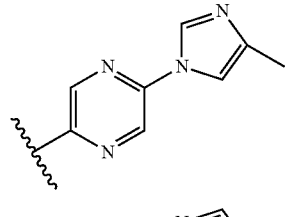
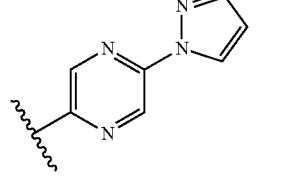
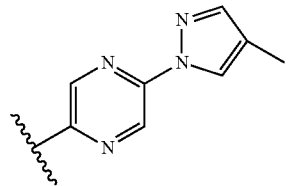
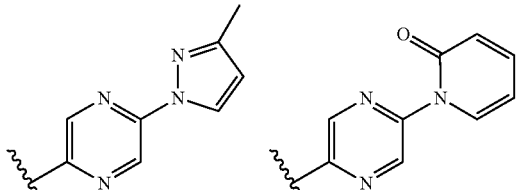
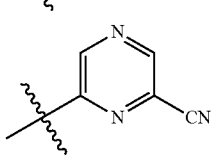
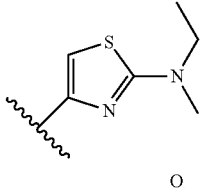
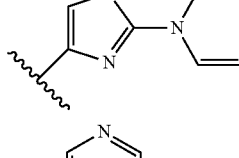
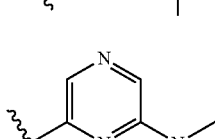
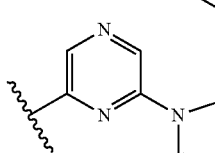
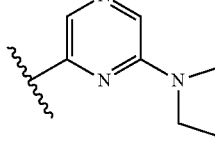
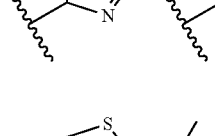
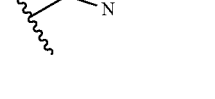

-continued

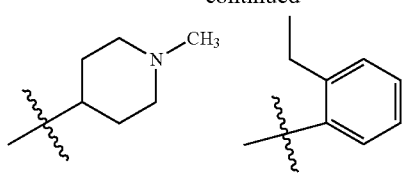
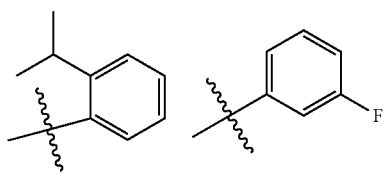
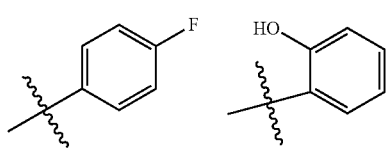
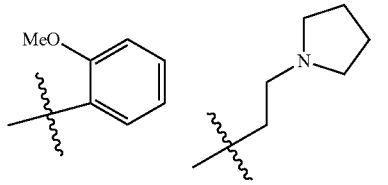
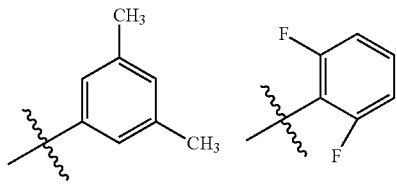
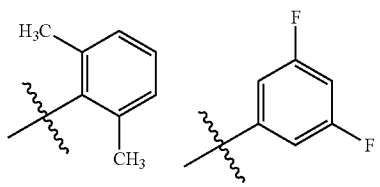
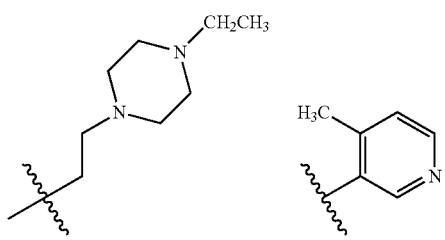
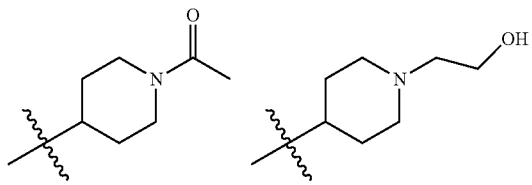
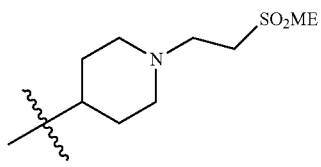

-continued

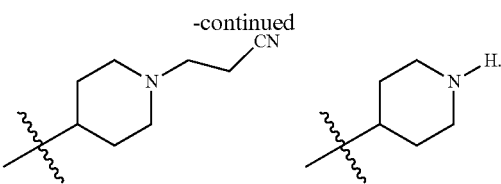

In some embodiments, B is one of the following moieties:

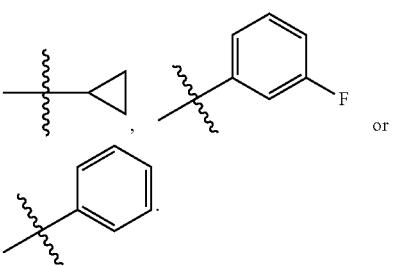 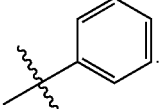

or

In some embodiments, B is substituted by one or more of alkyl, heteroalkyl, alkenyl, alkynyl, cycloalkyl, heterocycloalkyl, aryl, heteroaryl alkoxy, amido, amino, acyl, acyloxy, alkoxycarbonyl, sulfonamido, halo, cyano, hydroxy or nitro, each of which alkyl, heteroalkyl, alkenyl, alkynyl, cycloalkyl, heterocycloalkyl, aryl, heteroaryl, alkoxy, amido, amino, acyl, acyloxy, or sulfonamido, can itself be substituted.

In some embodiments, $R^1$ is selected from hydrogen, unsubstituted or substituted alkyl, unsubstituted or substituted heteroalkyl, unsubstituted or substituted alkenyl, unsubstituted or substituted alkynyl, unsubstituted or substituted cycloalkyl, and unsubstituted or substituted heterocycloalkyl. In some embodiments, $R^1$ is unsubstituted or substituted aryl, unsubstituted or substituted arylalkyl, unsubstituted or substituted heteroaryl, or unsubstituted or substituted heteroarylalkyl. In some embodiments, $R^1$ is unsubstituted or substituted alkoxy, unsubstituted or substituted amido, or unsubstituted or substituted amino. In some embodiments, $R^1$ is unsubstituted or substituted acyl, unsubstituted or substituted acyloxy, unsubstituted or substituted alkoxycarbonyl, or unsubstituted or substituted sulfonamido. In some embodiments, $R^1$ is halo which includes —Cl, —F, —I, and —Br. In some embodiments, $R^1$ is selected from cyano, hydroxy, nitro, unsubstituted or substituted phosphate, unsubstituted or substituted urea, and carbonate.

In some embodiments, when $R^1$ is alkyl, $R^1$ is methyl, ethyl, propyl, isopropyl, n-butyl, tert-butyl, sec-butyl, pentyl, hexyl or heptyl.

In some embodiments, when $R^1$ is alkyl, heteroalkyl, alkenyl, alkynyl, cycloalkyl, heterocycloalkyl, aryl, arylalkyl, heteroaryl, heteroarylalkyl, alkoxy, amido, amino, acyl, acyloxy, alkoxycarbonyl, sulfonamido, or hydroxy, $R^1$ is substituted by phosphate, unsubstituted urea, substituted urea, carbonic acid, or carbonate.

In some embodiments, when $R^1$ is alkyl, heteroalkyl, alkenyl, alkynyl, cycloalkyl, heterocycloalkyl, aryl, arylalkyl, heteroaryl, heteroarylalkyl, alkoxy, amido, amino, acyl, acyloxy, alkoxycarbonyl, or sulfonamido, $R^1$ is substituted by one or more of alkyl, heteroalkyl, alkenyl, alkynyl, cycloalkyl, heterocycloalkyl, aryl, arylalkyl, heteroaryl, heteroarylalkyl, alkoxy, amido, amino, acyl, acyloxy, alkoxycarbonyl, sulfonamido, halo, cyano, hydroxy or nitro, each of which alkyl, heteroalkyl, alkenyl, alkynyl, cycloalkyl, heterocycloalkyl, aryl, arylalkyl, heteroaryl, heteroarylalkyl, alkoxy, amido, amino, acyl, acyloxy, alkoxycarbonyl, or sulfonamido can itself be substituted.

In some embodiments, q is an integer of 0. In some embodiments, q is an integer of 1. In some embodiments, q is an integer of 2. In some embodiments, q is an integer of 3. In some embodiments, q is an integer of 4.

In some embodiments, $R^2$ is selected from unsubstituted or substituted alkyl, unsubstituted or substituted heteroalkyl, unsubstituted or substituted alkenyl, unsubstituted or substituted alkynyl, unsubstituted or substituted cycloalkyl, and unsubstituted or substituted heterocycloalkyl. In some embodiments, $R^2$ is unsubstituted or substituted aryl, unsubstituted or substituted arylalkyl, unsubstituted or substituted heteroaryl, or unsubstituted or substituted heteroarylalkyl. In some embodiments, $R^2$ is unsubstituted or substituted alkoxy, unsubstituted or substituted amido, or unsubstituted or substituted amino. In some embodiments, $R^2$ is unsubstituted or substituted acyl, unsubstituted or substituted acyloxy, unsubstituted or substituted alkoxycarbonyl, or unsubstituted or substituted sulfonamido. In some embodiments, $R^2$ is halo, which is —I, —F, —Cl, or —Br. In some embodiments, $R^2$ is selected from cyano, hydroxy, nitro, a carbonic acid, and a carbonate. In some embodiments, $R^2$ is unsubstituted or substituted phosphate. In some embodiments, $R^2$ is unsubstituted or substituted urea. In some embodiments, when $R^2$ is alkyl, $R^2$ is methyl, ethyl, propyl, isopropyl, n-butyl, tert-butyl, sec-butyl, pentyl, hexyl or heptyl.

In some embodiments, when $R^2$ is alkyl, heteroalkyl, alkenyl, alkynyl, cycloalkyl, heterocycloalkyl, aryl, arylalkyl, heteroaryl, heteroarylalkyl, alkoxy, amido, amino, acyl, acyloxy, alkoxycarbonyl, sulfonamido, or hydroxy, it is substituted by phosphate, substituted by urea, or substituted by carbonate.

In some embodiments, when $R^2$ is alkyl, heteroalkyl, alkenyl, alkynyl, cycloalkyl, heterocycloalkyl, aryl, arylalkyl, heteroaryl, heteroarylalkyl, alkoxy, amido, amino, acyl, acyloxy, alkoxycarbonyl, or sulfonamido, $R^2$ is substituted by one or more of alkyl, heteroalkyl, alkenyl, alkynyl, cycloalkyl, heterocycloalkyl, aryl, heteroaryl, alkoxy, amido, amino, acyl, acyloxy, alkoxycarbonyl, sulfonamido, halo, cyano, hydroxy or nitro, each of which alkyl, heteroalkyl, alkenyl, alkynyl, cycloalkyl, heterocycloalkyl, aryl, heteroaryl, alkoxy, amido, amino, acyl, acyloxy, alkoxycarbonyl, or sulfonamido can itself be substituted.

In some embodiments, $R^3$ is a 5-membered heteroaryl group. Such groups include, for example, pyrrole, furan, thiophene, triazole, oxazole, pyrazole, and isoxazole. In other embodiments, $R^3$ is a 5-membered nonaromatic heterocycle, including, but not limited to, oxazoline and oxazolidinone. In still other embodiments, $R^3$ is a 6-membered heteroaryl group such as pyridine, pyrazine, pyrimidine and pyridazine. In another embodiment, $R^3$ is a 6-membered nonaromatic heterocycle, including moieties such as morpholino or piperidino. In other embodiments, $R^3$ is a fused 5/6-bicyclic heteroaryl, for example benzothiazole, benzoxazole, benzisoxazole, indazole, benzimidazole, benzothiophene, indole, isoindole, purine, or pyrazolopyrimidine. In yet other embodiments, $R^3$ is a fused 5/6-bicyclic nonaromatic heterocycle.

In some embodiments, $R^3$ is a $C_1$-$C_6$ alkyl group substituted with a 5-membered heteroaryl, a 5-membered nonaromatic heterocycle, a 6-membered heteroaryl, a 6-membered nonaromatic heterocycle, a fused 5/6-bicyclic heteroaryl, or a fused 5/6-bicyclic nonaromatic heterocycle. In other embodiments, $R^3$ is a heteroatom selected from N, S, and O, wherein the heteroatom has a covalent bond either directly or through a $C_1$-$C_6$ alkyl group to a 5-membered heteroaryl, a 5-membered nonaromatic heterocycle, a 6-membered heteroaryl, a 6-membered nonaromatic heterocycle, a fused 5/6-bicyclic heteroaryl, or a fused 5/6-bicyclic nonaromatic heterocycle.

In other embodiments, $R^3$ is a $C_1$-$C_6$ alkyl group substituted with a fused polycyclic group, wherein the polycyclic group has greater than two rings and is carbocyclic or heterocyclic; $C_1$-$C_6$ alkyl group substituted with a bridged cycloalkyl or bridged heterocyclic group; $C_1$-$C_6$ alkyl group substituted with a spirocyclic cycloalkyl or spirocyclic heterocyclic group; or branched $C_4$-$C_{12}$ alkyl group, wherein said branched alkyl group contains at least one terminal t-butyl group.

Each of the embodiments named above for $R^3$ is unsubstituted or optionally additionally substituted with an alkyl, heteroalkyl, alkenyl, alkynyl, cycloalkyl, heterocycloalkyl, aryl, heteroaryl, alkoxy, amido, amino, acyl, acyloxy, alkoxycarbonyl, sulfonamido, halo, cyano, hydroxy or nitro group.

In certain embodiments, $R^3$ is a substituted or unsubstituted group selected from pyridine, pyrazole, piperazine, and pyrrolidine, wherein the substituent can be a $C_1$-$C_6$ alkyl group or a halogen.

In some embodiments, a compound is provided wherein $R^3$ is selected from a 5-membered heteroaryl selected from pyrrole, a furan, and a thiophene group; 5-membered nonaromatic heterocycle selected from a pyrrolidine, a tetrahydrofuran, and a tetrahydrothiophene group; 6-membered heteroaryl selected from pyridine, pyrazine, pyrimidine, and pyridazine; 6-membered nonaromatic heterocycle selected from piperidine, tetrahydropyran, and thiane; and fused 5/6-bicyclic heteroaryl selected from indole, isoindole, benzofuran, isobenzofuran, benzothiophene, benzimidazole, indazole, benzoxazole, benzisoxazole, and purine. In certain embodiments, $R^3$ is a substituted or unsubstituted group selected from pyridine, pyrazole, piperazine, and pyrrolidine. By way of non-limiting example, the $R^3$ group can be substituted with a $C_1$-$C_6$ alkyl group or a halogen. For example, the $R^3$ group can be substituted with a methyl group.

In some embodiments, a compound is provided wherein $R^3$ is selected from

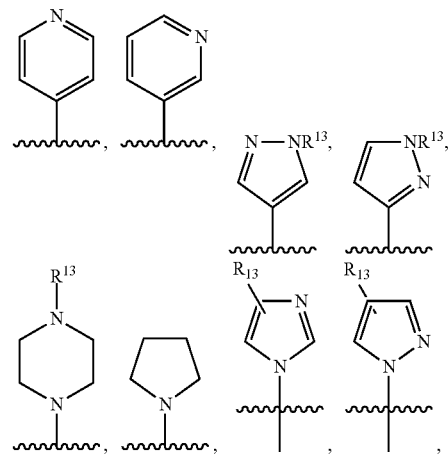

-continued

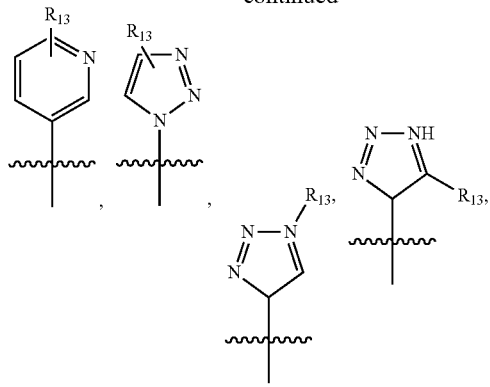

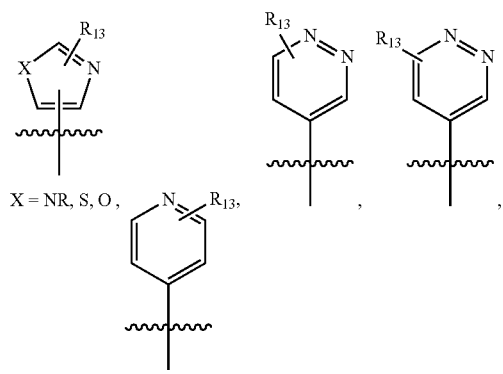

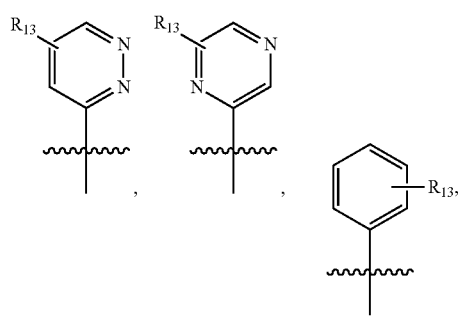

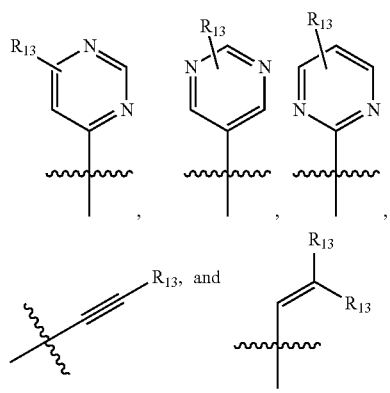

wherein $R^{13}$ is H or $C_1$-$C_6$ alkyl. In certain embodiments, $R^{13}$ is methyl. In some embodiments, $R^3$ is selected from the following:

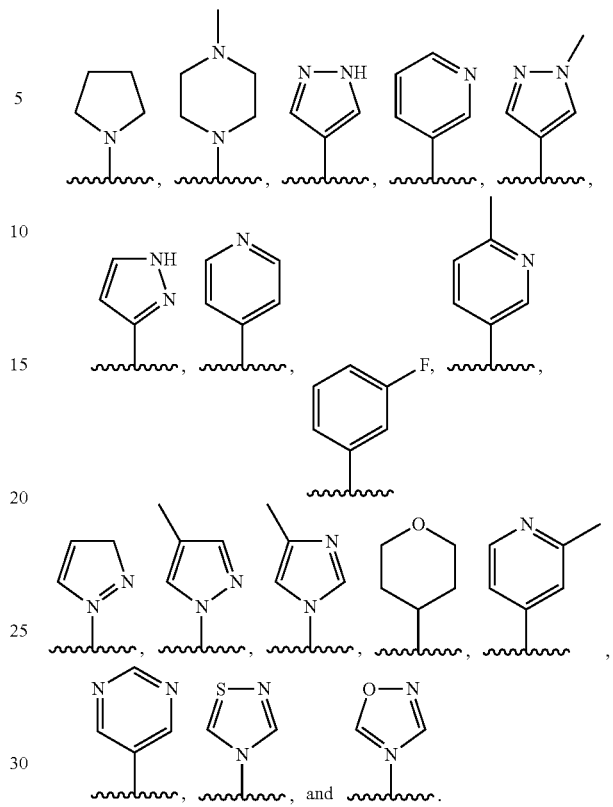

In some embodiments, $R^5$, $R^6$, $R^7$, and $R^8$ are each independently hydrogen, unsubstituted or substituted alkyl (including, but not limited to, unsubstituted or substituted $C_1$-$C_4$ alkyl). In some embodiments, $R^5$, $R^6$, $R^7$, and $R^8$ are each independently unsubstituted or substituted alkenyl including, but not limited to, unsubstituted or substituted $C_2$-$C_5$ alkenyl. In some embodiments, $R^5$, $R^6$, $R^7$, and $R^8$ are each independently unsubstituted or substituted alkynyl including, but not limited to, unsubstituted or substituted $C_2$-$C_5$ alkynyl. In some embodiments, $R^5$, $R^6$, $R^7$, and $R^8$ are each independently unsubstituted or substituted cycloalkyl including, but not limited to, unsubstituted or substituted $C_3$-$C_5$ cycloalkyl. In some embodiments, $R^5$, $R^6$, $R^7$, and $R^8$ are each independently unsubstituted or substituted heterocycloalkyl. In some embodiments, $R^5$, $R^6$, $R^7$, and $R^8$ are each independently unsubstituted or substituted heteroalkyl including, but not limited to, unsubstituted or substituted $C_1$-$C_4$ heteroalkyl. In some embodiments, $R^5$, $R^6$, $R^7$, and $R^8$ are each independently unsubstituted or substituted alkoxy including, but not limited to, unsubstituted or substituted $C_1$-$C_4$ alkoxy. In some embodiments, $R^5$, $R^6$, $R^7$, and $R^8$ are each independently unsubstituted or substituted amido including, but not limited to, unsubstituted or substituted $C_1$-$C_4$ amido. In some embodiments, $R^5$, $R^6$, $R^7$, and $R^8$ are each independently unsubstituted or substituted amino. In some embodiments, $R^5$, $R^6$, $R^7$, and $R^8$ are each independently unsubstituted or substituted acyl, unsubstituted or substituted acyloxy, unsubstituted or substituted $C_1$-$C_4$ acyloxy, unsubstituted or substituted alkoxycarbonyl, unsubstituted or substituted sulfonamido, or unsubstituted or substituted $C_1$-$C_4$ sulfonamido. In some embodiments, $R^5$, $R^6$, $R^7$, and $R^8$ are each independently halo, which is —I, —F, —Cl, or —Br. In some embodiments, $R^5$, $R^6$, $R^7$, and $R^8$ are each independently selected from cyano, hydroxy, and nitro. In some other embodiments, $R^5$, $R^6$, $R^7$, and $R^8$ are each independently —$CH_3$, —$CH_2CH_3$, n-propyl, isopropyl, —$OCH_3$, —$OCH_2CH_3$, or —$CF_3$.

In some embodiments, when $R^5$, $R^6$, $R^7$, and $R^8$ are each independently alkyl, alkenyl, alkynyl, cycloalkyl, heteroalkyl, acyl, alkoxy, amido, amino, acyloxy, alkoxycarbonyl, or sulfonamido, $R^5$, $R^6$, $R^7$, and $R^8$ are each independently optionally substituted with one or more of alkyl, heteroalkyl, alkenyl, alkynyl, cycloalkyl, heterocycloalkyl, aryl, heteroaryl, alkoxy, amido, amino, acyl, acyloxy, alkoxycarbonyl, sulfonamido, halo, cyano, hydroxy or nitro, each of which alkyl, heteroalkyl, alkenyl, alkynyl, cycloalkyl, heterocycloalkyl, aryl, heteroaryl, alkoxy, amido, amino, acyl, acyloxy, alkoxycarbonyl, or sulfonamido can itself be substituted.

In some embodiments, $R^5$, $R^6$, $R^7$, and $R^8$ are H.

In some embodiments, X is absent. In some embodiments, X is —$(CH(R^9))_z$, and z is an integer of 1, 2, 3 or 4.

In some embodiments, $R^9$ is unsubstituted or substituted alkyl including, but not limited to, unsubstituted or substituted $C_1$-$C_{10}$ alkyl. In some embodiments, $R^9$ is unsubstituted or substituted cycloalkyl including but not limited to unsubstituted or substituted $C_3$-$C_7$ cycloalkyl. In some embodiments, $R^9$ is ethyl, methyl or hydrogen. In some embodiments, $R^9$ is unsubstituted or substituted heterocycloalkyl including, but not limited to, unsubstituted or substituted $C_2$-$C_{10}$ heteroalkyl. In some embodiments, $R^9$ is unsubstituted or substituted heteroalkyl including, but not limited to, unsubstituted or substituted $C_2$-$C_{10}$ heteroalkyl.

In some embodiments, provided herein is a compound of Formula I (e.g., a compound of formula (I), (Ia), (Ib) or (Ic)) wherein $R^9$ is hydrogen, and X is —$CH_2$—, —$CH_2CH_2$—, —$CH_2CH_2CH_2$—, —$CH(CH_3)$—, or —$CH(CH_2CH_3)$—. In other embodiments, X is —$(CH(R^9))_z$, $R^9$ is alkyl, or heterocycloalkyl, and z is an integer of 1. When X is —$CH(R^9)$— and $R^9$ is alkyl, or heterocycloalkyl, then the compound can adopt either an (S)- or (R)-stereochemical configuration with respect to carbon X. In some embodiments, the compound is a racemic mixture of (S)- and (R)-isomers with respect to carbon X. In other embodiments, provided herein is a mixture of compounds of Formula I wherein individual compounds of the mixture exist predominately in an (S)- or (R)-isomeric configuration. For example, the compound mixture has an (S)-enantiomeric excess of greater than about 55%, about 60%, about 65%, about 70%, about 75%, about 80%, about 85%, about 90%, about 95%, about 96%, about 97%, about 98%, about 99%, about 99.5%, or more at the X carbon. In other embodiments, the compound mixture has an (S)-enantiomeric excess of greater than about 55% to about 99.5%, greater than about about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more.

In other embodiments, the compound mixture has an (R)-enantiomeric purity of greater than about 55%, about 60%, about 65%, about 70%, about 75%, about 80%, about 85%, about 90%, about 95%, about 96%, about 97%, about 98%, about 99%, about 99.5% or more at the X carbon. In some other embodiments, the compound mixture has an (R)-enantiomeric excess of greater than about 55% to about 99.5%, greater than about about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5% or more.

In other embodiments, the compound mixture contains identical chemical entities except for their stereochemical orientations, namely (S)- or (R)-isomers. For instance, in the compounds of Formula I, when X is —$CH(R^9)$—, and $R^9$ is not hydrogen, then the —$CH(R^9)$— is in an (S)- or (R)-stereochemical orientation for each of the identical chemical entities. In some embodiments, the mixture of identical chemical entities of Formula I is a racemic mixture of (S)- and (R)-isomers at the carbon represented by X. In another embodiment, the mixture of the identical chemical entities (except for their stereochemical orientations), contain predominately (S)-isomers or predominately (R)-isomers. For example, the (S)-isomers in the mixture of identical chemical entities are present at about 55%, about 60%, about 65%, about 70%, about 75%, about 80%, about 85%, about 90%, about 95%, about 96%, about 97%, about 98%, about 99%, about 99.5%, or more, relative to the (R)-isomers. In some embodiments, the (S)-isomers in the mixture of identical chemical entities are present at an (S)-enantiomeric excess of greater than about 55% to about 99.5%, greater than about about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5% or more.

In another embodiment, the (R)-isomers in the mixture of identical chemical entities (except for their stereochemical orientations), are present at about 55%, about 60%, about 65%, about 70%, about 75%, about 80%, about 85%, about 90%, about 95%, about 96%, about 97%, about 98%, about 99%, about 99.5%, or more, relative to the (S)-isomers. In some embodiments, the (R)-isomers in the mixture of identical chemical entities (except for their stereochemical orientations), are present at a (R)-enantiomeric excess greater than about 55% to about 99.5%, greater than about about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more.

In some embodiments, the compound of Formula I, X is —$CH(R^9)$—, $R^9$ is methyl or ethyl, and the compound is the (S)-isomer.

In some embodiments of the compound of Formula I, Y is absent. In some embodiments, Y is —O—, —S—, —S(=O)—, —S(=O)$_2$—, —C(=O)—, —N($R^9$)(C=O)—, —N($R^9$)(C=O)NH—, —N($R^9$)C($R^9$)$_2$— (such as —N($R^9$)CH$_2$—, specifically —N(CH$_3$)CH$_2$—, N(CH(CH$_3$)$_2$)CH$_2$— or N(CH$_2$CH$_3$)CH$_2$—), —N($R^9$)—, —N(CH₃)—, —N(CH₂CH₃)—, or —N(CH(CH₃)₂)—. In some embodiments, Y is —C(=O)—(CHR⁹)$_z$— and z is an integer of 1, 2, 3, or 4.

In some embodiments, at least one of X and Y is present. In some embodiments of the compound of Formula I, —XY— is —CH₂—, —CH₂—N(CH₃), —CH₂—N(CH₂CH₃), —CH(CH₃)—NH—, (S)—CH(CH₃)—NH—, or (R) —CH(CH₃)—NH—. In other embodiments, X—Y is —N(CH₃)_CH₂—, N(CH₂CH₃) CH₂—, —N(CH(CH₃)₂) CH₂—, or —NHCH₂—. In some embodiments, other compounds of Formula I are provided wherein when X-Y is X is —(CH(R⁹))$_z$N(R⁹)—, z is an integer of 1, 2, 3 or 4, and —N(R⁹)— is not —NH—, then —XY— is not connected to purinyl.

In some embodiments, W$_d$ in a formula disclosed herein (including but not limited to I, I-1, IV, IV-A, V, V-A, V-A2, V-B, VI and VI-A), is selected from unsubstituted or substituted heterocycloalkyl, unsubstituted or substituted aryl, and unsubstituted or substituted heteroaryl.

In various embodiments, W$_d$ is unsubstituted or substituted monocyclic heteroaryl (including, but not limited to, pyrimidinyl, pyrrolyl, pyrazinyl, triazinyl, or pyridazinyl) or unsubstituted or substituted bicyclic heteroaryl.

In some embodiments, W$_d$ is a monocyclic heteroaryl of the following formula:

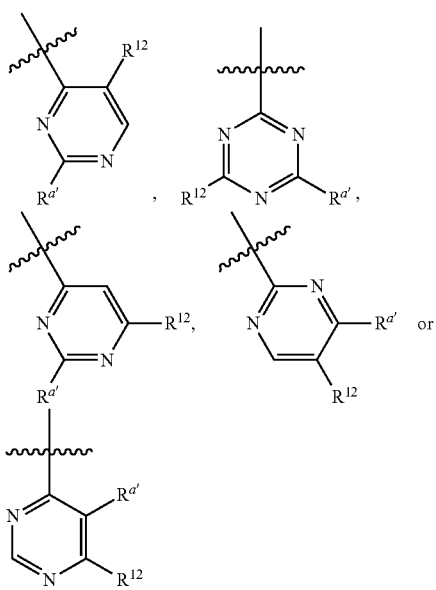

wherein R$^{a'}$ is hydrogen, halo, phosphate, urea, a carbonate, unsubstituted or substituted amino, unsubstituted or substituted alkyl, unsubstituted or substituted alkenyl, unsubstituted or substituted alkynyl, unsubstituted or substituted cycloalkyl, unsubstituted or substituted heteroalkyl, or unsubstituted or substituted heterocycloalkyl; and R¹² is hydrogen, unsubstituted or substituted alkyl, unsubstituted or substituted cyano, unsubstituted or substituted alkynyl, unsubstituted or substituted alkenyl, halo, unsubstituted or substituted aryl, unsubstituted or substituted heteroaryl, unsubstituted or substituted heterocycloalkyl, unsubstituted or substituted cycloalkyl, unsubstituted or substituted amino, carboxylic acid, unsubstituted or substituted alkoxycarbonyl, unsubstituted or substituted amido, unsubstituted or substituted acyl, or unsubstituted or substituted sulfonamido.

Provided herein are monocyclic heteroaryl W$_d$ including, but not limited to, one of the following formulae:

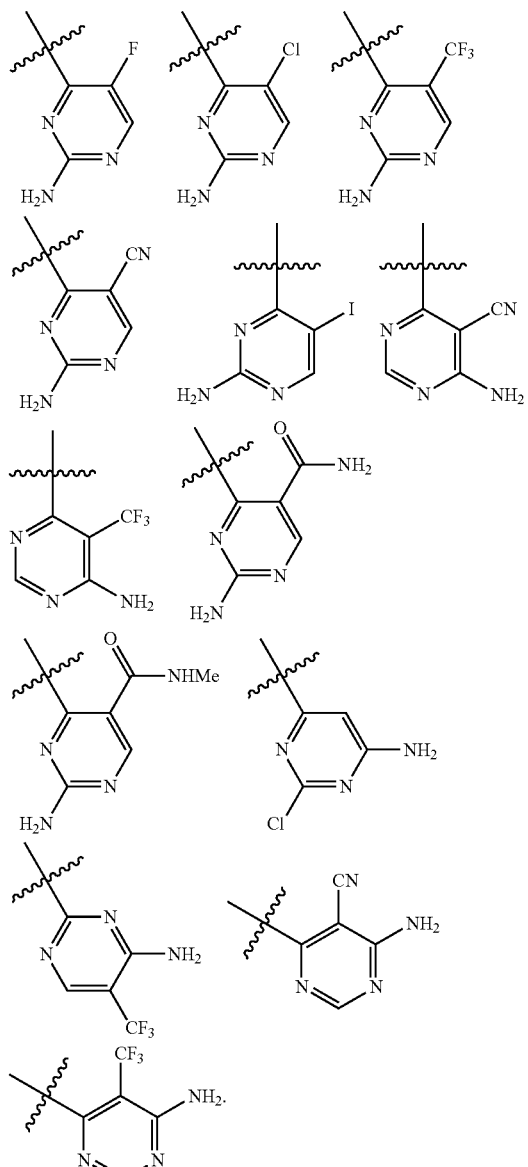

In some embodiments, W$_d$ in a formula disclosed herein (including but not limited to I, I-1, IV, IV-A, V, V-A, V-A2, V-B, VI and VI-A), is a bicyclic heteroaryl having at least one heteroatom, e.g., a bicyclic heteroaryl having at least one nitrogen ring atom. In some embodiments, W$_d$ is a bicyclic heteroaryl having at least two heteroatoms, e.g., a bicyclic heteroaryl having at least two nitrogen ring atoms. In some embodiments, W$_d$ is a bicyclic heteroaryl having two heteroatoms in the ring which is connected to XY. In some embodiments, W$_d$ is a bicyclic heteroaryl having two nitrogen ring atoms in the ring to which XY is connected. In some embodiments, W$_d$ is a bicyclic heteroaryl having four heteroatoms, e.g., a bicyclic heteroaryl having four nitrogen ring atoms. In some embodiments, W$_d$ is unsubstituted or substituted 4-amino-1H-pyrazolo[3,4-d]pyrimidin-1-yl, unsubstituted or substituted 7-amino-2-methyl-2H-pyrazolo

[4,3-d]pyrimidin-3-yl, unsubstituted or substituted 6-methylenyl-9H-purin-6-yl, or unsubstituted or substituted 6-amino-9H-purin-9-yl.

In some embodiments $W_d$ is one of the following:

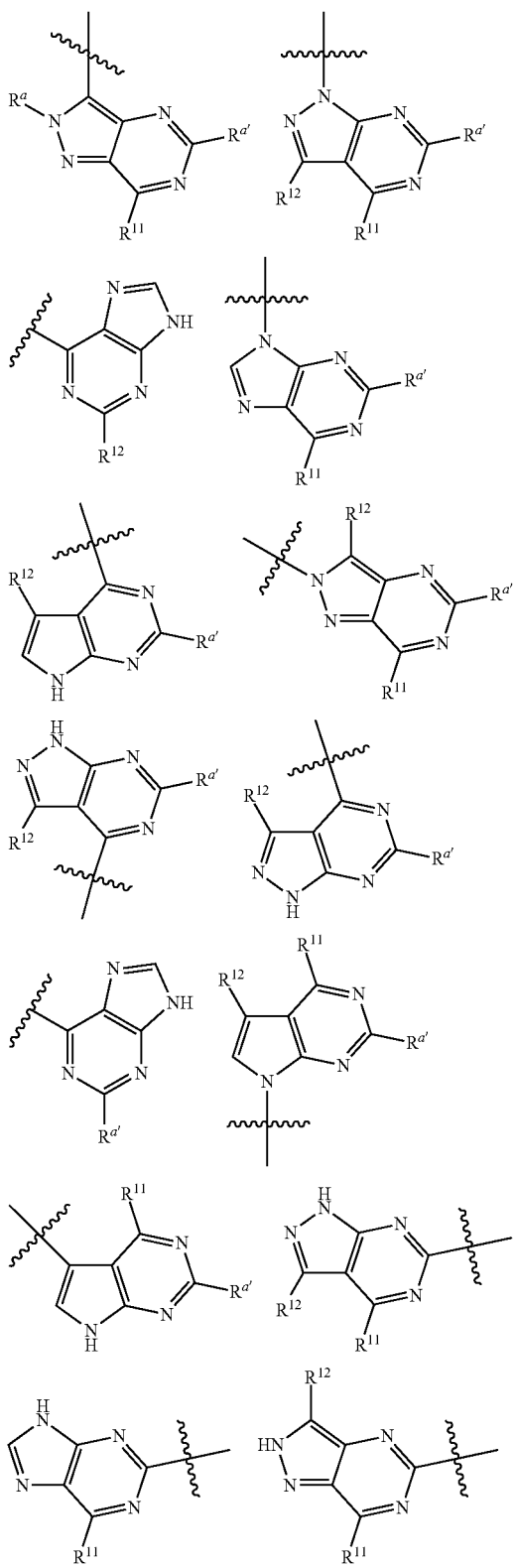

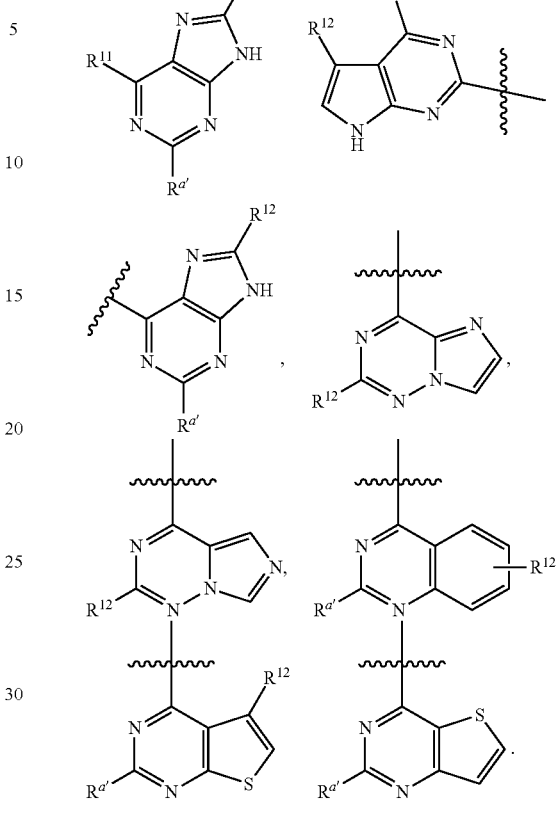

wherein $R^{a'}$ is hydrogen, halo, phosphate, urea, a carbonate, unsubstituted or substituted amino, unsubstituted or substituted alkyl, unsubstituted or substituted alkenyl, unsubstituted or substituted alkynyl, unsubstituted or substituted cycloalkyl, unsubstituted or substituted heteroalkyl, or unsubstituted or substituted heterocycloalkyl; $R^{11}$ is hydrogen, unsubstituted or substituted alkyl, halo (which includes —I, —F, —Cl, or —Br), unsubstituted or substituted amino, unsubstituted or substituted amido, hydroxy, or unsubstituted or substituted alkoxy, phosphate, unsubstituted or substituted urea, or carbonate; and $R^{12}$ is H, unsubstituted or substituted alkyl, unsubstituted or substituted cyano, unsubstituted or substituted alkynyl, unsubstituted or substituted alkenyl, halo, unsubstituted or substituted aryl, unsubstituted or substituted heteroaryl, unsubstituted or substituted heterocycloalkyl, unsubstituted or substituted cycloalkyl, unsubstituted or substituted amino, carboxylic acid, unsubstituted or substituted alkoxycarbonyl, unsubstituted or substituted amido, unsubstituted or substituted acyl, or unsubstituted or substituted sulfonamido.

In certain embodiments, $W_d$ is

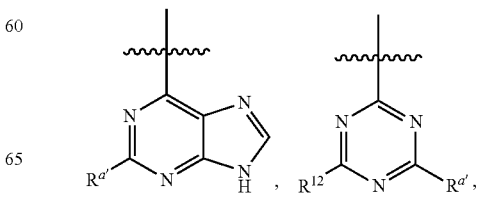

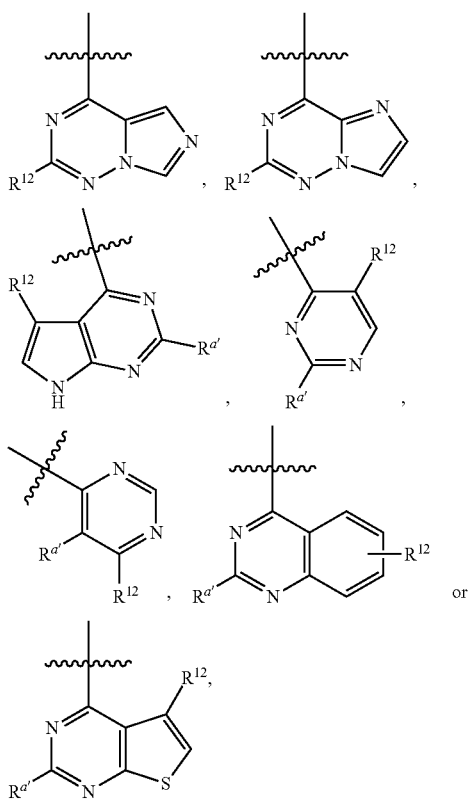

wherein $R^{a'}$ and $R^{12}$ are as defined herein.

In some embodiments of $W_d$ of the compounds of Formula I, when $R^{a'}$ is alkyl, alkynyl, cycloalkyl, heteroalkyl, or heterocycloalkyl, it is substituted by phosphate, urea, or carbonate.

In some embodiments of $W_d$ of the compounds of Formula I, when $R^{11}$ is alkyl, amino, amido, hydroxy, or alkoxy, it is substituted by phosphate, urea, or carbonate.

In some embodiments of the compound of Formula I, —X—Y—$W_d$ is one of the following moieties:

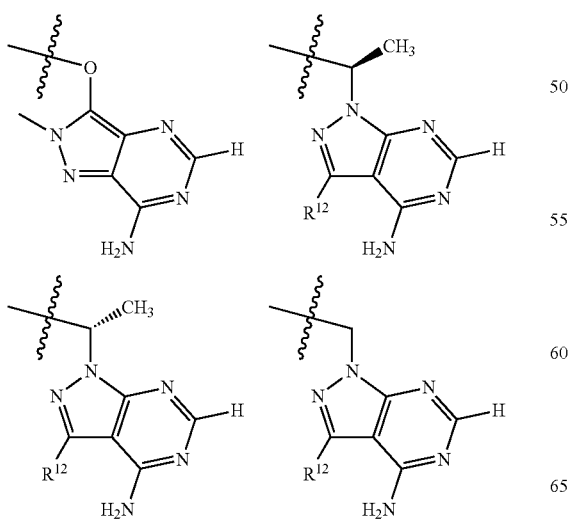

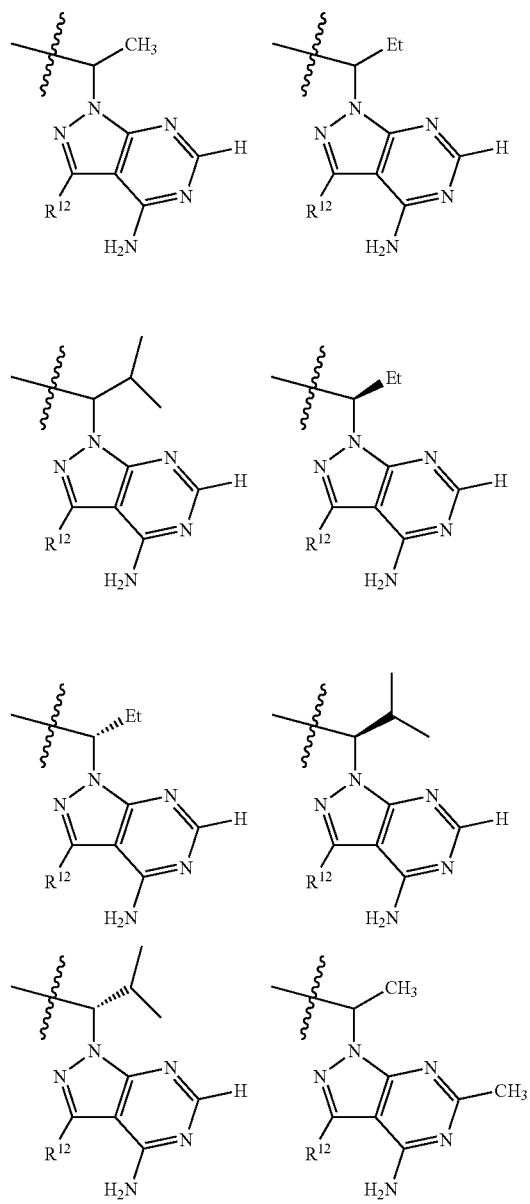

85
-continued
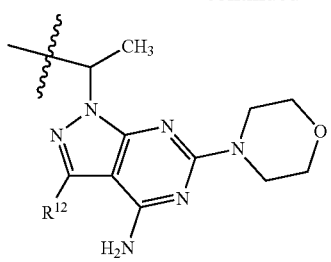
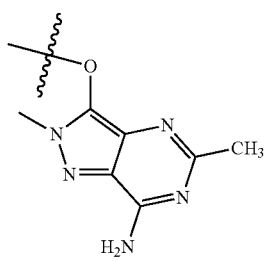
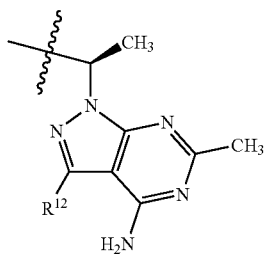
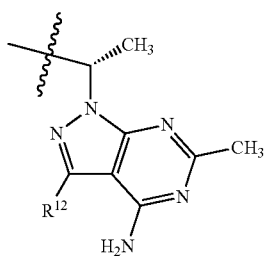
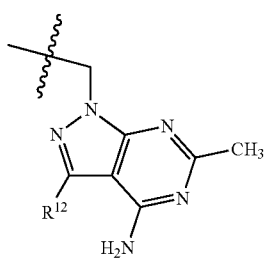
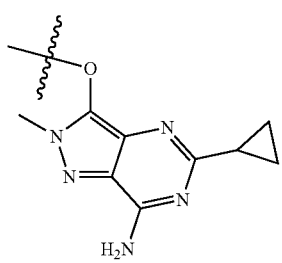
86
-continued
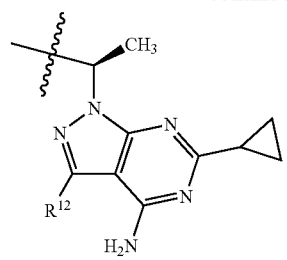
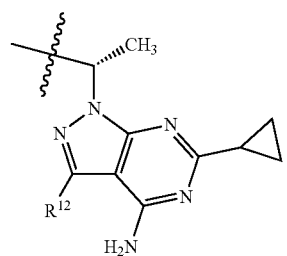
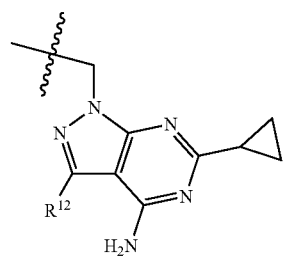
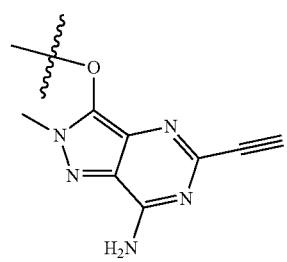
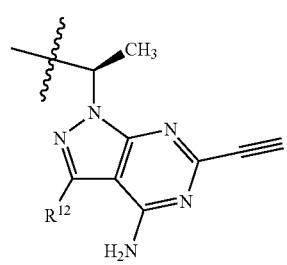
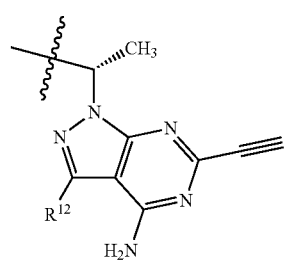

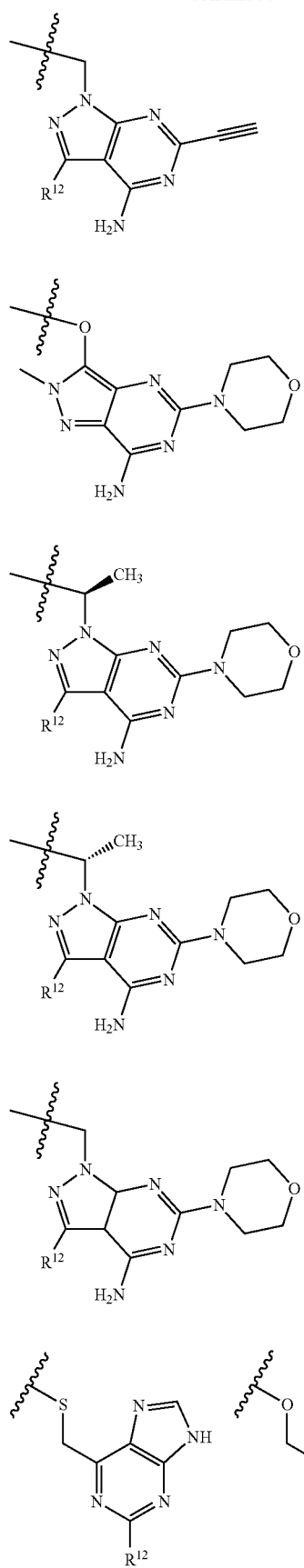
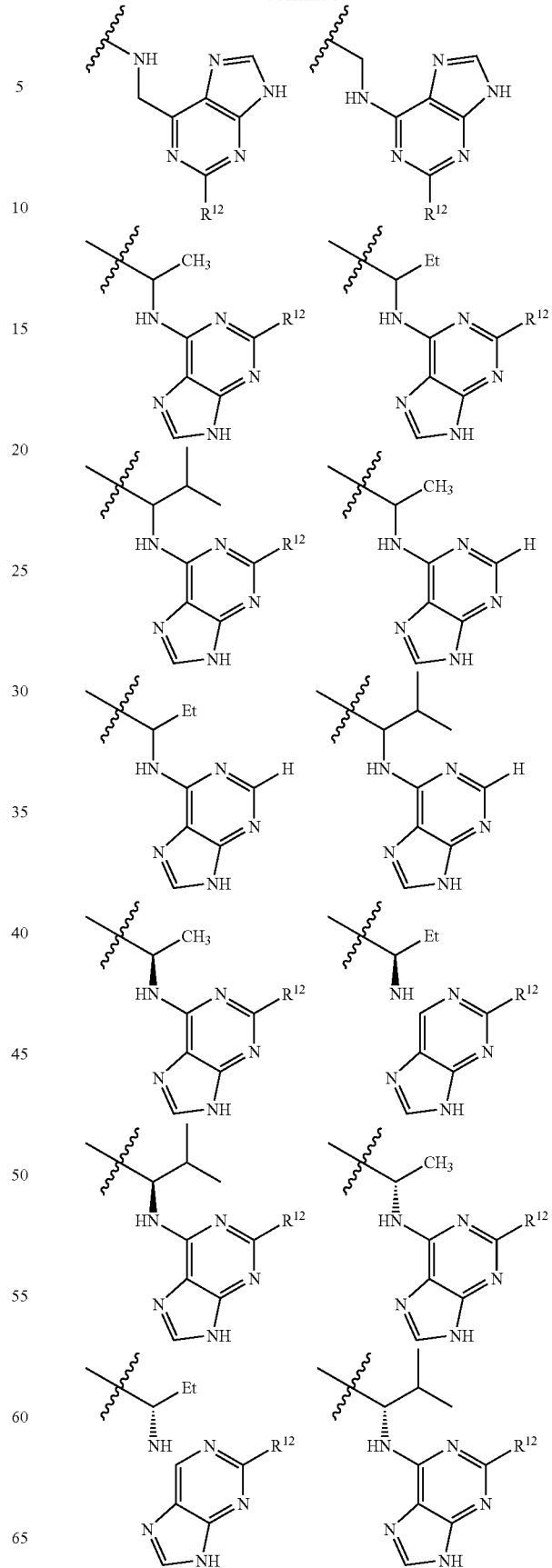

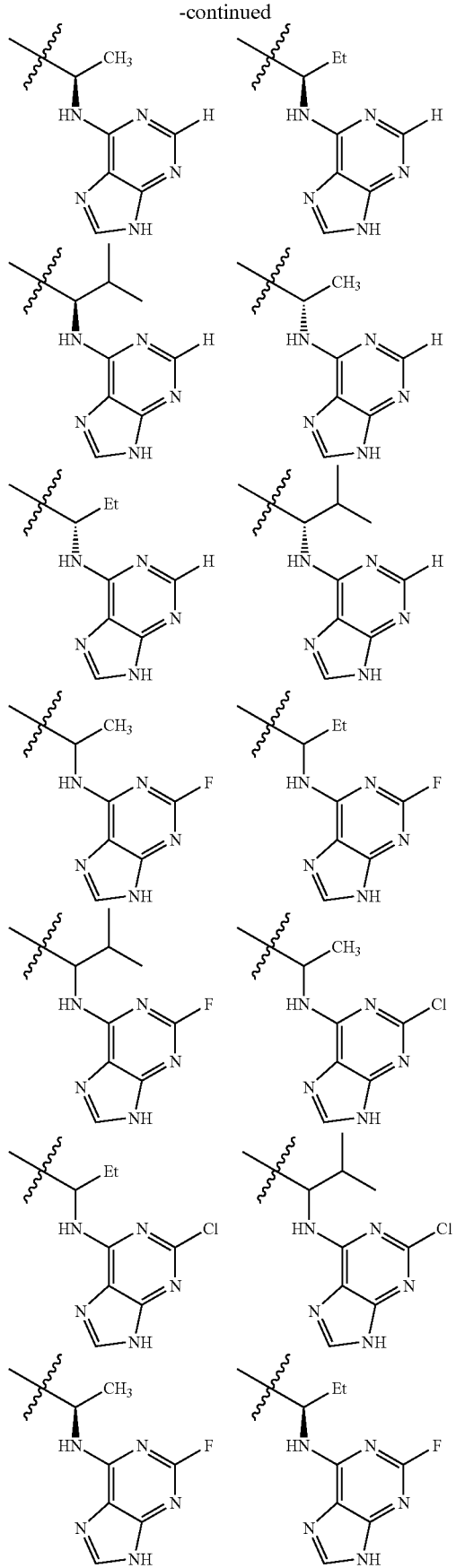
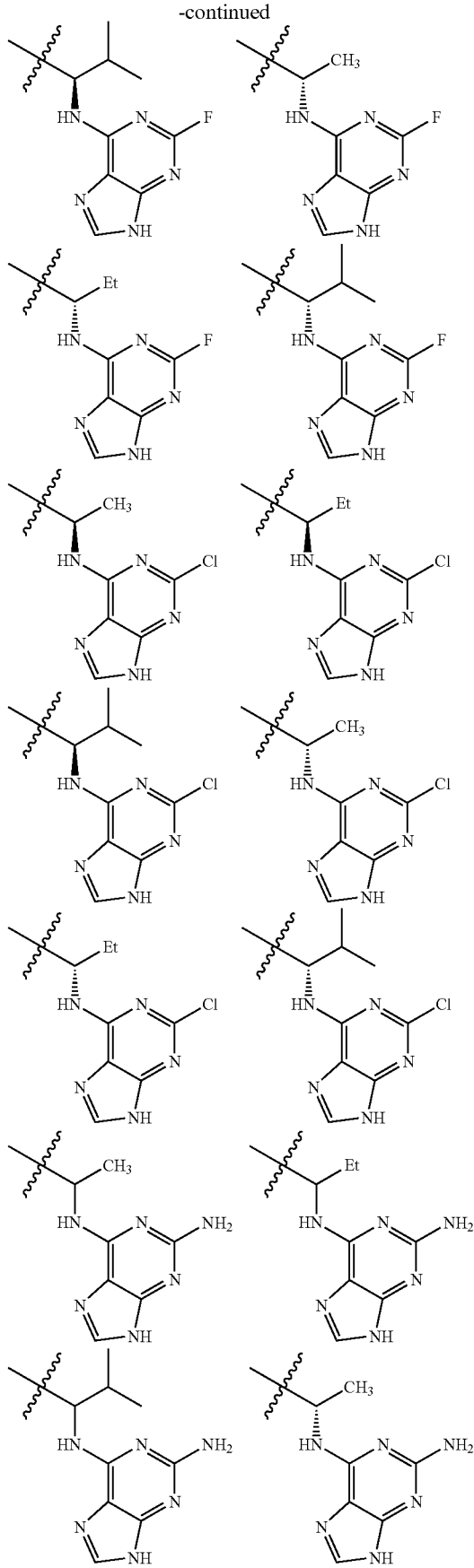

91
-continued
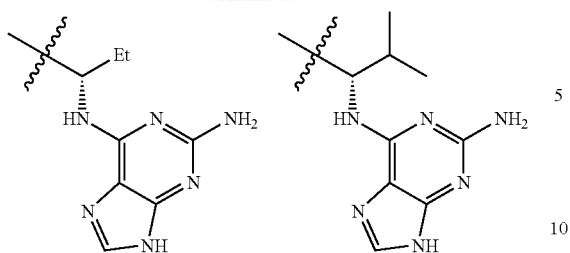
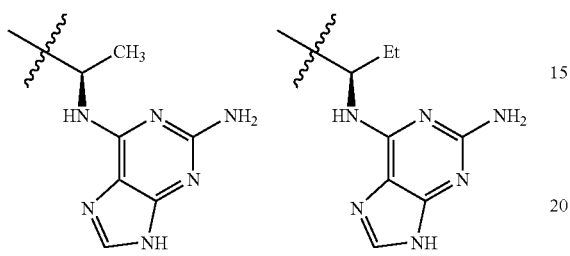
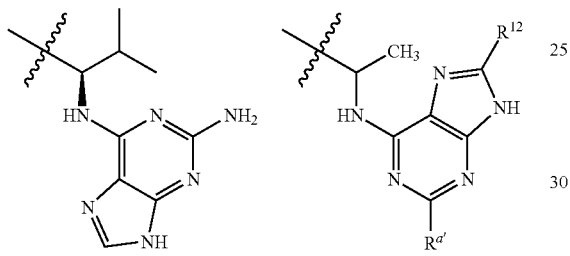
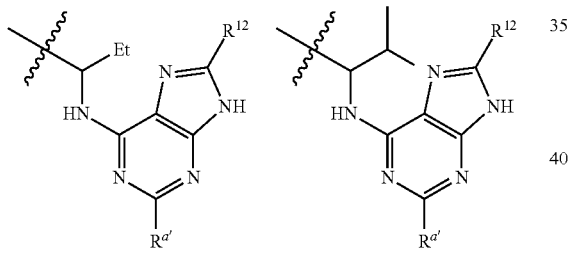
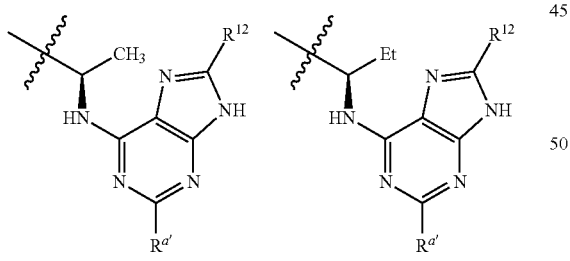
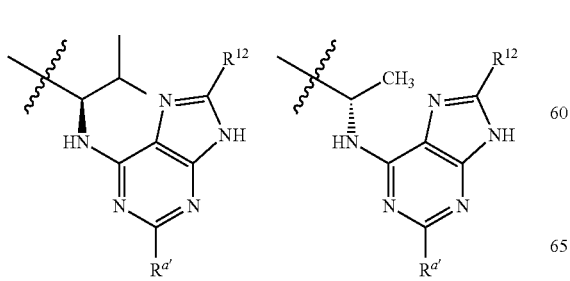
92
-continued
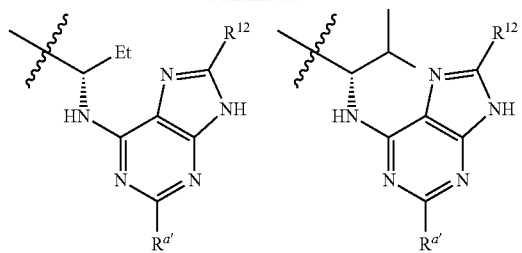
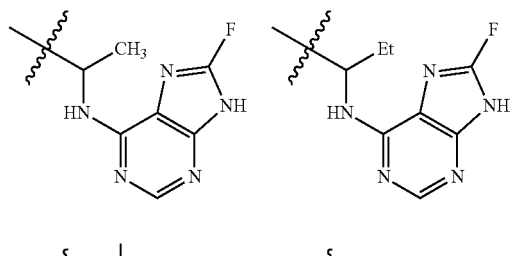
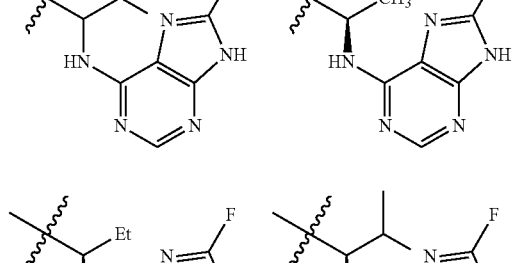
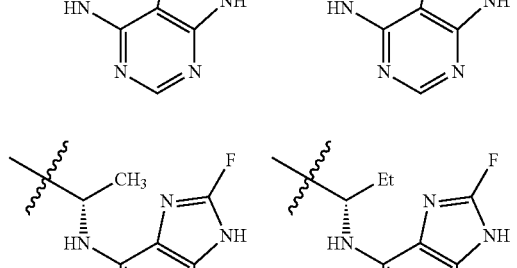
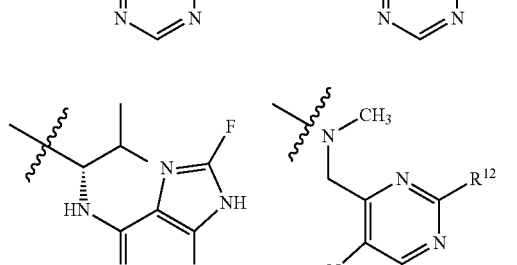
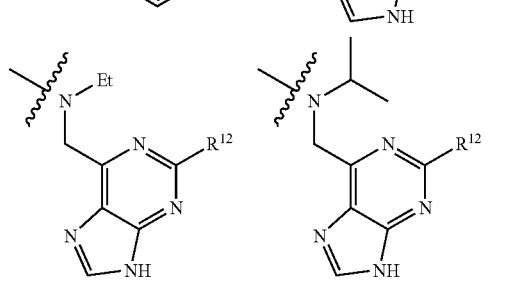

93
-continued
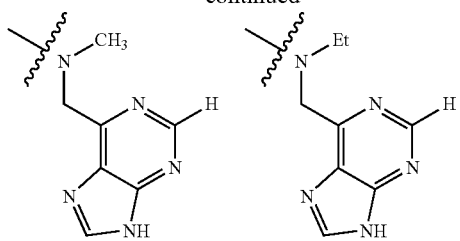
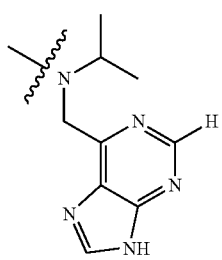
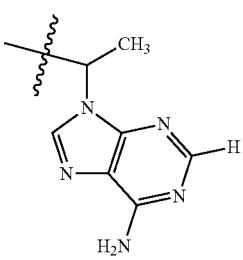
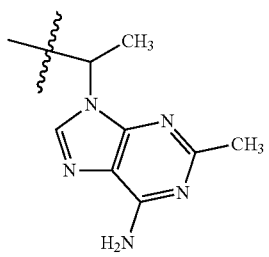
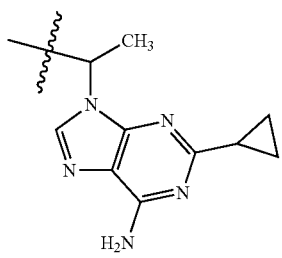
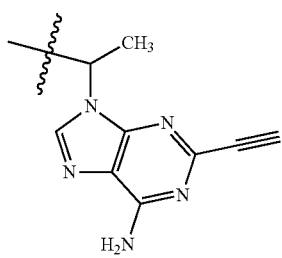
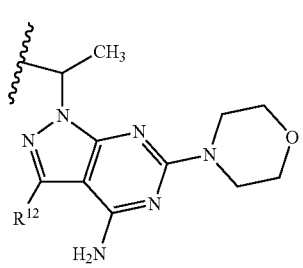
94
-continued
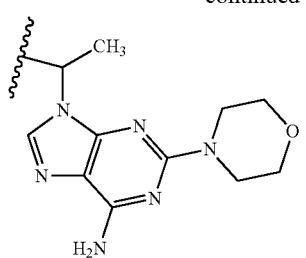
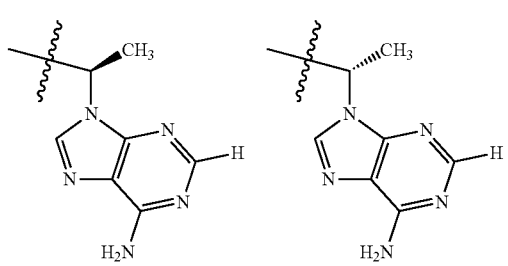
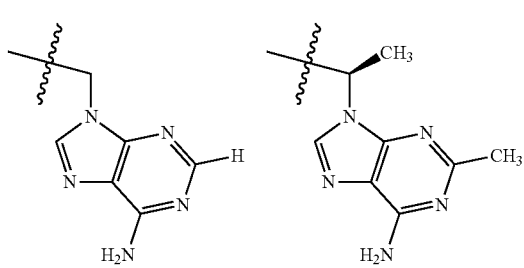
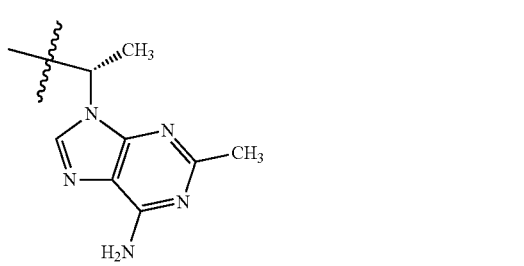
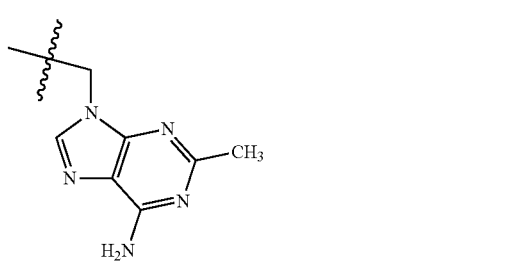
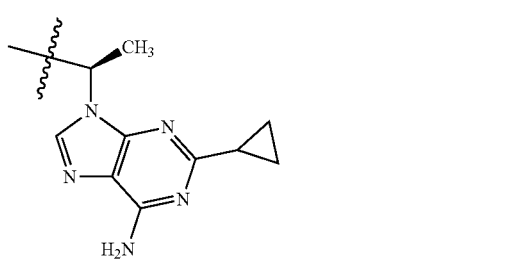

95
-continued
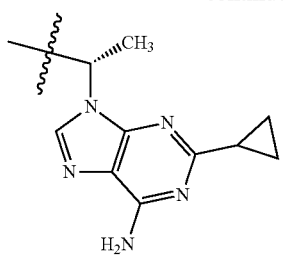
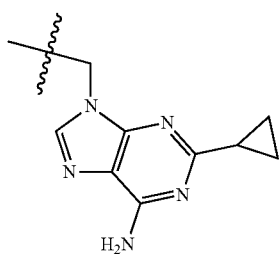
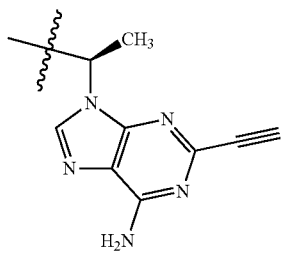
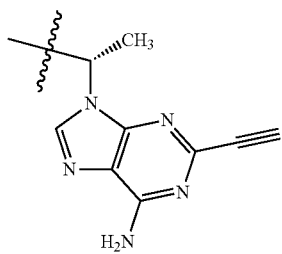
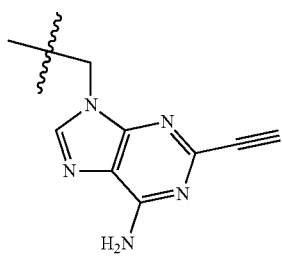
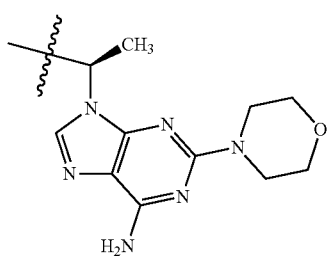
96
-continued
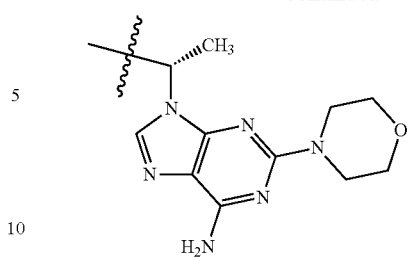
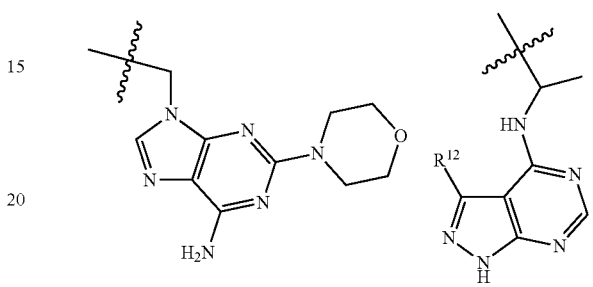
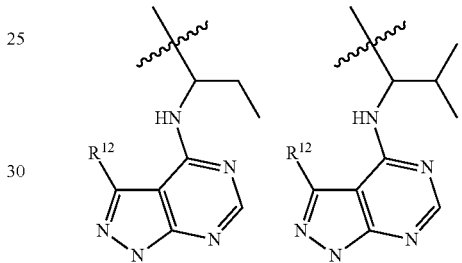
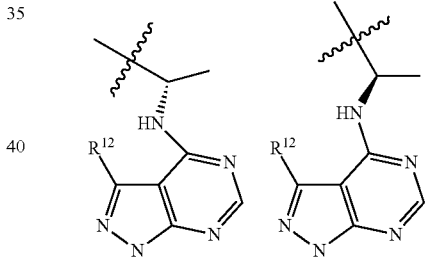
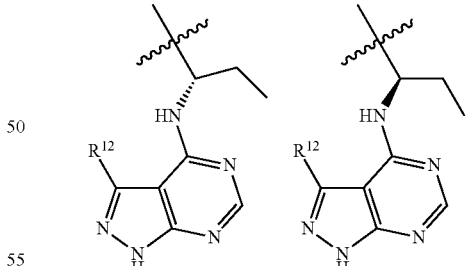
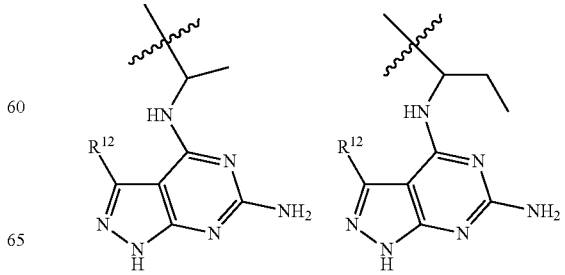

-continued
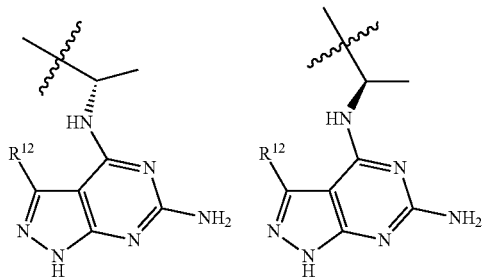
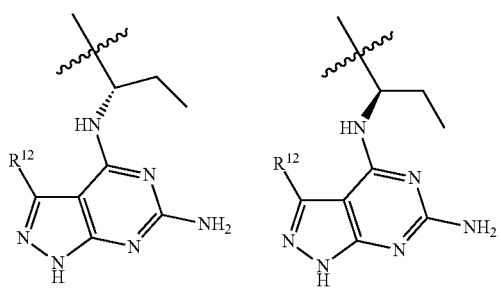
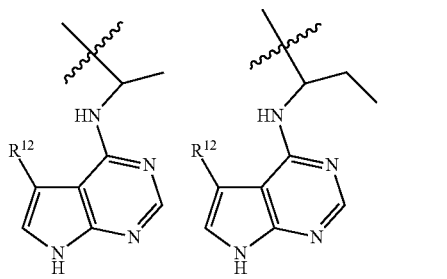
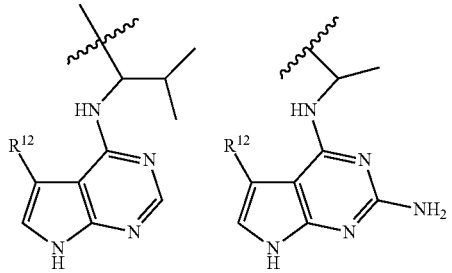
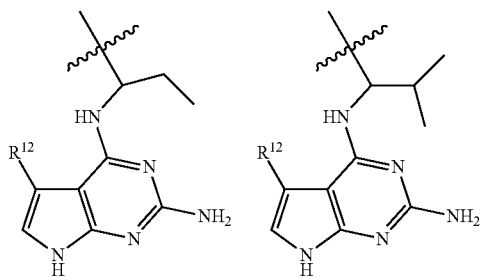
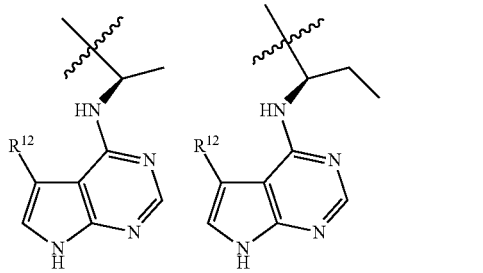
-continued
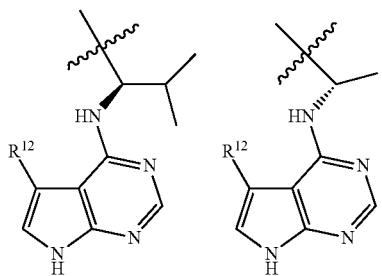
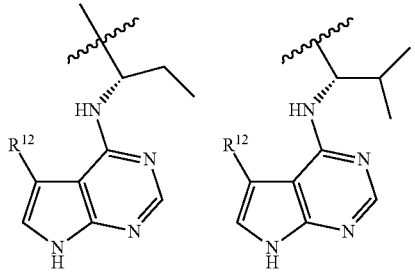
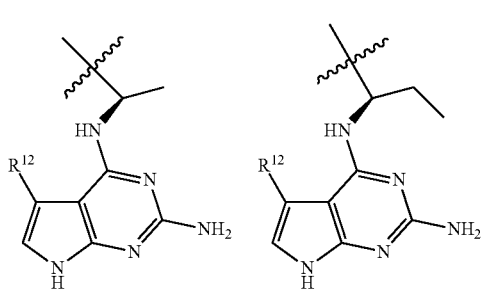
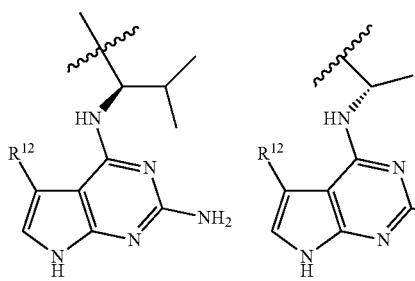
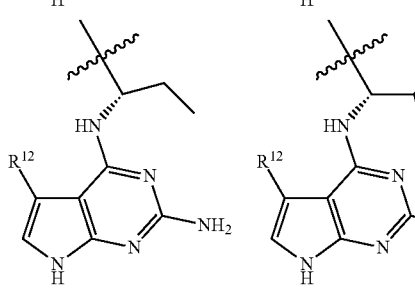
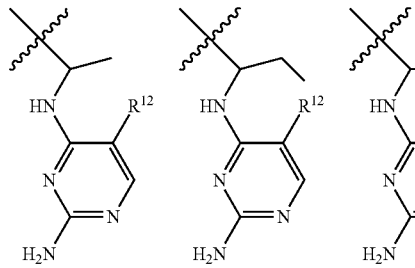

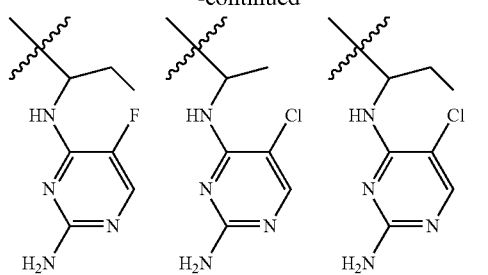
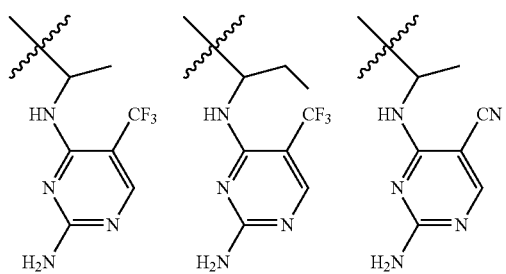
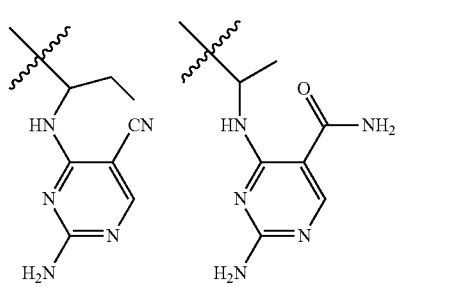
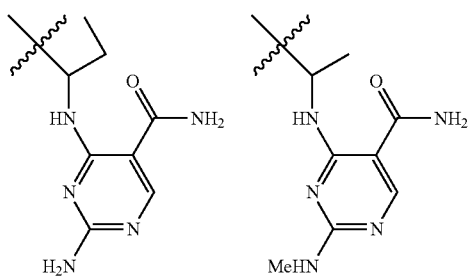
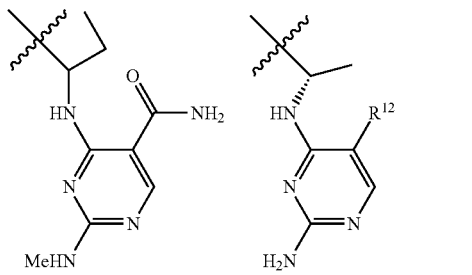
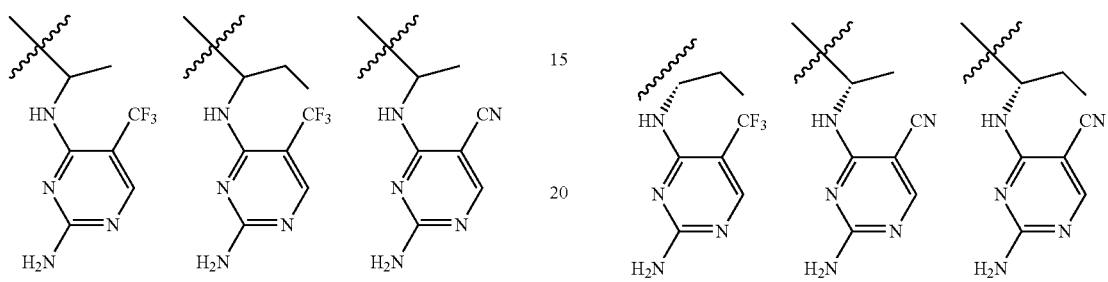
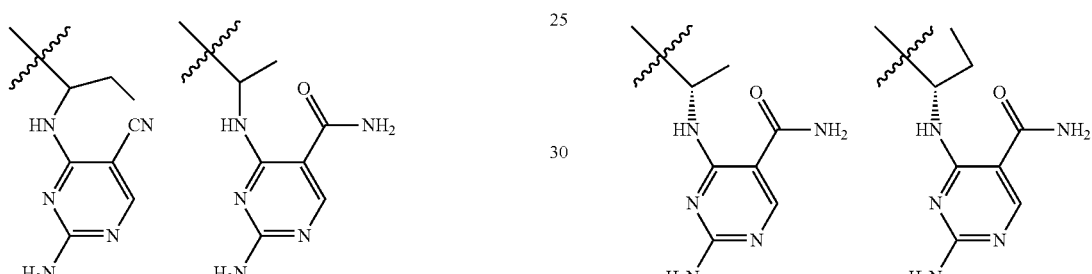
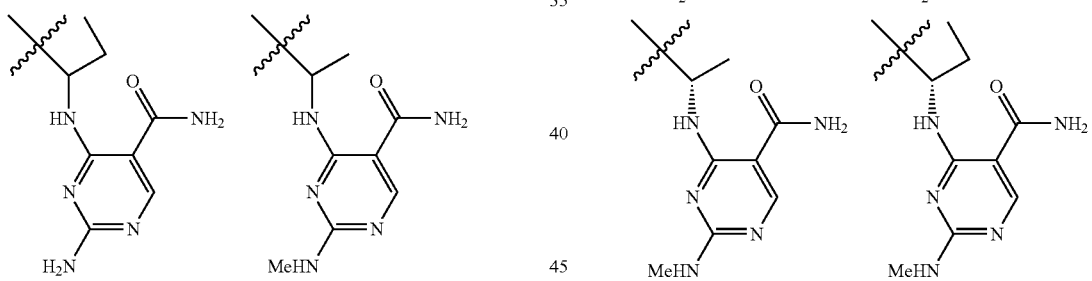
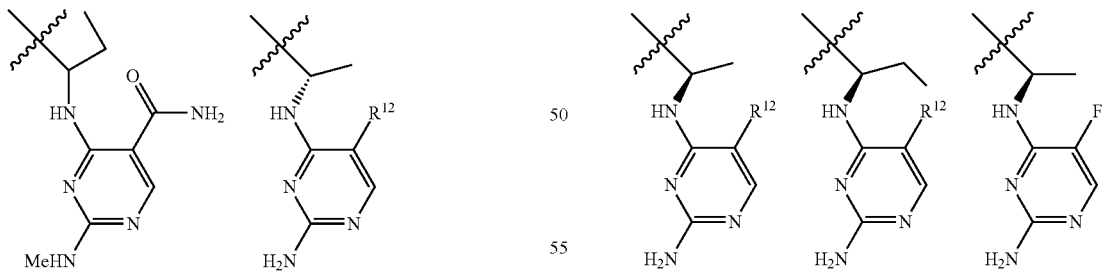
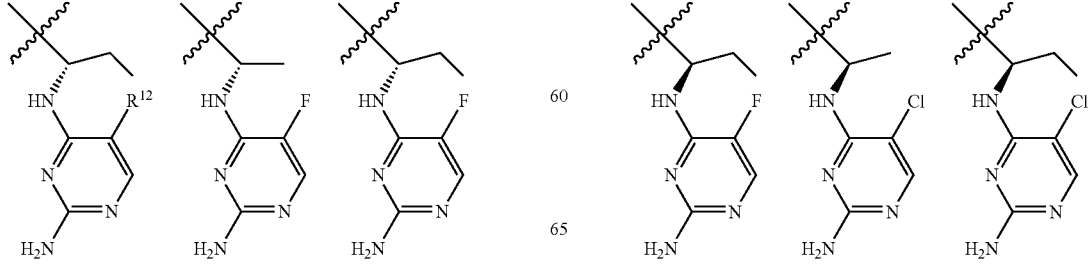

101
-continued
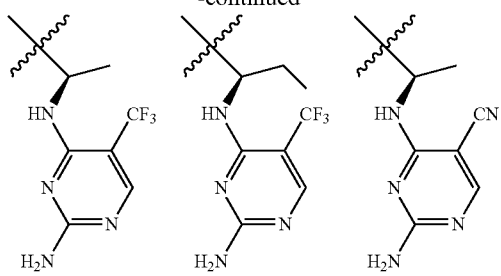
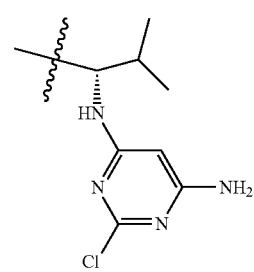
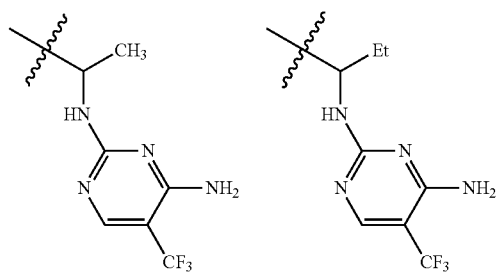
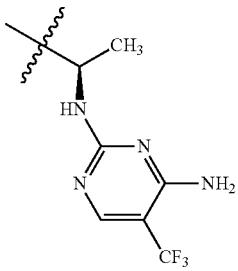
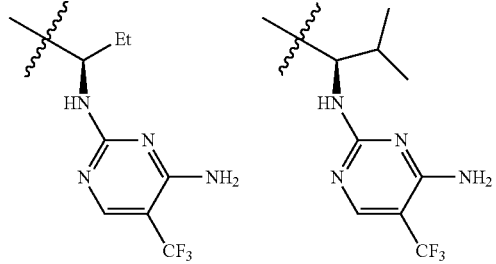
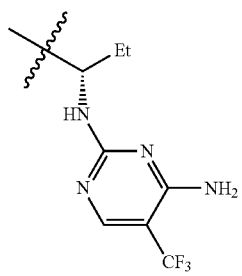
102
-continued
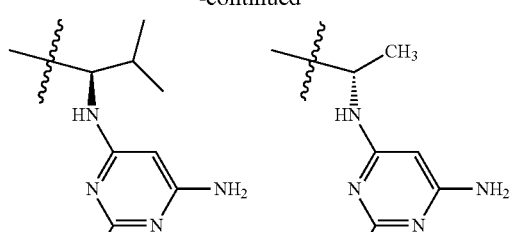

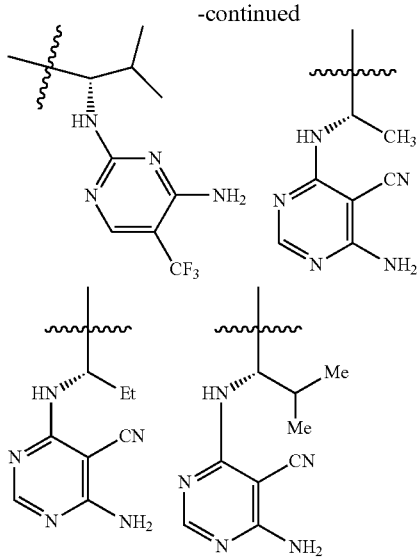

In some embodiments of the compound of Formula I, $R^{12}$ is selected from hydrogen, cyano, halo, unsubstituted or substituted alkyl, unsubstituted or substituted alkynyl, and unsubstituted or substituted alkenyl. In some embodiments, $R^{12}$ is unsubstituted or substituted aryl. In some embodiments, $R^{12}$ is unsubstituted or substituted heteroaryl, which includes, but is not limited to, heteroaryl having a five membered ring, heteroaryl having a six membered ring, heteroaryl with at least one nitrogen ring atom, heteroaryl with two nitrogen ring atoms, monocylic heteroaryl, and bicylic heteroaryl. In some embodiments, $R^{12}$ is unsubstituted or substituted heterocycloalkyl, which includes, but is not limited to, heterocycloalkyl with one nitrogen ring atom, heterocycloalkyl with one oxygen ring atom, heterocycloalkyl with one sulfur ring atom, 5 membered heterocycloalkyl, 6 membered heterocycloalkyl, saturated heterocycloalkyl, unsaturated heterocycloalkyl, heterocycloalkyl having an unsaturated moiety connected to the heterocycloalkyl ring, heterocycloalkyl substituted by oxo, and heterocycloalkyl substituted by two oxo. In some embodiments, $R^{12}$ is unsubstituted or substituted cycloalkyl, including but not limited to cyclopropyl, cyclobutyl, cyclopentyl, cyclohexyl, cycloalkyl substituted by one oxo, or cycloalkyl having an unsaturated moiety connected to the cycloalkyl ring. In some embodiments, $R^{12}$ is unsubstituted or substituted amido, carboxylic acid, unsubstituted or substituted acyloxy, unsubstituted or substituted alkoxycarbonyl, unsubstituted or substituted acyl, or unsubstituted or substituted sulfonamido.

In some embodiments, when $R^{12}$ is alkyl, alkynyl, alkenyl, aryl, heteroaryl, heterocycloalkyl, or cycloalkyl, it is substituted with phosphate. In some embodiments, when $R^{12}$ is alkyl, alkynyl, alkenyl, aryl, heteroaryl, heterocycloalkyl, or cycloalkyl, it is substituted with urea. In some embodiments, when $R^{12}$ is alkyl, alkynyl, alkenyl, aryl, heteroaryl, heterocycloalkyl, or cycloalkyl, it is substituted with carbonate.

In some embodiments, when $R^{12}$ is alkyl, alkynyl, alkenyl, aryl, heteroaryl, heterocycloalkyl, cycloalkyl, alkoxycarbonyl, amido, acyloxy, acyl, or sulfonamido, it is substituted with one or more of alkyl, heteroalkyl, alkenyl, alkynyl, cycloalkyl, heterocycloalkyl, aryl, heteroaryl, alkoxy, amido, amino, acyl, acyloxy, alkoxycarbonyl, sulfonamido, halo, cyano, hydroxy or nitro, each of which alkyl, heteroalkyl, alkenyl, alkynyl, cycloalkyl, heterocycloalkyl, aryl, heteroaryl, alkoxy, amido, amino, acyl, acyloxy, alkoxycarbonyl, or sulfonamido can itself be substituted.

In some embodiments, $R^{12}$ of $W_d$ is one of the following moieties:

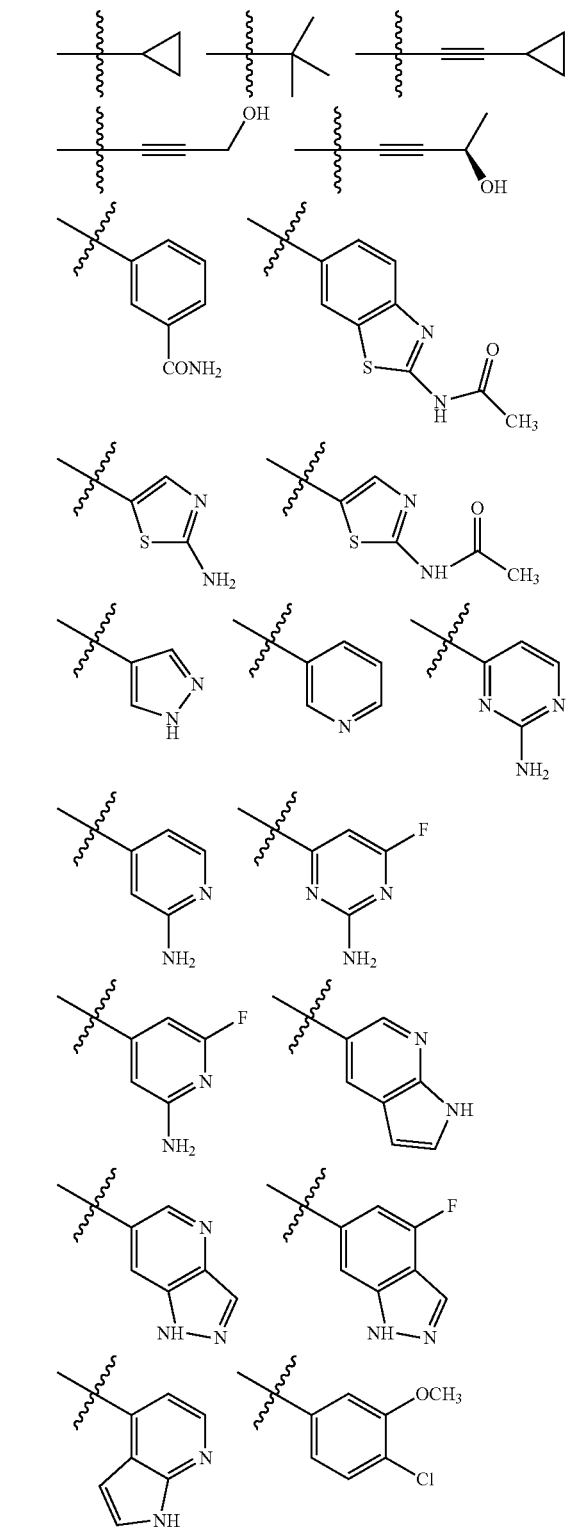

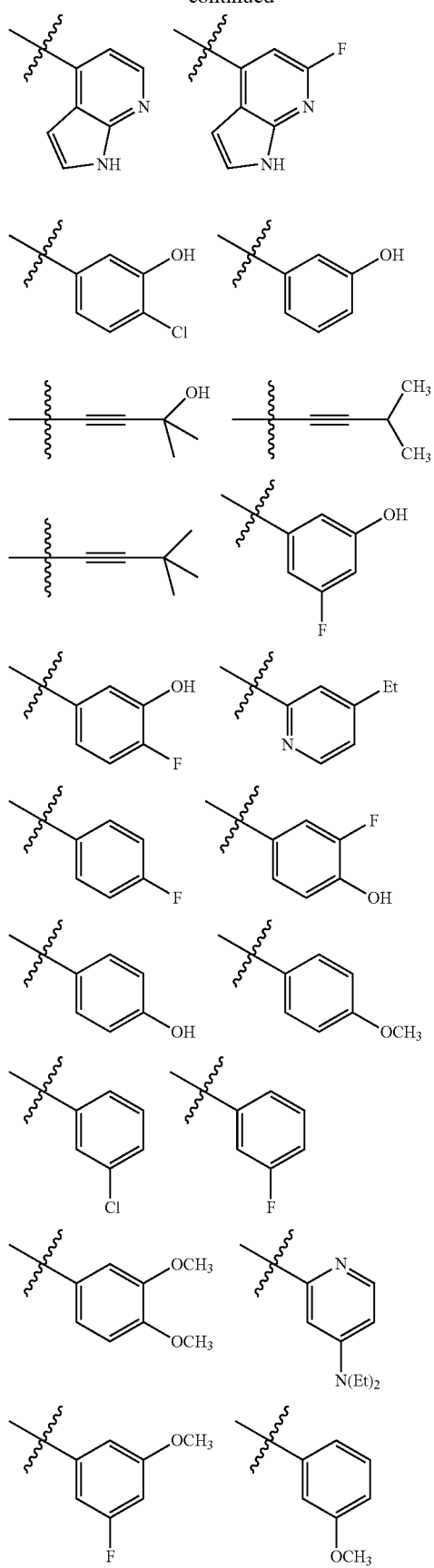
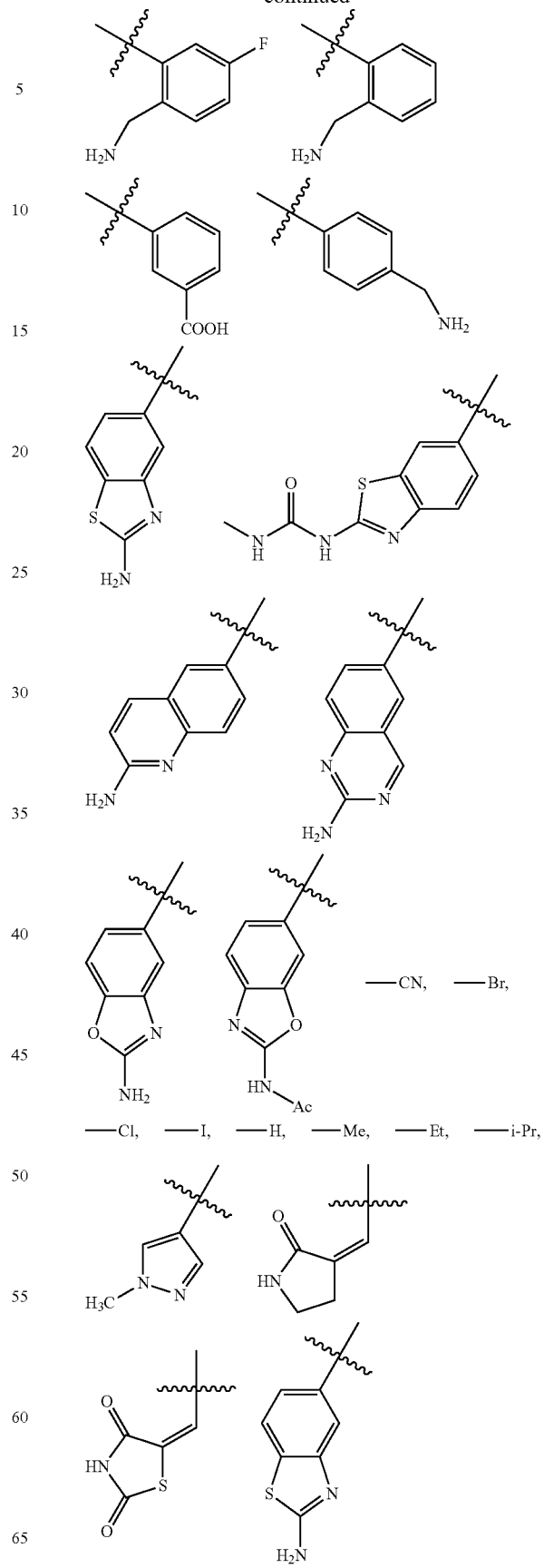

-continued

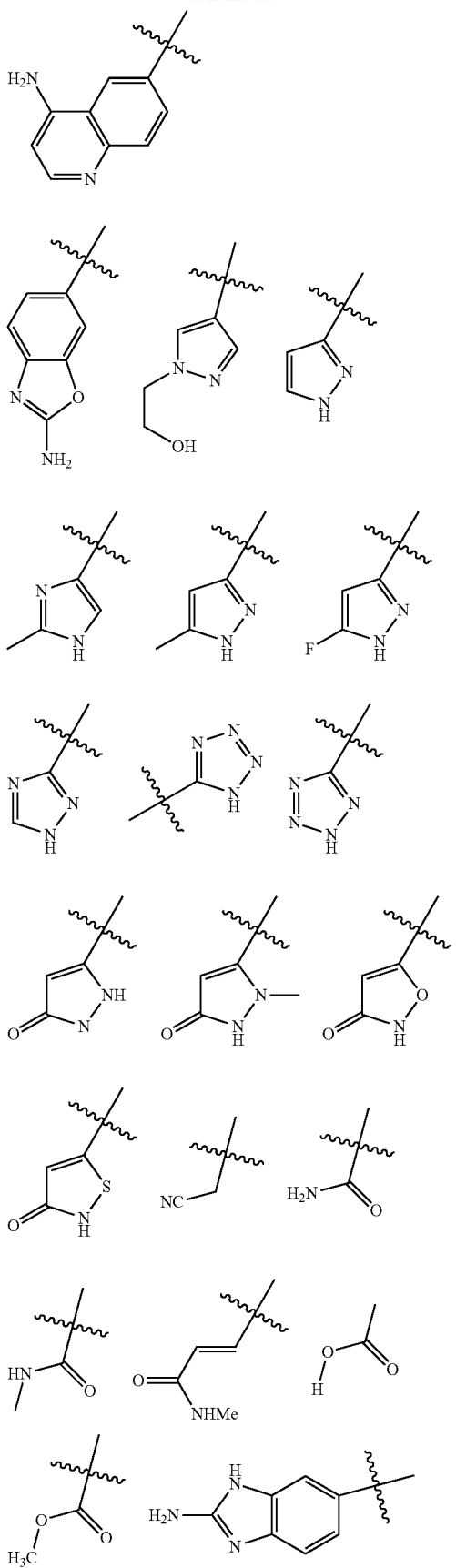

-continued

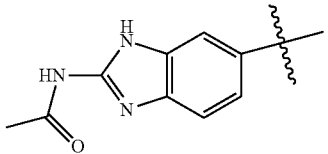

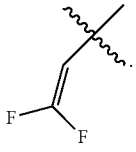

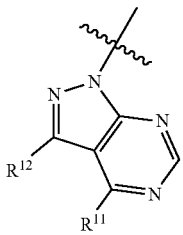

In some embodiments, $W_d$ is a pyrazolopyrimidine of Formula III:

Formula III

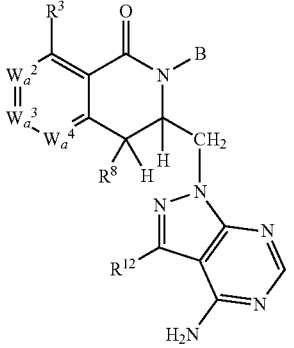

wherein $R^{11}$ is H, alkyl, halo, amino, amido, hydroxy, or alkoxy, and $R^{12}$ is H, alkyl, alkynyl, alkenyl, halo, aryl, heteroaryl, heterocycloalkyl, or cycloalkyl. In some embodiments, $R^{11}$ is amino and $R^{12}$ is H, alkyl, alkynyl, alkenyl, halo, aryl, heteroaryl, heterocycloalkyl, or cycloalkyl. In some embodiments, $R^{11}$ is amino and $R^{12}$ is alkyl, halo, aryl, heteroaryl, heterocycloalkyl, or cycloalkyl. In some embodiments, $R^{11}$ is amino and $R^{12}$ is monocyclic heteroaryl. In some embodiments, $R^{11}$ is amino and $R^{12}$ is bicyclic heteroaryl. In some embodiments, $R^{11}$ is amino and $R^{12}$ is cyano, amino, carboxylic acid, acyloxy, alkoxycarbonyl, or amido.

In some embodiments, the compound of Formula I is a compound which has a structure selected from Formula XXIII-A, XXIII-B, XXIV-A, XXIV-B, XXV, XXVI, XXVI-A, XXVII, XXVII-A, XXVII-B, XXVII-C, XXVII-C1, XXVII-C2, XXVII-D, and XXVII-D:

Formula XXIII-A

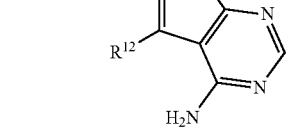

Formula XXIII-B
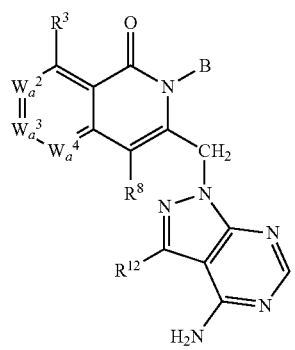
Formula XXIV-A
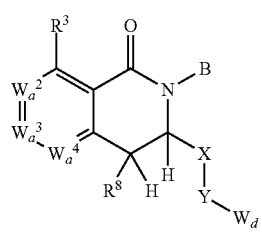
Formula XXIV-B
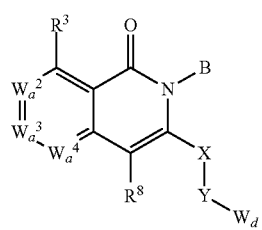
Formula XXV
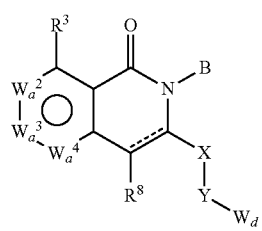
Formula XXVI
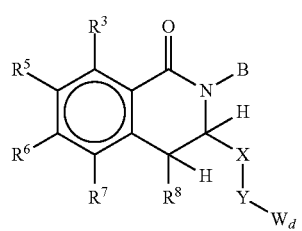
Formula XXVI-A
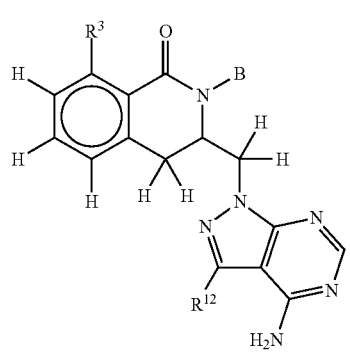
Formula XXVII
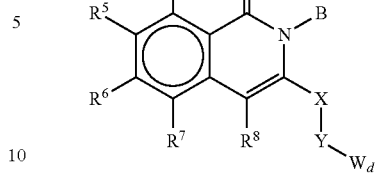
Formula XXVII-A
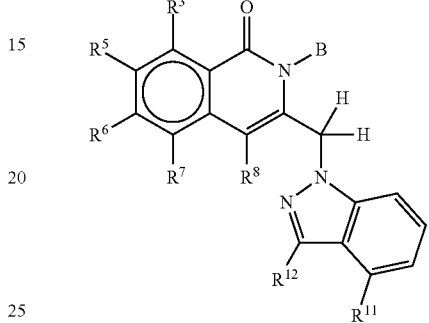
Formula XXVII-A1
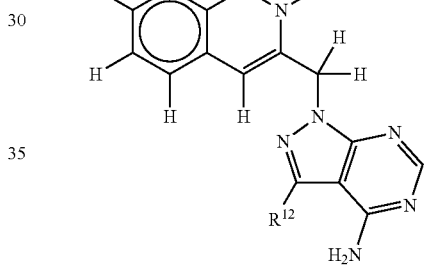
Formula XXVII-B
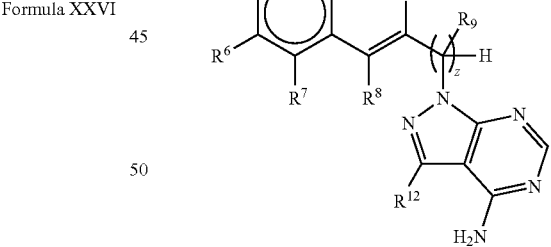
Formula XXVII-C
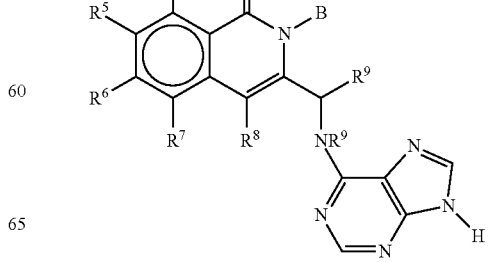

-continued

Formula XXVII-C1

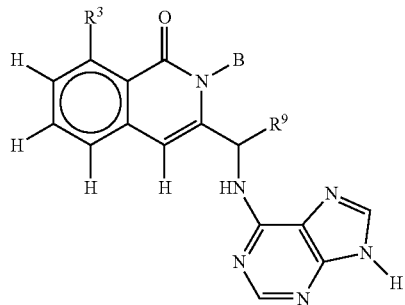

Formula XXVII-C2

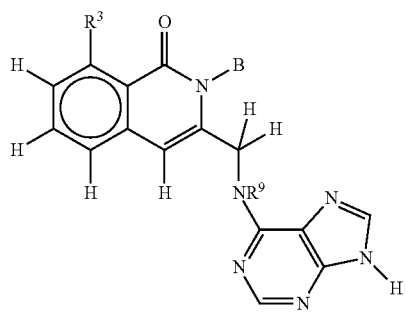

Formula XXVII-D

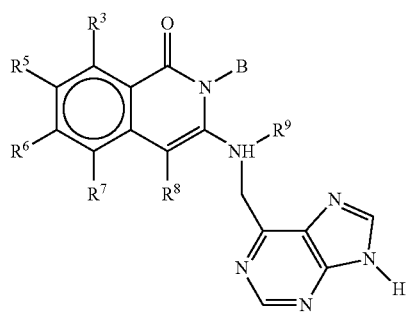

Formula XXVII-D

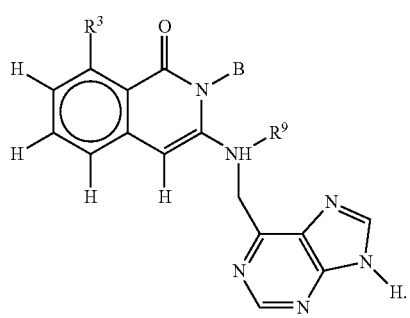

In another embodiment, the compound of Formula I is a compound which has a structure selected from Formula XXVIII, XXVIII-A, XXIX, XXIX-A, and XXIX-A1:

Formula XXVIII

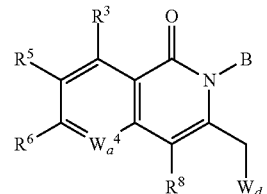

Formula XXVIII-A

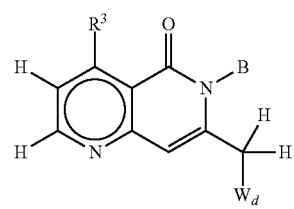

Formula XXIX

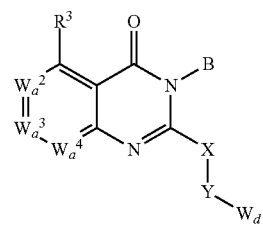

Formula XXIX-A

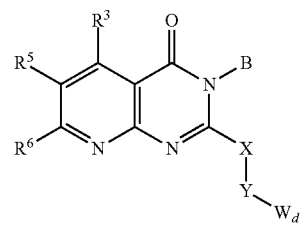

Formula XXIX-A1

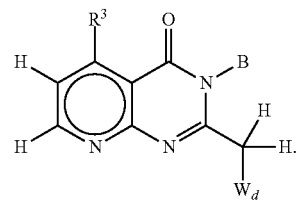

In one aspect, for compounds described herein, $R_3$ is H, $CH_3$, $CF_3$, Cl, F, aryl, or heteroaryl; B is alkyl or a moiety of Formula II:

Formula II

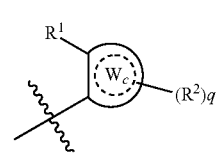

wherein $W_c$ is aryl, heteroaryl, heterocycloalkyl, or cycloalkyl; $R^1$ is H, —F, —Cl, —CN, —$CH_3$, isopropyl, —$CF_3$, —$OCH_3$, nitro, or phosphate; $R^2$ is halo, hydroxy, cyano, nitro, or phosphate; q is an integer of 0, 1, 2, 3, or 4; $R^5$, $R^6$, $R^7$, and $R^8$ are H; X is absent or $(CH_2)_z$; z is 1; Y is absent, —$N(R^9)$—, or —$N(R^9)$ $CH(R^9)$—; $R^9$ is hydrogen, $C_1$-$C_{10}$ alkyl, $C_3$-$C_7$ cycloalkyl, or $C_2$-$C_{10}$ heteroalkyl; and $W_d$ is pyrazolopyrimidine or purine.

TABLE 1

Illustrative B moieties of compounds of Formula I include, but are not limited to:

| Sub-class # | B |
|---|---|
| B-1 | cyclopentyl |
| B-2 | 4-(N-isopropyl)piperidinyl |
| B-3 | —CH(CH₃)₂ |
| B-4 | 2-(trifluoromethyl)phenyl |
| B-5 | cyclopropyl |
| B-6 | 2-chlorophenyl |
| B-7 | 2-methylphenyl |
| B-8 | 3-methylpyridin-2-yl |
| B-9 | 2-ethylphenyl |
| B-10 | 2-fluorophenyl |
| B-11 | 4-(N-methyl)piperidinyl |
| B-12 | 2-isopropylphenyl |
| B-13 | 2-methoxyphenyl |
| B-14 | 3-fluorophenyl |
| B-15 | 2-hydroxyphenyl |
| B-16 | 2-cyanophenyl |
| B-17 | 3-cyanophenyl |
| B-18 | 4-cyanophenyl |
| B-19 | 2-(morpholin-4-yl)ethyl |
| B-20 | phenyl |
| B-21 | 2-methyl-4-methoxyphenyl |

TABLE 1-continued

Illustrative B moieties of compounds of Formula I include, but are not limited to:

| Sub-class # | B |
|---|---|
| B-22 | 4-methylpyridin-3-yl |
| B-23 | 3-nitrophenyl |
| B-24 | 2-(2-morpholinoethoxy)phenyl |
| B-25 | tetrahydro-2H-pyran-4-yl |
| B-26 | 3-(4-methylpiperazin-1-yl)propyl |
| B-27 | pyridin-2-yl |
| B-28 | 6-chloropyridin-2-yl |
| B-29 | 6-methylpyridin-2-yl |
| B-30 | 5-methylpyridin-2-yl |
| B-31 | 4-methylpyridin-2-yl |
| B-32 | 6-methoxypyridin-2-yl |
| B-33 | 2-(trifluoromethyl)pyridin-4-yl |
| B-34 | 1H-indazol-5-yl |
| B-35 | 1H-indazol-6-yl |
| B-36 | 5-aminopyridin-2-yl |
| B-37 | 6-aminopyridin-2-yl |
| B-38 | 6-cyanopyridin-2-yl |
| B-39 | methyl 6-(pyridin-2-yl)nicotinate ester |

TABLE 1-continued

Illustrative B moieties of compounds of Formula I include, but are not limited to:

| Sub-class # | B |
|---|---|
| B-40 | 5-chloropyrazin-2-yl |
| B-41 | methyl 6-pyridine-2-carboxylate (6-linked) |
| B-42 | methyl 4-pyridine-2-carboxylate |
| B-43 | 2-cyanopyridin-4-yl |
| B-44 | 2-methylpyridin-4-yl |
| B-45 | 6-oxo-1,6-dihydropyridin-2-yl |
| B-46 | 5-hydroxypyridin-2-yl |
| B-47 | 5-fluoropyridin-2-yl |
| B-48 | 2-aminopyridin-4-yl |
| B-49 | 5-methoxypyrazin-2-yl |
| B-50 | 5-aminopyrazin-2-yl |
| B-51 | 5-methylpyrazin-2-yl |
| B-52 | 5-(dimethylamino)pyrazin-2-yl |
| B-53 | 5-(N-methyl-N-ethylamino)pyrazin-2-yl |
| B-54 | 5-(diethylamino)pyrazin-2-yl |
| B-55 | 5-(4-methylpiperazin-1-yl)pyrazin-2-yl |
| B-56 | 5-(pyrrolidin-1-yl)pyrazin-2-yl |
| B-57 | 5-(piperidin-1-yl)pyrazin-2-yl |

TABLE 1-continued

Illustrative B moieties of compounds of Formula I include, but are not limited to:

| Sub-class # | B |
|---|---|
| B-58 | pyrazine-morpholine |
| B-59 | pyrazine-(4-methylpiperidine) |
| B-60 | pyrazine-(2-methylpiperidine) |
| B-61 | pyrazine-pyrrole |
| B-62 | pyrazine-imidazole |
| B-63 | pyrazine-(2-methylimidazole) |
| B-64 | pyrazine-(4-methylimidazole) |
| B-65 | pyrazine-pyrazole |
| B-66 | pyrazine-(4-methylpyrazole) |
| B-67 | pyrazine-(3-methylpyrazole) |
| B-68 | pyrazine-(2-oxopyridine) |
| B-69 | pyrazine-CN |
| B-70 | pyrazine-OMe |
| B-71 | pyrazine-NMe$_2$ |
| B-72 | pyrazine-NEt$_2$ |

TABLE 1-continued

Illustrative B moieties of compounds of Formula I include, but are not limited to:

| Sub-class # | B |
| --- | --- |
| B-73 | pyrazine with morpholine |
| B-74 | chloropyrazine |
| B-75 | pyrazine with imidazole |
| B-76 | pyrazine with pyridinone |
| B-77 | pyrazine with pyrrolidine |
| B-78 | pyrazine |
| B-79 | thiazole |
| B-80 | 2-methylthiazole |
| B-81 | 2-isopropylthiazole |
| B-82 | 2-(N-methyl-N-ethylamino)thiazole |
| B-83 | 2-(diethylamino)thiazole |
| B-84 | thiazole with pyridinone |
| B-85 | thiazole with imidazole |
| B-86 | cyclohexyl |
| B-87 | —CH₃ |
| B-88 | —CH₂CH₃ |
| B-89 | cyclobutyl |
| B-90 | 4-methylpyridin-3-yl |
| B-91 | pyrrolidinylpropyl |
| B-92 | 3,5-dimethylphenyl |

TABLE 1-continued

Illustrative B moieties of compounds of Formula I include, but are not limited to:

| Sub-class # | B |
|---|---|
| B-93 | 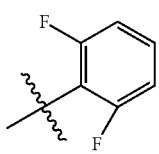 [SMILES: *c1c(F)cccc1F] |
| B-94 | 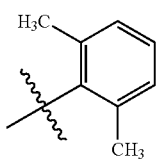 |
| B-95 | 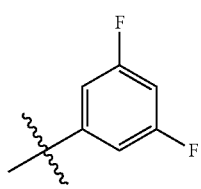 [SMILES: *c1cc(F)cc(F)c1] |
| B-96 | 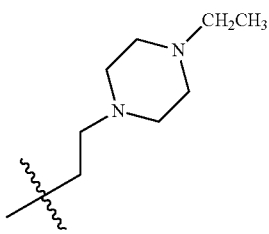 [SMILES: *CCN1CCN(CC)CC1] |
| B-97 | 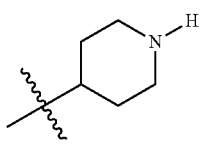 [SMILES: *C1CCNCC1] |
| B-98 | 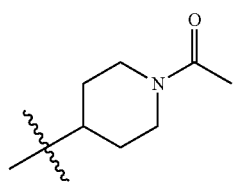 [SMILES: *C1CCN(C(C)=O)CC1] |
| B-99 | 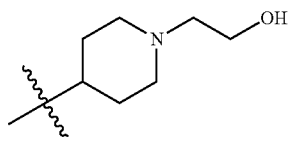 [SMILES: *C1CCN(CCO)CC1] |
| B-100 | 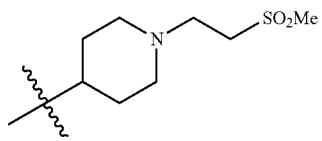 [SMILES: *C1CCN(CCS(C)(=O)=O)CC1] |

TABLE 1-continued

Illustrative B moieties of compounds of Formula I include, but are not limited to:

| Sub-class # | B |
|---|---|
| B-101 | 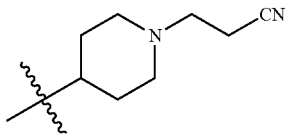 [SMILES: *C1CCN(CCC#N)CC1] |
| B-102 | 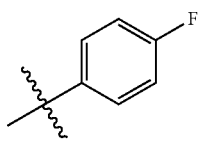 [SMILES: *c1ccc(F)cc1] |

TABLE 2

Illustrative $R^{12}$ moieties of compounds of Formula I include, but are not limited to:

| Sub-class # | $R^{12}$ |
|---|---|
| 12-1 | —CN |
| 12-2 | —Br |
| 12-3 | —Cl |
| 12-4 | —CH$_2$CH$_3$ |
| 12-5 | —CH$_3$ |
| 12-6 | —CH(CH$_3$)$_2$ |
| 12-7 | 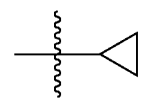 [SMILES: *C1CC1] |
| 12-8 | 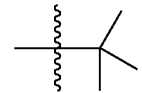 [SMILES: *C(C)(C)C] |
| 12-9 | 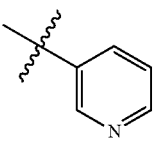 [SMILES: *c1cccnc1] |
| 12-10 | 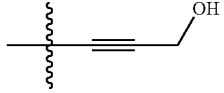 |
| 12-11 | 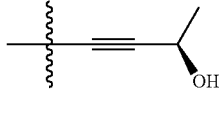 |
| 12-12 | 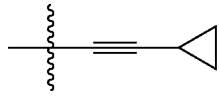 |
| 12-13 | 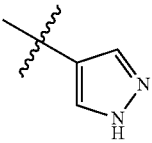 |

TABLE 2-continued

Illustrative $R^{12}$ moieties of compounds of Formula I include, but are not limited to:

| Sub-class # | $R^{12}$ |
|---|---|
| 12-14 | 3-carbamoylphenyl |
| 12-15 | 5-(2-acetamido)thiazolyl |
| 12-16 | 6-(2-acetamido)benzothiazolyl |
| 12-17 | 5-(2-amino)thiazolyl |
| 12-18 | 4-(2-amino)pyridyl |
| 12-19 | 4-(2-amino-6-fluoro)pyridyl |
| 12-20 | 4-(2-amino)pyrimidinyl |
| 12-21 | 4-(2-amino-6-fluoro)pyrimidinyl |
| 12-22 | 5-(7-azaindolyl) |
| 12-23 | 6-indazolyl |
| 12-24 | 6-(4-fluoro)indazolyl |
| 12-25 | 4-(7-azaindolyl) |
| 12-26 | 3-methoxyphenyl |
| 12-27 | 4-(6-fluoro-7-azaindolyl) |
| 12-28 | 3-hydroxy-3-methylbut-1-ynyl |

TABLE 2-continued
Illustrative R[12] moieties of compounds of Formula I include, but are not limited to:
| Sub-class # | R[12] |
|---|---|
| 12-29 | 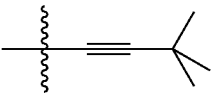 [SMILES: *C#CC(C)(C)C] |
| 12-30 | 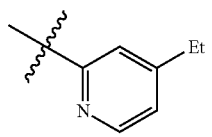 [SMILES: *c1cc(CC)ccn1] |
| 12-31 | 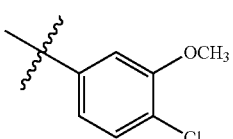 |
| 12-32 | 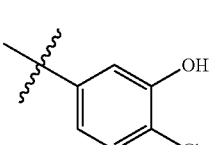 |
| 12-33 | 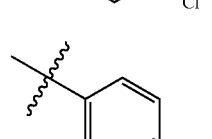 |
| 12-34 | 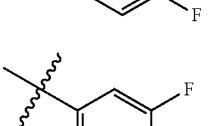 |
| 12-35 | —H |
| 12-36 | 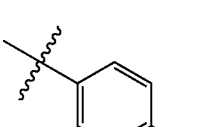 |
| 12-37 | 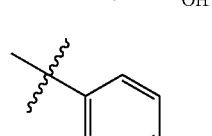 |
| 12-38 | 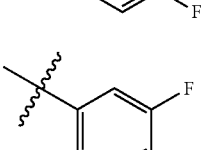 |
| 12-39 | 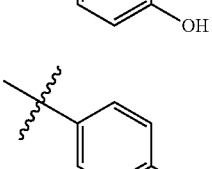 |
| 12-40 | 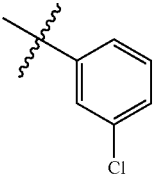 [SMILES: *c1cccc(Cl)c1] |
| 12-41 | 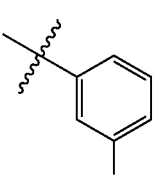 |
| 12-42 | 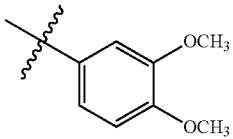 |
| 12-43 | 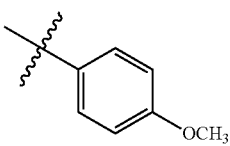 [SMILES: *c1ccc(OC)cc1] |
| 12-44 | 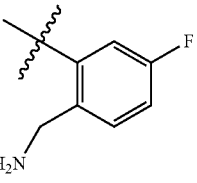 |
| 12-45 | 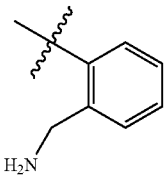 [SMILES: *c1ccccc1CN] |
| 12-46 | 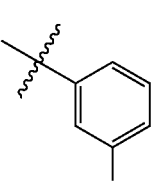 |
| 12-47 | 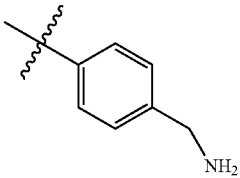 [SMILES: *c1ccc(CN)cc1] |

TABLE 2-continued
Illustrative R$^{12}$ moieties of compounds of Formula I include, but are not limited to:
| Sub-class # | R$^{12}$ |
|---|---|
| 12-48 | 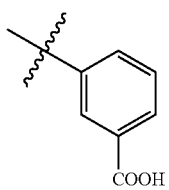 [SMILES: *c1cccc(C(=O)O)c1] |
| 12-49 | 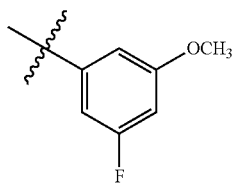 [SMILES: *c1cc(F)cc(OC)c1] |
| 12-50 | 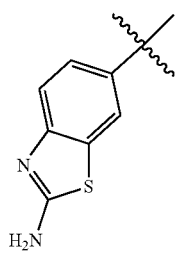 [SMILES: *c1ccc2nc(N)sc2c1] |
| 12-51 | 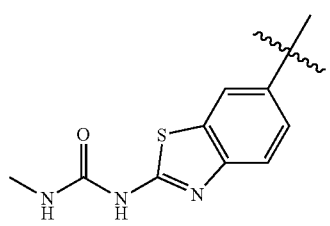 [SMILES: *c1ccc2nc(NC(=O)NC)sc2c1] |
| 12-52 | 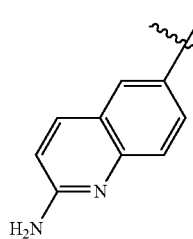 |
| 12-53 | 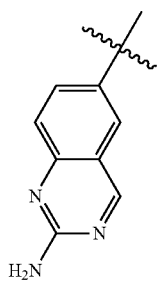 [SMILES: *c1ccc2nc(N)ncc2c1] |
TABLE 2-continued
Illustrative R$^{12}$ moieties of compounds of Formula I include, but are not limited to:
| Sub-class # | R$^{12}$ |
|---|---|
| 12-54 | 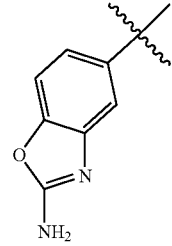 [SMILES: *c1ccc2oc(N)nc2c1] |
| 12-55 | 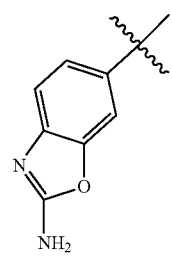 |
| 12-56 | 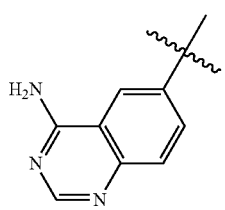 [SMILES: *c1ccc2ncnc(N)c2c1] |
| 12-57 | 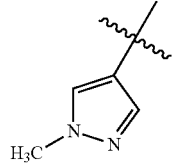 |
| 12-58 | 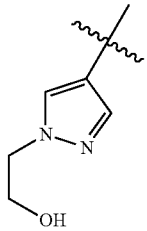 [SMILES: *c1cnn(CCO)c1] |
| 12-59 | 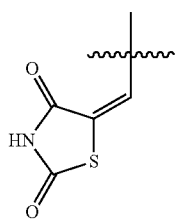 [SMILES: */C=C1/SC(=O)NC1=O] |

TABLE 2-continued

Illustrative R$^{12}$ moieties of compounds of Formula I include, but are not limited to:

| Sub-class # | R$^{12}$ |
|---|---|
| 12-60 | (pyrrolidinone with exocyclic =CH-) |
| 12-61 | —I |
| 12-62 | 3-hydroxyphenyl |
| 12-63 | 3-hydroxy-5-fluorophenyl |
| 12-64 | 3-hydroxy-4-fluorophenyl |
| 12-65 | —C≡C—CH(CH$_3$)$_2$ |
| 12-66 | 4-(diethylamino)pyridin-2-yl |
| 12-67 | 2-aminobenzothiazol-6-yl |
| 12-68 | 1H-pyrazol-3-yl |
| 12-69 | 2-methyl-1H-imidazol-4-yl |
| 12-70 | 5-methyl-1H-pyrazol-3-yl |
| 12-71 | 5-fluoro-1H-pyrazol-3-yl |
| 12-72 | 1H-1,2,4-triazol-3-yl |
| 12-73 | 5-oxo-2,5-dihydro-1H-pyrazol-3-yl |
| 12-74 | 1-methyl-5-oxo-2,5-dihydro-1H-pyrazol-3-yl |
| 12-75 | 3-oxo-2,3-dihydroisoxazol-5-yl |
| 12-76 | 3-oxo-2,3-dihydroisothiazol-5-yl |

TABLE 2-continued

Illustrative R[12] moieties of compounds of Formula I include, but are not limited to:

| Sub-class # | R[12] |
|---|---|
| 12-77 | NC– |
| 12-78 | H2N–C(=O)– |
| 12-79 | MeHN–C(=O)– |
| 12-80 | (E)-MeHN–C(=O)–CH=CH– |
| 12-81 | morpholin-4-ylmethyl |
| 12-82 | H3C–O–C(=O)– |
| 12-83 | H–O–C(=O)– |
| 12-84 | HO–HN–C(=O)– |
| 12-85 | 2-amino-1H-benzimidazol-6-yl |
| 12-86 | 2-(acetylamino)-1H-benzimidazol-6-yl |
| 12-87 | 2,2-difluorovinyl |
| 12-88 | 1H-pyrazol-3-yl |
| 12-89 | 1-methyl-1H-pyrazol-4-yl |
| 12-90 | –CH2–C(=O)–NH2 |
| 12-91 | 2-(acetylamino)-1,3-benzoxazol-6-yl |
| 12-92 | (E)-4-morpholin-4-yl-4-oxobut-2-en-2-yl |

TABLE 2-continued
Illustrative R[12] moieties of compounds of Formula I include, but are not limited to:
| Sub-class # | R[12] |
|---|---|
| 12-93 | 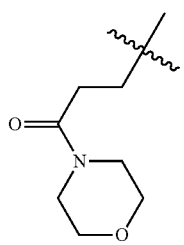 [SMILES: *CCC(=O)N1CCOCC1] |
| 12-94 | 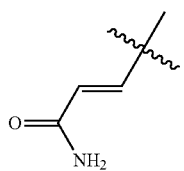 |
| 12-95 | 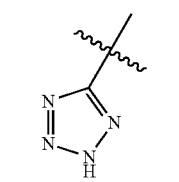 |
| 12-96 | 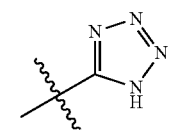 [SMILES: *c1nnn[nH]1] |
TABLE 3
Illustrative X-Y-W$_d$ of compounds of Formula I include, but are not limited to:
| Sub-class # | X-Y-W$_d$ |
|---|---|
| 1 | 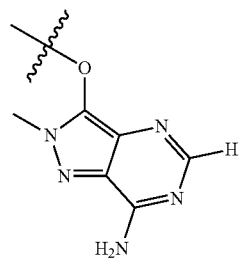 [SMILES: *Oc1c2ncnc(N)c2nn1C] |
| 2 | 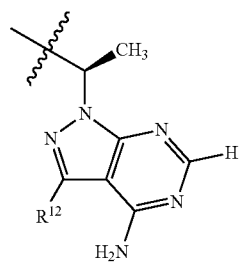 |
| 3 | 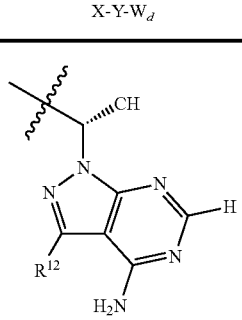 |
| 4 | 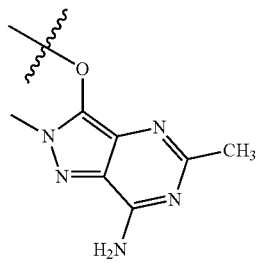 |
| 5 | 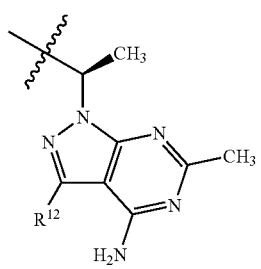 |
| 6 | 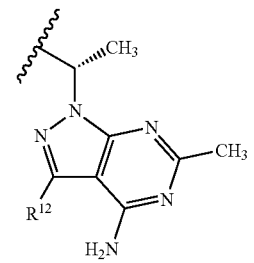 |
| 7 | 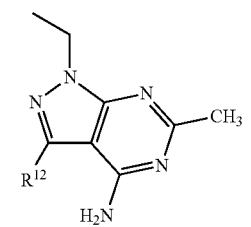 |

TABLE 3-continued
Illustrative X-Y-W$_d$ of compounds of Formula I include, but are not limited to:
| Sub-class # | X-Y-W$_d$ |
|---|---|
| 8 | 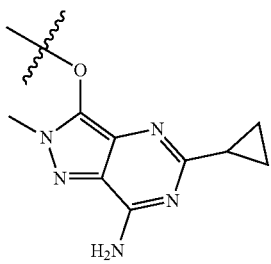 [SMILES: *Oc1c2nc(C3CC3)nc(N)c2nn1C] |
| 9 | 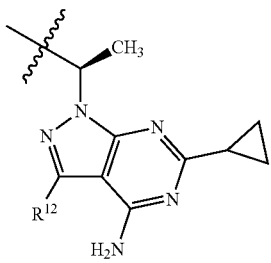 |
| 10 | 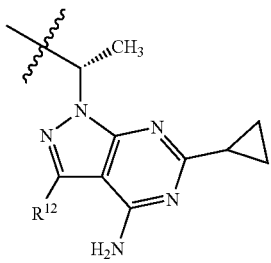 |
| 11 | 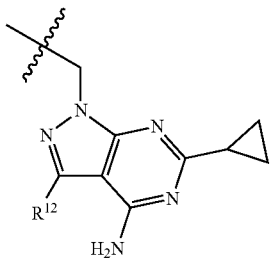 |
| 12 | 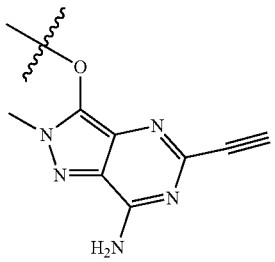 [SMILES: *Oc1c2nc(C#C)nc(N)c2nn1C] |
TABLE 3-continued
Illustrative X-Y-W$_d$ of compounds of Formula I include, but are not limited to:
| Sub-class # | X-Y-W$_d$ |
|---|---|
| 13 | 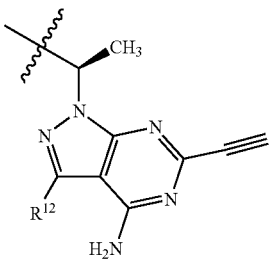 |
| 14 | 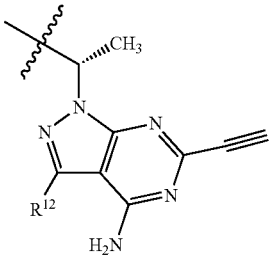 |
| 15 | 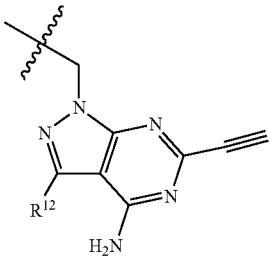 |
| 16 | 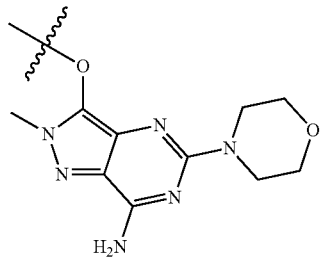 [SMILES: *Oc1c2nc(N3CCOCC3)nc(N)c2nn1C] |
| 17 | 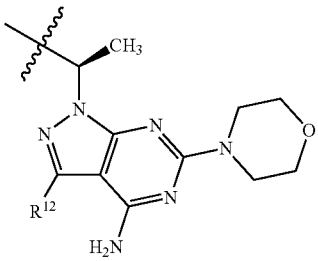 |

TABLE 3-continued

Illustrative X-Y-W$_d$ of compounds of Formula I include, but are not limited to:

| Sub-class # | X-Y-W$_d$ |
|---|---|
| 18 | [structure: pyrazolopyrimidine with morpholine, NH$_2$, R$^{12}$, and chiral CH$_3$ linker] |
| 19 | [structure: pyrazolopyrimidine with morpholine, NH$_2$, R$^{12}$, and CH$_2$ linker] |
| 20 | [structure: purine with S-CH$_2$ linker and R$^{12}$] |
| 21 | [structure: purine with O-CH$_2$ linker and R$^{12}$] |
| 22 | [structure: purine with NH-CH$_2$ linker and R$^{12}$] |
| 23 | [structure: 2-R$^{12}$-6-aminopurine with NH-CH$_2$ linker] |
| 24 | [structure: adenine N9-linked via chiral CH(CH$_3$)] |
| 25 | [structure: adenine N9-linked via chiral CH(CH$_3$)] |
| 26 | [structure: adenine N9-linked via CH$_2$] |
| 27 | [structure: 2-methyladenine N9-linked via chiral CH(CH$_3$)] |

TABLE 3-continued
Illustrative X-Y-W$_d$ of compounds of Formula I
include, but are not limited to:
| Sub-class # | X-Y-W$_d$ |
|---|---|
| 28 | 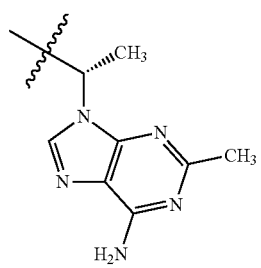 [SMILES: *[C@H](C)n1cnc2c(N)nc(C)nc21] |
| 29 | 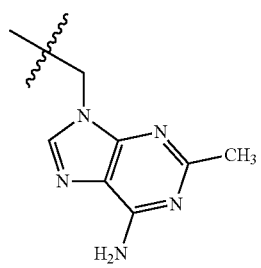 [SMILES: *Cn1cnc2c(N)nc(C)nc21] |
| 30 | 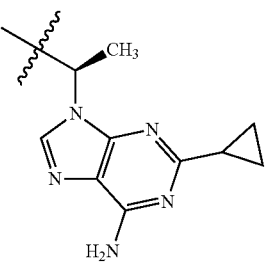 [SMILES: *[C@@H](C)n1cnc2c(N)nc(C3CC3)nc21] |
| 31 | 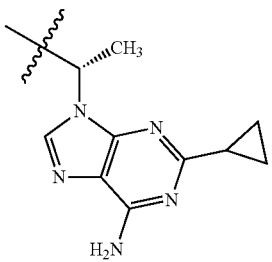 [SMILES: *[C@H](C)n1cnc2c(N)nc(C3CC3)nc21] |
| 32 | 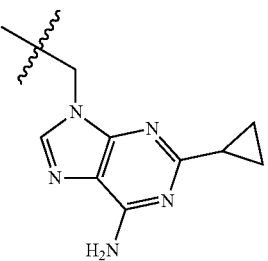 [SMILES: *Cn1cnc2c(N)nc(C3CC3)nc21] |
TABLE 3-continued
Illustrative X-Y-W$_d$ of compounds of Formula I
include, but are not limited to:
| Sub-class # | X-Y-W$_d$ |
|---|---|
| 33 | 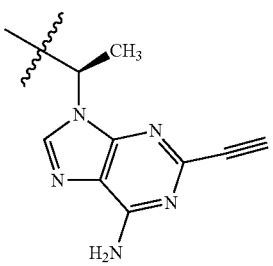 [SMILES: *[C@@H](C)n1cnc2c(N)nc(C#C)nc21] |
| 34 | 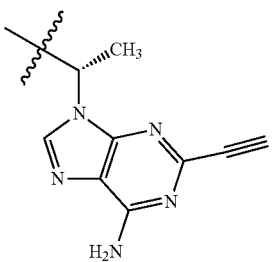 [SMILES: *[C@H](C)n1cnc2c(N)nc(C#C)nc21] |
| 35 | 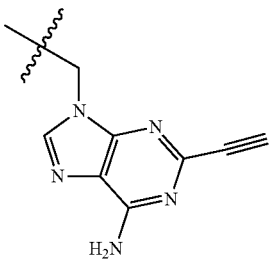 [SMILES: *Cn1cnc2c(N)nc(C#C)nc21] |
| 36 | 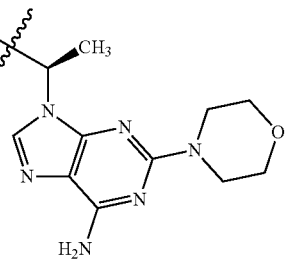 |
| 37 | 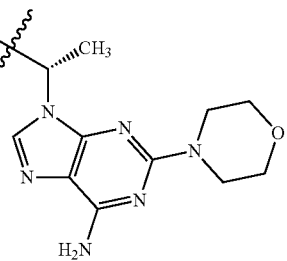 |

TABLE 3-continued

Illustrative X-Y-W_d of compounds of Formula I include, but are not limited to:

| Sub-class # | X-Y-W_d |
|---|---|
| 38 | (9-substituted 6-amino-2-morpholinopurine) |
| 39 | (1-substituted 3-R^12-4-amino-pyrazolo[3,4-d]pyrimidine) |
| 40 | (9-(1-methyl) substituted 8-R^12-6-amino-purine) |
| 41 | (1-(1-ethyl) substituted 3-R^12-4-amino-pyrazolo[3,4-d]pyrimidine) |
| 42 | (1-(1-isopropyl) substituted 3-R^12-4-amino-pyrazolo[3,4-d]pyrimidine) |
| 43 | (N-(1-methyl) substituted 2-R^12-6-amino-purine) |
| 44 | (N-(1-ethyl) substituted 2-R^12-6-amino-purine) |
| 45 | (N-(1-isopropyl) substituted 2-R^12-6-amino-purine) |
| 46 | (N-(1-methyl) substituted 6-amino-purine) |
| 47 | (N-(1-ethyl) substituted 6-amino-purine) |
| 48 | (N-(1-isopropyl) substituted 6-amino-purine) |

TABLE 3-continued

Illustrative X-Y-W$_d$ of compounds of Formula I include, but are not limited to:

| Sub-class # | X-Y-W$_d$ |
|---|---|
| 49 | (structure with N-CH$_3$, purine, H) |
| 50 | (structure with N-Et, purine, H) |
| 51 | (structure with N-iPr, purine, H) |
| 52 | (structure with N-CH$_3$, purine, R$^{12}$) |
| 53 | (structure with N-Et, purine, R$^{12}$) |
| 54 | (structure with N-iPr, purine, R$^{12}$) |
| 55 | (structure with NH, purine, R$^{12}$) |

In some embodiments, one or more subject compounds bind specifically to a PI3 kinase.

In some embodiments, the IC$_{50}$ of a subject compound for p110α, p110β, p110γ, or p110δ is less than about 1 uM, less than about 100 nM, less than about 50 nM, less than about 10 nM, less than 1 nM or even less than about 0.5 nM. In some embodiments, the IC$_{50}$ of a subject compound for mTor is less than about 1 μM, less than about 100 nM, less than about 50 nM, less than about 10 nM, less than 1 nM or even less than about 0.5 nM. In some other embodiments, one or more subject compounds exhibit dual binding specificity and are capable of inhibiting a PI3 kinase (e.g., a class I PI3 kinase) as well as a protein kinase (e.g., mTor) with an IC$_{50}$ value less than about 1 μM, less than about 100 nM, less than about 50 nM, less than about 10 nM, less than 1 nM or even less than about 0.5 nM. One or more subject compounds are capable of inhibiting tyrosine kinases including, for example, DNA-dependent protein kinase DNA-dependent protein kinase (Pubmed protein accession number (PPAN) AAA79184), Abl tyrosine kinase (CAA52387), Bcr-Abl, hemopoietic cell kinase (PPAN CAI19695), Src (PPAN CAA24495), vascular endothelial growth factor receptor 2 (PPAN ABB82619), vascular endothelial growth factor receptor-2 (PPAN ABB82619), epidermal growth factor receptor (PPAN AG43241), EPH receptor B4 (PPAN EAL23820), stem cell factor receptor (PPAN AAF22141), Tyrosine-protein kinase receptor TIE-2 (PPAN Q02858), fms-related tyrosine kinase 3 (PPAN NP_004110), platelet-derived growth factor receptor alpha (PPAN NP_990080), RET (PPAN CAA73131), and functional mutants thereof. In some embodiments, the tyrosine kinase is Abl, Bcr-Abl, EGFR, or Flt-3, and any other kinases listed in the Tables herein.

In some embodiments, non-limiting exemplary compounds exhibit one or more functional characteristics disclosed herein. For example, one or more subject compounds bind specifically to a PI3 kinase. In some embodiments, the IC$_{50}$ of a subject compound for p110α, p110β, p110γ, or p110δ is less than about 1 μM, less than about 100 nM, less than about 50 nM, less than about 10 nM, less than about 1 nM, less than about 0.5 nM, less than about 100 pM, or less than about 50 pM.

In some embodiments, one or more of the subject compound can selectively inhibit one or more members of type I or class I phosphatidylinositol 3-kinases (PI3-kinase) with an IC$_{50}$ value of about 100 nM, 50 nM, 10 nM, 5 nM, 100 pM, 10 pM or 1 pM, or less as measured in an in vitro kinase assay.

In some embodiments, one or more of the subject compounds can selectively inhibit one or two members of type I or class I phosphatidylinositol 3-kinases (PI3-kinase) such as PI3-kinase α, PI3-kinase β, PI3-kinase γ, and PI3-kinase δ. In some aspects, some of the subject compounds selectively inhibit PI3-kinase δ as compared to all other type I PI3-kinases. In other aspects, some of the subject compounds selectively inhibit PI3-kinase δ and PI3-kinase γ as compared to the rest of the type I PI3-kinases. In yet other aspects, some of the subject compounds selectively inhibit PI3-kinase α and PI3-kinase β as compared to the rest of the type I PI3-kinases. In still yet some other aspects, some of the subject compounds selectively inhibit PI3-kinase δ and PI3-kinase α as compared to the rest of the type I PI3-kinases. In still yet some other aspects, some of the subject compounds selectively inhibit PI3-kinase δ and PI3-kinase β as compared to the rest of the type I PI3-kinases, or selectively inhibit PI3-kinase δ and PI3-kinase α as compared to the rest of the type I PI3-kinases, or selectively inhibit PI3-kinase α and PI3-kinase γ as compared to the rest of the type I PI3-kinases, or selectively inhibit PI3-kinase γ and PI3-kinase β as compared to the rest of the type I PI3-kinases.

In yet another aspect, an inhibitor that selectively inhibits one or more members of type I PI3-kinases, or an inhibitor that selectively inhibits one or more type I PI3-kinase mediated signaling pathways, alternatively can be understood to refer to a compound that exhibits a 50% inhibitory concentration ($IC_{50}$) with respect to a given type I PI3-kinase, that is at least about 10-fold, at least about 20-fold, at least about 50-fold, at least about 100-fold, at least about 1000-fold, at least about 10,000-fold, or lower, than the inhibitor's $IC_{50}$ with respect to the rest of the other type I PI3-kinases. In one embodiment, an inhibitor selectively inhibits PI3-kinase δ as compared to PI3-kinase β with at least about 10-fold lower $IC_{50}$ for PI3-kinase δ. In certain embodiments, the $IC_{50}$ for PI3-kinase δ is below about 100 nM, while the $IC_{50}$ for PI3-kinase β is above about 1000 nM. In certain embodiments, the $IC_{50}$ for PI3-kinase δ is below about 50 nM, while the $IC_{50}$ for PI3-kinase β is above about 5000 nM. In certain embodiments, the $IC_{50}$ for PI3-kinase δ is below about 10 nM, while the $IC_{50}$ for PI3-kinase is above about 1000 nM, above about 5,000 nM, or above about 10,000 nM.

Pharmaceutical Compositions

In some embodiments, provided herein are pharmaceutical compositions comprising one or more compounds as disclosed herein and one or more pharmaceutically acceptable excipients. In some embodiments, the pharmaceutical composition comprises a compound as disclosed herein and one or more pharmaceutically acceptable excipients.

In some embodiments, provided herein are pharmaceutical compositions for treating diseases or conditions related to an undesirable, over-active, harmful or deleterious immune response in a subject. Such undesirable immune response can be associated with or result in, e.g., asthma, emphysema, bronchitis, psoriasis, allergy, anaphylaxsis, auto-immune diseases, rhuematoid arthritis, graft versus host disease, and lupus erythematosus. The pharmaceutical compositions can be used to treat other respiratory diseases including, but not limited to, diseases affecting the lobes of the lung, pleural cavity, bronchial tubes, trachea, upper respiratory tract, or the nerves and muscle responsible for breathing.

In some embodiments, provided herein are pharmaceutical compositions for the treatment of multiorgan failure. Also provided herein are pharmaceutical compositions for the treatment of liver diseases (including diabetes), gall bladder disease (including gallstones), pancreatitis or kidney disease (including proliferative glomerulonephritis and diabetes-induced renal disease) or pain in a subject.

In some embodiments, provided herein are pharmaceutical compositions for the prevention of blastocyte implantation in a subject.

In some embodiments, provided herein are pharmaceutical compositions for treating a disease related to vasculogenesis or angiogenesis in a subject which can manifest as tumor angiogenesis, chronic inflammatory disease such as rheumatoid arthritis, inflammatory bowel disease, atherosclerosis, skin diseases such as bullous pemphigoid (BP), psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

In some embodiments, provided herein are pharmaceutical compositions for the treatment of disorders involving platelet aggregation or platelet adhesion, including but not limited to Idiopathic thrombocytopenic purpura, Bernard-Soulier syndrome, Glanzmann's thrombasthenia, Scott's syndrome, von Willebrand disease, Hermansky-Pudlak Syndrome, and Gray platelet syndrome.

In some embodiments, pharmaceutical compositions are provided for treating a disease which is skeletal muscle atrophy, skeletal or muscle hypertrophy. In some embodiments, provided herein are pharmaceutical compositions for the treatment of disorders that include, but are not limited to, cancers as discussed herein, transplantation-related disorders (e.g., lowering rejection rates, graft-versus-host disease, etc.), muscular sclerosis (MS), allergic disorders (e.g., arthritis, allergic encephalomyelitis) and other immunosuppressive-related disorders, metabolic disorders (e.g., diabetes), reducing intimal thickening following vascular injury, and misfolded protein disorders (e.g., Alzheimer's Disease, Gaucher's Disease, Parkinson's Disease, Huntington's Disease, cystic fibrosis, macular degeneration, retinitis pigmentosa, and prion disorders) (as mTOR inhibition can alleviate the effects of misfolded protein aggregates). The disorders also include hamartoma syndromes, such as tuberous sclerosis and Cowden Disease (also termed Cowden syndrome and multiple hamartoma syndrome)

In some embodiments, the disclosure provides a pharmaceutical composition for treating ophthalmic disorders. The pharmaceutical composition is formulated for ocular administration and it contains an effective amount of a compound as disclosed herein and a pharmaceutical excipient suitable for ocular administration. Pharmaceutical compositions suitable for ocular administration can be presented as discrete dosage forms, such as drops or sprays each containing a predetermined amount of an active ingredient a solution, or a suspension in an aqueous or non-aqueous liquid, an oil-in-water emulsion, or a water-in-oil liquid emulsion. Eye drops can be prepared by dissolving the active ingredient in a sterile aqueous solution such as physiological saline, buffering solution, etc., or by combining powder compositions to be dissolved before use. Other vehicles can be chosen, as is known in the art, including, but not limited to: balance salt solution, saline solution, water soluble polyethers such as polyethyene glycol, polyvinyls, such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate. In some embodiments, additives ordinarily used in the eye drops can be added. Such additives include isotonizing agents (e.g., sodium chloride, etc.), buffer agent (e.g., boric acid, sodium monohydrogen phosphate, sodium dihydrogen phosphate, etc.), preservatives (e.g., benzalkonium chloride, benzethonium chloride, chlorobutanol, etc.), thickeners (e.g., saccharide such as lactose, mannitol, maltose, etc.; e.g., hyaluronic acid or its salt such as sodium hyaluronate, potassium hyaluronate, etc.; e.g., mucopolysaccharide such as chondroitin sulfate, etc.; e.g., sodium polyacrylate, carboxyvinyl polymer, crosslinked polyacrylate, polyvinyl alcohol, polyvinyl pyrrolidone, methyl cellulose, hydroxy propyl methylcellulose, hydroxyethyl cellulose, carboxymethyl cellulose, hydroxy propyl cellulose or other agents known to those skilled in the art).

The subject pharmaceutical compositions are typically formulated to provide a therapeutically effective amount of a compound as disclosed herein as the active ingredient, or a pharmaceutically acceptable form, salt, ester, prodrug or derivative thereof. Where desired, the pharmaceutical compositions contain a pharmaceutically acceptable form, such as a salt and/or coordination complex thereof, and one or more pharmaceutically acceptable excipients, carriers, including inert solid diluents and fillers, diluents, including sterile aqueous solution and various organic solvents, permeation enhancers, solubilizers and adjuvants.

The subject pharmaceutical compositions can be administered alone or in combination with one or more other agents, which are also typically administered in the form of pharmaceutical compositions. In some embodiments, the subject compounds and other agent(s) can be mixed into a preparation or both components can be formulated into separate preparations to use them in combination separately or at the same time.

In some embodiments, the concentration of one or more of the compounds provided in the disclosed pharmaceutical compositions is less than about 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, the concentration of one or more of the compounds as disclosed herein is greater than about 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, the concentration of one or more of the compounds as disclosed herein is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v. v/v.

In some embodiments, the concentration of one or more of the compounds as disclosed herein is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of one or more of the compounds as disclosed herein is equal to or less than about 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of one or more of the compounds as disclosed herein is more than about 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

In some embodiments, the amount of one or more of the compounds as disclosed herein is in the range of about 0.0001-10 g, 0.0005-9 g, 0.001-8 g, 0.005-7 g, 0.01-6 g, 0.05-5 g, 0.1-4 g, 0.5-4 g, or 1-3 g.

The compounds as disclosed herein are effective over a wide dosage range. For example, in the treatment of adult humans, dosages from about 0.01 to 1000 mg, from about 0.5 to 100 mg, from about 1 to 50 mg per day, and from about 5 to 40 mg per day are examples of dosages that can be used. An exemplary dosage is about 10 to 30 mg per day. The exact dosage will depend upon the route of administration, the form in which the compound is administered, the subject to be treated, the body weight of the subject to be treated, and the preference and experience of the attending physician.

Described below are non-limiting exemplary pharmaceutical compositions and methods for preparing the same.

Pharmaceutical compositions for oral administration: In some embodiments, provided herein are pharmaceutical compositions for oral administration containing a compound as disclosed herein, and a pharmaceutical excipient suitable for oral administration.

In some embodiments, provided herein are solid pharmaceutical compositions for oral administration containing: (i) an effective amount of a disclosed compound; optionally (ii) an effective amount of a second agent; and (iii) a pharmaceutical excipient suitable for oral administration. In some embodiments, the pharmaceutical composition further contains: (iv) an effective amount of a third agent.

In some embodiments, the pharmaceutical composition can be a liquid pharmaceutical composition suitable for oral consumption. Pharmaceutical compositions suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more ingredients. In general, the pharmaceutical compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

The present disclosure further encompasses anhydrous pharmaceutical compositions and dosage forms comprising an active ingredient, since water can facilitate the degradation of some compounds. For example, water can be added (e.g., about 5%) in the pharmaceutical arts as a means of simulating long-term storage in order to determine characteristics such as shelf-life or the stability of formulations over time. Anhydrous pharmaceutical compositions and dosage forms can be prepared using anhydrous or low moisture containing ingredients and low moisture or low humidity conditions. For example. pharmaceutical compositions and dosage forms which contain lactose can be made anhydrous if substantial contact with moisture and/or humidity during manufacturing, packaging, and/or storage is expected. An anhydrous pharmaceutical composition can be prepared and stored such that its anhydrous nature is maintained. Accordingly, anhydrous pharmaceutical compositions can be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the pharmaceutical compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. In some embodiments, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants can be used in the pharmaceutical compositions as provided herein to provide tablets that disintegrate when exposed to an aqueous environment. Too much of a disintegrant can produce tablets which can disintegrate in the bottle. Too little may be insufficient for disintegration to occur and can thus alter the rate and extent of release of the active ingredient(s) from the dosage form. Thus, a sufficient amount of disintegrant that is neither too little nor too much to detrimentally alter the release of the active ingredient(s) can be used to form the dosage forms of the compounds disclosed herein. The amount of disintegrant used can vary based upon the type of formulation and mode of administration, and can be readily discernible to those of ordinary skill in the art. About 0.5 to about 15 weight percent of disintegrant, or about 1 to about 5 weight percent of disintegrant, can be used in the pharmaceutical composition. Disintegrants that can be used to form pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the active ingredient therein can be combined with various sweetening or flavoring agents, coloring matter or dyes and, for example, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical compositions and dosage forms include, but are not limited to, hydrophilic surfactants, lipophilic surfactants, and mixtures thereof. That is, a mixture of hydrophilic surfactants can be employed, a mixture of lipophilic surfactants can be employed, or a mixture of at least one hydrophilic surfactant and at least one lipophilic surfactant can be employed.

A suitable hydrophilic surfactant can generally have an HLB value of at least about 10, while suitable lipophilic surfactants can generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants can be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants can be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants can include, but are not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of triglycerides, vegetable oils, and hydrogenated vegetable oils. The polyol can be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters;

polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of glycerides, vegetable oils, hydrogenated vegetable oils, fatty acids and sterols; oil-soluble vitamins/vitamin derivatives; and mixtures thereof. Within this group, non-limiting examples of lipophilic surfactants include glycerol fatty acid esters, propylene glycol fatty acid esters, and mixtures thereof, or are hydrophobic transesterification products of a polyol with at least one member of vegetable oils, hydrogenated vegetable oils, and triglycerides.

In one embodiment, the pharmaceutical composition can include a solubilizer to ensure good solubilization and/or dissolution of a compound as provided herein and to minimize precipitation of the compound. This can be especially important for pharmaceutical compositions for non-oral use, e.g., pharmaceutical compositions for injection. A solubilizer can also be added to increase the solubility of the hydrophilic drug and/or other components, such as surfactants, or to maintain the pharmaceutical composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers can also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. In some embodiments, solubilizers include sorbitol, glycerol, triacetin, ethyl alcohol, PEG-400, glycofurol and propylene glycol.

The amount of solubilizer that can be included is not particularly limited. The amount of a given solubilizer can be limited to a bioacceptable amount, which can be readily determined by one of skill in the art. In some circumstances, it can be advantageous to include amounts of solubilizers far in excess of bioacceptable amounts, for example to maximize the concentration of the drug, with excess solubilizer removed prior to providing the pharmaceutical composition to a subject using conventional techniques, such as distillation or evaporation. Thus, if present, the solubilizer can be in a weight ratio of about 10%, 25%, 50%, 100%, or up to about 200% by weight, based on the combined weight of the drug, and other excipients. If desired, very small amounts of solubilizer can also be used, such as about 5%, 2%, 1% or even less. Typically, the solubilizer can be present in an amount of about 1% to about 100%, more typically about 5% to about 25% by weight.

The pharmaceutical composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base can be incorporated into the pharmaceutical composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl)aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Examples can include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

Pharmaceutical compositions for injection. In some embodiments, provided herein are pharmaceutical compositions for injection containing a compound qas disclosed herein and a pharmaceutical excipient suitable for injection. Components and amounts of agents in the pharmaceutical compositions are as described herein.

The forms in which the disclosed pharmaceutical compositions can be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils can also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound as disclosed herein in the required amount in the appropriate solvent with various other ingredients as enumerated above, as appropriate, followed by filtered sterilization. Generally, dispersions are prepared by incorporating the various sterilized active ingredients into a sterile vehicle which contains the basic dispersion medium and the appropriate other ingredients from those enumerated above. In the case of sterile powders for the preparation of sterile injectable solutions, certain methods of preparation are vacuum-drying and freeze-drying techniques which yield a powder of the active ingredient plus any additional ingredient from a previously sterile-filtered solution thereof.

Pharmaceutical compositions for topical (e.g., transdermal) delivery. In some embodiments, provided herein are pharmaceutical compositions for transdermal delivery containing a compound as disclosed herein and a pharmaceutical excipient suitable for transdermal delivery.

Pharmaceutical compositions provided herein can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation can provide more immediate exposure of the active ingredient to the chosen area.

The pharmaceutical compositions also can comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the disclosed methods employs transdermal delivery devices ("patches"). Such transdermal patches can be used to provide continuous or discontinuous infusion of a compound as provided herein in controlled amounts, either with or without another agent.

The construction and use of transdermal patches for the delivery of pharmaceutical agents is well known in the art. See, e.g., U.S. Pat. Nos. 5,023,252, 4,992,445 and 5,001,139. Such patches can be constructed for continuous, pulsatile, or on demand delivery of pharmaceutical agents.

Pharmaceutical compositions for inhalation. Pharmaceutical compositions for inhalation or insufflation include solutions and suspensions in pharmaceutically acceptable, aqueous or organic solvents, or mixtures thereof, and powders. The liquid or solid pharmaceutical compositions can contain suitable pharmaceutically acceptable excipients as described herein. In some embodiments, the pharmaceutical compositions are administered by the oral or nasal respiratory route for local or systemic effect. Pharmaceutical compositions in pharmaceutically acceptable solvents can be nebulized by use of inert gases. Nebulized solutions can be inhaled directly from the nebulizing device or the nebulizing device can be attached to a face mask tent, or intermittent positive pressure breathing machine. Solution, suspension, or powder pharmaceutical compositions can be administered, e.g., orally or nasally, from devices that deliver the formulation in an appropriate manner.

Pharmaceutical compositions can also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., Anderson, Philip O.; Knoben, James E.; Troutman, William G, eds., *Handbook of Clinical Drug Data*, Tenth Edition, McGraw-Hill, 2002; Pratt and Taylor, eds., *Principles of Drug Action*, Third Edition, Churchill Livingston, N. Y., 1990; Katzung, ed., *Basic and Clinical Pharmacology*, Ninth Edition, McGraw Hill, 20037ybg; Goodman and Gilman, eds., *The Pharmacological Basis of Therapeutics*, Tenth Edition, McGraw Hill, 2001; *Remingtons Pharmaceutical Sciences,* 20th Ed., Lippincott Williams & Wilkins, 2000; Martindale, *The Extra Pharmacopoeia*, Thirty-Second Edition (The Pharmaceutical Press, London, 1999); all of which are incorporated by reference herein in their entirety.

Administration of the compounds or pharmaceutical compositions as disclosed herein can be effected by any method that enables delivery of the compounds to the site of action. These methods include oral routes, intraduodenal routes, parenteral injection (including intravenous, intraarterial, subcutaneous, intramuscular, intravascular, intraperitoneal or infusion), topical (e.g., transdermal application), rectal administration, via local delivery by catheter or stent or through inhalation. Compounds can also be administered intraadiposally or intrathecally.

The amount of the compound administered will be dependent on the subject being treated, the severity of the disorder or condition, the rate of administration, the disposition of the compound and the discretion of the prescribing physician. However, an effective dosage can be in the range of about 0.001 to about 100 mg per kg body weight per day, such as from about 1 to about 35 mg/kg/day, in single or divided doses. For a 70 kg human, this would amount to about 0.05 to about 7 g/day, such as about 0.05 to about 2.5 g/day. In some instances, dosage levels below the lower limit of the aforesaid range can be more than adequate, while in other cases still larger doses can be employed without causing any harmful side effect, e.g., by dividing such larger doses into several small doses for administration throughout the day.

In some embodiments, a compound as provided herein is administered in a single dose. Typically, such administration will be by injection, e.g., intravenous injection, in order to introduce the agent quickly. However, other routes can be used as appropriate. A single dose of a compound as provided herein can also be used for treatment of an acute condition.

In some embodiments, a compound as provided herein is administered in multiple doses. Dosing can be about once, twice, three times, four times, five times, six times, or more than six times per day. Dosing can be about once a month, once every two weeks, once a week, or once every other day. In another embodiment, a compound as disclosed herein and another agent are administered together about once per day to about 6 times per day. In another embodiment, the administration of a compound as provided herein and an agent continues for less than about 7 days. In yet another embodiment, the administration continues for more than about 6, 10, 14, 28 days, two months, six months, or one year. In some cases, continuous dosing is achieved and maintained as long as necessary.

Administration of the agents as disclosed herein can continue as long as necessary. In some embodiments, an agent as disclosed herein is administered for more than 1, 2, 3, 4, 5, 6, 7, 14, or 28 days. In some embodiments, an agent as disclosed herein is administered for less than 28, 14, 7, 6, 5, 4, 3, 2, or 1 day. In some embodiments, an agent as disclosed herein is administered chronically on an ongoing basis, e.g., for the treatment of chronic effects.

An effective amount of a compound as disclosed herein can be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

The pharmaceutical compositions provided herein can also be delivered via an impregnated or coated device such as a stent, for example, or an artery-inserted cylindrical polymer. Such a method of administration can, for example, aid in the prevention or amelioration of restenosis following procedures such as balloon angioplasty. Without being bound by theory, compounds as disclosed herein can slow or inhibit the migration and proliferation of smooth muscle cells in the arterial wall which contribute to restenosis. A compound as disclosed herein can be administered, for example, by local delivery from the struts of a stent, from a stent graft, from grafts, or from the cover or sheath of a stent. In some embodiments, a compound as disclosed herein is admixed with a matrix. Such a matrix can be a polymeric matrix, and can serve to bond the compound to the stent. Polymeric matrices suitable for such use, include, for example, lactone-based polyesters or copolyesters such as polylactide, polycaprolactonglycolide, polyorthoesters, polyanhydrides, polyaminoacids, polysaccharides, polyphosphazenes, poly(ether-ester) copolymers (e.g., PEO-PLLA); polydimethylsiloxane, poly(ethylene-vinylacetate), acrylate-based polymers or copolymers (e.g., polyhydroxyethyl methylmethacrylate, polyvinyl pyrrolidinone), fluorinated polymers such as polytetrafluoroethylene and cellulose esters. Suitable matrices can be nondegrading or can degrade with time, releasing the compound or compounds. Compounds as disclosed herein can be applied to the surface of the stent by various methods such as dip/spin coating, spray coating, dip-coating, and/or brush-coating. The compounds can be applied in a solvent and the solvent can be allowed to evaporate, thus forming a layer of compound onto the stent. Alternatively, the compound can be located in the body of the stent or graft, for example in microchannels or micropores. When implanted, the compound diffuses out of the body of the stent to contact the arterial wall. Such stents can be prepared by dipping a stent manufactured to contain such micropores or microchannels into a solution of the compound as disclosed herein in a suitable solvent, followed by evaporation of the solvent. Excess drug on the surface of the stent can be removed via an additional brief solvent wash. In yet other embodiments, compounds as disclosed herein can be covalently linked to a stent or graft. A covalent linker can be used which degrades in vivo, leading to the release of the compound as disclosed herein. Any bio-labile linkage can be used for such a purpose, such as ester, amide or anhydride linkages. Compounds provided herein can additionally be administered intravascularly from a balloon used during angioplasty. Extravascular administration of the compounds via the pericard or via advential application of formulations provided herein can also be performed to decrease restenosis.

A variety of stent devices which can be used as described are disclosed, for example, in the following references, all of which are hereby incorporated by reference: U.S. Pat. Nos. 5,451,233; 5,040,548; 5,061,273; 5,496,346; 5,292,331; 5,674,278; 3,657,744; 4,739,762; 5,195,984; 5,292,331; 5,674,278; 5,879,382; 6,344,053.

The compounds provided herein can be administered in dosages. It is known in the art that due to intersubject variability in compound pharmacokinetics, individualization of dosing regimen is necessary for optimal therapy. Dosing for a compound provided herein can be found by routine experimentation in light of the instant disclosure.

When a compound provided herein, is administered in a pharmaceutical composition that comprises one or more agents, and the agent has a shorter half-life than the compound provided herein unit dose forms of the agent and the compound provided herein can be adjusted accordingly.

The subject pharmaceutical composition can, for example, be in a form suitable for oral administration as a tablet, capsule, pill, powder, sustained release formulations, solution, or suspension, for parenteral injection as a sterile solution, suspension or emulsion, for topical administration as an ointment or cream or for rectal administration as a suppository. The pharmaceutical composition can be in unit dosage forms suitable for single administration of precise dosages. The pharmaceutical composition will include a conventional pharmaceutical carrier or excipient and a compound as provided herein as an active ingredient. In addition, it can include other medicinal or pharmaceutical agents, carriers, adjuvants, etc.

Exemplary parenteral administration forms include solutions or suspensions of active compound in sterile aqueous solutions, for example, aqueous propylene glycol or dextrose solutions. Such dosage forms can be suitably buffered, if desired.

In some embodiments, provided herein are kits. The kits include a compound or compounds as described herein, in suitable packaging, and written material that can include instructions for use, discussion of clinical studies, listing of side effects, and the like. Such kits can also include information, such as scientific literature references, package insert materials, clinical trial results, and/or summaries of these and the like, which indicate or establish the activities and/or advantages of the pharmaceutical composition, and/or which describe dosing, administration, side effects, drug interactions, or other information useful to the health care provider. Such information can be based on the results of various studies, for example, studies using experimental animals involving in vivo models and studies based on human clinical trials. The kit can further contain another agent. In some embodiments, the compound as disclosed herein and the agent are provided as separate pharmaceutical compositions in separate containers within the kit. In some embodiments, the compound as disclosed herein and the agent are provided as a single pharmaceutical composition within a container in the kit. Suitable packaging and additional articles for use (e.g., measuring cup for liquid preparations, foil wrapping to minimize exposure to air, and the like) are known in the art and can be included in the kit. Kits described herein can be provided, marketed and/or promoted to health providers, including physicians, nurses, pharmacists, formulary officials, and the like. Kits can also, in some embodiments, be marketed directly to the consumer.

Phosphoinositide 3-kinases (PI3Ks) are members of a conserved family of lipid kinases that regulate numerous cell functions, including proliferation, differentiation, cell survival and metabolism. Several classes of PI3Ks exist in mammalian cells, including Class IA subgroup (e.g., PI3K-α, β, δ), which are generally activated by receptor tyrosine kinases (RTKs); Class IB (e.g., PI3K-γ), which is activated by G-protein coupled receptors, among others. PI3Ks exert their biological activities via a "PI3K-mediated signaling pathway" that includes several components that directly and/or indirectly transduce a signal triggered by a PI3K, including the generation of secondary messenger phophotidylinositol, 3,4,5-triphosphate (PIP3) at the plasma membrane, activation of heterotrimeric G protein signaling, and generation of further second messengers such as cAMP, DAG, and IP3, all of which leads to an extensive cascade of protein kinase activation (reviewed in Vanhaesebroeck, B. et al. (2001) Annu Rev Biochem. 70:535-602). For example, PI3K-δ is activated by cellular receptors through interaction between the PI3K regulatory subunit (p85) SH2 domains, or through direct interaction with RAS. PIP3 produced by PI3K activates effector pathways downstream through interaction with plextrin homology (PH) domain containing enzymes (e.g., PDK-1 and AKT [PKB]). (Fung-Leung W P. (2011) Cell Signal. 23(4):603-8). Unlike PI3K-δ, PI3K-γ is not a Class 1A PI3K, and is not associated with a regulatory subunit of the P85 family, but rather with a regulatory subunit in the p101 family. PI3K-γ is associated with G-protein coupled receptors (GPCRs), and is responsible for the very rapid induction of PIP3, and can be also activated by RAS.

As used herein, a "PI3K-mediated disorder" refers to a disease or condition involving aberrant PI3K-mediated signaling pathway. In one embodiment, provided herein is a method of treating a PI3K mediated disorder in a subject, the method comprising administering a therapeutically effective amount of a compound or a pharmaceutical composition as disclosed herein. In some embodiments, provided herein is a method of treating a PI3K-δ or PI3K-γ mediated disorder in a subject, the method comprising administering a therapeutically effective amount of a compound or a pharmaceutical composition as disclosed herein. In some embodiments, provided herein is a method for inhibiting at least one of PI3K-δ or PI3K-γ, the method comprising contacting a cell expressing PI3K in vitro or in vivo with an effective amount of the compound or composition disclosed herein PI3Ks have been associated with a wide range of conditions, including immunity, cancer and thrombosis (reviewed in Vanhaesebroeck, B. et al. (2010) Current Topics in Microbiology and Immunology, DOI 10.1007/82201065). For example, Class I PI3Ks, particularly PI3Kγ and PI3Kδ isoforms, are highly expressed in leukocytes and have been associated with adaptive and innate immunity; thus, these PI3Ks are believed to be important mediators in inflammatory disorders and hematologic malignancies (reviewed in Harris, S J et al. (2009) Curr Opin Investig Drugs 10(11):1151-62); Rommel C. et al. (2007) Nat Rev Immunol 7(3):191-201; Durand C A et al. (2009) J Immunol. 183(9):5673-84; Dil N, Marshall A J. (2009) Mol Immunol. 46(10):1970-8; Al-Alwan M M et al. (2007) J Immunol. 178(4):2328-35; Zhang T T, et al. (2008) J Allergy Clin Immunol. 2008; 122(4):811-819.e2; Srinivasan L, et al. (2009) Cell 139(3):573-86).

Numerous publications support roles of PI3K-δ, PI3K-γ, and PI3K-β in the differentiation, maintenance, and activation of immune and malignant cells, as described in more detail below.

The importance of PI3K-δ in the development and function of B-cells is supported from inhibitor studies and genetic models. PI3K-δ is an important mediator of B-cell receptor (BCR) signaling, and is upstream of AKT, calcium flux, PLCγ, MAP kinase, P70S6k, and FOXO3a activation. PI3K-δ is also important in IL4R, S1P, and CXCR5 signaling, and has been shown to modulate responses to toll-like receptors 4 and 9 Inhibitors of PI3K-δ have shown the importance of PI3K-δ in B-cell development (Marginal zone and B1 cells), B-cell activation, chemotaxis, migration and homing to lymphoid tissue, and in the control of immunoglobulin class switching leading to the production of IgE. Clayton E et al. (2002) J Exp Med. 196(6):753-63; Bilancio A, et al. (2006) Blood 107(2):642-50; Okkenhaug K. et al. (2002) Science 297(5583):1031-4; Al-Alwan M M et al. (2007) J Immunol. 178(4):2328-35; Zhang T T, et al. (2008) J Allergy Clin Immunol. 2008; 122(4):811-819.e2; Srinivasan L, et al. (2009) Cell 139(3):573-86)

In T-cells, PI3K-δ has been demonstrated to have a role in T-cell receptor and cytokine signaling, and is upstream of AKT, PLCγ, and GSK3b. In PI3K-δ deletion or kinase-dead knock-in mice, or in inhibitor studies, T-cell defects including proliferation, activation, and differentiation have been observed, leading to reduced T helper cell 2 (TH2) response, memory T-cell specific defects (DTH reduction), defects in antigen dependent cellular trafficking, and defects in chemotaxis/migration to chemokines (e.g., S1P, CCR7, CD62L). (Garcon F. et al. (2008) Blood 111(3):1464-71; Okkenhaug K et al. (2006). J Immunol. 177(8):5122-8; Soond D R, et al. (2010) Blood 115(11):2203-13; Reif K, (2004). J Immunol 2004; 173(4):2236-40; Ji H. et al. (2007) Blood 110(8):2940-7; Webb L M, et al. (2005) J Immunol. 175(5):2783-7; Liu D, et al. (2010) J Immunol. 184(6):3098-105; Haylock-Jacobs S, et al. (2011) J Autoimmun. 2011; 36(3-4):278-87; Jarmin S J, et al. (2008) J Clin Invest. 118(3):1154-64).

In neutrophils, PI3K-δ along with PI3K-γ, and PI3K-β, contribute to the responses to immune complexes, FCgRII signaling, including migration and neutrophil respiratory burst. Human neutrophils undergo rapid induction of PIP3 in response to formyl peptide receptor (FMLP) or complement component C5a (C5a) in a PI3K-γ dependent manner, followed by a longer PIP3 production period that is PI3K-δ dependent, and is essential for respiratory burst. The response to immune complexes is contributed by PI3K-δ, PI3K-γ, and PI3K-β, and is an important mediator of tissue damage in models of autoimmune disease (Randis T M et al. (2008) Eur J Immunol. 38(5):1215-24; Pinho V, (2007) J Immunol. 179(11):7891-8; Sadhu C. et al. (2003) J Immunol. 170(5):2647-54; Condliffe A M et al. (2005) Blood 106(4):1432-40).

In macrophages collected from patients with chronic obstructive pulmonary disease (COPD), glucocorticoid responsiveness can be restored by treatment of the cells with inhibitors of PI3K-δ. Macrophages also rely on PI3K-δ and PI3K-γ for responses to immune complexes through the arthus reaction (FCgR and C5a signaling) (Randis T M, et al. (2008) *Eur J Immunol.* 38(5):1215-24; Marwick J A et al. (2009) *Am J Respir Crit Care Med.* 179(7):542-8; Konrad S, et al. (2008) *J Biol Chem.* 283(48):33296-303).

In mast cells, stem cell factor—(SCF) and IL3-dependent proliferation, differentiation and function are PI3K-δ dependent, as is chemotaxis. The allergen/IgE crosslinking of FCgR1 resulting in cytokine release and degranulation of the mast cells is severely inhibited by treatment with PI3K-δ inhibitors, suggesting a role for PI3K-δ in allergic disease (Ali K et al. (2004) *Nature* 431(7011):1007-11; Lee K S, et al. (2006) *FASEB J.* 20(3):455-65; Kim M S, et al. (2008) *Trends Immunol.* 29(10):493-501).

Natural killer (NK) cells are dependent on both PI3K-δ and PI3K-γ for efficient migration towards chemokines including CXCL10, CCL3, S1P and CXCL12, or in response to LPS in the peritoneum (Guo H, et al. (2008) *J Exp Med.* 205(10):2419-35; Tassi I, et al. (2007) *Immunity* 27(2):214-27; Saudemont A, (2009) *Proc Natl Acad Sci USA.* 106(14):5795-800; Kim N, et al. (2007) *Blood* 110(9): 3202-8).

The roles of PI3K-δ, PI3K-γ, and PI3K-β in the differentiation, maintenance, and activation of immune cells support a role for these enzymes in inflammatory disorders ranging from autoimmune diseases (e.g., rheumatoid arthritis, multiple sclerosis) to allergic inflammatory disorders, such as asthma and COPD. Extensive evidence is available in experimental animal models, or can be evaluated using art-recognized animal models. In an embodiment, described herein is a method of treating inflammatory disorders ranging from autoimmune diseases (e.g., rheumatoid arthritis, multiple sclerosis) to allergic inflammatory disorders, such as asthma and COPD using a compound described herein.

For example, inhibitors of PI3Kδ and/or γ have been shown to have anti-inflammatory activity in several autoimmune animal models for rheumatoid arthritis (Williams, O. et al. (2010) *Chem Biol,* 17(2):123-34; WO 2009/088986; WO2009/088880; WO 2011/008302). PI3Kδ is expressed in the RA synovial tissue (especially in the synovial lining which contains fibroblast-like synoviocytes (FLS), and selective PI3Kd inhibitors have been shown to be effective in inhibiting synoviocyte growth and survival (Bartok et al. (2010) *Arthritis Rheum* 62 Suppl 10:362). Several PI3K δ and γ inhibitors have been shown to ameliorate arthritic symptoms (e.g., swelling of joints, reduction of serum-induced collagen levels, reduction of joint pathology and/or inflammation), in art-recognized models for RA, such as collagen-induced arthritis and adjuvant induced arthritis (WO 2009/088986; WO2009/088880; WO 2011/008302).

The role of PI3K-δ has also been shown in models of T-cell dependent response, including the DTH model. In the murine experimental autoimmune encephalomyelitis (EAE) model of multiple sclerosis, the PI3K-g/d-double mutant mice are resistant. PI3K-δ inhibitors have also been shown to block EAE disease induction and development of TH-17 cells both in vitro and in vivo (Haylock-Jacobs, S. et al. (2011) *J. Autoimmunity* 36(3-4):278-87).

Systemic lupus erythematosus (SLE) is a complex disease that at different stages requires memory T-cells, B-cell polyclonal expansion and differentiation into plasma cells, and the innate immune response to endogenous damage associated molecular pattern molecules (DAMPS), and the inflammatory responses to immune complexes through the complement system as well as the $F_c$ receptors. The role of PI3K-δ and PI3K-γ together in these pathways and cell types suggest that blockade with an inhibitor would be effective in these diseases. A role for PI3K in lupus is also predicted by two genetic models of lupus. The deletion of phosphatase and tensin homolog (PTEN) leads to a lupus-like phenotype, as does a transgenic activation of Class1A PI3Ks, which includes PI3K-δ. The deletion of PI3K-γ in the transgenically activated class 1A lupus model is protective, and treatment with a PI3K-γ selective inhibitor in the murine MLR/lpr model of lupus improves symptoms (Barber, D F et al. (2006) *J. Immunol.* 176(1): 589-93).

In allergic disease, PI3K-δ has been shown by genetic models and by inhibitor treatment to be essential for mast-cell activation in a passive cutaneous anaphalaxis assay (Ali K et al. (2008) *J Immunol.* 180(4):2538-44; Ali K, (2004) *Nature* 431(7011):1007-11). In a pulmonary measure of response to immune complexes (Arthus reaction) a PI3K-δ knockout is resistant, showing a defect in macrophage activation and C5a production. Knockout studies and studies with inhibitors for both PI3K-δ and PI3K-γ support a role for both of these enzymes in the ovalbumin induced allergic airway inflammation and hyper-responsiveness model (Lee K S et al. (2006) *FASEB J.* 20(3):455-65). Reductions of infiltration of eosinophils, neutrophils, and lymphocytes as well as TH2 cytokines (IL4, IL5, and IL13) were seen with both PI3K-δ specific and dual PI3K-δ and PI3K-γ inhibitors in the Ova induced asthma model (Lee K S et al. (2006) *J Allergy Clin Immunol* 118(2):403-9).

PI3K-δ and PI3K-γ inhibition can be used in treating COPD. In the smoked mouse model of COPD, the PI3K-δ knockout does not develop smoke induced glucocorticoid resistance, while wild-type and PI3K-γ knockout mice do. An inhaled formulation of dual PI3K-δ and PI3K-γ inhibitor blocked inflammation in a LPS or smoke COPD models as measured by neutrophilia and glucocorticoid resistance (Doukas J, et al. (2009) *J Pharmacol Exp Ther.* 328(3):758-65).

Class I PI3Ks, particularly PI3Kδ and PI3Kγ isoforms, are also associated with cancers (reviewed, e.g., in Vogt, P K et al. (2010) *Curr Top Microbiol Immunol* 347:79-104; Fresno Vara, J A et al. (2004) *Cancer Treat Rev.* 30(2):193-204; Zhao, L and Vogt, P K. (2008) *Oncogene* 27(41):5486-96). Inhibitors of PI3K, e.g., PI3Kδ and/or γ, have been shown to have anti-cancer activity (e.g., Courtney, K D et al. (2010) *J Clin Oncol.* 28(6):1075-1083); Markman, B et al. (2010) Ann Oncol. 21(4):683-91; Kong, D and Yamori, T (2009) Curr Med Chem. 16(22):2839-54; Jimeno, A et al. (2009) J Clin Oncol. 27:156s (suppl; abstr 3542); Flinn, I W et al. (2009) *J Clin Oncol.* 27:156s (suppl; abstr 3543); Shapiro, G et al. (2009) J Clin Oncol. 27:146s (suppl; abstr 3500); Wagner, A J et al. (2009) *J Clin Oncol.* 27:146s (suppl; abstr 3501); Vogt, P K et al. (2006) Virology 344(1):131-8; Ward, S et al. (2003) *Chem Biol.* 10(3):207-13; WO 2011/041399; US 2010/0029693; US 2010/0305096; US 2010/0305084). In an embodiment, described herein is a method of treating cancer.

Types of cancer that can be treated with an inhibitor of PI3K (particularly, PI3Kδ and/or γ) include, e.g., leukemia, chronic lymphocytic leukemia, acute myeloid leukemia, chronic myeloid leukemia (e.g., Salmena, L et al. (2008) *Cell* 133:403-414; Chapuis, N et al. (2010) *Clin Cancer Res.* 16(22):5424-35; Khwaja, A (2010) *Curr Top Microbiol Immunol.* 347:169-88); lymphoma, e.g., non-Hodgkin's lymphoma (e.g., Salmena, L et al. (2008) *Cell* 133:403-414);

lung cancer, e.g., non-small cell lung cancer, small cell lung cancer (e.g., Herrera, V A et al. (2011) *Anticancer Res.* 31(3):849-54); melanoma (e.g., Haluska, F et al. (2007) *Semin Oncol.* 34(6):546-54); prostate cancer (e.g., Sarker, D et al. (2009) *Clin Cancer Res.* 15(15):4799-805); glioblastoma (e.g., Chen, J S et al. (2008) Mol Cancer Ther. 7:841-850); endometrial cancer (e.g., Bansal, N et al. (2009) Cancer Control. 16(1):8-13); pancreatic cancer (e.g., Furukawa, T (2008) *J Gastroenterol.* 43(12):905-11); renal cell carcinoma (e.g., Porta, C and Figlin, R A (2009) *J Urol.* 182(6):2569-77); colorectal cancer (e.g., Saif, M W and Chu, E (2010) Cancer J. 16(3):196-201); breast cancer (e.g., Torbett, N E et al. (2008) *Biochem J.* 415:97-100); thyroid cancer (e.g., Brzezianska, E and Pastuszak-Lewandoska, D (2011) *Front Biosci.* 16:422-39); and ovarian cancer (e.g., Mazzoletti, M and Broggini, M (2010) *Curr Med Chem.* 17(36):4433-47).

Numerous publications support a role of PI3K-δ and PI3K-γ in treating hematological cancers. PI3K-δ and PI3K-γ are highly expressed in the heme compartment, and some solid tumors, including prostate, breast and glioblastomas (Chen J. S. et al. (2008) *Mol Cancer Ther.* 7(4):841-50; Ikeda H. et al. (2010) *Blood* 116(9):1460-8). In hematological cancers including acute myeloid leukemia (AML), multiple myeloma (MM), and chronic lymphocytic leukemia (CLL), overexpression and constitutive activation of PI3K-δ supports the model that PI3K-δ inhibition would be therapeutic Billottet C, et al. (2006) *Oncogene* 25(50):6648-59; Billottet C, et al. (2009) *Cancer Res.* 69(3):1027-36; Meadows, S A, $52^{nd}$ Annual ASH Meeting and Exposition; 2010 Dec. 4-7; Orlando, Fla.; Ikeda H, et al. (2010) *Blood* 116(9):1460-8; Herman S E et al. (2010) *Blood* 116(12): 2078-88; Herman S E et al. (2011). *Blood* 117(16):4323-7. In an embodiment, described herein is a method of treating hematological cancers including, but not limited to acute myeloid leukemia (AML), multiple myeloma (MM), and chronic lymphocytic leukemia (CLL).

A PI3K-δ inhibitor (CAL-101) has been evaluated in a phase 1 trial in patients with haematological malignancies, and showed activity in CLL in patients with poor prognostic characteristics. In CLL, inhibition of PI3K-δ not only affects tumor cells directly, but it also affects the ability of the tumor cells to interact with their microenvironment. This microenvironment includes contact with and factors from stromal cells, T-cells, nurse like cells, as well as other tumor cells. CAL-101 suppresses the expression of stromal and T-cell derived factors including CCL3, CCL4, and CXCL13, as well as the CLL tumor cells' ability to respond to these factors. CAL-101 treatment in CLL patients induces rapid lymph node reduction and redistribution of lymphocytes into the circulation, and affects tonic survival signals through the BCR, leading to reduced cell viability, and an increase in apoptosis. Single agent CAL-101 treatment was also active in mantle cell lymphoma and refractory non Hodgkin's lymphoma (Furman, R R, et al. $52^{nd}$ Annual ASH Meeting and Exposition; 2010 Dec. 4-7; Orlando, Fla.; Hoellenriegel, J, et al. $52^{nd}$ Annual ASH Meeting and Exposition; 2010 Dec. 4-7; Orlando, Fla.; Webb, H K, et al. $52^{nd}$ Annual ASH Meeting and Exposition; 2010 Dec. 4-7; Orlando, Fla.; Meadows, et al. $52^{nd}$ Annual ASH Meeting and Exposition; 2010 Dec. 4-7; Orlando, Fla.; Kahl, B, et al. $52^{nd}$ Annual ASH Meeting and Exposition; 2010 Dec. 4-7; Orlando, Fla.; Lannutti B J, et al. (2011) *Blood* 117(2):591-4).

PI3K-δ inhibitors have shown activity against PI3K-δ positive gliomas in vitro (Kashishian A, et al. Poster presented at: The American Association of Cancer Research $102^{nd}$ Annual Meeting; 2011 Apr. 2-6; Orlando, Fla.). PI3K-β is the PI3K isoform that is most commonly activated in tumors where the PTEN tumor suppressor is mutated (Ward S, et al. (2003) *Chem Biol.* 10(3):207-13). In this subset of tumors, treatment with the PI3K-δ inhibitor either alone or in combination with a cytotoxic agent can be effective.

Another mechanism for PI3K-δ inhibitors to have an affect in solid tumors involves the tumor cells' interaction with their micro-environment. PI3K-δ, PI3K-γ, and PI3K-β are expressed in the immune cells that infiltrate tumors, including tumor infiltrating lymphocytes, macrophages, and neutrophils. PI3K-δ inhibitors can modify the function of these tumor-associated immune cells and how they respond to signals from the stroma, the tumor, and each other, and in this way affect tumor cells and metastasis (Hoellenriegel, J, et al. $52^{nd}$ Annual ASH Meeting and Exposition; 2010 Dec. 4-7; Orlando, Fla.).

PI3K-δ is also expressed in endothelial cells. It has been shown that tumors in mice treated with PI3K-δ selective inhibitors are killed more readily by radiation therapy. In this same study, capillary network formation is impaired by the PI3K inhibitor, and it is postulated that this defect contributes to the greater killing with radiation. PI3K-δ inhibitors can affect the way in which tumors interact with their microenvironment, including stromal cells, immune cells, and endothelial cells and be therapeutic either on its own or in conjunction with another therapy (Meadows, S A, et al. Paper presented at: $52^{nd}$ Annual ASH Meeting and Exposition; 2010 Dec. 4-7; Orlando, Fla.; Geng L, et al. (2004) *Cancer Res.* 64(14):4893-9).

In some embodiments, provided herein are methods of using the compounds or pharmaceutical compositions to treat disease conditions, including but not limited to diseases associated with malfunctioning of one or more types of PI3 kinase. A detailed description of conditions and disorders mediated by p110δ kinase activity is set forth in Sadu et al., WO 01/81346, which is incorporated herein by reference in its entirety for all purposes.

The treatment methods provided herein comprise administering to the subject a therapeutically effective amount of a compound as disclosed herein.

In some embodiments, the disclosure relates to a method of treating a hyperproliferative disorder in a subject that comprises administering to said subject a therapeutically effective amount of a compound as disclosed herein, or a pharmaceutically acceptable form, salt, ester, prodrug or derivative thereof. In some embodiments, said method relates to the treatment of cancer such as acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS-related (e.g., Lymphoma and Kaposi's Sarcoma) or viral-induced cancer. In some embodiments, said method relates to the treatment of a non-cancerous hyperproliferative disorder such as benign hyperplasia of the skin (e.g., psoriasis), restenosis, or prostate (e.g., benign prostatic hypertrophy (BPH)).

In one embodiment, provided herein is a method of treating an inflammation disorder, including autoimmune diseases in a subject. The method comprises administering to said subject a therapeutically effective amount of a compound as disclosed herein, or a pharmaceutically acceptable form, salt, ester, prodrug or derivative thereof. Examples of autoimmune diseases includes but is not limited to acute disseminated encephalomyelitis (ADEM), Addison's disease, antiphospholipid antibody syndrome (APS), aplastic anemia, autoimmune hepatitis, coeliac disease, Crohn's disease, Diabetes mellitus (type 1), Goodpasture's syndrome, Graves' disease, Guillain-Barr-syndrome (GBS), Hashimoto's disease, lupus erythematosus, multiple sclerosis, myasthenia gravis, opsoclonus myoclonus syndrome (OMS), optic neuritis, Ord's thyroiditis, oemphigus, polyarthritis, primary biliary cirrhosis, psoriasis, rheumatoid arthritis, Reiter's syndrome, Takayasu's arteritis, temporal arteritis (also known as "giant cell arteritis"), warm autoimmune hemolytic anemia, Wegener's granulomatosis, alopecia universalis, Chagas disease, chronic fatigue syndrome, dysautonomia, endometriosis, hidradenitis suppurativa, interstitial cystitis, neuromyotonia, sarcoidosis, scleroderma, ulcerative colitis, vitiligo, and vulvodynia. Other disorders include bone-resorption disorders and thrombosis.

In some embodiments, provided herein aremethods for treating disorders or conditions in which the δ isoform of PI3K is implicated to a greater extent than other PI3K isoforms such as PI3K α and/or β Selective inhibition of PI3K-δ and/or PI3K-γ can provide advantages over using less selective compounds which inhibit PI3K α and/or β, such as an improved side effects profile or lessened reduction in the ability to reduce a bacterial, viral, and/or fungal infection.

In certain embodiments, a method of treating inflammatory or autoimmune diseases is provided comprising administering to a subject (e.g., a mammal) a therapeutically effective amount of one or more compounds as disclosed herein that selectively inhibit PI3K-δ and/or PI3K-γ as compared to all other type I PI3 kinases. Such selective inhibition of PI3K-δ and/or PI3K-γ can be advantageous for treating any of the diseases or conditions described herein. For example, selective inhibition of PI3K-δ can inhibit inflammatory responses associated with inflammatory diseases, autoimmune disease, or diseases related to an undesirable immune response including but not limited to asthma, emphysema, allergy, dermatitis, rheumatoid arthritis, psoriasis, lupus erythematosus, or graft versus host disease. Selective inhibition of PI3K-δ can further provide for a reduction in the inflammatory or undesirable immune response without a concomitant reduction in the ability to reduce a bacterial, viral, and/or fungal infection. Selective inhibition of both PI3K-δ and PI3K-γ can be advantageous for inhibiting the inflammatory response in the subject to a greater degree than that would be provided for by inhibitors that selectively inhibit PI3K-δ or PI3K-γ alone. In one aspect, one or more of the subject methods are effective in reducing antigen specific antibody production in vivo by about 2-fold, 3-fold, 4-fold, 5-fold, 7.5-fold, 10-fold, 25-fold, 50-fold, 100-fold, 250-fold, 500-fold, 750-fold, or about 1000-fold or more. In another aspect, one or more of the subject methods are effective in reducing antigen specific IgG3 and/or IgGM production in vivo by about 2-fold, 3-fold, 4-fold, 5-fold, 7.5-fold, 10-fold, 25-fold, 50-fold, 100-fold, 250-fold, 500-fold, 750-fold, or about 1000-fold or more.

In one aspect, one of more of the subject methods are effective in ameliorating symptoms associated with rhuematoid arthritis including but not limited to a reduction in the swelling of joints, a reduction in serum anti-collagen levels, and/or a reduction in joint pathology such as bone resorption, cartilage damage, pannus, and/or inflammation. In another aspect, the subject methods are effective in reducing ankle inflammation by at least about 2%, 5%, 10%, 15%, 20%, 25%, 30%, 50%, 60%, or about 75% to 90%. In another aspect, the subject methods are effective in reducing knee inflammation by at least about 2%, 5%, 10%, 15%, 20%, 25%, 30%, 50%, 60%, or about 75% to 90% or more. In still another aspect, the subject methods are effective in reducing serum anti-type II collagen levels by at least about 10%, 12%, 15%, 20%, 24%, 25%, 30%, 35%, 50%, 60%, 75%, 80%, 86%, 87%, or about 90% or more. In another aspect, the subject methods are effective in reducing ankle histopathology scores by about 5%, 10%, 15%, 20%, 25%, 30%, 40%, 50%, 60%, 75%, 80%, 90% or more. In still another aspect, the subject methods are effective in reducing knee histopathology scores by about 5%, 10%, 15%, 20%, 25%, 30%, 40%, 50%, 60%, 75%, 80%, 90% or more.

In other embodiments, provided herein are methods of using the compounds or pharmaceutical compositions to treat respiratory diseases including but not limited to diseases affecting the lobes of lung, pleural cavity, bronchial tubes, trachea, upper respiratory tract, or the nerves and muscle for breathing. For example, methods are provided to treat obstructive pulmonary disease. Chronic obstructive pulmonary disease (COPD) is an umbrella term for a group of respiratory tract diseases that are characterized by airflow obstruction or limitation. Conditions included in this umbrella term include, but are not limited to: chronic bronchitis, emphysema, and bronchiectasis.

In another embodiment, the compounds described herein are used for the treatment of asthma. Also, the compounds or pharmaceutical compositions described herein can be used for the treatment of endotoxemia and sepsis. In one embodiment, the compounds or pharmaceutical compositions described herein are used to for the treatment of rheumatoid arthritis (RA). In yet another embodiment, the compounds or pharmaceutical compositions described herein is used for the treatment of contact or atopic dermatitis. Contact dermatitis includes irritant dermatitis, phototoxic dermatitis, allergic dermatitis, photoallergic dermatitis, contact urticaria, systemic contact-type dermatitis and the like. Irritant dermatitis can occur when too much of a substance is used on the skin of when the skin is sensitive to certain substance. Atopic dermatitis, sometimes called eczema, is a kind of dermatitis, an atopic skin disease.

In some embodiments, the disclosure provides a method of treating diseases related to vasculogenesis or angiogenesis in a subject that comprises administering to said subject a therapeutically effective amount of a compound as disclosed herein, or a pharmaceutically acceptable form, salt, ester, prodrug, or derivative thereof. In some embodiments, said method is for treating a disease selected from tumor angiogenesis, chronic inflammatory disease such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

Patients that can be treated with compounds as disclosed herein, or pharmaceutically acceptable form, salt, ester, prodrug or derivative of said compounds, according to the methods as disclosed herein include, for example, but not limited to, patients that have been diagnosed as having psoriasis; restenosis; atherosclerosis; BPH; breast cancer such as a ductal carcinoma in duct tissue in a mammary gland, medullary carcinomas, colloid carcinomas, tubular carcinomas, and inflammatory breast cancer; ovarian cancer, including epithelial ovarian tumors such as adenocarcinoma in the ovary and an adenocarcinoma that has migrated from the ovary into the abdominal cavity; uterine cancer; cervical cancer such as adenocarcinoma in the cervix epithelial including squamous cell carcinoma and adenocarcinomas; prostate cancer, such as a prostate cancer selected from the following: an adenocarcinoma or an adenocarinoma that has migrated to the bone; pancreatic cancer such as epitheliod carcinoma in the pancreatic duct tissue and an adenocarcinoma in a pancreatic duct; bladder cancer such as a transitional cell carcinoma in urinary bladder, urothelial carcinomas (transitional cell carcinomas), tumors in the urothelial cells that line the bladder, squamous cell carcinomas, adenocarcinomas, and small cell cancers; leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), and myelodysplastic syndrome (MDS); bone cancer; lung cancer such as non-small cell lung cancer (NSCLC), which is divided into squamous cell carcinomas, adenocarcinomas, and large cell undifferentiated carcinomas, and small cell lung cancer; skin cancer such as basal cell carcinoma, melanoma, squamous cell carcinoma and actinic keratosis, which is a skin condition that sometimes develops into squamous cell carcinoma; eye retinoblastoma; cutaneous or intraocular (eye) melanoma; primary liver cancer (cancer that begins in the liver); kidney cancer; thyroid cancer such as papillary, follicular, medullary and anaplastic; AIDS-related lymphoma such as diffuse large B-cell lymphoma, B-cell immunoblastic lymphoma and small non-cleaved cell lymphoma; Kaposi's Sarcoma; viral-induced cancers including hepatitis B virus (HBV), hepatitis C virus (HCV), and hepatocellular carcinoma; human lymphotropic virus-type 1 (HTLV-1) and adult T-cell leukemia/lymphoma; and human papilloma virus (HPV) and cervical cancer; central nervous system cancers (CNS) such as primary brain tumor, which includes gliomas (astrocytoma, anaplastic astrocytoma, or glioblastoma multiforme), Oligodendroglioma, Ependymoma, Meningioma, Lymphoma, Schwannoma, and Medulloblastoma; peripheral nervous system (PNS) cancers such as acoustic neuromas and malignant peripheral nerve sheath tumor (MPNST) including neurofibromas and schwannomas, malignant fibrous cytoma, malignant fibrous histiocytoma, malignant meningioma, malignant mesothelioma, and malignant mixed Müllerian tumor; oral cavity and oropharyngeal cancer such as, hypopharyngeal cancer, laryngeal cancer, nasopharyngeal cancer, and oropharyngeal cancer; stomach cancer such as lymphomas, gastric stromal tumors, and carcinoid tumors; testicular cancer such as germ cell tumors (GCTs), which include seminomas and nonseminomas, and gonadal stromal tumors, which include Leydig cell tumors and Sertoli cell tumors; thymus cancer such as to thymomas, thymic carcinomas, Hodgkin disease, non-Hodgkin lymphomas carcinoids or carcinoid tumors; rectal cancer; and colon cancer.

In some embodiments, the disclosure relates to a method of treating diabetes in a subject that comprises administering to said subject a therapeutically effective amount of a compound as disclosed herein, or a pharmaceutically acceptable form, salt, ester, prodrug or derivative thereof.

In addition, the compounds described herein can be used to treat acne.

In addition, the compounds described herein can be used for the treatment of arteriosclerosis, including atherosclerosis. Arteriosclerosis is a general term describing any hardening of medium or large arteries. Atherosclerosis is a hardening of an artery specifically due to an atheromatous plaque.

Further, the compounds described herein can be used for the treatment of glomerulonephritis. Glomerulonephritis is a primary or secondary autoimmune renal disease characterized by inflammation of the glomeruli. It can be asymptomatic, or present with hematuria and/or proteinuria. There are many recognized types, divided in acute, subacute or chronic glomerulonephritis. Causes are infectious (bacterial, viral or parasitic pathogens), autoimmune or paraneoplastic.

Additionally, the compounds described herein can be used for the treatment of bursitis, lupus, acute disseminated encephalomyelitis (ADEM), Addison's disease, antiphospholipid antibody syndrome (APS), aplastic anemia, autoimmune hepatitis, coeliac disease, crohn's disease, diabetes mellitus (type 1), goodpasture's syndrome, graves' disease, guillain-barre syndrome (GBS), hashimoto's disease, inflammatory bowel disease, lupus erythematosus, myasthenia gravis, opsoclonus myoclonus syndrome (OMS), optic neuritis, ord's thyroiditis, ostheoarthritis, uveoretinitis, pemphigus, polyarthritis, primary biliary cirrhosis, reiter's syndrome, takayasu's arteritis, temporal arteritis, warm autoimmune hemolytic anemia, wegener's granulomatosis, alopecia universalis, chagas' disease, chronic fatigue syndrome, dysautonomia, endometriosis, hidradenitis suppurativa, interstitial cystitis, neuromyotonia, sarcoidosis, scleroderma, ulcerative colitis, vitiligo, vulvodynia, appendicitis, arteritis, arthritis, blepharitis, bronchiolitis, bronchitis, cervicitis, cholangitis, cholecystitis, chorioamnionitis, colitis, conjunctivitis, cystitis, dacryoadenitis, dermatomyositis, endocarditis, endometritis, enteritis, enterocolitis, epicondylitis, epididymitis, fasciitis, fibrositis, gastritis, gastroenteritis, gingivitis, hepatitis, hidradenitis, ileitis, iritis, laryngitis, mastitis, meningitis, myelitis, myocarditis, myositis, nephritis, omphalitis, oophoritis, orchitis, osteitis, otitis, pancreatitis, parotitis, pericarditis, peritonitis, pharyngitis, pleuritis, phlebitis, pneumonitis, proctitis, prostatitis, pyelonephritis, rhinitis, salpingitis, sinusitis, stomatitis, synovitis, tendonitis, tonsillitis, uveitis, vaginitis, vasculitis, or vulvitis.

In some embodiments, provided herein is a method of treating a cardiovascular disease in a subject that comprises administering to said subject a therapeutically effective amount of a compound as disclosed herein, or a pharmaceutically acceptable form, salt, ester, prodrug or derivative thereof. Examples of cardiovascular conditions include, but are not limited to, atherosclerosis, restenosis, vascular occlusion and carotid obstructive disease.

In another aspect, provided herein are methods of disrupting the function of a leukocyte or disrupting a function of an osteoclast. The method includes contacting the leukocyte or the osteoclast with a function disrupting amount of a compound as disclosed herein.

In another aspect, methods are provided for treating ophthalmic disease by administering one or more of the subject compounds or pharmaceutical compositions to the eye of a subject.

Methods are further provided for administering the compounds provided herein include via eye drop, intraocular injection, intravitreal injection, topically, or through the use of a drug eluting device, microcapsule, implant, or microfluidic device. In some cases, the compounds as disclosed herein are administered with a carrier or excipient that increases the intraocular penetration of the compound such as an oil and water emulsion with colloid particles having an oily core surrounded by an interfacial film. It is contemplated that all local routes to the eye can be used including topical, subconjunctival, periocular, retrobulbar, subtenon, intracameral, intravitreal, intraocular, subretinal, juxtascleral and suprachoroidal administration. Systemic or parenteral administration can be feasible including but not limited to intravenous, subcutaneous, and oral delivery. An exemplary method of administration will be intravitreal or subtenon injection of solutions or suspensions, or intravitreal or subtenon placement of bioerodible or non-bioerodible devices, or by topical ocular administration of solutions or suspensions, or posterior juxtascleral administration of a gel or cream formulation.

In some cases, the colloid particles include at least one cationic agent and at least one non-ionic sufactant such as a poloxamer, tyloxapol, a polysorbate, a polyoxyethylene castor oil derivative, a sorbitan ester, or a polyoxyl stearate. In some cases, the cationic agent is an alkylamine, a tertiary alkyl amine, a quarternary ammonium compound, a cationic lipid, an amino alcohol, a biguanidine salt, a cationic compound or a mixture thereof. In some cases, the cationic agent is a biguanidine salt such as chlorhexidine, polyaminopropyl biguanidine, phenformin, alkylbiguanidine, or a mixture thereof. In some cases, the quaternary ammonium compound is a benzalkonium halide, lauralkonium halide, cetrimide, hexadecyltrimethylammonium halide, tetradecyltrimethylammonium halide, dodecyltrimethylammonium halide, cetrimonium halide, benzethonium halide, behenalkonium halide, cetalkonium halide, cetethyldimonium halide, cetylpyridinium halide, benzododecinium halide, chlorallyl methenamine halide, rnyristylalkonium halide, stearalkonium halide or a mixture of two or more thereof. In some cases, cationic agent is a benzalkonium chloride, lauralkonium chloride, benzododecinium bromide, benzethenium chloride, hexadecyltrimethylammonium bromide, tetradecyltrimethylammonium bromide, dodecyltrimethylammonium bromide or a mixture of two or more thereof. In some cases, the oil phase is mineral oil and light mineral oil, medium chain triglycerides (MCT), coconut oil; hydrogenated oils comprising hydrogenated cottonseed oil, hydrogenated palm oil, hydrogenate castor oil or hydrogenated soybean oil; polyoxyethylene hydrogenated castor oil derivatives comprising poluoxyl-40 hydrogenated castor oil, polyoxyl-60 hydrogenated castor oil or polyoxyl-100 hydrogenated castor oil.

In some embodiments, provided herein are methods of modulating a PI3K kinase activity by contacting the kinase with an effective amount of a compound as disclosed herein. Modulation can be inhibiting or activating kinase activity. In some embodiments, provided herein are methods of inhibiting kinase activity by contacting the kinase with an effective amount of a compound as disclosed herein in solution. In some embodiments, provided herein are methods of inhibiting the kinase activity by contacting a cell, tissue, organ that express the kinase of interest. In some embodiments, provided herein are methods of inhibiting kinase activity in a subject by administering into the subject an effective amount of a compound as disclosed herein. In some embodiments, the percentage of inhibiting exceeds about 25%, 30%, 40%, 50%, 60%, 70%, 80%, or 90%.

In some embodiments, the kinase is a lipid kinase or a protein kinase. In some embodiments, the kinase is selected from a PI3 kinase including different isoforms such as PI3 kinase α, PI3 kinase β, PI3 kinase γ, PI3 kinase δ; DNA-PK; mTor; Abl, VEGFR, Ephrin receptor B4 (EphB4); TEK receptor tyrosine kinase (TIE2); FMS-related tyrosine kinase 3 (FLT-3); Platelet derived growth factor receptor (PDGFR); RET; ATM; ATR; hSmg-1; Hck; Src; Epidermal growth factor receptor (EGFR); KIT; Inulsin Receptor (IR) and IGFR.

In some embodiments, disclosed herein are methods of modulating PI3 kinase activity by contacting a PI3 kinase with an amount of a compound as disclosed herein sufficient to modulate the activity of the PI3 kinase. Modulate can be inhibiting or activating PI3 kinase activity. In some embodiments, provided herein are methods of inhibiting PI3 kinase activity by contacting a PI3 kinase with an amount of a compound as disclosed herein sufficient to inhibit the activity of the PI3 kinase. In some embodiments, provided herein are methods of inhibiting PI3 kinase activity. Such inhibition can take place in solution, in a cell expressing one or more PI3 kinases, in a tissue comprising a cell expressing one or more PI3 kinases, or in an organism expressing one or more PI3 kinases. In some embodiments, provided herein are methods of inhibiting PI3 kinase activity in a subject (including mammals such as humans) by contacting said subject with an amount of a compound as disclosed herein sufficient to inhibit the activity of the PI3 kinase in said subject.

In some embodiments, provided herein are methods for combination therapies in which an agent known to modulate other pathways, or other components of the same pathway, or even overlapping sets of target enzymes are used in combination with a compound as disclosed herein, or a pharmaceutically acceptable form, salt, ester, prodrug or derivative thereof. In one aspect, such therapy includes, but is not limited to, the combination of the subject compound with chemotherapeutic agents, therapeutic antibodies, and radiation treatment, to provide a synergistic or additive therapeutic effect.

In one aspect, the compounds or pharmaceutical compositions as disclosed herein can present synergistic or additive efficacy when administered in combination with agents that inhibit IgE production or activity. Such combination can reduce the undesired effect of high level of IgE associated with the use of one or more PI3Kδ inhibitors, if such effect occurs. This can be particularly useful in treatment of autoimmune and inflammatory disorders (AIID) such as rheumatoid arthritis. Additionally, the administration of PI3Kδ or PI3Kδ/γ inhibitors as disclosed herein in combination with inhibitors of mTOR can also exhibit synergy through enhanced inhibition of the PI3K pathway.

In a separate but related aspect, provided herein is a combination treatment of a disease associated with PI3Kδ comprising administering to a PI3Kδ inhibitor and an agent that inhibits IgE production or activity. Other exemplary PI3Kδ inhibitors are applicable for this combination and they are described, e.g., U.S. Pat. No. 6,800,620. Such combination treatment is particularly useful for treating autoimmune and inflammatory diseases (AIID) including but not limited to rheumatoid arthritis.

Agents that inhibit IgE production are known in the art and they include, but are not limited to, one or more of TEI-9874, 2-(4-(6-cyclohexyloxy-2-naphtyloxy)phenylacetamide)benzoic acid, rapamycin, rapamycin analogs (i.e., rapalogs), TORC1 inhibitors, TORC2 inhibitors, and any other compounds that inhibit mTORC1 and mTORC2. Agents that inhibit IgE activity include, for example, anti-IgE antibodies such as for example Omalizumab and TNX-901.

For treatment of autoimmune diseases, the subject compounds or pharmaceutical compositions can be used in combination with commonly prescribed drugs including but not limited to Enbrel®, Remicade®, Humira®, Avonex®, and Rebif®. For treatment of respiratory diseaseses, the subject compounds or pharmaceutical compositions can be administered in combination with commonly prescribed drugs including but not limited to Xolair®, Advair®, Singulair®, and Spiriva®.

The compounds as disclosed herein can be formulated or administered in conjunction with other agents that act to relieve the symptoms of inflammatory conditions such as encephalomyelitis, asthma, and the other diseases described herein. These agents include non-steroidal anti-inflammatory drugs (NSAIDs), e.g., acetylsalicylic acid; ibuprofen; naproxen; indomethacin; nabumetone; tolmetin; etc. Corticosteroids are used to reduce inflammation and suppress activity of the immune system. An exemplary drug of this type is Prednisone. Chloroquine (Aralen) or hydroxychloroquine (Plaquenil) can also be used in some individuals with lupus. They can be prescribed for skin and joint symptoms of lupus. Azathioprine (Imuran) and cyclophosphamide (Cytoxan) suppress inflammation and tend to suppress the immune system. Other agents, e.g., methotrexate and cyclosporin are used to control the symptoms of lupus. Anticoagulants are employed to prevent blood from clotting rapidly. They range from aspirin at very low dose which prevents platelets from sticking, to heparin/coumadin.

In another aspect, provided herein is a pharmaceutical composition for inhibiting abnormal cell growth in a subject which comprises an amount of a compound as disclosed herein, or a pharmaceutically acceptable form, salt, ester, prodrug or derivative thereof, in combination with an amount of an anti-cancer agent (e.g., a chemotherapeutic agent). Many chemotherapeutics are presently known in the art and can be used in combination with the compounds as disclosed herein.

In some embodiments, the chemotherapeutic is selected from mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. Non-limiting examples are chemotherapeutic agents, cytotoxic agents, and non-peptide small molecules such as Gleevec® (Imatinib Mesylate), Velcade® (bortezomib), Casodex (bicalutamide), Iressa®, and Adriamycin as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK.R™; razoxane; sizofiran; spirogermanium; tenuazonic acid; triaziquone; 2,2',2"-trichlorotriethyla-mine; urethan; vindesine; dacarbazine; mannomustine; mitobronitol; mitolactol; pipobroman; gacytosine; arabinoside ("Ara-C"); cyclophosphamide; thiotepa; taxanes, e.g., paclitaxel (TAXOL™, Bristol-Myers Squibb Oncology, Princeton, N.J.) and docetaxel (TAXOTERE™, Rhone-Poulenc Rorer, Antony, France) and ABRAXANE® (paclitaxel protein-bound particles); retinoic acid; esperamicins; capecitabine; and pharmaceutically acceptable forms, salts, acids or derivatives of any of the above. Also included as suitable chemotherapeutic cell conditioners are anti-hormonal agents that act to regulate or inhibit hormone action on tumors such as anti-estrogens including for example tamoxifen (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomerase inhibitor RFS 2000; difluoromethylornithine (DMFO). Where desired, the compounds or pharmaceutical composition as disclosed herein can be used in combination with commonly prescribed anti-cancer drugs such as Herceptin®, Avastin®, Erbitux®, Rituxan®, Taxol®, Arimidex®, Taxotere®, ABVD, AVICINE, Abagovomab, Acridine carboxamide, Adecatumumab, 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, Tris(2-chloroethyl)amine, Troxacitabine, Uramustine, Vadimezan, Vinflunine, ZD6126, and Zosuquidar.

In some embodiments, the chemotherapeutic is selected from hedgehog inhibitors including, but not limited to IPI-926 (See U.S. Pat. No. 7,812,164). Other suitable hedgehog inhibitors include, for example, those described and disclosed in U.S. Pat. No. 7,230,004, U.S. Patent Application Publication No. 2008/0293754, U.S. Patent Application Publication No. 2008/0287420, and U.S. Patent Application Publication No. 2008/0293755, the entire disclosures of which are incorporated by reference herein. Examples of other suitable hedgehog inhibitors include those described in U.S. Patent Application Publication Nos. US 2002/0006931, US 2007/0021493 and US 2007/0060546, and International Application Publication Nos. WO 2001/19800, WO 2001/26644, WO 2001/27135, WO 2001/49279, WO 2001/74344, WO 2003/011219, WO 2003/088970, WO 2004/020599, WO 2005/013800, WO 2005/033288, WO 2005/032343, WO 2005/042700, WO 2006/028958, WO 2006/050351, WO 2006/078283, WO 2007/054623, WO 2007/059157, WO 2007/120827, WO 2007/131201, WO 2008/070357, WO 2008/110611, WO 2008/112913, and WO 2008/131354. Additional examples of hedgehog inhibitors include, but are not limited to, GDC-0449 (also known as RG3616 or vismodegib) described in, e.g., Von Hoff D. et al., *N Engl. J Med.* 2009; 361(12):1164-72; Robarge K. D. et al., *Bioorg Med Chem Lett.* 2009; 19(19):5576-81; Yauch, R. L. et al. (2009) *Science* 326: 572-574; Sciencexpress: 1-3 (10.1126/science. 1179386); Rudin, C. et al. (2009) *New England J of Medicine* 361-366 (10.1056/nejma0902903); BMS-833923 (also known as XL139) described in, e.g., in Siu L. et al., *J. Clin. Oncol.* 2010; 28:15s (suppl; abstr 2501); and National Institute of Health Clinical Trial Identifier No. NCT006701891; LDE-225 described, e.g., in Pan S. et al., *ACS Med. Chem. Lett.*, 2010; 1(3): 130-134; LEQ-506 described, e.g., in National Institute of Health Clinical Trial Identifier No. NCT01106508; PF-04449913 described, e.g., in National Institute of Health Clinical Trial Identifier No. NCT00953758; Hedgehog pathway antagonists disclosed in U.S. Patent Application Publication No. 2010/0286114; SMOi2-17 described, e.g., U.S. Patent Application Publication No. 2010/0093625; SANT-1 and SANT-2 described, e.g., in Rominger C. M. et al., *J. Pharmacol. Exp. Ther.* 2009; 329(3):995-1005; 1-piperazinyl-4-arylphthalazines or analogues thereof, described in Lucas B. S. et al., *Bioorg. Med. Chem. Lett.* 2010; 20(12):3618-22.

In some embodiments, the chemotherapeutic is selected from HSP90 inhibitors. The HSP90 inhibitor can be a geldanamycin derivative, e.g., a benzoquinone or hygroquinone ansamycin HSP90 inhbitor (e.g., IPI-493 and/or IPI-504). Non-limiting examples of HSP90 inhibitors include IPI-493, IPI-504, 17-AAG (also known as tanespimycin or CNF-1010), BIIB-021 (CNF-2024), BIIB-028, AUY-922 (also known as VER-49009), SNX-5422, STA-9090, AT-13387, XL-888, MPC-3100, CU-0305, 17-DMAG, CNF-1010, Macbecin (e.g., Macbecin I, Macbecin II), CCT-018159, CCT-129397, PU-H71, or PF-04928473 (SNX-2112).

In some embodiments, the chemotherapeutic is selected from PI3K inhibitors (e.g., including those PI3K inhibitors disclosed herein and those PI3K inhibitors not disclosed herein). In some embodiment, the PI3K inhibitor is an inhibitor of delta and gamma isoforms of PI3K. In some embodiments, the the PI3K inhibitor is an inhibitor of alpha isoforms of PI3K. In other embodiments, the PI3K inhibitor is an inhibitor of one or more alpha, beta, delta and gamma isoforms of PI3K. Exemplary PI3K inhibitors that can be used in combination are described in, e.g., WO 2010/036380; WO 2010/006086, WO 09/114870, WO 05/113556.

Additional PI3K inhibitors that can be used in combination with the pharmaceutical compositions, include but are not limited to, GSK 2126458, GDC-0980, GDC-0941, Sanofi XL147, XL756, XL147, PF-46915032, BKM 120, CAL-101, CAL 263, SF1126, PX-886, and a dual PI3K inhibitor (e.g., Novartis BEZ235). In one embodiment, the PI3K inhibitor is an isoquinolinone. In one embodiment, the PI3K inhibitor is IPI-145 or a derivative thereof. In other embodiments, the PI3K inhibitor is INK1117 or a derivative thereof.

In some embodiments, provided herein is a method for using the compounds or pharmaceutical composition in combination with radiation therapy in inhibiting abnormal cell growth or treating the hyperproliferative disorder in the subject. Techniques for administering radiation therapy are known in the art, and these techniques can be used in the combination therapy described herein. The administration of the compound as disclosed herein in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g., At-211, I-131, I-125, Y-90, Re-186, Re-188, Sm-153, Bi-212, P-32, and radioactive isotopes of Lu). Suitable radiation sources for use as a cell conditioner as disclosed herein include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

Without being limited by any theory, the compounds as disclosed herein can render abnormal cells more sensitive to treatment with radiation for purposes of killing and/or inhibiting the growth of such cells. Accordingly, provided herein is a method for sensitizing abnormal cells in a subject to treatment with radiation which comprises administering to the subject an amount of a compound as disclosed herein or pharmaceutically acceptable forms, salt, ester, prodrug, or derivative thereof, which amount is effective is sensitizing abnormal cells to treatment with radiation. The amount of the compound, form, salt in this method can be determined according to the means for ascertaining effective amounts of such compounds described herein.

The compounds or pharmaceutical compositions as disclosed herein can be used in combination with an amount of one or more substances selected from anti-angiogenesis agents, signal transduction inhibitors, and antiproliferative agents, glycolysis inhibitors, or autophagy inhibitors.

Anti-angiogenesis agents, such as MMP-2 (matrix-metalloproteinase 2) inhibitors, MMP-9 (matrix-metalloproteinase 9) inhibitors, and COX-11 (cyclooxygenase 11) inhibitors, can be used in conjunction with a compound as disclosed herein and pharmaceutical compositions described herein. Anti-angiogenesis agents include, for example, rapamycin, temsirolimus (CCI-779), everolimus (RAD001), sorafenib, sunitinib, and bevacizumab. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931, 788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12, 1999), U.S. Pat. No. 5,863, 949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. In some embodiments, MMP-2 and MMP-9 inhibitors are those that have little or no activity inhibiting MMP-1. Other embodiments include those that selectively inhibit MMP-2 and/or AMP-9 relative to the other matrix-metalloproteinases (i.e., MAP-1, MMP-3, MMP-4, MMP-5, MMP-6, MMP-7, MMP-8, MMP-10, MMP-11, MMP-12, and MMP-13). Some non-limiting examples of MMP inhibitors are AG-3340, RO 32-3555, and RS 13-0830.

Autophagy inhibitors include, but are not limited to, chloroquine, 3-methyladenine, hydroxychloroquine (Plaquenil™), bafilomycin A1,5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, N6-mercaptopurine riboside, and vinblastine. In addition, antisense or siRNA that inhibits expression of proteins including but not limited to ATG5 (which are implicated in autophagy), can also be used.

In some embodiments, disclosed herein is a method of and/ora pharmaceutical composition for treating a cardiovascular disease in a subject which comprises an amount of a compound as disclosed herein, or a pharmaceutically acceptable form, salt, ester, prodrug or derivative thereof, or an isotopically-labeled derivative thereof, and an amount of one or more therapeutic agents use for the treatment of cardiovascular diseases.

Exemplary agents for use in cardiovascular disease applications are anti-thrombotic agents, e.g., prostacyclin and salicylates, thrombolytic agents, e.g., streptokinase, urokinase, tissue plasminogen activator (TPA) and anisoylated plasminogen-streptokinase activator complex (APSAC), anti-platelets agents, e.g., acetyl-salicylic acid (ASA) and clopidrogel, vasodilating agents, e.g., nitrates, calcium channel blocking drugs, anti-proliferative agents, e.g., colchicine and alkylating agents, intercalating agents, growth modulating factors such as interleukins, transformation growth factor-beta and congeners of platelet derived growth factor, monoclonal antibodies directed against growth factors, anti-inflammatory agents, both steroidal and non-steroidal, and other agents that can modulate vessel tone, function, arteriosclerosis, and the healing response to vessel or organ injury post intervention. Antibiotics can also be included in combinations or coatings. Moreover, a coating can be used to effect therapeutic delivery focally within the vessel wall. By incorporation of the active agent in a swellable polymer, the active agent will be released upon swelling of the polymer.

The compounds described herein can be formulated or administered in conjunction with liquid or solid tissue barriers also known as lubricants. Examples of tissue barriers include, but are not limited to, polysaccharides, polyglycans, seprafilm, interceed and hyaluronic acid.

Medicaments which can be administered in conjunction with the compounds described herein include any suitable drugs usefully delivered by inhalation for example, analgesics, e.g., codeine, dihydromorphine, ergotamine, fentanyl or morphine; anginal preparations, e.g., diltiazem; antiallergics, e.g. cromoglycate, ketotifen or nedocromil; anti-infectives, e.g., cephalosporins, penicillins, streptomycin, sulphonamides, tetracyclines or pentamidine; antihistamines, e.g., methapyrilene; anti-inflammatories, e.g., beclomethasone, flunisolide, budesonide, tipredane, triamcinolone acetonide or fluticasone; antitussives, e.g., noscapine; bronchodilators, e.g., ephedrine, adrenaline, fenoterol, formoterol, isoprenaline, metaproterenol, phenylephrine, phenylpropanolamine, pirbuterol, reproterol, rimiterol, salbutamol, salmeterol, terbutalin, isoetharine, tulobuterol, orciprenaline or (−)-4-amino-3,5-dichloro-α-[[[6-[2-(2-pyridinyl)ethoxy]hexyl]-amino]methyl]benzenemethanol; diuretics, e.g., amiloride; anticholinergics e.g., ipratropium, atropine or oxitropium; hormones, e.g., cortisone, hydrocortisone or prednisolone; xanthines e.g., aminophylline, choline theophyllinate, lysine theophyllinate or theophylline; and therapeutic proteins and peptides, e.g., insulin or glucagon. It will be clear to a person skilled in the art that, where appropriate, the medicaments can be used in the form of salts (e.g., as alkali metal or amine salts or as acid addition salts) or as esters (e.g., lower alkyl esters) to optimize the activity and/or stability of the medicament.

Other exemplary therapeutic agents useful for a combination therapy include, but are not limited to, agents as described above, radiation therapy, hormone antagonists, hormones and their releasing factors, thyroid and antithyroid drugs, estrogens and progestins, androgens, adrenocorticotropic hormone; adrenocortical steroids and their synthetic analogs; inhibitors of the synthesis and actions of adrenocortical hormones, insulin, oral hypoglycemic agents, and the pharmacology of the endocrine pancreas, agents affecting calcification and bone turnover: calcium, phosphate, parathyroid hormone, vitamin D, calcitonin, vitamins such as water-soluble vitamins, vitamin B complex, ascorbic acid, fat-soluble vitamins, vitamins A, K, and E, growth factors, cytokines, chemokines, muscarinic receptor agonists and antagonists; anticholinesterase agents; agents acting at the neuromuscular junction and/or autonomic ganglia; catecholamines, sympathomimetic drugs, and adrenergic receptor agonists or antagonists; and 5-hydroxytryptamine (5-HT, serotonin) receptor agonists and antagonists.

Therapeutic agents can also include agents for pain and inflammation such as histamine and histamine antagonists, bradykinin and bradykinin antagonists, 5-hydroxytryptamine (serotonin), lipid substances that are generated by biotransformation of the products of the selective hydrolysis of membrane phospholipids, eicosanoids, prostaglandins, thromboxanes, leukotrienes, aspirin, nonsteroidal anti-inflammatory agents, analgesic-antipyretic agents, agents that inhibit the synthesis of prostaglandins and thromboxanes, selective inhibitors of the inducible cyclooxygenase, selective inhibitors of the inducible cyclooxygenase-2, autacoids, paracrine hormones, somatostatin, gastrin, cytokines that mediate interactions involved in humoral and cellular immune responses, lipid-derived autacoids, eicosanoids, β-adrenergic agonists, ipratropium, glucocorticoids, methylxanthines, sodium channel blockers, opioid receptor agonists, calcium channel blockers, membrane stabilizers and leukotriene inhibitors.

Additional therapeutic agents contemplated herein include diuretics, vasopressin, agents affecting the renal conservation of water, rennin, angiotensin, agents useful in the treatment of myocardial ischemia, anti-hypertensive agents, angiotensin converting enzyme inhibitors, β-adrenergic receptor antagonists, agents for the treatment of hypercholesterolemia, and agents for the treatment of dyslipidemia.

Other therapeutic agents contemplated herein include drugs used for control of gastric acidity, agents for the treatment of peptic ulcers, agents for the treatment of gastroesophageal reflux disease, prokinetic agents, antiemetics, agents used in irritable bowel syndrome, agents used for diarrhea, agents used for constipation, agents used for inflammatory bowel disease, agents used for biliary disease, agents used for pancreatic disease. Therapeutic agents include, but are not limited to, those used to treat protozoan infections, drugs used to treat Malaria, Amebiasis, Giardiasis, Trichomoniasis, Trypanosomiasis, and/or Leishmaniasis, and/or drugs used in the chemotherapy of helminthiasis. Other therapeutic agents include, but are not limited to, antimicrobial agents, sulfonamides, trimethoprim-sulfamethoxazole quinolones, and agents for urinary tract infections, penicillins, cephalosporins, and other, β-Lactam antibiotics, an agent containing an aminoglycoside, protein synthesis inhibitors, drugs used in the chemotherapy of tuberculosis, mycobacterium avium complex disease, and leprosy, antifungal agents, antiviral agents including nonretroviral agents and antiretroviral agents.

Examples of therapeutic antibodies that can be combined with a subject compound include but are not limited to anti-receptor tyrosine kinase antibodies (cetuximab, panitumumab, trastuzumab), anti CD20 antibodies (rituximab, tositumomab), and other antibodies such as alemtuzumab, bevacizumab, and gemtuzumab.

Moreover, therapeutic agents used for immunomodulation, such as immunomodulators, immunosuppressive agents, tolerogens, and immunostimulants are contemplated by the methods herein. In addition, therapeutic agents acting on the blood and the blood-forming organs, hematopoietic agents, growth factors, minerals, and vitamins, anticoagulant, thrombolytic, and antiplatelet drugs.

For treating renal carcinoma, one can combine a compound as disclosed herein with sorafenib and/or avastin. For treating an endometrial disorder, one can combine a compound as disclosed herein with doxorubincin, taxotere (taxol), and/or cisplatin (carboplatin). For treating ovarian cancer, one can combine a compound as disclosed herein with cisplatin (carboplatin), taxotere, doxorubincin, topotecan, and/or tamoxifen. For treating breast cancer, one can combine a compound as disclosed herein with taxotere (taxol), gemcitabine (capecitabine), tamoxifen, letrozole, tarceva, lapatinib, PD0325901, avastin, herceptin, OSI-906, and/or OSI-930. For treating lung cancer, one can combine a compound as disclosed herein with taxotere (taxol), gemcitabine, cisplatin, pemetrexed, Tarceva, PD0325901, and/or avastin.

Further therapeutic agents that can be combined with a subject compound can be found in Goodman and Gilman's "*The Pharmacological Basis of Therapeutics*" Tenth Edition edited by Hardman, Limbird and Gilman or the Physician's Desk Reference, both of which are incorporated herein by reference in their entirety.

The compounds described herein can be used in combination with the agents disclosed herein or other suitable agents, depending on the condition being treated. Hence, in some embodiments, the compounds as disclosed herein will be co-administered with other agents as described above. When used in combination therapy, the compounds described herein can be administered with the second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound as disclosed herein and any of the agents described above can be simultaneously administered, wherein both the agents are present in separate formulations. In another alternative, a compound as disclosed herein can be administered just followed by and any of the agents described above, or vice versa. In the separate administration protocol, a compound as disclosed herein and any of the agents described above can be administered a few minutes apart, or a few hours apart, or a few days apart.

Administration of the compounds as disclosed herein can be effected by any method that enables delivery of the compounds to the site of action. An effective amount of a compound as disclosed herein can be administered in either single or multiple doses by any of the accepted modes of administration of agents having similar utilities, including rectal, buccal, intranasal and transdermal routes, by intraarterial injection, intravenously, intraperitoneally, parenterally, intramuscularly, subcutaneously, orally, topically, as an inhalant, or via an impregnated or coated device such as a stent, for example, or an artery-inserted cylindrical polymer.

When a compound as disclosed herein is administered in a pharmaceutical composition that comprises one or more agents, and the agent has a shorter half-life than the compound as disclosed herein, unit dose forms of the agent and the compound as disclosed herein can be adjusted accordingly.

The examples and preparations provided below further illustrate and exemplify the compounds as disclosed herein and methods of preparing such compounds. It is to be understood that the scope of the present disclosure is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers can be obtained by methods known to those skilled in the art.

EXAMPLES

Biological Activity Assessment

The activity of the compounds as described herein can be determined by the following procedure, as well as the procedures described in the examples below. The activity of the kinase is assessed by measuring the incorporation of γ-$^{33}$P-phosphate from γ-$^{33}$P-ATP onto N-terminal His tagged substrate, which is expressed in *E. coli* and is purified by conventional methods, in the presence of the kinase. The assay is carried out in 96-well polypropylene plate. The incubation mixture (100, μL) comprises of 25 mM Hepes, pH 7.4, 10 mM $MgCl_2$, 5 mM β-glycerolphosphate, 100 μM Na-orthovanadate, 5 mM DTT, 5 nM kinase, and 1 μM substrate Inhibitors are suspended in DMSO, and all reactions, including controls are performed at a final concentration of 1% DMSO. Reactions are initiated by the addition of 10 μM ATP (with 0.5 μCi γ-$^{33}$P-ATP/well) and incubated at ambient temperature for 45 minutes. Equal volume of 25% TCA is added to stop the reaction and precipitate the proteins. Precipitated proteins are trapped onto glass fiber B filterplates, and excess labeled ATP washed off using a Tomtec MACH III harvestor. Plates are allowed to air-dry prior to adding 30 μL/well of Packard Microscint 20, and plates are counted using a Packard TopCount.

Chemical Examples

The chemical entities described herein can be synthesized according to one or more illustrative schemes herein and/or techniques well known in the art.

Unless specified to the contrary, the reactions described herein take place at atmospheric pressure, generally within a temperature range from −10° C. to 200° C. Further, except as otherwise specified, reaction times and conditions are intended to be approximate, e.g., taking place at about atmospheric pressure within a temperature range of about −10° C. to about 110° C. over a period that is, for example, about 1 to about 24 hours; reactions left to run overnight in some embodiments can average a period of about 16 hours.

The terms "solvent," "organic solvent," or "inert solvent" each mean a solvent inert under the conditions of the reaction being described in conjunction therewith including, for example, benzene, toluene, acetonitrile, tetrahydrofuran ("THF"), dimethylformamide ("DMF"), chloroform, methylene chloride (or dichloromethane), diethyl ether, methanol, N-methylpyrrolidone ("NMP"), pyridine and the like. Unless specified to the contrary, the solvents used in the reactions described herein are inert organic solvents. Unless specified to the contrary, for each gram of the limiting reagent, one cc (or mL) of solvent constitutes a volume equivalent.

Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures are given by reference to the examples hereinbelow. However, other equivalent separation or isolation procedures can also be used.

When desired, the (R)- and (S)-isomers of the non-limiting exemplary compounds, if present, can be resolved by methods known to those skilled in the art, for example by formation of diastereoisomeric salts or complexes which can be separated, for example, by crystallization; via formation of diastereoisomeric derivatives which can be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. Alternatively, a specific enantiomer can be synthesized by asymmetric synthesis using optically active reagents, substrates, catalysts or solvents, or by converting one enantiomer to the other by asymmetric transformation.

The compounds described herein can be optionally contacted with a pharmaceutically acceptable acid to form the corresponding acid addition salts. Also, the compounds described herein can be optionally contacted with a pharmaceutically acceptable base to form the corresponding basic addition salts.

In some embodiments, disclosed compounds can generally be synthesized by an appropriate combination of generally well known synthetic methods. Techniques useful in synthesizing these chemical entities are both readily apparent and accessible to those of skill in the relevant art, based on the instant disclosure. Many of the optionally substituted starting compounds and other reactants are commercially available, e.g., from Aldrich Chemical Company (Milwaukee, Wis.) or can be readily prepared by those skilled in the art using commonly employed synthetic methodology.

The discussion below is offered to illustrate certain of the diverse methods available for use in making the disclosed compounds and is not intended to limit the scope of reactions or reaction sequences that can be used in preparing the compounds provided herein.

General Synthetic Methods

General method for the synthesis of Cl—$W_d$ heterocycles:

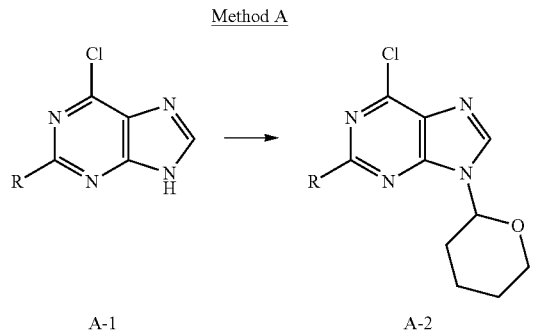

Method A

General Conditions for the Preparation of 6-chloro-9-(tetrahydro-2H-pyran-2-yl)-9H-purines:

To a solution of a given 6-chloro-9H-purine (A-1) (1.29 mol, 1 eq) and TsOH (0.02 mol, 0.015 eq) in ethyl acetate (1000 mL), 3,4-dihydro-2H-pyran (1.94 mol, 1.5 eq) is added and the resulting mixture is stirred at reflux for 2 h. The reaction mixture is allowed to cool to RT, aqueous $Na_2CO_3$ solution (3%, 500 mL) is added and the resulting mixture is stirred for 10 min. The organic layer is separated, washed with water (500 mL×2) and brine (500 mL), dried over anhydrous $Na_2SO_4$, and filtered. The filtrate is concentrated in vacuo. The product is dissolved in ethyl acetate (50 mL), and then n-heptane (500 mL) is added. The resulting mixture is stirred at RT for 1 h. The precipitate is collected by filtration, rinsed with heptane (100 mL) and dried in vacuo to afford the product 6-chloro-9-(tetrahydro-2H-pyran-2-yl)-9H-purine (A-2) as a yellowish solid.

Method B

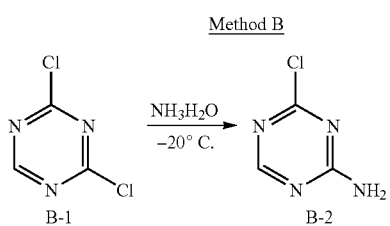

General Conditions for the Preparation of 4-chloro-1,3,5-triazin-2-amine:

2,4-Dichloro-1,3,5-triazine (B-1) (500 mg, 3.3 mmol, 1.0 eq) is dissolved in concentrated ammonium hydroxide (100 mL, 700 mmol, 212 eq) at −20° C. and the resulting mixture is stirred at this temperature for 10 min. The mixture is then filtered, rinsed with water (5 mL×3) and dried in vacuo to afford the product, 4-chloro-1,3,5-triazin-2-amine (B-2) as a solid.

Method C

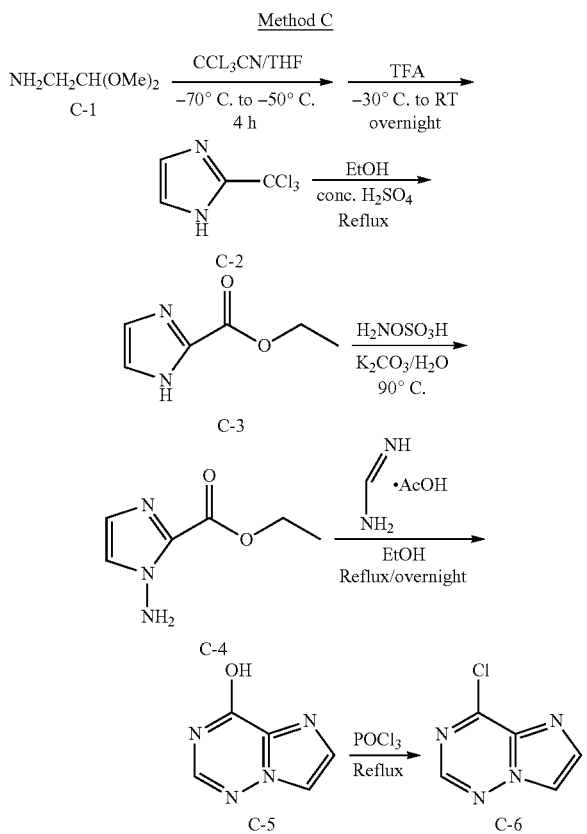

General Conditions for the Preparation of 4-chloroimidazo[1,2-f][1,2,4]triazine:

To a stirred solution of trichloroacetonitrile (28.8 g, 200 mmol, 1 eq) in anhydrous THF (70 mL) at −60° C. under an argon atmosphere, 2,2-dimethoxyethanamine (C-1) (21.8 mL, 200 mmol, 1.0 eq) is added dropwise over 5 min. The resulting mixture is allowed to warm to RT and stirred at RT for 4 h. The mixture is concentrated in vacuo and the residue is added in portions to a stirred solution of trifluoroacetic acid (100 mL) at −30° C. under argon. The resulting mixture is then stirred from −30° C. to RT overnight. The reaction mixture is concentrated in vacuo to afford the product, 2-(trichloromethyl)-1H-imidazole (C-2). The product is used in the next step without further purification.

The above-obtained residue (C-2) is dissolved in EtOH (300 mL). To this solution, conc. $H_2SO_4$ (98%, 30 mL, 522 mmol, 2.76 eq) is added dropwise while keeping the reaction temperature below 25° C. The resulting mixture is stirred at reflux for 7 h and then stirred at RT overnight. The mixture is concentrated in vacuo to remove EtOH. The resulting suspension is diluted with ice-water (200 mL) and neutralized with concentrated ammonium hydroxide to adjust the pH to 5-6 while keeping the temperature below 5° C. The solid is collected by filtration, rinsed with water (10 mL×3), and dried in vacuo to afford a first portion of the product. The filtrate is extracted with ethyl acetate (200 mL×2). The combined organic layers are washed with brine, dried over $Na_2SO_4$ and filtered. The filtrate is concentrated in vacuo. The resulting residue is combined with the first portion of product and then recrystallized in isopropyl ether to afford the product, ethyl 1H-imidazole-2-carboxylate (C-3).

To a stirred solution of hydroxylamine-o-sulfonic acid (26.64 g, 235.8 mmol, 3.0 eq) in $H_2O$ (17 mL) at 0° C., ethyl 1H-imidazole-2-carboxylate (C-3) (11.0 g, 78.6 mmol, 1.0 eq) is added and the resulting mixture is stirred at 90° C. for 30 min. The mixture is cooled to RT and $K_2CO_3$ (3.6 g, 26.2 mmol, 1.0 eq) is added in portions. The resulting mixture is stirred at RT overnight, filtered and rinsed with $H_2O$ (10 mL×3). The filtrate is extracted with ethyl acetate (50 mL×5). The combined organic layer is washed with brine, dried over $Na_2SO_4$ and filtered. The filtrate is evaporated in vacuo and the residue is purified by flash column chromatography on silica gel (1% MeOH-DCM) to afford the product, ethyl 1-amino-1H-imidazole-2-carboxylate (C-4) as a colorless oil.

A mixture of ethyl 1-amino-1H-imidazole-2-carboxylate (C-4) (800 mg, 5.16 mmol, 1.0 eq) and formamidine acetate (2.68 g, 25.78 mmol, 5.0 eq) in EtOH (100 mL) is stirred at reflux overnight. The resulting mixture is cooled to RT. The solid is collected by filtration, rinsed with EtOH (3×2 mL) and petroleum ether (2 mL×3), and then dried in vacuo to afford the product, imidazo[1,2-f][1,2,4]triazin-4-ol (C-5).

Imidazo[1,2-f][1,2,4]triazin-4-ol (C-5) (400 mg, 2.94 mmol, 1.0 eq) is dissolved in $POCl_3$ (10 mL, 109.2 mmol, 37.1 eq) and the resulting mixture is stirred at reflux for 2 h. The mixture is concentrated in vacuo to remove $POCl_3$. The residue is poured into ice water (30 mL) and neutralized with saturated aqueous $NaHCO_3$ solution to adjust the pH to 6-7 while keeping the temperature below 5° C. The mixture is extracted with ethyl acetate (30 mL×4). The combined organic layers are washed with brine, dried over $Na_2SO_4$ and filtered. The filtrate is concentrated in vacuo and the residue is purified by flash column chromatography on silica gel (16% ethyl acetate in petro ether) to afford the product, 4-chloroimidazo[1,2-f][1,2,4]triazine (C-6).

Method D

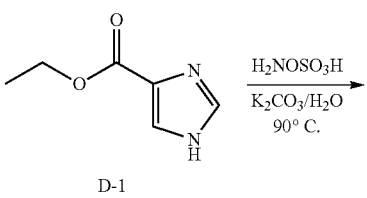

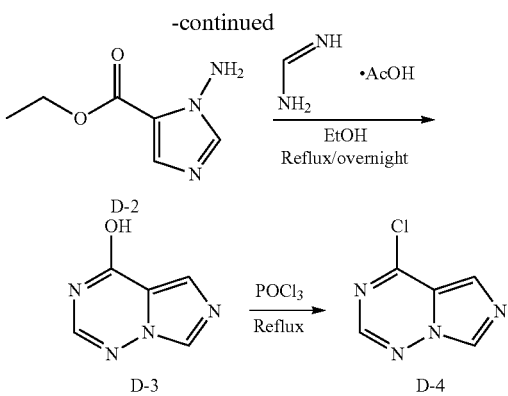

General Conditions for the Preparation of 4-chloroimidazo[1,5-f][1,2,4]triazine:

4-Chloroimidazo[1,5-f][1,2,4]triazine (D-4) is prepared from commercially available material (D-1) through a three-step sequence in analogous fashion to the synthesis of 4-chloroimidazo[1,2-f][1,2,4]triazine (C-6) from compound (C-3B) in Method C.

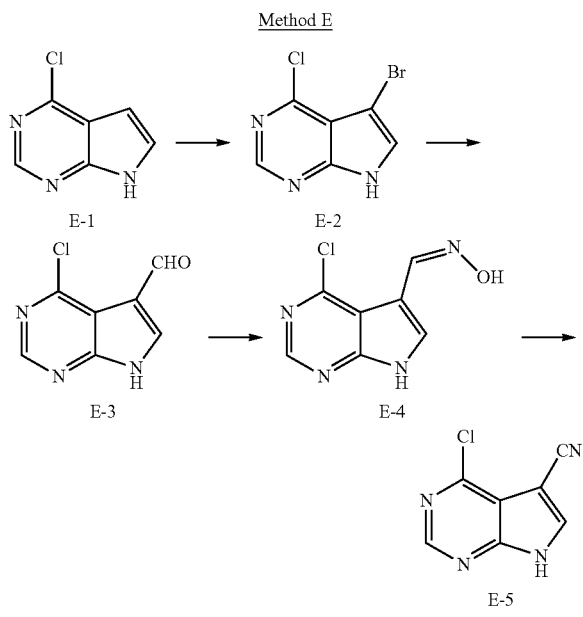

General Method for the Synthesis of 4-chloro-7H-pyrrolo[2,3-d]pyrimidine-5-carbonitrile:

To a suspension of 4-chloro-7H-pyrrolo[2,3-d]pyrimidine (E-1) (3.99 g, 26.0 mmol, 1.0 eq) in dry DCM (150 mL) under argon, N-bromosuccinimide (6.02 g, 33.8 mmol, 1.3 eq) is added and the resulting mixture is stirred at RT for 3 h. The reaction mixture is diluted with MeOH (30 mL) and then concentrated in vacuo to yield a slight brown solid. The residue is triturated with $H_2O$ (150 mL). The solid is collected by filtration and then re-crystallized in MeOH to afford the product, 5-bromo-4-chloro-7H-pyrrolo[2,3-d]pyrimidine (E-2).

To a solution of 5-bromo-4-chloro-7H-pyrrolo[2,3-d]pyrimidine (E-2) (2.33 g, 10.0 mmol, 1.0 eq) in anhydrous THF (100 mL) at −78° C. under argon, n-BuLi solution (2.5 M in THF, 8.8 mL, 22.0 mmol, 2.2 eq) is added dropwise (over 10 min). The resulting mixture is stirred at −78° C. for 1 h and then DMF (2.0 g, 11.0 mmol, 1.1 eq) is added dropwise (over 10 min) The mixture is stirred at −78° C. for an additional 30 min and then stirred at RT overnight. The reaction mixture is quenched with $H_2O$ (50 mL) and then concentrated in vacuo. The residue is triturated with saturated aqueous $NH_4Cl$ solution. The solid is collected by filtration, rinsed with ethyl acetate, and dried in vacuo to afford the product, 4-chloro-7H-pyrrolo[2,3-d]pyrimidine-5-carbaldehyde (E-3).

To a suspension of 4-chloro-7H-pyrrolo[2,3-d]pyrimidine-5-carbaldehyde (E-3) (1.17 g, 6.47 mmol, 1.0 eq) and hydroxylamine hydrochloride (0.54 g, 7.77 mmol, 1.2 eq) in EtOH (25 mL), aqueous NaOH solution (0.31 g, 7.77 mmol, 1.2 eq) in $H_2O$ (4 mL) is added dropwise. The resulting mixture is stirred at RT for 30 min and then is diluted with a sufficient amount of EtOH to allow stirring for additional 30 min. The solid is collected by filtration, rinsed with $H_2O$ and dried in vacuo to afford the product, 4-chloro-7H-pyrrolo[2,3-d]pyrimidine-5-carbaldehyde oxime (E-4) as a mixture of isomers.

To a suspension of 4-chloro-7H-pyrrolo[2,3-d]pyrimidine-5-carbaldehyde oxime (E-4) (865 mg, 4.40 mmol, 1.0 eq) in DCM (20 mL), thionyl chloride (3.1 mL, 43.7 mmol, 10.0 eq) is added and the resulting mixture is stirred at RT overnight. The reaction mixture is concentrated in vacuo. The residue is suspended in water (60 mL) and saturated aqueous $NaHCO_3$ is added to adjust the pH to 4. The solid is collected by filtration, rinsed with water followed by ethyl acetate to afford a first portion of product. The filtrate is then extracted with ethyl acetate (50 mL×3). The combined organic layers are washed with brine, dried over $Na_2SO_4$ and filtered. The filtrate is concentrated in vacuo and the residue is combined with the first portion of product. The product is then re-crystallized in ethyl acetate/hexanes (1:1) and dried in vacuo to afford the final product, 4-chloro-7H-pyrrolo[2,3-d]pyrimidine-5-carbonitrile (E-5) as a pale solid.

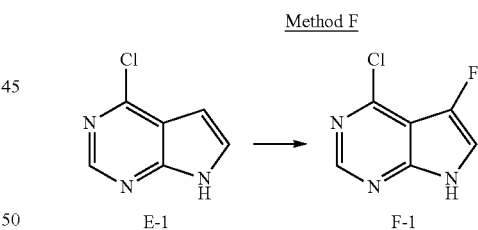

General Method for the Synthesis of 4-chloro-5-fluoro-7H-pyrrolo[2,3-d]pyrimidine:

4-Chloro-7H-pyrrolo[2,3-d]pyrimidine (E-1) (5.01 g, 32.6 mmol, 1 eq) and Selectfluor (17.32 g, 48.9 mmol, 1.5 eq) are dissolved in a mixture of dry acetonitrile (250 mL) and AcOH (50 mL). The resulting mixture is stirred at 70° C. under argon for 16 h. The mixture is concentrated in vacuo. The residue is dissolved in a mixture of DCM-ethyl acetate (1:1, 50 mL) and filtered through celite. The filtrate is concentrated in vacuo and the residue is purified by flash chromatography on silica gel (0-0.7% MeOH-DCM) to afford the product, 4-chloro-5-fluoro-7H-pyrrolo[2,3-d]pyrimidine (F-1) as a pink solid.

Method G

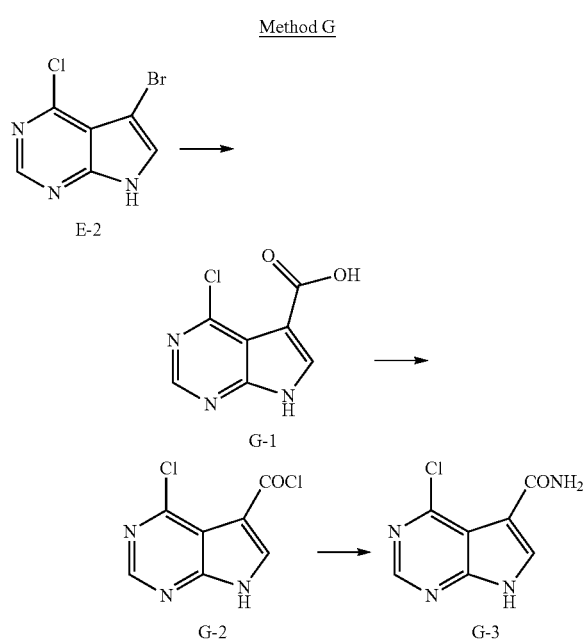

General Method for the Synthesis of 4-chloro-7H-pyrrolo[2,3-d]pyrimidine-5-carboxamide:

To a mixture of 5-bromo-4-chloro-7H-pyrrolo[2,3-d]pyrimidine (E-2) (6.24 g, 26.8 mmol, 1.0 eq) in anhydrous THF (100 mL) at 78° C. under argon, n-BuLi solution (2.5 M in THF, 23.6 mL, 59.0 mmol, 2.2 eq) is added dropwise (over 30 min) The reaction mixture is then stirred at −78° C. for 1 h and then dry ice (300 g) is added in portions under an argon atmosphere. The resulting mixture is allowed to warm to RT and then stirred at RT overnight. The reaction mixture is then diluted with H$_2$O (200 mL) and extracted with ethyl acetate (50 mL×4). The aqueous layer is acidified with con. HCl to adjust the pH to 3-4. The precipitate is then collected by filtration, rinsed with H$_2$O (30 mL) and dried in vacuo to afford the product, 4-chloro-7H-pyrrolo[2,3-d]pyrimidine-5-carboxylic acid (G-1).

To a stirred suspension of 4-chloro-7H-pyrrolo[2,3-d]pyrimidine-5-carboxylic acid (G-1) (3.11 g, 15.7 mmol, 1.0 eq) and a catalytic amount of DMF in a mixture of DCM (40 mL) and THF (40 mL) at RT, oxalyl dichloride (2.0 mL, 23.5 mmol, 1.5 eq) is added dropwise. The resulting mixture is stirred for 2 h and then concentrated in vacuo. The residue (G2) is dissolved in DCM (50 mL) and the resulting solution is added dropwise to saturated aqueous ammonium hydroxide (200 mL) at RT. The resulting mixture is stirred for 30 min and then filtered. The filter cake is then rinsed with H$_2$O (30 mL×2). The filtrate is acidified with con. HCl to adjust the pH to 4-5. The solid is collected by filtration, rinsed with water and dried in vacuo to afford the product, 4-chloro-7H-pyrrolo[2,3-d]pyrimidine-5-carboxamide (G-3).

Method H

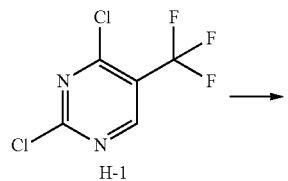

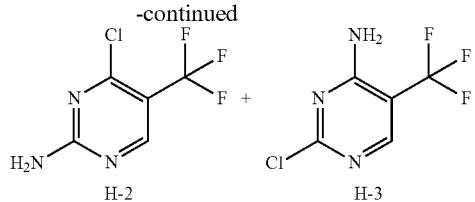

General Method for the Synthesis of 4-chloro-5-(trifluoromethyl)pyrimidin-2-amine:

Ammonia in methanol (7N solution, 15 mL) is added dropwise to the stirred neat 2,4-dichloro-5-(trifluoromethyl)pyrimidine (H-1) (5.0 g, 23.04 mmol) under argon, and the resulting mixture is stirred at RT for 2 h. The reaction mixture is quenched with water and then extracted with ethyl acetate (200 mL×2). The combined organic layers are washed with brine, dried over Na$_2$SO$_4$ and filtered. The filtrate is concentrated in vacuo and the residue is purified by flash chromatography on silica gel (0-20% ethyl acetate-hexanes) to afford the product, 4-chloro-5-(trifluoromethyl)pyrimidin-2-amine (H-2) as a white solid. The regionalisomer, 2-chloro-5-(trifluoromethyl)pyrimidin-4-amine (H-3) can also be isolated as a white solid.

General Method for the Synthesis of Amine Cores:

Method I

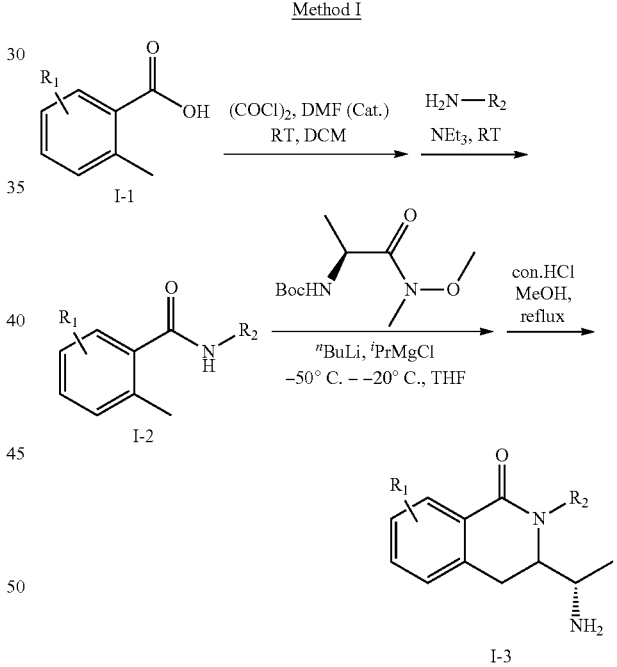

General Conditions for the Preparation of (S)-3-(1-aminoethyl)-isoquinolin-1(2H)-ones To a stirred mixture of a given o-methylbenzoic acid (I-1) (1.5 mol, 1 eq) and DMF (2 mL) in DCM (1275 mL) at RT, oxalyl chloride (1.65 mol, 1.1 eq) is added over 5 min and the resulting mixture is stirred at RT for 2 h. The mixture is then concentrated in vacuo. The residue is dissolved in DCM (150 mL) and the resulting solution (solution A) is used directly in the next step.

To a stirred mixture of aniline (1.58 mol, 1.05 eq) and triethylamine (3.15 mol, 2.1 eq) in DCM (1350 mL), the above solution A (150 mL) is added dropwise while the reaction temperature is maintained between 25° C. to 40° C.

by an ice-water bath. The resulting mixture is stirred at RT for 2 h and then water (1000 mL) was added. The organic layers are separated and washed with water (1000 mL×2), dried over Na₂SO₄ and filtered. The filtrate is concentrated in vacuo. The product is suspended in n-heptanes (1000 mL) and stirred at RT for 30 min. The precipitate is collected by filtration, rinsed with heptanes (500 mL) and further dried in vacuo to afford the amide (I-2) as a yellow solid.

To a stirred mixture of amide (I-2) (173 mmol, 1 eq) in anhydrous THF (250 mL) at −30° C. under an argon atmosphere, a solution of n-butyllithium in hexanes (432 mol, 2.5 eq) is added dropwise over 30 min while keeping inner temperature between −30° C. and −10° C. The resulting mixture is then stirred at −30° C. for 30 min.

To a stirred mixture of (S)-tert-butyl 1-(methoxy(methyl)amino)-1-oxopropan-2-ylcarbamate (260 mmol, 1.5 eq) in anhydrous THF (250 mL) at −30° C. under an argon atmosphere, a solution of isopropylmagnesium chloride in THF (286 mmol, 1.65 eq) is added dropwise over 30 min while keeping inner temperature between −30° C. and −10° C. The resulting mixture is stirred at −30° C. for 30 min. This solution is then slowly added to above reaction mixture while keeping inner temperature between −30° C. and −10° C. The resulting mixture is stirred at −15° C. for 1 h. The reaction mixture is quenched with water (50 mL) and then acidified with conc. HCl at −10° C.-0° C. to adjust the pH to 1-3. The mixture is allowed to warm to RT and concentrated in vacuo. The residue is dissolved in MeOH (480 mL), and then conc. HCl (240 mL) is added quickly at RT. The resulting mixture is stirred at reflux for 1 h. The reaction mixture is concentrated in vacuo to reduce the volume to about 450 mL. The residue is extracted with a 2:1 mixture of heptane and ethyl acetate (500 mL×2). The aqueous layer is basified with concentrated ammonium hydroxide to adjust the pH value to 9-10 while keeping the inner temperature between −10° C. and 0° C. The mixture is then extracted with DCM (300 mL×3), washed with brine, dried over MgSO₄ and filtered. The filtrate is concentrated in vacuo and the residue is dissolved in MeOH (1200 mL) at RT. To this solution, D-(−)-tartaric acid (21 g, 140 mmol, 0.8 eq) is added in one portion at RT. After stirring at RT for 30 min, white solid precipitates out and the mixture is slurried at RT for 10 h. The solid is collected by filtration and rinsed with MeOH (50 mL×3). The collected solid is suspended in water (500 mL) and then neutralized with concentrated ammonium hydroxide solution at RT to adjust the pH to 9-10. The mixture is extracted with DCM (200 mL×3). The combined organic layers are washed with brine, dried over MgSO₄ and filtered. The filtrate is concentrated in vacuo to afford (S)-3-(1-aminoethyl)-isoquinolin-1(2H)-ones (I-3).

Method J

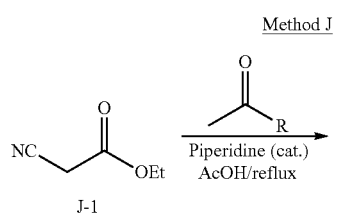

J-1

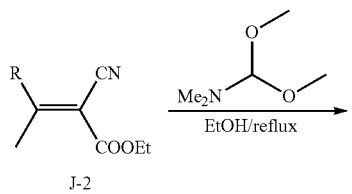

J-2

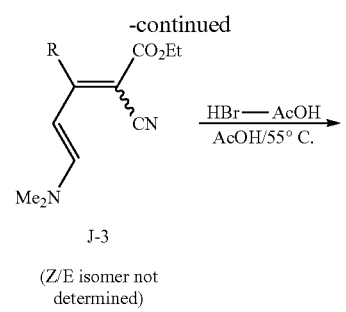

J-3

(Z/E isomer not determined)

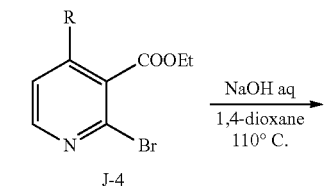

J-4

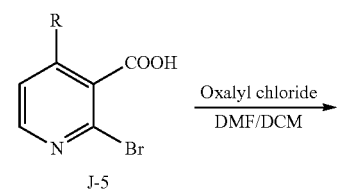

J-5

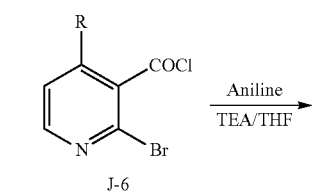

J-6

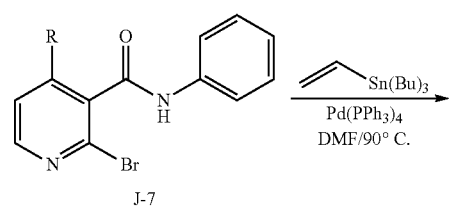

J-7

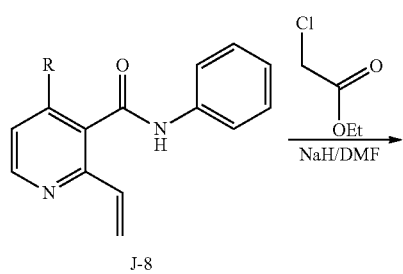

J-8

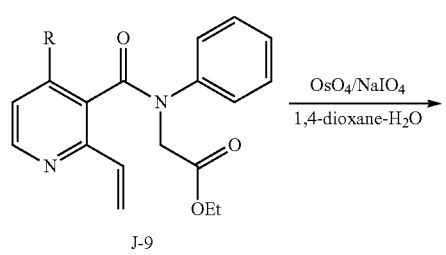

J-9

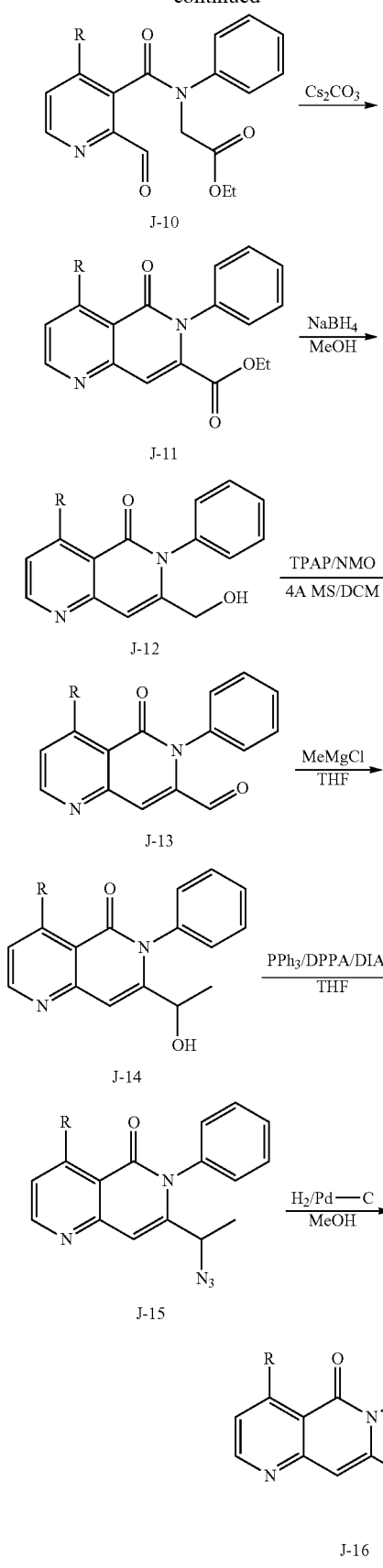

General Conditions for the Preparation of 7-(1-aminoethyl-6-phenyl-1,6-naphthyridin-5(6H)-ones:

To a mixture of ethyl 2-cyanoacetate (J-1) (45.2 g, 400 mmol) and a given ketone (800 mmol) in glacial acetic acid (50 mL), piperidine (2 mL, 20 mmol) is added and the resulting mixture is stirred at reflux for 24 h. The reaction mixture is allowed to cool to RT, and then concentrated in vacuo. The residue is diluted with water (200 mL) and extracted with ethyl acetate (200 mL×3). The combined organic layers are washed with brine (50 mL), dried over $Na_2SO_4$ and filtered. The filtrate is concentrated in vacuo and the residue is purified by flash column chromatography on silica gel (0-2% EA/PE) to afford the product (J-2) as a white solid.

To a solution of (J-2) (285 mol) in absolute EtOH (300 mL), N,N-dimethylformamide dimethyl acetal (37.3 g, 313 mmol) is added dropwise and the resulting mixture is stirred at reflux 6 h. The mixture is allowed to cool to RT, and concentrated in vacuo to afford the product (J-3) in as a yellow solid. This material is used in the next step without further purification.

Dienoate (J-3) (148 mmol) is dissolved in AcOH (120 mL) and the mixture is stirred at 40° C. A solution of 45% HBr-AcOH (120 mL) is added dropwise, and then the mixture is stirred at 55° C. for 2 h. The mixture is allowed to cool to RT, poured onto ice, neutralized with solid $Na_2CO_3$, and extracted with ethyl acetate (150 mL×3). The combined organic layers are washed with brine (50 mL), dried over $Na_2SO_4$ and filtered. The filtrate is concentrated in vacuo and the residue is purified by flash column chromatography on silica gel (5-20% EA/PE) to afford the product (J-4) as a yellow oil.

To a solution of 4-substituted ethyl 2-bromonicotinate (J-4) (52 mmol) in 1,4-dioxane (15 mL), a solution of NaOH (8.0 g, 200 mmol) in $H_2O$ (15 mL) is added and the resulting mixture is stirred at reflux for 12 h. The mixture is allowed to cool to RT, diluted with $H_2O$, and washed with ethyl acetate (30 mL×3). The aqueous layer is acidified with concentrated hydrochloric acid to pH to 1, and then extracted with ethyl acetate (50 mL×3). The combined organic layers are washed with brine (25 mL), dried over $Na_2SO_4$ and filtered. The filtrate is concentrated in vacuo to afford the product nicotinic acid (J-5) as a white solid.

To a solution of (J-5) (60 mmol) and DMF (3 drops) in $CH_2Cl_2$ (150 mL), oxalyl chloride (11.4 g, 90 mmol) is added dropwise and the resulting mixture is stirred at RT for 2 h. The reaction mixture is concentrated in vacuo to afford the nicotinoyl chloride (J-6) as a yellow oil.

To a solution of nicotinoyl chloride (J-6) (23.26 mmol) in anhydrous THF (70 mL) at 0° C., aniline (25.59 mmol) and triethylamine (3.6 mL, 25.59 mmol) is added slowly. The resulting mixture is stirred at RT for 1 h. The reaction mixture is quenched with water and extracted with ethyl acetate. The combined organic layers are washed with brine, dried over $Na_2SO_4$ and filtered. The filtrate is concentrated in vacuo to afford the amide (J-7) as a tan solid.

To a solution of nicotinamide (J-7) (6.77 g, 23.25 mmol) and tributyl(vinyl)tin (10.2 mL, 34.88 mmol) in DMF (250 mL) under argon, $Pd(PPh_3)_4$ (1.07 g, 0.93 mmol) is added and the resulting mixture is stirred at 90° C. for 1 h. The mixture is allowed to cool to RT, quenched with water and extracted with ethyl acetate (100 mL×2). The organic layer is washed with brine, dried over $Na_2SO_4$, and filtered. The filtrate is concentrated in vacuo and the residue is purified by ISCO (silica gel cartridge, 0-60% EA/Hexanes) to afford the vinylnicotinamide (J-8) as a red solid.

To a solution of 2-vinylnicotinamide (J-8) (30.21 mmol) in anhydrous DMF (100 mL) at RT, sodium hydride (60% in mineral oil, 6.04 g, 151.08 mmol) is slowly added in portions. The resulting mixture is stirred at RT for 45 min. To this mixture, ethyl chloroacetate (16 mL, 151.08 mmol) is added dropwise and the resulting mixture is stirred for 2 h. The reaction is quenched with water and extracted with ethyl acetate. The combined organic layers are washed with brine, dried over Na$_2$SO$_4$ and filtered. The filtrate is concentrated in vacuo to afford (J-9).

To a solution of (J-9) (17.36 mmol) in 1,4-dioxane-H$_2$O (3:1, 150 mL) at RT, osmium tetraoxide (4% wt in H$_2$O, 2.72 mL, 0.35 mmol) is added and the resulting mixture is stirred at RT for 30 min. To this mixture, sodium periodate (14.85 g, 69.44 mmol) is added and the resulting mixture is stirred at RT for 16 h. The mixture is filtered through celite and the filtrate is extracted with ethyl acetate (2×100 mL). The combined organic layers are washed with brine, dried over Na$_2$SO$_4$ and filtered. The filtrate is concentrated in vacuo to afford the product (J-10) as a tan/yellow solid.

To a solution of (J-10) (17.35 mmol) in EtOH-ethyl acetate (3:1, 200 mL) is added cesium carbonate (6.22 g, 19.09 mmol) and the resulting mixture is stirred at 50° C. for 2 h. The mixture is allowed to cool to RT and filtered through celite. The filtrate is concentrated in vacuo and the residue is partitioned between water and ethyl acetate. The organic layer is washed with brine, dried over Na$_2$SO$_4$ and filtered. The filtrate is concentrated in vacuo and the residue is purified by ISCO (silica gel cartridge, 0-50% EA/Hex) to afford the product (J-11) as an off white solid.

To a solution of (J-11) (6.97 mmol) in anhydrous MeOH (40 mL), sodium borohydride (2.62 g, 69.34 mmol) is added in two portions. The mixture is stirred at RT for 16 h, quenched with water and extracted with ethyl acetate. The combined organic layers are washed with brine, dried over Na$_2$SO$_4$ and filtered. The filtrate is concentrated in vacuo to afford product (J-12).

To a solution of (J-12) (13.61 mmol) in anhydrous DCM (50 mL) at RT, 4A molecular sieves (powder, 3.62 g), NMO (1.59 G, 13.6 mmol) and TPAP (tetrapropylammonium perruthenate) (119.5 mg, 0.34 mmol) are added sequentially. The resulting mixture is stirred at RT for 16 h (overnight). The mixture is filtered through a celite/silica gel pad and the filtrate is concentrated in vacuo to afford the product (J-13).

To a solution of (J-13) (6.80 mmol) in anhydrous THF (100 mL) at −78° C. under argon, methylmagnesium chloride solution (3.0 M in THF, 6.8 mL, 20.41 mmol) is added dropwise and the resulting mixture was stirred from −78° C. to RT for 2 h. An additional amount of methylmagnesium chloride solution (2 mL) is added to bring reaction to completion. The reaction mixture is quenched with water (150 mL) and extracted with ethyl acetate (200 mL×2). The combined organic layers are washed with brine, dried over Na$_2$SO$_4$ and filtered. The filtrate is concentrated in vacuo and the residue is purified by ISCO (silica gel cartridge, 0-10% MeOH-DCM) to afford the product (J-14) as a white solid.

To a solution of (J-14) (4.28 mmol) in anhydrous THF (25 mL) at 0° C. under argon, triphenyl phosphine (2.24 g, 8.56 mmol) is added and the resulting mixture was stirred for 5 min. To this mixture, diphenyl phosphoryl azide (2.31 mL, 10.7 mmol) is added followed by slow addition of diisopropyl azodicarboxylate (1.69 mL, 8.56 mmol) over 20 min period of time. The resulting mixture is stirred from 0° C. to RT for 2 h. The mixture is then partitioned between ethyl acetate and water. The organic layer is washed with brine, dried over Na$_2$SO$_4$ and filtered. The filtrate is concentrated in vacuo and the residue is purified by ISCO (silica gel cartridge, 0-70% EA/Hex) to afford the product, (J-15) as a white solid.

A mixture of (J-15) (3.08 mmol) and palladium (10% weight on carbon, 190 mg, 20% of starting material by weight) in anhydrous MeOH (25 mL) are degassed and flushed with hydrogen (three cycles). The reaction mixture is stirred under a hydrogen atmosphere (hydrogen balloon) at RT for 30 min. The mixture is then filtered through celite over a Buchner funnel and rinsed with ethyl acetate. The filtrate is concentrated in vacuo to afford the product (J-16) as an off-white solid.

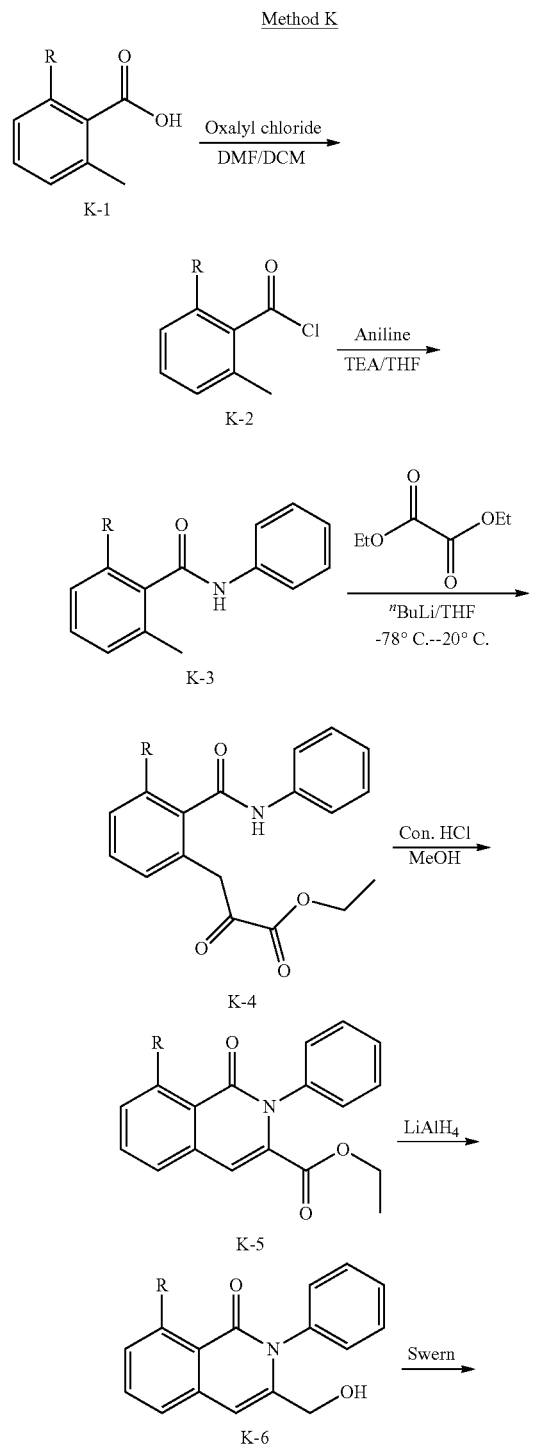

Method K

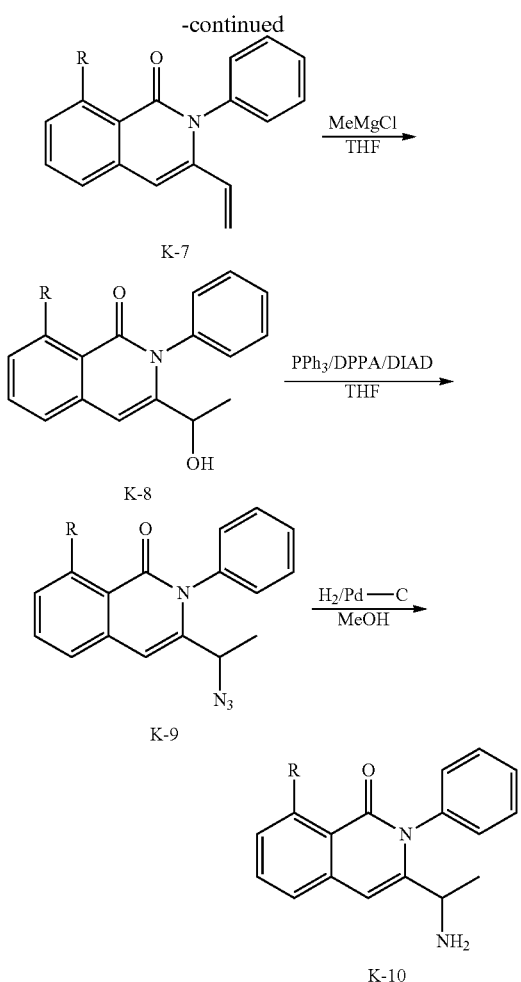

General Conditions for the Preparation of 3-(1-aminoethyl)-2-phenyl-3,4-dihydroisoquinolin-1(2H)-ones:

A mixture of benzoic acid (K-1) (400 mmol), oxalyl chloride (101 g, 800 mmol) and DMF (0.2 ml) in DCM (400 mL) is stirred at RT for 2 h. The mixture is concentrated in vacuo to afford the acid chloride (K-2) as a yellow oil. The product obtained is used directly in the next step without purification.

A mixture of aniline (420 mmol) and triethylamine (71 g, 700 mmol) in DCM (300 mL) is stirred at RT for 10 min. To this mixture, acid chloride (K-2) (64 g, 400 mmol) is added dropwise, and the resulting mixture is stirred at RT for 30 min. The reaction mixture is poured into water (300 mL) and extracted with DCM (200 mL×3), dried over anhydrous $Na_2SO_4$ and filtered. The filtrate is concentrated in vacuo to afford the product. The product is suspended in isopropyl ether (300 mL), stirred at reflux for 30 min, and then cooled to 0-5° C. The precipitate is collected by filtration and further dried in vacuo to afford the product amide (K-3) as a yellow solid.

To a stirred solution of amide (K-3) (0.1 mol, 1.0 eq) in anhydrous THF (225 mL) at −78° C. under an argon atmosphere, a solution of n-butyllithium in hexanes (120 mL, 2.5 M, 0.3 mol, 3 eq) is added dropwise over 1 h period of time while keeping inner temperature between −78° C. to −50° C. The resulting mixture is stirred at −70° C. for 1 h, and then diethyl oxalate (17.5 g, 0.12 mol, 1.2 eq) is quickly added (with an increase in temperature to −20° C. upon addition). The mixture is stirred at −50° C. for 10 min, and then quenched with water (100 mL). The inorganic salt is removed by filtration, and the filtrate is extracted with ethyl acetate (100 mL×2). The combined organic layers are washed with brine (100 mL), dried over $MgSO_4$ and filtered. The filtrate is concentrated in vacuo to afford the product as a semi-solid. The product is slurried in isopropyl ether (100 mL) at RT for 10 min. The solid is collected by filtration and further dried in vacuo to afford the product (K-4) as a white solid. The product obtained is used directly in the next step.

Compound (K-4) (88 mmol, 1 eq) is dissolved in HCl/MeOH (10 M, 100 mL, 10 mL/1 g of K-4), and the resulting mixture is stirred at reflux for 1 h. The reaction mixture is concentrated in vacuo, and the residue is slurried in ethyl acetate (100 mL) at RT for 30 min. The solid is collected by filtration, rinsed with ethyl acetate (50 mL×3), and further dried in vacuo to afford the product (K-5) as a white solid.

To a stirred suspension of lithium aluminum hydride (15.6 g, 410 mmol) in anhydrous THF (500 mL) at −78° C. under a nitrogen atmosphere, (K-5) (137 mmol) is slowly added over a 10 min period of time. The resulting mixture is allowed to warm to −30° C. and stirred for 30 min (TLC shows the completion of the reaction). Then the mixture is cooled to −78° C., and quenched carefully with water (100 mL). The mixture is allowed to warm to RT, filtered through silica gel (20 g), and the filtrate is concentrated in vacuo. The product is poured into $H_2O$ (200 mL) and extracted with ethyl acetate (200 mL×3). The combined organic layers are washed with brine (100 mL), dried over $Na_2SO_4$ and filtered. The filtrate is concentrated in vacuo. The product is suspended in ethyl acetate (30 mL) and stirred for 10 min. The solid is collected by filtration and further dried in vacuo to afford the product (K-6) as a white solid.

To a stirred solution of oxalyl chloride (2.0 M in DCM, 12.8 mL) in anhydrous DCM (100 mL) at −78° C. under argon, DMSO (4.82 mL, 68 mmol) is slowly added and the resulting mixture is stirred at −78° C. for 50 min. To this reaction mixture, a solution of (K-6) (17 mmol) in DCM (50 mL) is added slowly. The resulting mixture is stirred at −78° C. for 1 h and then triethylamine (11.8 mL, 85 mmol) is added. The mixture is stirred from −78° C. to RT for 1 h and quenched with water (100 mL). The organic layer is separated and the aqueous layer is extracted with DCM (50 mL×2). The combined organic layers are washed with brine, dried over $Na_2SO_4$ and filtered. The filtrate is concentrated in vacuo to afford the product, (K-7).

To a solution of (K-7) (17.0 mmol) in anhydrous THF (120 mL) at −78° C. under argon, methylmagnesium chloride solution (3.0 M in THF, 14.9 mL, 44.2 mmol) is added dropwise and the resulting mixture is stirred at −78° C. for 3 h. The mixture is quenched with saturated $NH_4Cl$ aqueous solution (50 mL) and extracted with ethyl acetate (200 mL×2). The combined organic layers are washed with brine, dried over $Na_2SO_4$ and filtered. The filtrate is concentrated in vacuo and the residue was triturated with 20% ethyl acetate-hexanes to afford the product (K-8) as a yellowish solid.

To a solution of (K-8) (7.88 mmol) in anhydrous THF (60 mL) at 0° C. under argon, triphenyl phosphine (3.1 g, 11.81 mmol) is added and the resulting mixture was stirred for 5 min. To this mixture, diphenyl phosphoryl azide (3.41 mL, 15.76 mmol) is added followed by slow addition of diisopropyl azodicarboxylate (2.32 mL, 11.81 mmol) over 20 min. The resulting mixture is stirred from 0° C. to RT for 5 h. The mixture is then partitioned between ethyl acetate and water. The organic layer is washed with brine, dried over $Na_2SO_4$ and filtered. The filtrate is concentrated in vacuo and the residue is purified by ISCO (silica gel cartridge, 0-100% ethyl acetate/hexanes) to afford the product azide (K-9).

A mixture of azide (K-9) (1.1 mmol) and palladium (10% weight on carbon, 100 mg, 30% of starting material by weight) in anhydrous methanol (20 mL) is degassed and flushed with hydrogen (three cycles). The reaction mixture is stirred under a hydrogen atmosphere (hydrogen balloon) at RT for 24 h. The mixture is filtered through celite over a Buchner funnel and rinsed with ethyl acetate. The filtrate is concentrated in vacuo to afford the amine (K-10) as a yellow solid.

General Method for the Capping of Amine Cores with Cl—$W_d$:

Method L

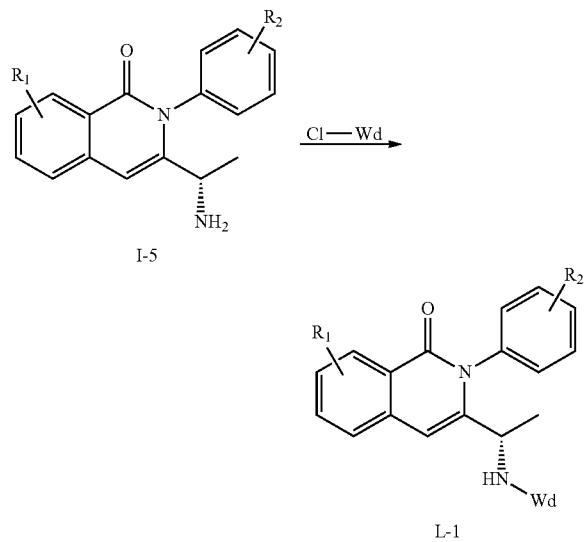

An (S)-3-(1-Aminoethyl)-isoquinolin-1(2H)-one (I-5) (115 mmol, 1.0 eq), Cl-Wd (173 mmol, 1.5 eq) and triethylamine (344 mmol, 3.0 eq) are dissolved in n-BuOH (350 mL) and the mixture is stirred at reflux for 16 h. The reaction mixture is cooled to RT and concentrated in vacuo. The residue is slurried in a mixture of $H_2O$ (200 mL) and ethyl acetate (100 mL) and stirred at RT for 30 min. The solid is then collected by filtration, rinsed with ethyl acetate (25 mL) and dried in vacuo to afford the product (L-1).

General Method for the Elaboration of $W_d$ Heterocycles:

Method M

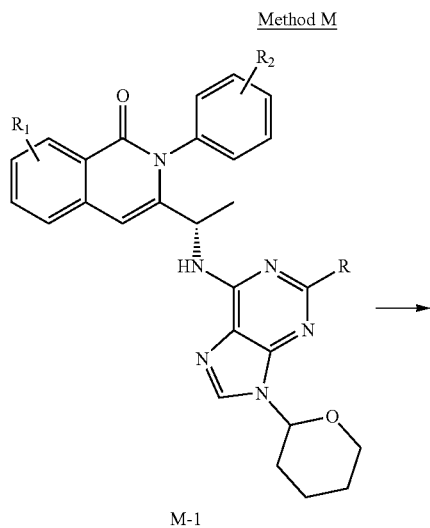

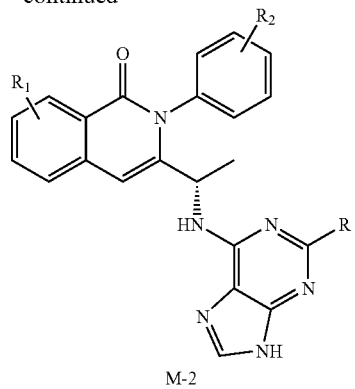

A mixture of tetrahydro-2H-pyran-intermediate (M-1) in ethanol (4 vol)/water (2 vol) followed by addition of conc. HCl solution (2 vol) is stirred at RT for 1 h. The resulting mixture is diluted with cold water, neutralized with saturated aqueous $NaHCO_3$ to adjust the pH to 8-9 and then extracted with DCM (20 vol×3). The combined organic layers are washed with brine, dried over $Na_2SO_4$ and filtered. The filtrate is concentrated in vacuo. The resultant residue is suspended in petroleum ether with ultrasonic vibration for 5 min. The solid is collected by filtration and dried in vacuo to afford the product (M-2).

Method N

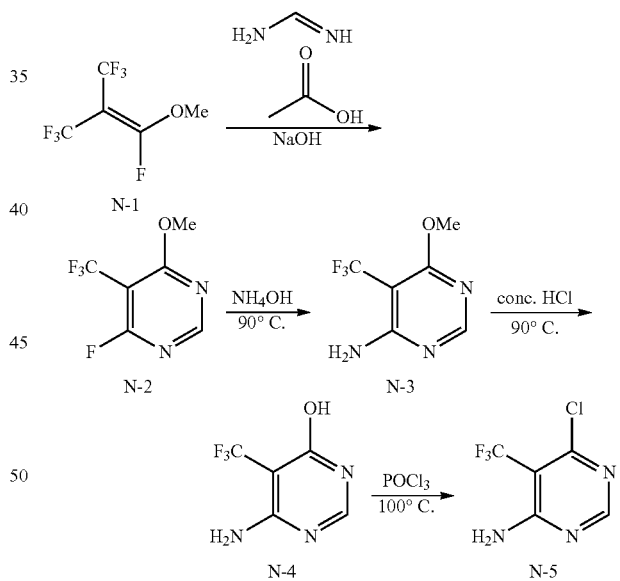

General Method for the Synthesis of 6-chloro-5-(trifluoromethyl)pyrimidin-4-amine:

To a rapidly stirred mixture of 1,1,1,3-tetrafluoro-2-(trifluoromethyl)-4-oxapent-2-ene (N–1) (10.0 g, 47.15 mmol) and formamidine acetate (7.37 g, 70.73 mmol) in a mixture of water (50 mL) and dichloromethane (50 mL) at 0° C., a solution of sodium hydroxide (7.54 g, 189 mmol) in water (40 mL) is added dropwise and the resulting mixture is stirred for 30 min after complete addition. The dichloromethane layer is separated, washed with 1M aqueous HCl solution and water, dried over $Na_2SO_4$ and filtered. The filtrate is concentrated in vacuo to afford 4-fluoro-6- methoxy-5-(trifluoromethyl)pyrimidine (N-2) as a yellow solid. The product is used directly in the next step without further purification.

To a solution of 4-fluoro-6-methoxy-5-(trifluoromethyl) pyrimidine (N-2) (1.10 g, 5.61 mmol) in n-butanol (4 mL) in a pressure vessel, ammonium hydroxide (5 mL) is added and the resulting mixture is stirred at 90° C. for 1 h. The mixture is allowed to cool to RT, quenched with water, and extracted with ethyl acetate (100 mL×2). The combined organic layers are washed with brine, dried over Na₂SO₄ and filtered. The filtrate is concentrated in vacuo to afford the product 6-methoxy-5-(trifluoromethyl)pyrimidin-4-amine (N-3) as an off-white solid. The product is used directly in the next step without further purification.

To a solution of 6-methoxy-5-(trifluoromethyl)pyrimidin-4-amine (N-3) (420 mg, 2.18 mmol) in 1,4-dioxane (10 mL), concentrated HCl (1.81 mL, 21.8 mmol) is added and the resulting mixture is stirred at 90° C. for 3 h. The mixture is allowed to cool to RT and then concentrated in vacuo to afford the product, 6-amino-5-(trifluoromethyl)pyrimidin-4-ol (N-4) as yellowish solid.

The mixture of 6-amino-5-(trifluoromethyl)pyrimidin-4-ol (N-4) (300 mg, 1.66 mmol) in POCl₃ (8 mL) in a pressure vessel is stirred at 100° C. for 1 h. The mixture is allowed to cool to RT and concentrated in vacuo. The residue is taken up in water (20 mL), basified with saturated NaHCO₃ aqueous solution to pH=9 and then extracted with DCM (30 mL×3). The combined organic layers are washed with brine, dried over Na₂SO₄ and filtered. The filtrate is concentrated in vacuo to afford the desired product, 6-chloro-5-(trifluoromethyl)pyrimidin-4-amine (N-5) as a yellow solid.

Example 1

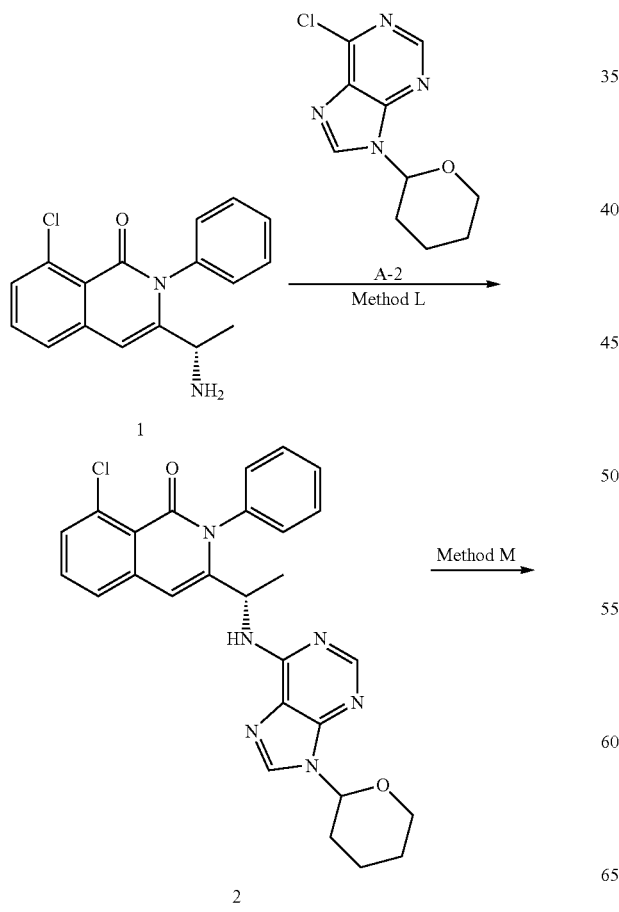

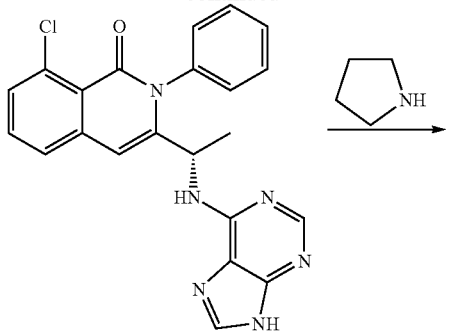

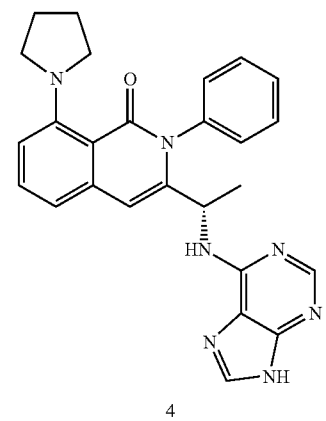

Isoquinolinone 4 was prepared from compound 1 through a 3-step sequence. Compound 1 was prepared using Method I and was then converted to 2 by coupling with A-2 according to Method L. Compound 2 was converted to compound 3 according to Method M. Compound 4 was then prepared according to the following procedure:

To a solution of (S)-3-(1-((9H-purin-6-yl)amino)ethyl)-8-chloro-2-phenylisoquinolin-1(2H)-one (3) (100 mg, 0.24 mmol) in 1,4-dioxane (3 mL) in a sealed tube, pyrrolidine (1.25 mL, excess amount) was added and the resulting mixture was stirred at 135° C. for 17 h. The mixture was allowed to cool to RT, partitioned between ethyl acetate and water. The organic layer was washed with brine, dried over Na₂SO₄ and filtered. The filtrate was concentrated in vacuo and the residue was purified by ISCO (silica gel cartridge, 0-10% MeOH-DCM) to afford the product, (S)-3-(1-((9H-purin-6-yl)amino)ethyl)-2-phenyl-8-(pyrrolidin-1-yl)isoquinolin-1 (2H)-one (4) as an off-white solid. ESI-MS m/z: 452.2 [M+H]⁺.

Example 2

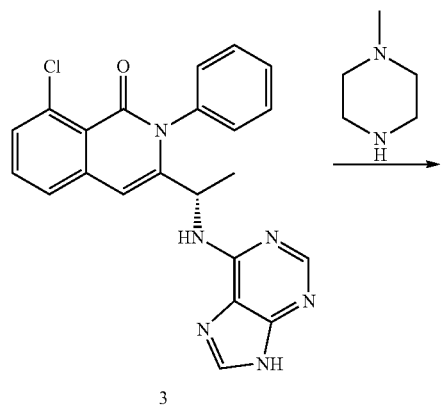

Example 3

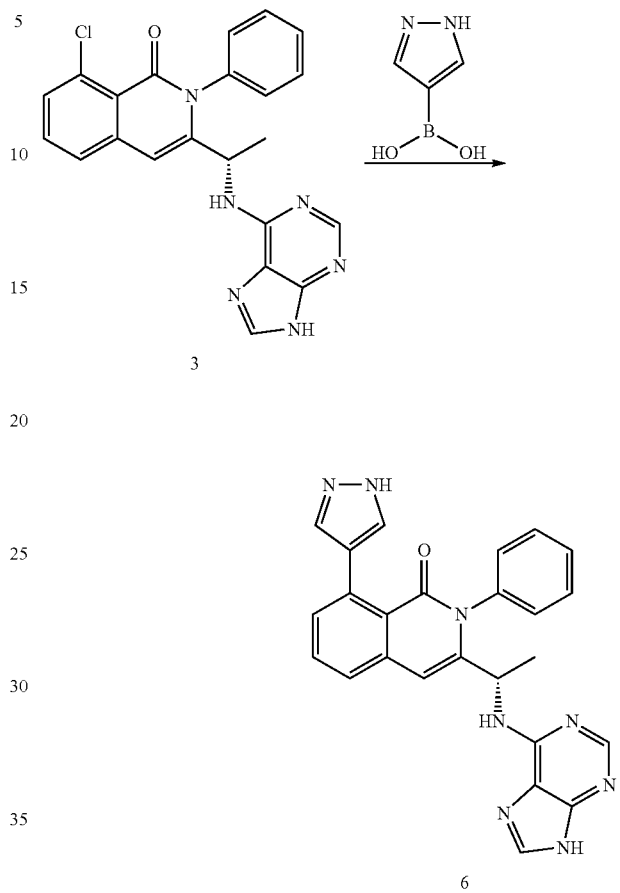

Isoquinolinone 5 was prepared from compound 3 according to the following procedure:

(S)-3-(1-((9H-purin-6-yl)amino)ethyl)-8-chloro-2-phenylisoquinolin-1(2H)-one (3) (200 mg, 0.48 mmol) and 1-methylpiperazine (0.267 mL, 2.4 mmol) were dissolved in anhydrous NMP (8 mL) and the resulting solution was degassed and back-filled with argon (two cycles). To this mixture, $Na_2CO_3$ (102 mg, 0.96 mmol), $Pd(OAc)_2$ (11 mg, 0.048 mmol) and di-(1-adamantyl)-n-butylphosphine (52 mg, 0.144 mmol) were added sequentially. The resulting mixture was degassed and back-filled with argon (two cycles) and then stirred at 160° C. under argon for 16 h. The reaction mixture was allowed to cool to RT and then partitioned between water and ethyl acetate. The organic layers were separated and the aqueous layer was extracted with ethyl acetate. The combined organic layers were washed with brine, dried over $Na_2SO_4$ and filtered. The filtrate was concentrated in vacuo and the residue was purified by ISCO (silica gel cartridge, 0-10% MeOH-DCM with 0.1% TEA) to afford the product, (S)-3-(1-((9H-purin-6-yl)amino)ethyl)-8-(4-methylpiperazin-1-yl)-2-phenylisoquinolin-1(2H)-one (5) as a yellowish solid. ESI-MS m/z: 481.2 $[M+H]^+$.

Isoquinolinone 6 was prepared from compound 3 by coupling with 1H-pyrazole-4-boronic acid using the following procedure:

(S)-3-(1-((9H-purin-6-yl)amino)ethyl)-8-chloro-2-phenylisoquinolin-1(2H)-one (3) (200 mg, 0.48 mmol) and 1H-pyrazole-4-boronic acid (108 mg, 0.96 mmol) were dissolved in anhydrous NMP (8 mL) and the resulting solution was degassed and back-filled with argon (two cycles). To this mixture, $Na_2CO_3$ (152 mg, 1.44 mmol), $Pd(OAc)_2$ (22 mg, 0.096 mmol) and di-(1-adamantyl)-n-butylphosphine (104 mg, 0.288 mmol) were added sequentially. The resulting mixture was degassed and back-filled with argon (two cycles) and then stirred at 160° C. under argon for 3 h. The reaction mixture was allowed to cool to RT and then partitioned between water and ethyl acetate. The organic layer was separated and the aqueous layer was extracted with ethyl acetate. The combined organic layers were washed with brine, dried over $Na_2SO_4$ and filtered. The filtrate was concentrated in vacuo and the residue was triturated with $Et_2O$ to afford the product, (S)-3-(1-((9H-purin-6-yl)amino)ethyl)-2-phenyl-8-(1H-pyrazol-3-yl)isoquinolin-1(2H)-one (6) as a yellowish solid. ESI-MS m/z: 449.2 $[M+H]^+$.

Example 4

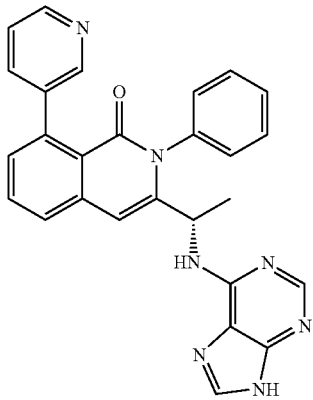

7

Isoquinolinone 7 was prepared from compound 3 in analogous fashion to compound 6 in Example 3 except that pyridin-3-ylboronic acid was used in place of 1H-pyrazole-4-boronic acid. ESI-MS m/z: 460.2 [M+H]$^+$.

Example 5

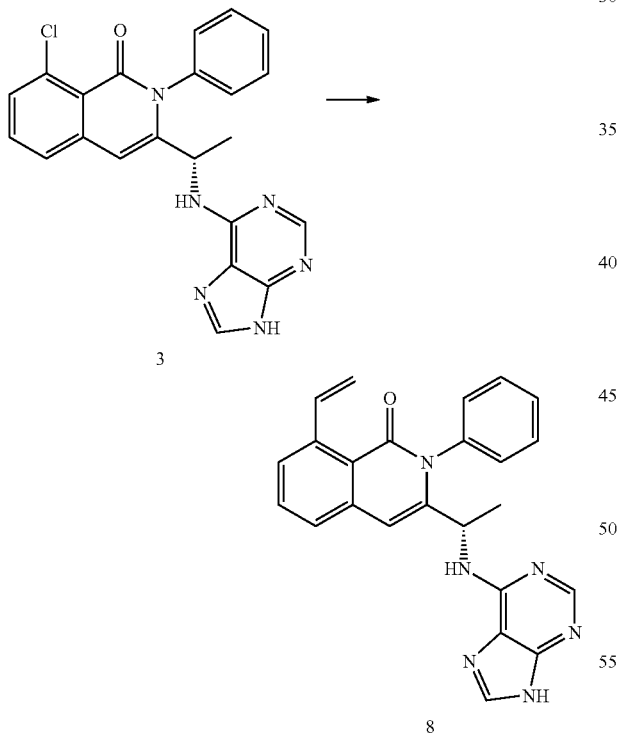

Isoquinolinone 8 was prepared from compound 3 according to the following procedure:

(S)-3-(1-((9H-purin-6-yl)amino)ethyl)-8-chloro-2-phenylisoquinolin-1(2H)-one (3) (417 mg, 1.0 mmol) and tributyl(vinyl)tin (0.58 mL, 2.0 mmol) were dissolved in anhydrous NMP (10 mL) and the resulting solution was degassed and back-filled with argon (two cycles). To this mixture, Na$_2$CO$_3$ (212 mg, 2.0 mmol), Pd(OAc)$_2$ (45 mg, 0.2 mmol) and di-(1-adamantyl)-n-butylphosphine (215 mg, 0.6 mmol) were added sequentially. The resulting mixture was degassed and back-filled with argon (two cycles) and then stirred at 160° C. under argon for 1 h. The reaction mixture was allowed to cool to RT and then partitioned between water and ethyl acetate. The organic layer was separated and the aqueous layer was extracted with ethyl acetate. The combined organic layers were washed with brine, dried over Na$_2$SO$_4$ and filtered. The filtrate was concentrated in vacuo and the residue was purified by ISCO (silica gel cartridge, 0-10% MeOH-DCM) to afford the product, (S)-3-(1-((9H-purin-6-yl)amino)ethyl)-2-phenyl-8-vinylisoquinolin-1(2H)-one (8) as an off-while solid. ESI-MS m/z: 409.2 [M+H]$^+$.

Example 6

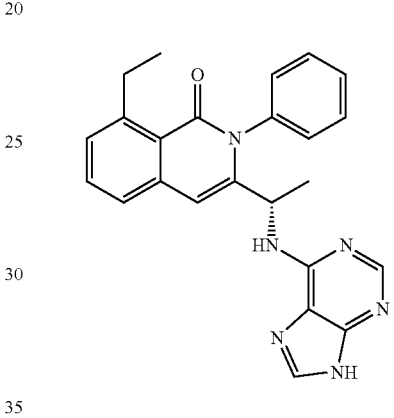

9

Isoquinolinone 9 was prepared from compound 8 according to the following procedure:

A mixture of (S)-3-(1-((9H-purin-6-yl)amino)ethyl)-2-phenyl-8-vinylisoquinolin-1(2H)-one (8) (120 mg, 0.29 mmol) and palladium (10% weight on carbon, 24 mg) in anhydrous MeOH (25 mL) was degassed and flushed with hydrogen (three cycles). The reaction mixture was stirred under a hydrogen atmosphere (hydrogen balloon) at RT for 1 h. The mixture was filtered through Celite and rinsed with ethyl acetate. The filtrate was concentrated in vacuo and the residue was purified by ISCO (silica gel cartridge, 0-10% MeOH-DCM) to afford the product, (S)-3-(1-((9H-purin-6-yl)amino)ethyl)-8-ethyl-2-phenylisoquinolin-1(2H)-one (9). ESI-MS m/z: 411.2 [M+H]$^+$.

Example 7

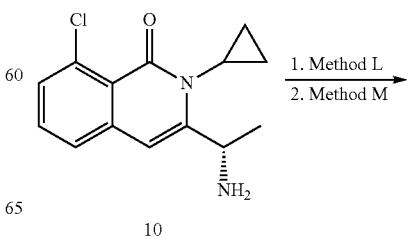

10

205

-continued

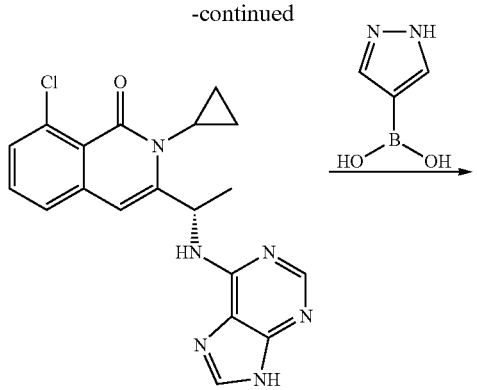

11

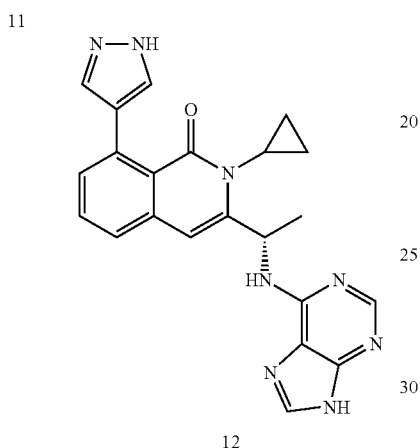

12

Isoquinoline 12 was prepared in 3 steps according to the following procedures Amine 10 was prepared using Method I. The amine was then converted to 11 according to Method L followed by Method M. Compound 11 was then converted to compound 12 in analogous fashion to compound 6 in Example 3. ESI-MS m/z: 413.2 [M+H]$^+$.

Example 8

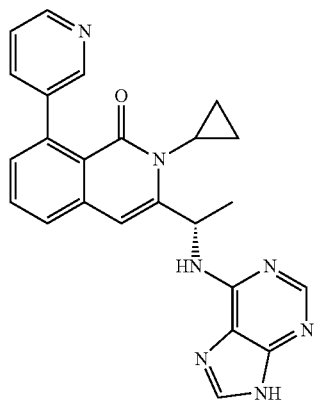 [SMILES: C[C@@H](Nc1ncnc2[nH]cnc12)c1cc2cccc(-c3cccnc3)c2c(=O)n1C1CC1]

13

Isoquinolinone 13 was prepared from compound 11 in analogous fashion to compound 12 in Example 7 except that pyridin-3-ylboronic acid was used in place of 1H-pyrazole-4-boronic acid. ESI-MS m/z: 424.2 [M+H]$^+$.

206

Example 9

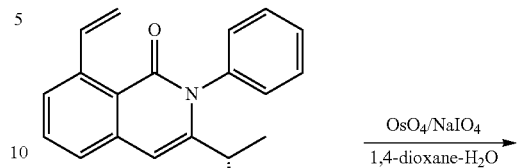

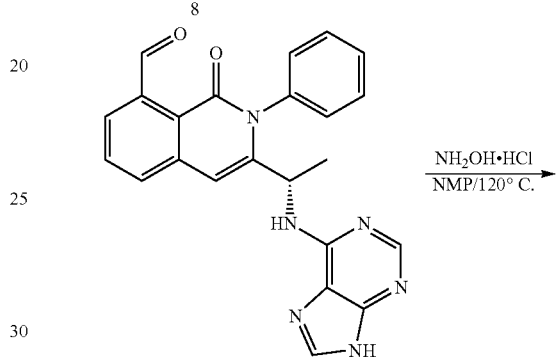

15

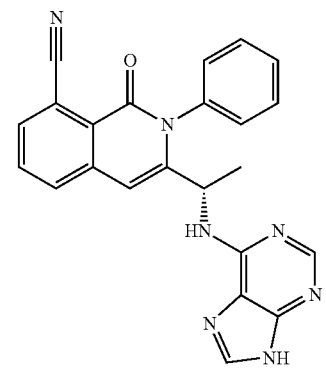

16

Isoquinoline 16 was prepared from compound 8 according to the following procedure:

To a solution of ethyl 2-(4-methyl-N-phenyl-2-vinylnicotinamido)acetate (8) (767 mg, 1.88 mmol) in 1,4-dioxane-H$_2$O (3:1, 20 mL) at RT, osmium tetraoxide (2.5% wt in H$_2$O, 0.5 mL, 0.05 mmol) was added and the resulting mixture was stirred at RT for 30 min. To this mixture, sodium periodate (1.21 g, 5.53 mmol) was added and the resulting mixture was stirred at RT for 30 h. The mixture was filtered through celite and the filtrate was extracted with ethyl acetate (100 mL×2). The combined organic layer was washed with brine, dried over Na$_2$SO$_4$ and filtered. The filtrate was concentrated in vacuo to afford the product, (S)-3-(1-((9H-purin-6-yl)amino)ethyl)-1-oxo-2-phenyl-1,2-dihydroisoquinoline-8-carbaldehyde (15) (730 mg, 95% yield) as a yellowish solid. ESI-MS m/z: 411.2 [M+H]$^+$.

To a solution of (S)-3-(1-((9H-purin-6-yl)amino)ethyl)-1-oxo-2-phenyl-1,2-dihydroisoquinoline-8-carbaldehyde (15)

(50 mg, 0.12 mmol) in anhydrous 1-methyl-2-pyrrolidinone (3 mL), hydroxylamine hydrochloride (17 mg, 0.24 mmol) was added and the resulting mixture was stirred at 120° C. for 16 h. The mixture was allowed to cool to RT, partitioned between ethyl acetate and water. The organic layer was washed with brine, dried over $Na_2SO_4$ and filtered. The filtrate was concentrated in vacuo and the residue was purified by ISCO (silica gel cartridge, 0-10% MeOH-DCM) to afford the product, (S)-3-(1-((9H-purin-6-yl)amino)ethyl)-1-oxo-2-phenyl-1,2-dihydroisoquinoline-8-carbonitrile (16) (14 mg, 28% yield) as a while solid. ESI-MS m/z: 408.2 $[M+H]^+$.

Example 10

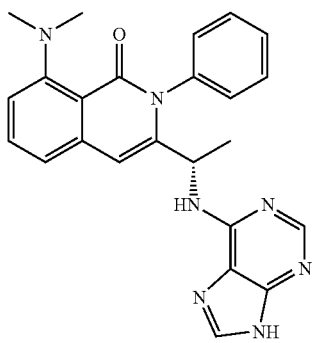 [SMILES: C[C@@H](Nc1ncnc2[nH]cnc12)c1cc2cccc(N(C)C)c2c(=O)n1-c1ccccc1]

17

Isoquinolinone 17 was prepared in analogous fashion to compound 5 in Example 2 except that dimethylamine THF solution was used in place of 1-methylpiperazine. ESI-MS m/z: 426.20 $[M+H]^+$.

Example 11

18

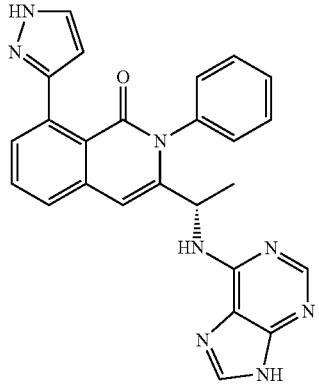 [SMILES: C[C@@H](Nc1ncnc2[nH]cnc12)c1cc2cccc(-c3cc[nH]n3)c2c(=O)n1-c1ccccc1]

Isoquinolinone 18 was prepared from compound 3 in analogous fashion to compound 6 in Example 3 except that 1H-pyrazol-3-boronic acid was used in place of 1H-pyrazole-4-boronic acid. ESI-MS m/z: 449.2 $[M+H]^+$.

Example 12

19

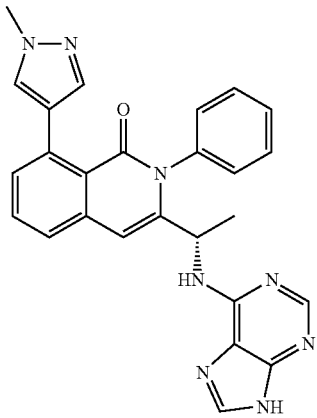 [SMILES: C[C@@H](Nc1ncnc2[nH]cnc12)c1cc2cccc(-c3cnn(C)c3)c2c(=O)n1-c1ccccc1]

Isoquinolinone 19 was prepared from compound 3 in analogous fashion to compound 6 in Example 3 except that (1-methyl-1H-pyrazol-4-yl)boronic acid was used in place of 1H-pyrazole-4-boronic acid. ESI-MS m/z: 463.2 $[M+H]^+$.

Example 13

20

Isoquinolinone 20 was prepared from compound 11 in analogous fashion to compound 12 in Example 7 except that (1-methyl-1H-pyrazol-4-yl)boronic acid was used in place of 1H-pyrazole-4-boronic acid. ESI-MS m/z: 427.2 $[M+H]^+$.

Example 14

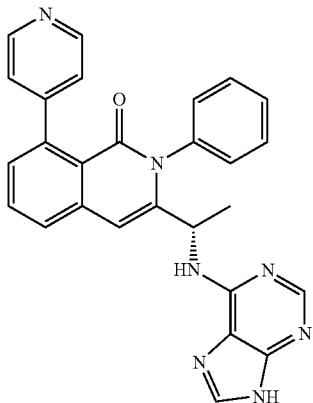 [SMILES: C[C@@H](Nc1ncnc2[nH]cnc12)c1cc2cccc(-c3ccncc3)c2c(=O)n1-c1ccccc1]

Isoquinolinone 21 was prepared from compound 3 in analogous fashion to compound 6 in Example 3 except that pyridine-4-boronic acid was used in place of 1H-pyrazole-4-boronic acid. ESI-MS m/z: 458.2 [M+H]+.

Example 15

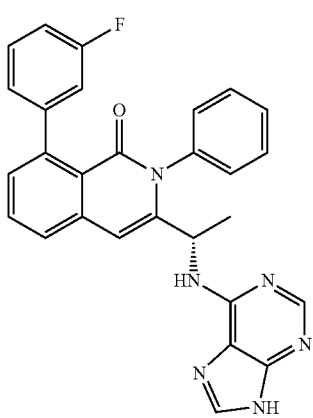

Isoquinolinone 25 was prepared from compound 3 in analogous fashion to compound 6 in Example 3 except that (3-fluorophenyl)boronic acid was used in place of 1H-pyrazole-4-boronic acid. ESI-MS m/z: 477.2 [M+H]+.

Example 16

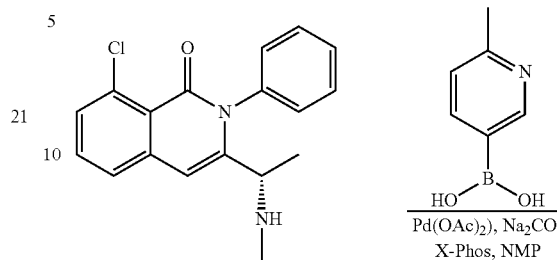

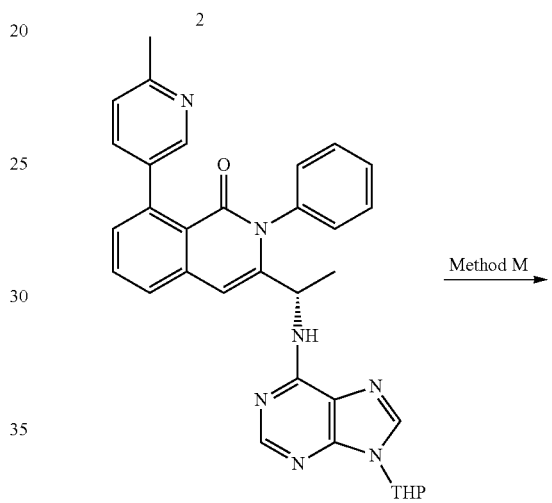

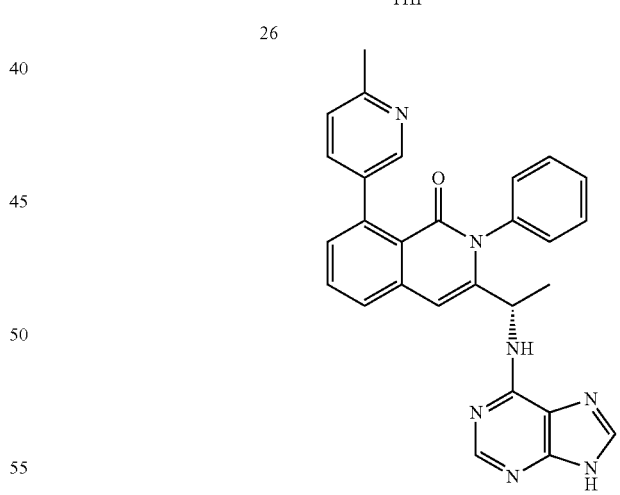

Isoquinolinone 27 was prepared from compound 2 in 2 steps:

Compound 2 was converted to compound 26 according to the following Suzuki coupling procedure. 8-Chloro-2-phenyl-3-((S)-1-(9-(tetrahydro-2H-pyran-2-yl)-9H-purin-6-ylamino)ethyl)isoquinolin-1(2H)-one (2) (100 mg, 0.2 mmol, 1.0 eq), 6-methylpyridin-3-ylboronic acid (56 mg, 0.41 mmol, 2.0 eq), Pd(OAc)₂ (9 mg, 0.04 mmol, 0.2 eq), 2-(dicyclohexylphosphino)-2',4',6'-triisopropylbiphenyl (58 mg, 0.12 mmol, 0.6 eq) and Na₂CO₃ (64 mg, 0.6 mmol, 3.0 eq) were dissolved in 1-methyl-2-pyrrolidinone (10 mL). The resulting mixture was degassed and back-filled with argon three times, and then stirred at 160° C. under an argon atmosphere for 1.5 h. The reaction was complete based on TLC analysis. The mixture was concentrated in vacuo and the residue was purified by flash column chromatography on silica gel (1:30 MeOH-DCM) to afford the product, 8-(6-methylpyridin-3-yl)-2-phenyl-3-((S)-1-(9-(tetrahydro-2H-pyran-2-yl)-9H-purin-6-ylamino)ethyl) isoquinolin-1(2H)-one (26); ESI-MS m/z: 558.30 [M+H]⁺.

Compound 26 was then converted to the product 27 using Method M. ESI-MS m/z: 474.20 [M+H]⁺.

Example 17

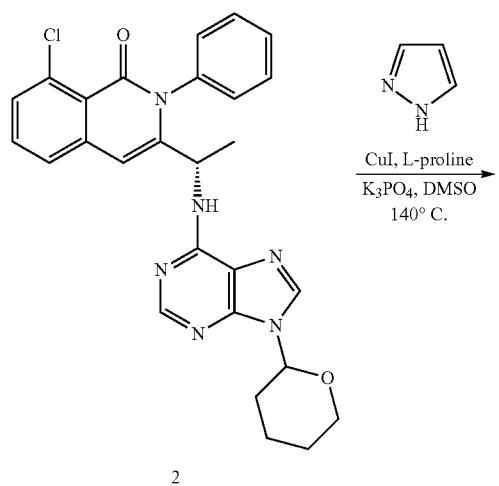

2

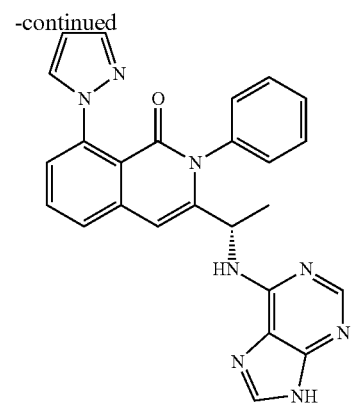

29

Isoquinolinone 29 was prepared from compound 2 in 2 steps:

Compound 2 first was converted to compound 28 using the following Buchwald-Hartwig coupling procedure: A mixture of 8-chloro-2-phenyl-3-((S)-1-(9-(tetrahydro-2H-pyran-2-yl)-9H-purin-6-ylamino)ethyl) isoquinolin-1(2H)-one (2) (300 mg, 0.6 mmol, 1.0 eq), pyrazole (61 mg, 0.9 mmol, 1.5 eq), L-proline (14 mg, 0.12 mmol, 0.2 eq), copper(I) iodide (12 mg, 0.06 mmol, 0.1 eq), and potassium phosphate (318 mg, 1.5 mmol, 2.5 eq) was suspended in DMSO (10 mL). The resulting mixture was degassed and back-filled with argon three times and stirred at 140° C. under an argon atmosphere overnight. After the reaction mixture was cooled to RT, it was diluted with water (50 mL) and extracted with ethyl acetate (30 mL×3). The combined organic layers were washed with brine (30 mL×2), dried over Na₂SO₄ and filtered. The filtrate was concentrated in vacuo. The resultant residue was purified by flash column chromatography on silica gel (1% MeOH-DCM) to afford the product, 2-phenyl-8-(1H-pyrazol-1-yl)-3-((S)-1-(9-(tetrahydro-2H-pyran-2-yl)-9H-purin-6-ylamino)ethyl)isoquinolin-1(2H)-one (28). ESI-MS m/z: 533.30 [M+H]⁺.

Compound 28 was then converted to compound 29 using Method M. ESI-MS m/z: 449.25 [M+H]⁺.

Example 18

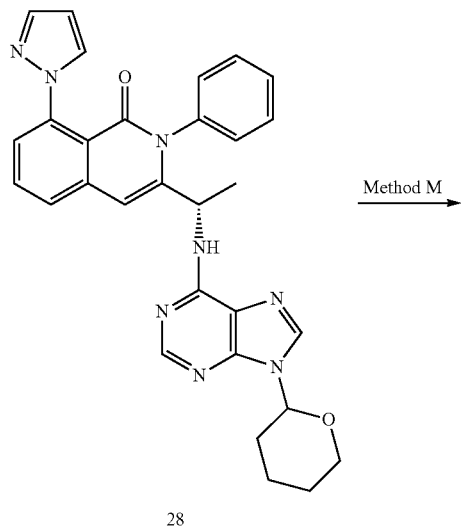

28

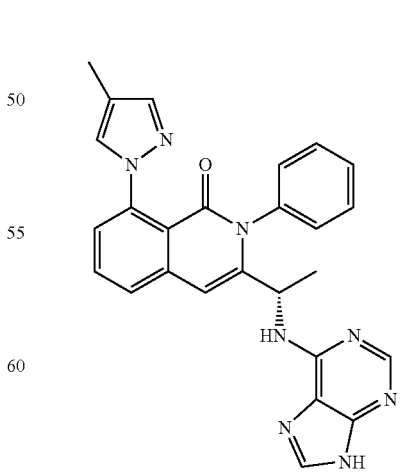

30

Isoquinolinone 30 was prepared from compound 2 in analogous fashion to compound 29 in Example 17 except that 4-methyl-1H-pyrazole was used in place of 1H-pyrazole. ESI-MS m/z: 463.25 [M+H]+.

Example 19

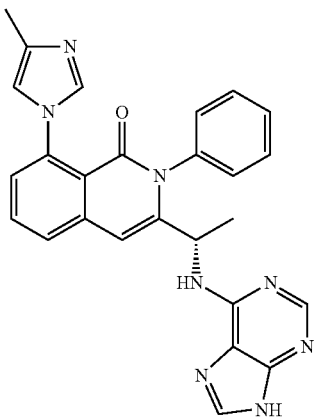

31

Isoquinolinone 31 was prepared from compound 2 in analogous fashion to compound 29 in Example 17 except that 4-methyl-1H-imidazole was used in place of 1H-pyrazole. ESI-MS m/z: 463.20 [M+H]+.

Example 20

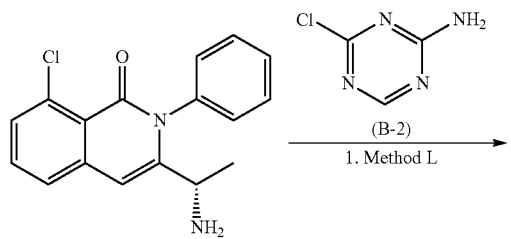

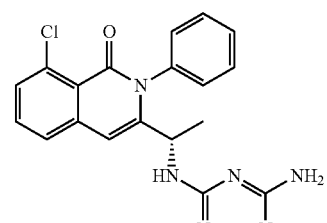

32

-continued

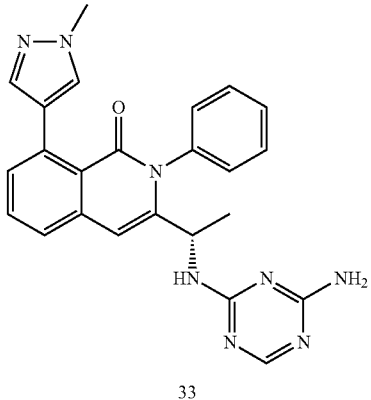

33

Isoquinolinone 33 was prepared from compound 1 in 2 steps. Compound 1 was converted to compound 32 using Method L (intermediate B-2 was prepared by Method B). Compound 32 was then converted to 33 according to the following procedure:

(S)-3-(1-(4-Amino-1,3,5-triazin-2-ylamino)ethyl)-8-chloro-2-phenylisoquinolin-1(2H)-one (32) (100 mg, 0.26 mmol, 1.0 eq), 1-methyl-4-(4,4,5,5-tetramethyl-1,3,2-dioxaborolan-2-yl)-1H-pyrazole (106 mg, 0.51 mmol, 2 eq), PdCl$_2$(dppf) (16 mg, 0.02 mmol, 0.08 eq), and Na$_2$CO$_3$ (81 mg, 0.765 mmol, 3.0 eq) were suspended in a mixture of N,N-dimethylacetamide (20 mL) and water (1 mL). The resulting mixture was degassed and back-filled with argon three times and stirred at 120° C. under an argon atmosphere for 16 h. The mixture was concentrated in vacuo and the residue was purified by flash column chromatography on silica gel (1-4% MeOH-DCM) to afford the product, 3-((S)-1-(4-amino-1,3,5-triazin-2-ylamino)ethyl)-8-(1-methyl-1H-pyrazol-4-yl)-2-phenylisoquinolin-1(2H)-one (33). ESI-MS m/z: 439.25 [M+H]+.

Example 21

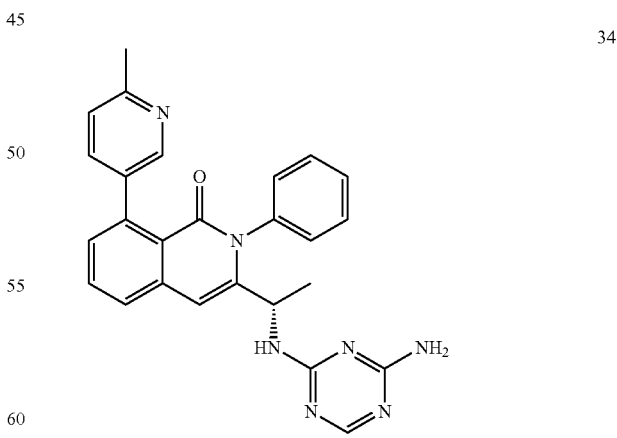

34

Isoquinolinone 34 was prepared from compound 32 in analogous fashion to compound 33 in Example 20 except that 6-methylpyridin-3-ylboronic acid was used in place of 1-methyl-4-(4,4,5,5-tetramethyl-1,3,2-dioxaborolan-2-yl)-1H-pyrazole. ESI-MS m/z: 450.25 [M+H]+.

Example 22

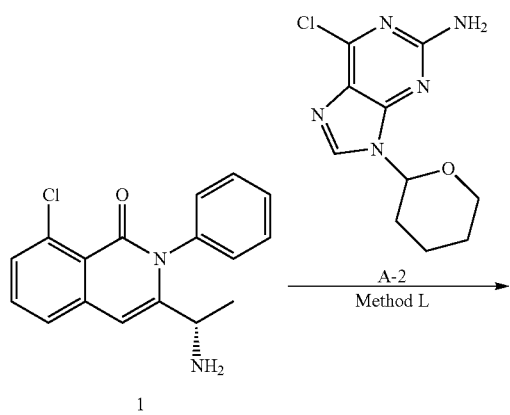

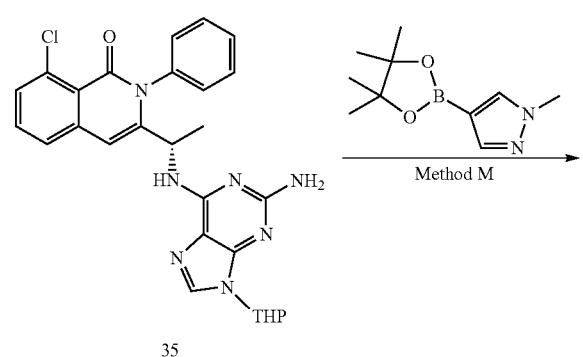

Isoquinolinone 36 was prepared from compound 1 in 3 steps. Compound 1 was first converted to compound 35 using Method L. Compound 35 was then coupled to 1-methyl-4-(4,4,5,5-tetramethyl-1,3,2-dioxaborolan-2-yl)-1H-pyrazole using the analogous procedures for compound 33 in Example 20 after which it was converted to compound 36 using Method M. ESI-MS m/z: 478.2 [M+H]+.

Example 23

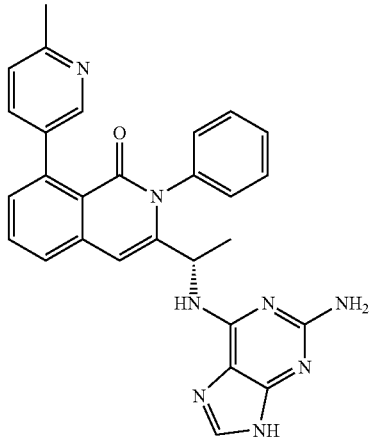

Isoquinolinone 37 was prepared from compound 35 in analogous fashion to compound 36 in Example 22 except that 6-methylpyridin-3-ylboronic acid was used in place of 1-methyl-4-(4,4,5,5-tetramethyl-1,3,2-dioxaborolan-2-yl)-1H-pyrazole. ESI-MS m/z: 487.2 [M−H]−.

Example 24

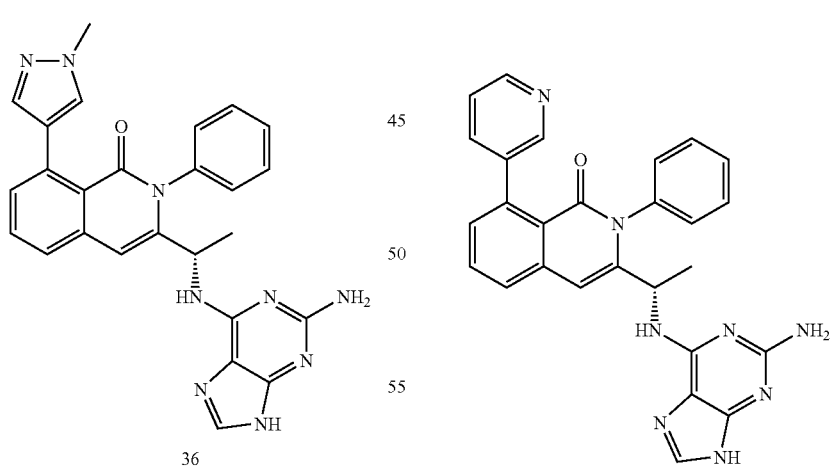

Isoquinolinone 38 was prepared from compound 35 in analogous fashion to compound 36 in Example 22 except that pyridin-3-ylboronic acid was used in place of 1-methyl-4-(4,4,5,5-tetramethyl-1,3,2-dioxaborolan-2-yl)-1H-pyrazole. ESI-MS m/z: 475.30 [M+H]+.

Example 25

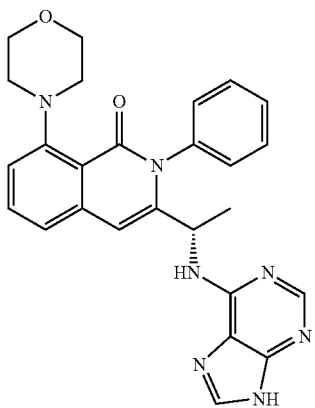

39

Isoquinolinone 39 was prepared in analogous fashion to compound 4 in Example 1 except that morpholine was used in place of pyrrolidine. ESI-MS m/z: 468.0 [M+H]⁺.

Example 26

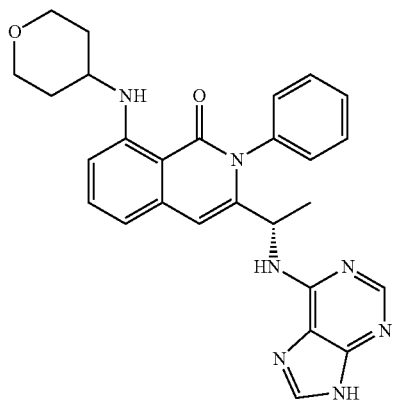

Isoquinolinone 40 was prepared in analogous fashion to compound 4 in Example 1 except that tetrahydro-2H-pyran-4-amine was used in place of pyrrolidine. ESI-MS m/z: 482.2 [M+H]⁺.

Example 27

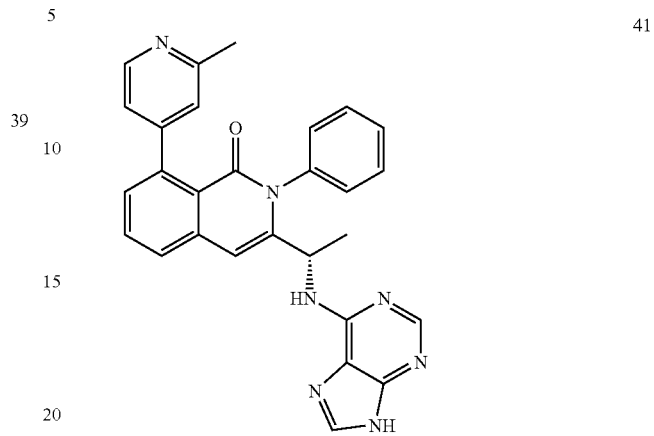

41

Isoquinolinone 41 was prepared from compound 2 in analogous fashion to compound 27 in Example 16 except that 2-methylpyridin-4-ylboronic acid was used in place of 6-methylpyridin-3-ylboronic acid. ESI-MS m/z: 474.30 [M+H]⁺.

Example 28

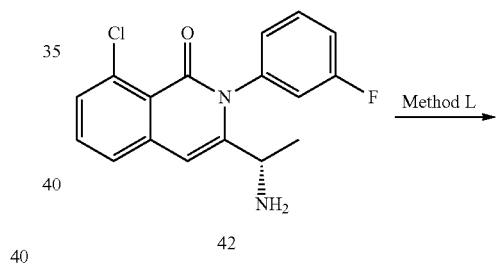

42

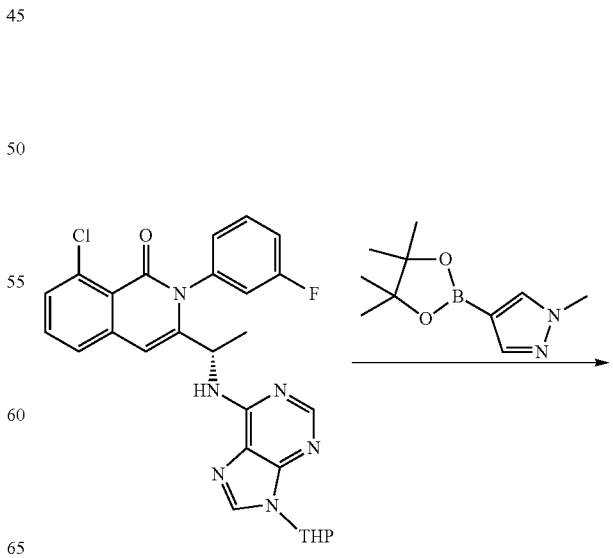

43

-continued

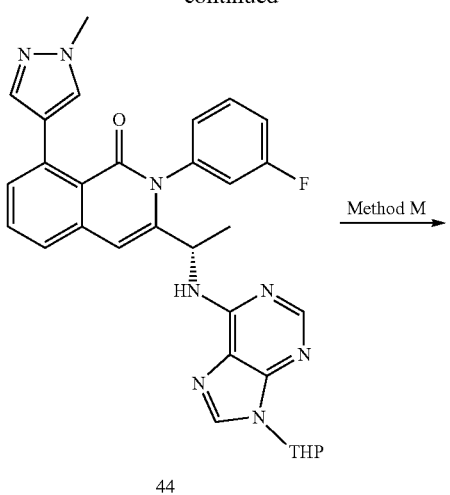

44

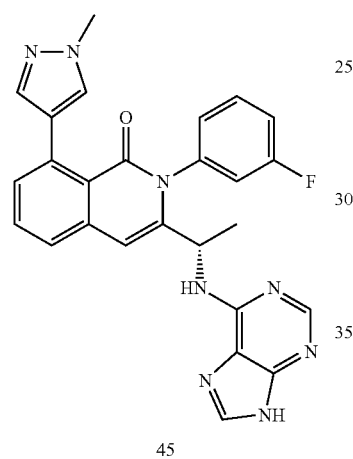

45

Isoquinolinone 45 was prepared according to the following sequences: Amine 42 was prepared by Method I and converted to compound 43 using Method L. The compound 44 was then obtained in analogous fashion to compound 27 in Example 16. Compound 44 was then converted to compound 45 using Method M. ESI-MS m/z: 481.45 (M+H)⁺.

Example 29

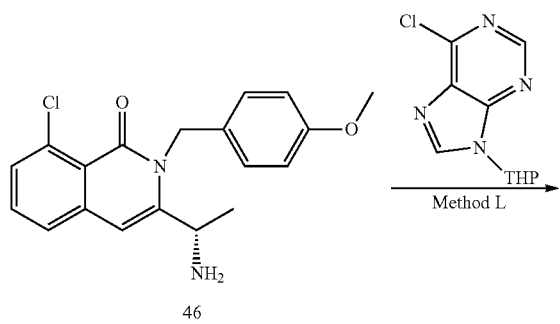

46

-continued

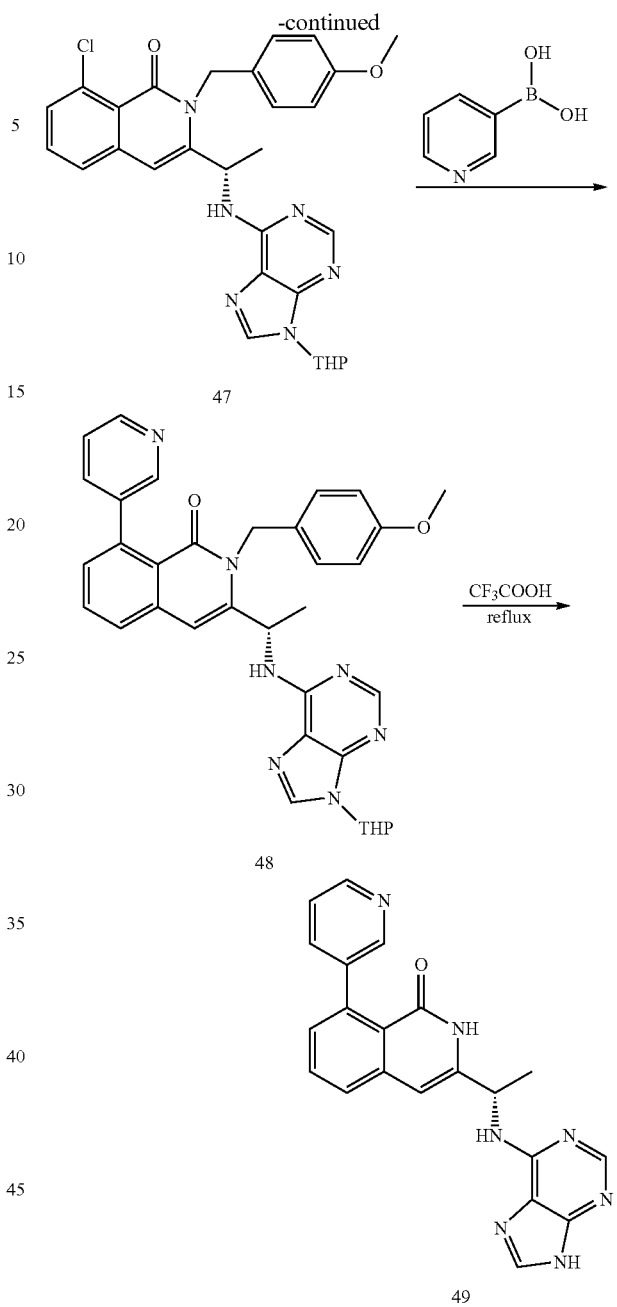

Isoquinoline 49 was prepared according to the following sequences: Amine 46 was prepared by Method I and converted to compound 47 using Method L. Compound 48 was then coupled to pyridin-3-ylboronic using the analogous procedure in Example 20 after which it was converted to the compound 49 according to the following procedure:

Compound 48 (290 mg, 0.49 mmol) was dissolved in trifluoroacetic acid (20 mL) and the resulting mixture was stirred at reflux for 48 h. The mixture was allowed to cool RT and then concentrated in vacuo to remove the excess amount of trifluoroacetic acid. The residue was diluted with water (50 mL), neutralized with aqueous Na₂CO₃ solution to adjust the PH to 8 and then extracted with DCM (100 mL×3). The combined organic layer was dried over anhydrous Na₂SO₄ and filtered. The filtrate was concentrated to dryness in vacuo and the residue was purified by flash chromatography on silica gel (gradient of 1-20% methanol/methylene chloride) to give the product 49 (80 mg, 42.6% yield) as an off-white solid. ESI-MS m/z: 384.2 [M+H]$^+$.

Example 30

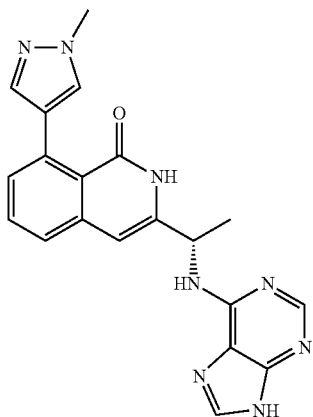

Compound 50 was prepared in analogous fashion to compound 49 in Example 29 except that 1-methyl-4-(4,4,5,5-tetramethyl-1,3,2-dioxaborolan-2-yl)-1H-pyrazole was used in place of 3-pyridylboronic acid. ESI-MS m/z: 387.2 [M+H]$^+$.

Example 31

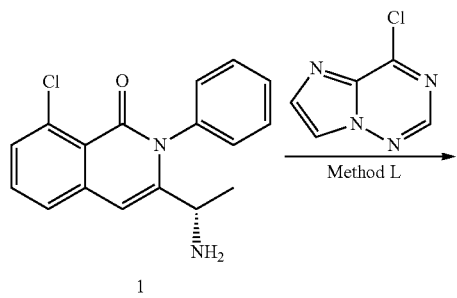

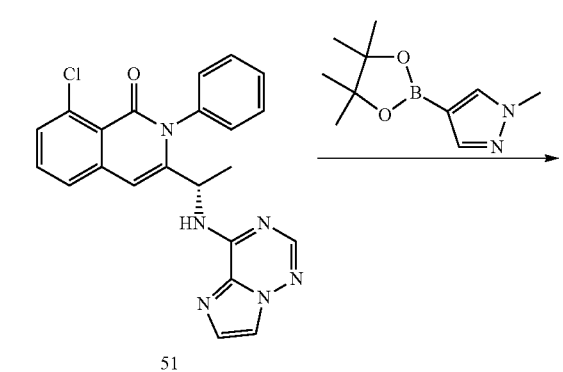

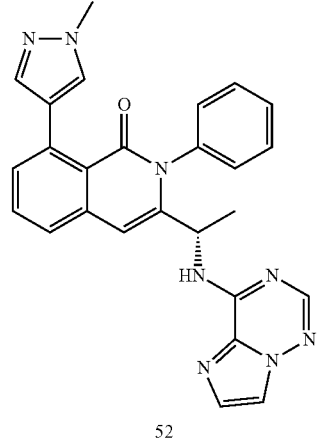

Isoquinolinone 52 was prepared from compound 1 in 2 steps. Compound 1 was converted to compound 51 using Method L. Compound 51 was then coupled to 1-methyl-4-(4,4,5,5-tetramethyl-1,3,2-dioxaborolan-2-yl)-1H-pyrazole using the analogous conditions from Example 20 to provide compound 52. ESI-MS m/z: 463.4 [M+H]$^+$.

Example 32

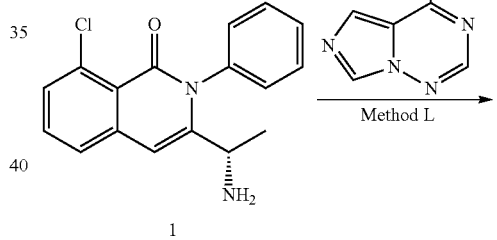

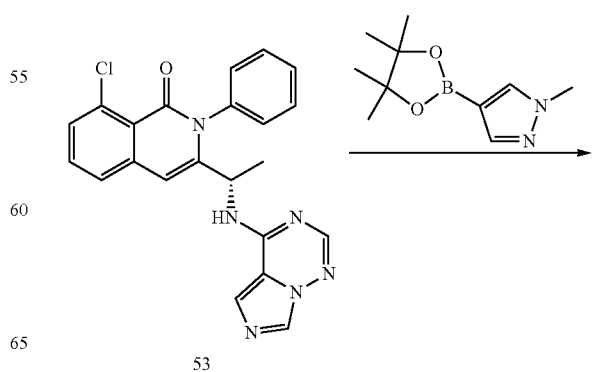

-continued

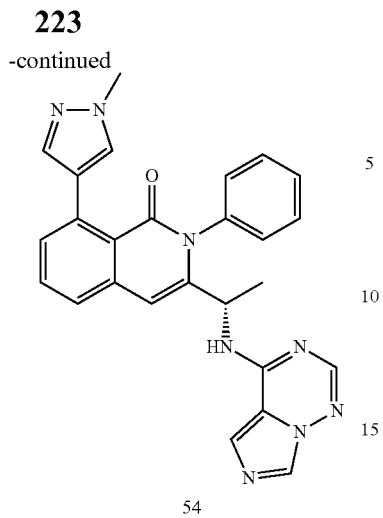

54

Isoquinolinone 54 was prepared from compound 1 in 2 steps. Compound 1 was converted to compound 53 using Method L. Compound 53 was then coupled to 1-methyl-4-(4,4,5,5-tetramethyl-1,3,2-dioxaborolan-2-yl)-1H-pyrazole using the analogous conditions from Example 20 to provide compound 54. ESI-MS m/z: 463.35 [M+H]$^+$.

Example 33

-continued

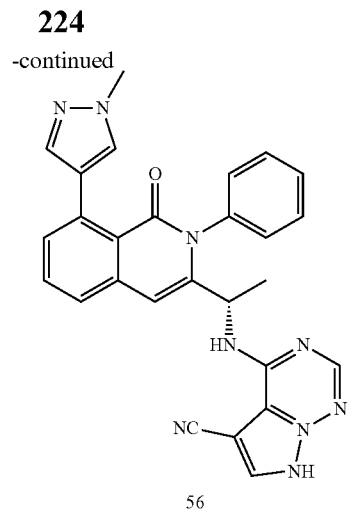

56

Isoquinolinone 56 was prepared from compound 1 in 2 steps. Compound 1 was converted to compound 55 using Method L. Compound 55 was then coupled to 1-methyl-4-(4,4,5,5-tetramethyl-1,3,2-dioxaborolan-2-yl)-1H-pyrazole using the analogous conditions from Example 20 to provide compound 56. ESI-MS m/z::487.2 [M+H]$^+$.

Example 34

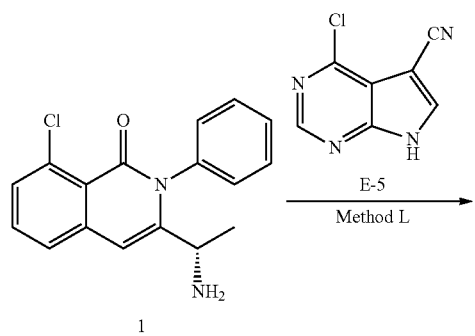

1

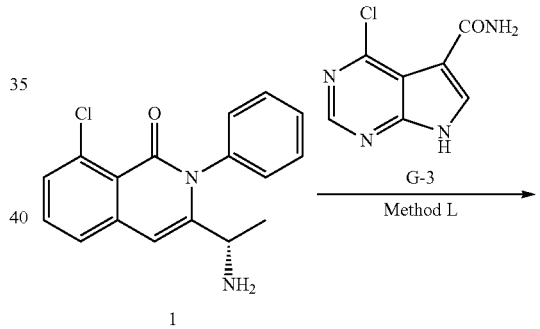

1

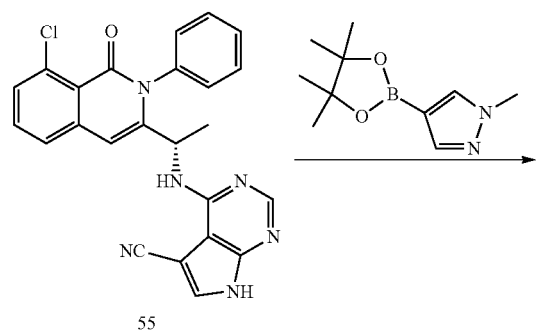

55

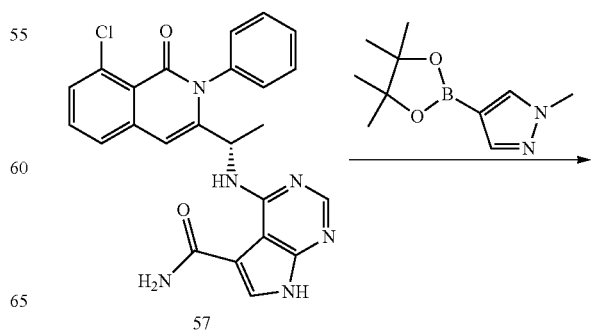

57

-continued

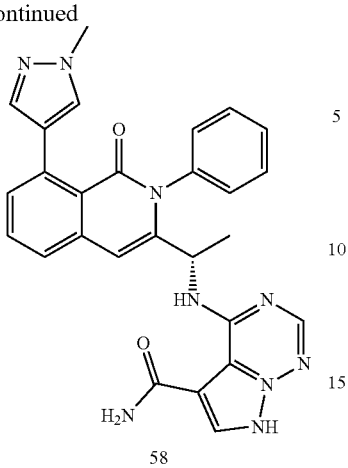
58

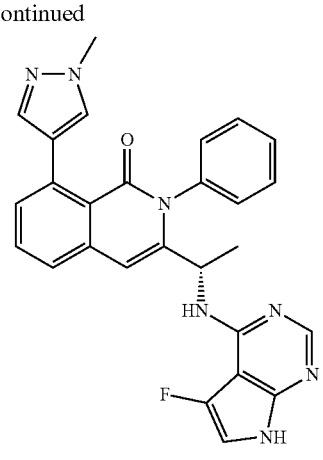
60

Isoquinolinone 58 was prepared from compound 1 in 2 steps. Compound 1 was converted to compound 57 using Method L. Compound 57 was then coupled to 1-methyl-4-(4,4,5,5-tetramethyl-1,3,2-dioxaborolan-2-yl)-1H-pyrazole using the analogous conditions from Example 20 to provide compound 58. ESI-MS m/z: 505.2 [M+H]$^+$.

Isoquinolinone 60 was prepared from compound 1 in 2 steps. Compound 1 was converted to compound 59 using Method L. Compound 59 was then coupled to 1-methyl-4-(4,4,5,5-tetramethyl-1,3,2-dioxaborolan-2-yl)-1H-pyrazole using the analogous conditions from Example 20 to provide compound 60. ESI-MS m/z: 480.2 [M+H]$^+$.

Example 35

Example 36

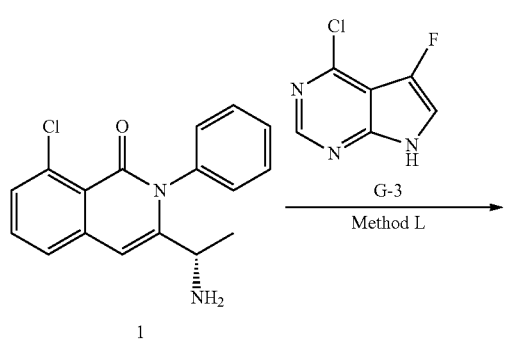

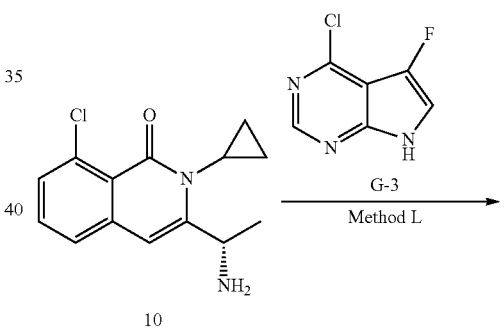

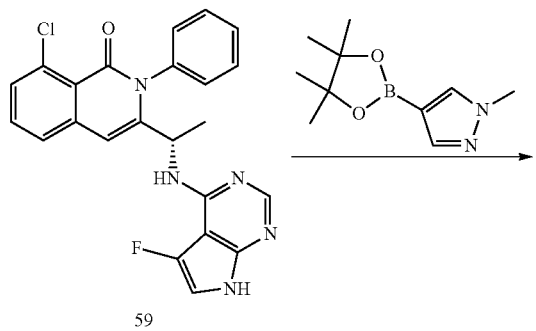
59

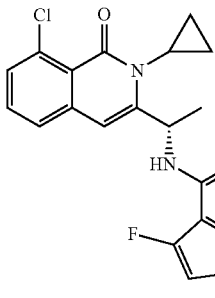
61

-continued

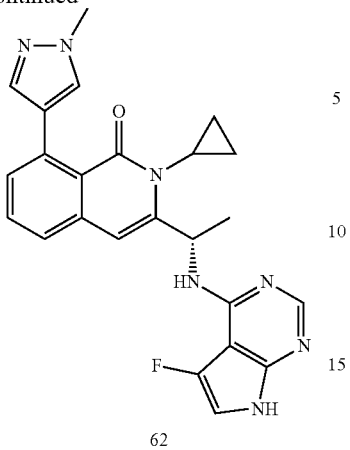

62

Isoquinolinone 62 was prepared from compound 10 in 2 steps. Compound 10 was converted to compound 61 using Method L. Compound 61 was then coupled to 1-methyl-4-(4,4,5,5-tetramethyl-1,3,2-dioxaborolan-2-yl)-1H-pyrazole using the analogous conditions from Example 20 to provide compound 62. ESI-MS m/z: 444.2 [M+H]$^+$.

Example 37

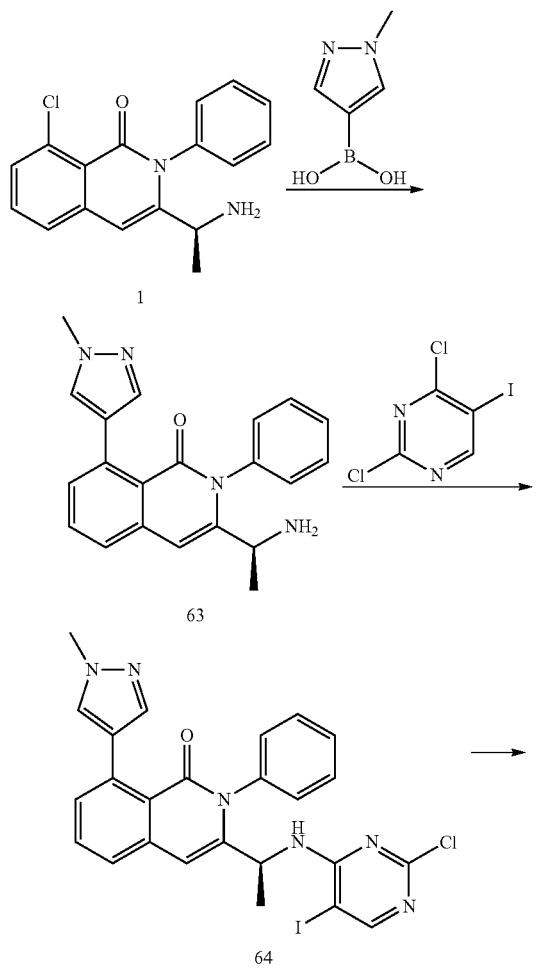

-continued

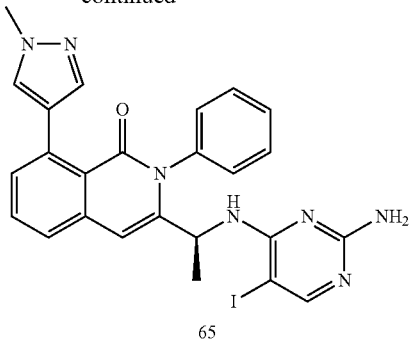

65

To a mixture of (S)-3-(1-aminoethyl)-8-chloro-2-phenylisoquinolin-1(2H)-one (1) (1.0 g, 3.35 mmol) and 1-methyl-1 h-pyrazole-4-boronic acid (815 mg, 5.02 mmol) in anhydrous DMA (10 mL) in a sealed tube, PdCl$_2$(dppf) (219 mg, 0.27 mmol) and aqueous Na$_2$CO$_3$ solution (1 M, 10.0 mL, 10.0 mmol) were added and the resulting mixture was stirred at 120° C. for 3 h. The reaction mixture was allowed to cool to RT, quenched with water, and then extracted with ethyl acetate (200 mL×3). The combined organic layers were washed with brine, dried over Na$_2$SO$_4$ and filtered. The filtrate was concentrated in vacuo and the residue was purified by ISCO (silica gel cartridge, 0-8% MeOH-DCM) to afford the product, (S)-3-(1-aminoethyl)-8-(1-methyl-1H-pyrazol-4-yl)-2-phenylisoquinolin-1(2H)-one (63) (990 mg, 85% yield) as a pink/magenta solid. ESI-MS m/z: 345.2 [M+H]$^+$.

(S)-3-(1-Aminoethyl)-8-(1-methyl-1H-pyrazol-4-yl)-2-phenylisoquinolin-1(2H)-one (63) (570 mg, 1.66 mmol), 2,4-dichloro-5-iodopyrimidine (455 mg, 1.66 mmol) and DIEA (0.27 mL, 1.66 mmol) were dissolved in n-butanol (12 mL) in a sealed tube, and the resulting mixture was stirred at 100° C. for 16 h. The mixture was allowed to cool to RT, quenched with water and extracted with ethyl acetate (150 mL×2). The combined organic layers were washed with brine, dried over Na$_2$SO$_4$ and filtered. The filtrate was concentrated in vacuo to afford the product (S)-3-(1-((2-chloro-5-iodopyrimidin-4-yl)amino)ethyl)-8-(1-methyl-1H-pyrazol-4-yl)-2-phenylisoquinolin-1(2H)-one (64) as an oil. The product obtained was used in the next step without purification. ESI-MS m/z: 583.0 [M+H]$^+$.

To a solution of (S)-3-(1-((2-chloro-5-iodopyrimidin-4-yl)amino)ethyl)-8-(1-methyl-1H-pyrazol-4-yl)-2-phenylisoquinolin-1(2H)-one (64) (964 mg, 1.65 mmol) in anhydrous 1,4-dioxane (5 mL) in a sealed tube, ammonium hydroxide (6 mL) was added and the resulting mixture was stirred at 110° C. for 16 h. An additional amount of ammonium hydroxide (3 mL) was added to the reaction mixture and stirring was continued for 16 h. The mixture was allowed to cool to RT, quenched with water and extracted with ethyl acetate (100 mL×2). The combined organic layers were washed with brine, dried over Na$_2$SO$_4$ and filtered. The filtrate was concentrated in vacuo and the residue was purified by ISCO (silica gel cartridge, 0-8% MeOH-DCM) to afford the product, (S)-3-(1-((2-amino-5-iodopyrimidin-4-yl)amino)ethyl)-8-(1-methyl-1H-pyrazol-4-yl)-2-phenylisoquinolin-1(2H)-one (65) (532 mg, 57% yield) as a light tan solid. ESI-MS m/z: 564.0 [M+H]$^+$.

Example 38

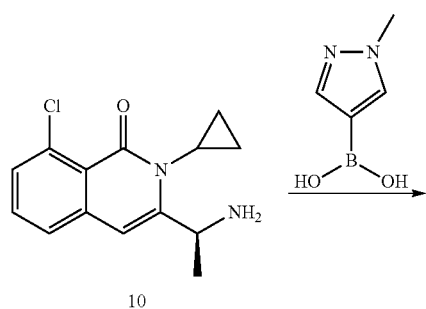

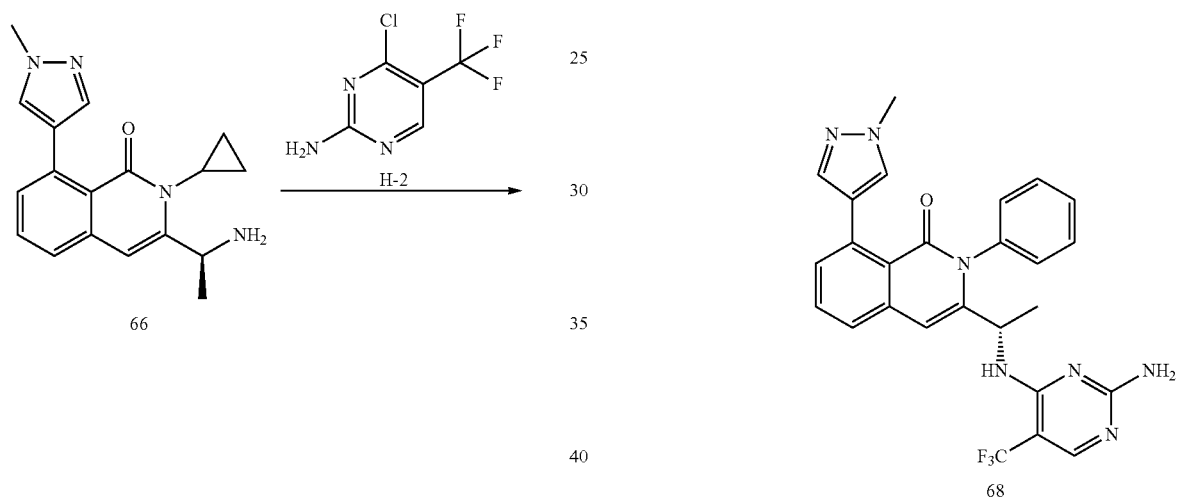

Compound 67 was prepared in 2 steps from amine 10. Compound 66 was prepared using analogous Suzuki coupling procedures as in the conversion of 1 to 63 in Example 37. Compound 66 was then converted to 67 using the same conditions in Example 37 except that H-2 was used in place of 2,4-dichloro-5-iodopyrimidine. ESI-MS m/z: 470.2 [M+H]+.

Example 39

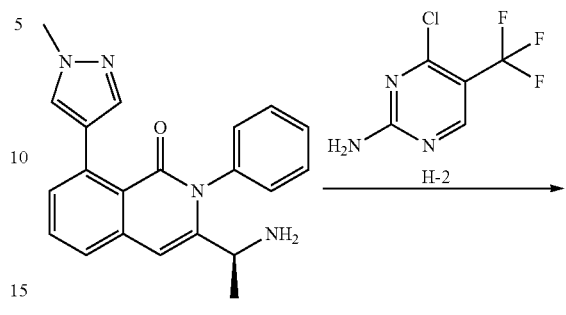

Compound 68 was prepared in analogous fashion to compound 64 in Example 37 except that H-2 was used in place of 2,4-dichloro-5-iodopyrimidine. ESI-MS m/z: 506.2 [M+H]+.

Example 40

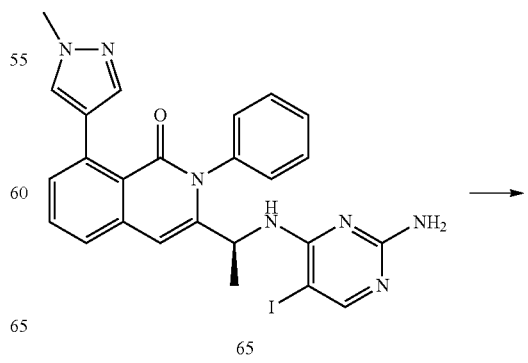

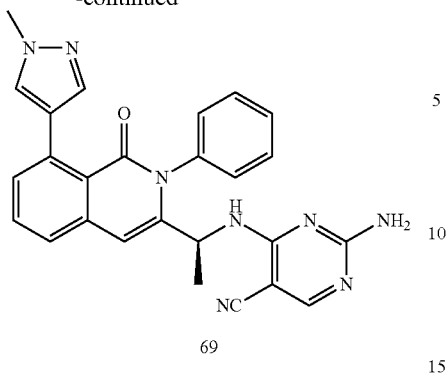

69

To a solution of (S)-3-(1-((2-amino-5-iodopyrimidin-4-yl)amino)ethyl)-8-(1-methyl-1H-pyrazol-4-yl)-2-phenyliso-quinolin-1(2H)-one (65) (240 mg, 0.43 mmol) in anhydrous acetonitrile (12 mL) in a sealed tube, sodium cyanide (209 mg, 4.26 mmol), tetrakis(triphenylphosphine) palladium(0) (246 mg, 0.21 mmol), and copper iodide (57 mg, 0.30 mmol) were added and the resulting mixture was stirred at 80° C. for 16 h. The mixture was allowed to cool to RT, quenched with water and extracted with ethyl acetate (50 mL×2). The combined organic layer was washed with brine, dried over Na$_2$SO$_4$ and filtered. The filtrate was concentrated in vacuo and the residue was purified by ISCO (silica gel cartridge, 0-10% MeOH-DCM) to afford the product, (S)-2-amino-4-((1-(8-(1-methyl-1H-pyrazol-4-yl)-1-oxo-2-phenyl-1,2-di-hydroiso-quinolin-3-yl)ethyl)amino)pyrimidine-5-carboni-trile (69) (60 mg, 30% yield). ESI-MS m/z: 463.2 [M+H]$^+$.

Example 41

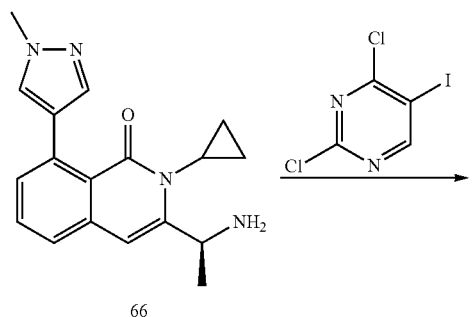

66

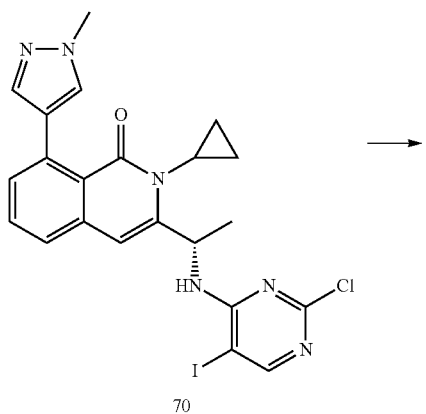

70

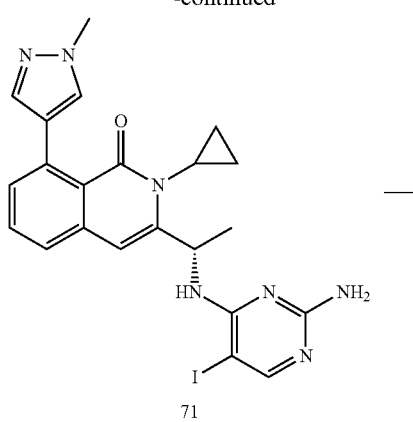

71

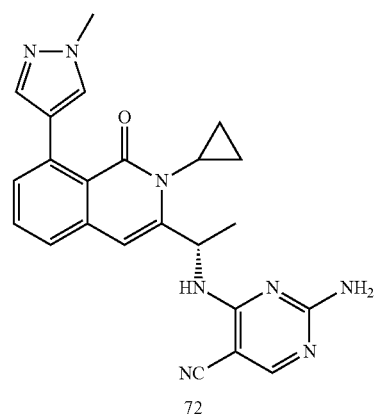

72

Compound 72 was prepared in 3 steps from compound 66. Compound 66 was converted to 70 and then 71 using the analogous procedures in Example 37. Compound 71 was then converted to the product 72 using the procedure in Example 40. ESI-MS m/z: 427.2 [M+H]$^+$.

Example 42

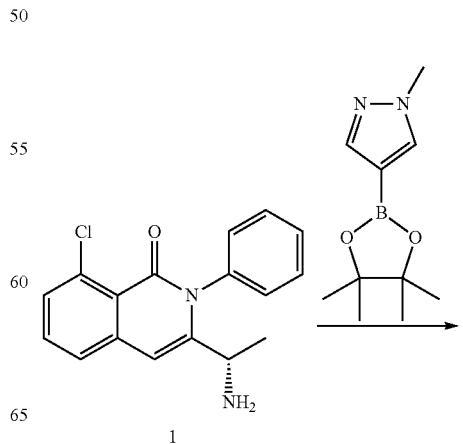

1

-continued

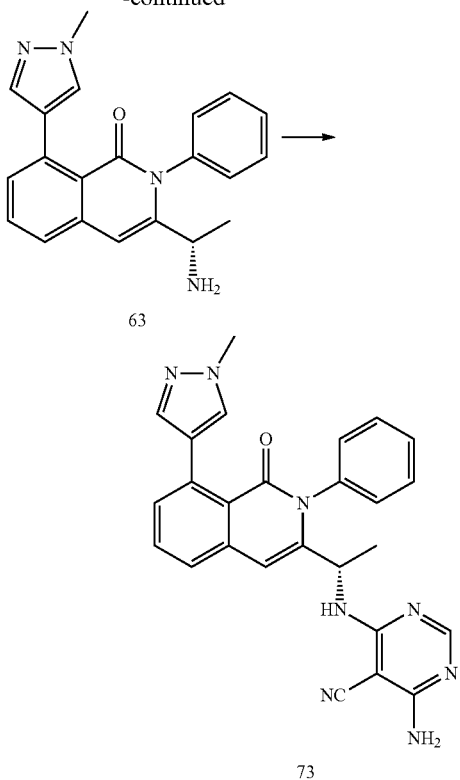

63

73

Compound 73 was prepared in two steps from compound 1 according to the following procedures: Compound 1 (860 mg, 2.9 mmol, 1 eq.), 1-methylpyrazole-4-boronic acid pinacol ester (1.8 g, 3 eq.), sodium carbonate (1.6 g, 5 eq.), palladium diacetate (100 mg, 0.15 eq.) and RuPhos (400 mg, 0.30 eq) were combined in a 20 mL septum-sealed microwave reaction tube with stir bar. The tube was purged with vacuum and refilled with dry argon three times, then charged with 1,4-dioxane (16 mL) and water (4 mL), and subjected to microwave heating at 125° C. for 3 h. The reaction mixture was then purified using flash silica gel chromatography (30 g of silica gel packed using a solution of 1% triethylamine in methylene chloride, mobile phase was a gradient of 1-4% methanol:methylene chloride) NMR analysis revealed this material to be a mixture of the amine 63 and 2.6 eq. of pinacol; this mixture was taken forward without further purification.

A 15 mL thick-walled tube with o-ring seal and stir bar was charged with amine intermediate Z (53% by mass, 300 mg, 0.46 mmol, 1 eq.), n-butanol (5 mL), diisopropylethylamine (160 uL, 2 eq.), and 4-chloro-5-cyano-6-aminopyrimidine (110 mg, 1.5 eq., commercially available from Ark Pharm, Inc.), capped tightly, and heated in a 120° C. bath during 3d. The solvent was removed in vacuo, the residue taken up in DCM and treated with silica gel, and concentrated. The compound was initially purified using flash silica gel chromatography (gradient of 0-5% methanol:methylene chloride). A sample of this material was further purified by partitioning between diethyl ether and 5% acetic acid in water, discarding the ether layer, and extracting the aqueous three times with methylene chloride. The combine organic layers were dried over sodium sulfate to provide compound 73 in 31% yield. ESI-MS m/z: 463.26 [M+H]+.

Example 43

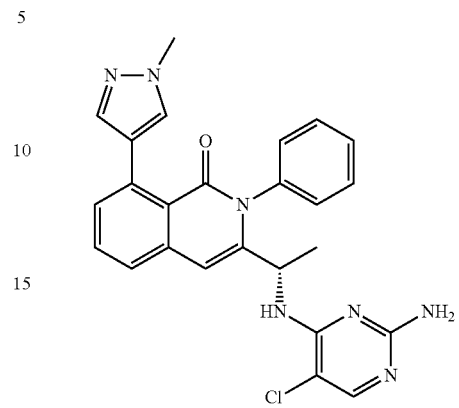

74

Compound 74 was prepared in analogous fashion to compound 72 in Example 41 except that 2,4,5-trichloropyrimidine was used in place of 2,4-dichloro-5-iodopyrimidine. ESI-MS m/z: 472.2 [M+H]+.

Example 44

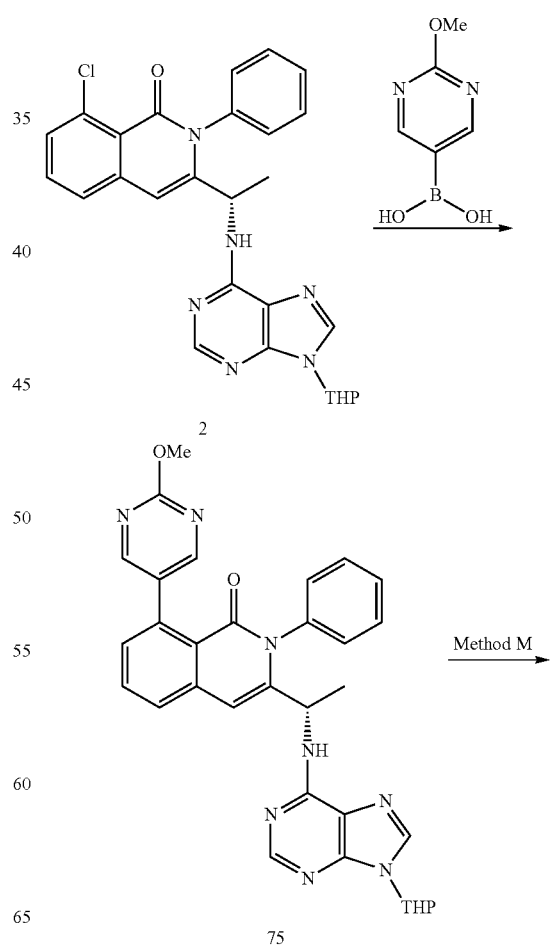

2

75

Method M

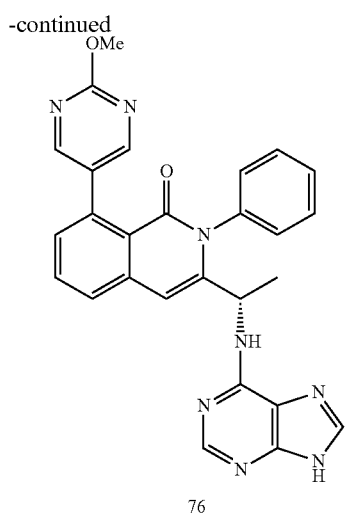

76

Compound 76 was prepared from compound 2 in two steps: A 2 mL thick-walled microwave-reaction tube with stir bar was charged with compound 2 (120 mg, 0.24 mmol, 1 eq.), 2-methoxypyrimidine-5-boronic acid (74 mg, 2 eq.), sodium carbonate (130 mg, 5 eq.), palladium diacetate (8 mg, 0.15 eq.) and RuPhos (34 mg, 0.30 eq.), then capped with a septum and purged three time with vacuum, refilling with dry argon. 1,4-Dioxane (1.6 mL) and water (0.4 mL) were added and the reaction subjected to microwave heating at 125° C. during 3 h, at which time LC/MS showed complete consumption of the starting chloride. The reaction mixture was diluted with DCM, treated with silica gel (0.5 g) and concentrated, then purified by flash chromatography, eluting 15 g silica gel (gradient 1-4% methanol/methylene chloride) to provide 140 mg of compound 75 as an off-white powder. ESI-MS m/z 575.36 [M+H]+.

Compound 75 was then converted to compound 76 using Method M. ESI-MS m/z: 491.22 [M+H]+.

Example 45

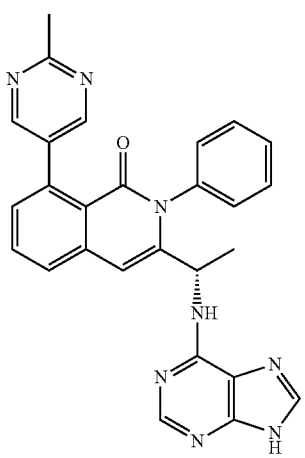

77

Compound 77 was prepared in analogous fashion to compound 75 in Example 44 except that 2-methylpyrimidin-5-ylboronic acid was used in place of 2-methoxypyrimidin-5-ylboronic acid. ESI-MS m/z 475.21 [M+H]+

Example 46

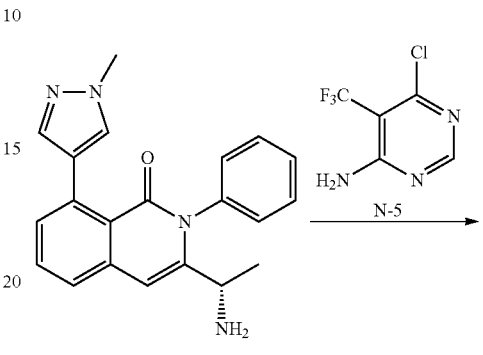

63

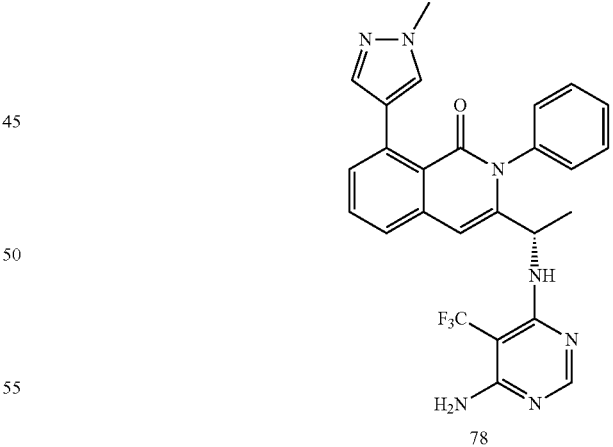

78

Compound 78 was prepared in analogous fashion to compound 64 in Example 37 except that N-5 was used in place of 2,4-dichloro-5-iodopyrimidine and isopropanol was used in place of n-butanol. ESI-MS m/z: 506.2 [M+H]+.

Example 47

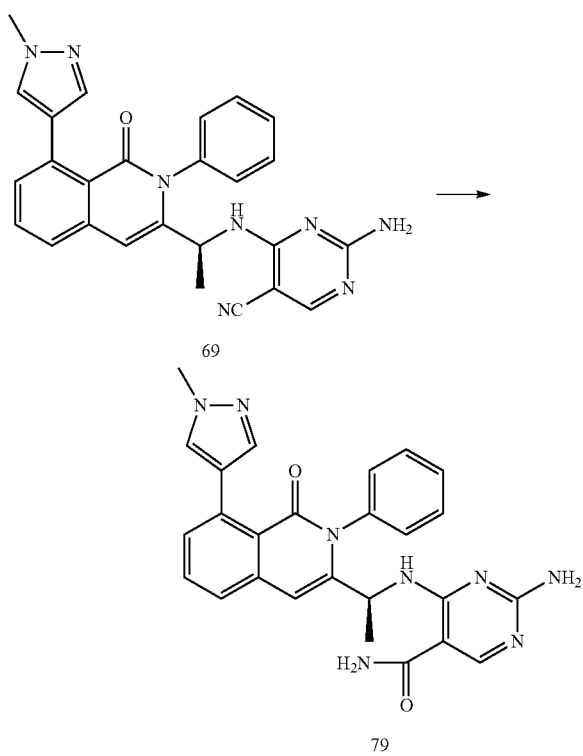

Compound 79 was prepared from 69 according to the following procedure:

To a solution of (S)-2-amino-4-((1-(8-(1-methyl-1H-pyrazol-4-yl)-1-oxo-2-phenyl-1,2-dihydroisoquinolin-3-yl)ethyl)amino)pyrimidine-5-carbonitrile (69) (30.4 mg, 0.066 mmol) in anhydrous toluene (1 mL), acetaldoxime (10 μL, 0.13 mmol), palladium acetate (2 mg, 0.0066 mmol) and triphenyl phosphine (4 mg, 0.013 mmol) were added and the resulting mixture was stirred at 80° C. for 2 h. Additional amounts of acetaldoxime (10 μL, 0.13 mmol), palladium acetate (2 mg, 0.0066 mmol) and triphenyl phosphine (4 mg, 0.013 mmol) were added and stirring was continued at 80° C. for 2 h. The mixture was allowed to cool to RT, quenched with water (30 mL), and then extracted with ethyl acetate (30 mL×2). The combined organic layers were washed with brine, dried over $Na_2SO_4$ and filtered. The filtrate was concentrated in vacuo and the residue was purified by ISCO column chromatography (silica gel cartridge, 0-8.5% MeOH-DCM) to afford the desired product, (S)-2-amino-4-((1-(8-(1-methyl-1H-pyrazol-4-yl)-1-oxo-2-phenyl-1,2-dihydroisoquinolin-3-yl)ethyl)amino)pyrimidine-5-carboxamide (79) as a white solid. ESI-MS m/z: 481.2 [M+H]+.

TABLE 4

In Vitro $IC_{50}$ data for selected compounds.

| $IC_{50}$ (nM) | + (greater than 10 microMolar) | ++ (less than 10 microMolar) | +++ (less than 1 microMolar) | ++++ (less than 100 nM) |
| --- | --- | --- | --- | --- |
| PI3K δ | Compound No. | Compound No. 4, 17, 50, 54, | Compound No. 5, 29, 30, 34, 39, 40 | Compound No. 6, 7, 9, 12, 13, 16, 18, 19, 20, 21, 8, 25, 27, 31, 33, 36, 37, 38, 56, 41, 58, 45, 49, 52, 62, 67, 68, 65, 69, 72, 73, 74, 76 |
| PI3K γ | Compound No. 5, 50, 54 | Compound No. 4, 17, 29, 30, 31, 33, 34, 40, 76 | Compound No. 6, 20, 39, 49, 52, 62, 74 | Compound No. 7, 9, 12, 13, 16, 18, 19, 21, 8, 25, 27, 36, 37, 38, 56, 41, 58, 45, 67, 68, 65, 69, 72, 73 |
| PI3K α | Compound No. 4, 5, 16, 17, 18, 19, 29, 30, 31, 33, 34, 39, 40, 49, 50, 54, 67, 68, 65, 69, 74 | Compound No. 6, 7, 9, 13, 20, 21, 8, 25, 27, 58, 45, 52, 62, 72, 73, 76 | Compound No. 12, 349, 36, 37, 38, 56, 41 | Compound No. |
| PI3K β | Compound No. 4, 5, 6, 17, 18, 19, 27, 29, 30, 31, 33, 34, 39, 40, 45, 49, 52, 50, 54, 67, 68, 65, 69, 73, 74, 76 | Compound No. 7, 9, 16, 20, 21, 8, 25, 36, 37, 38, 56, 41, 58, 62 | Compound No. 12, 13, 349 | Compound No. 72 |
| B cell proliferation $EC_{50}$ (nM) | Compound No. | Compound No. | Compound No. 4, 29, 30, 34 | Compound No. 5, 6, 7, 9, 12, 13, 16, 17, 18, 19, 20, 21, 8, 25, 27, 31, 33, 36, 37, 56, 41, 45, 49, 52, 62, 67, 68 |

TABLE 5
Structures of the Compounds for the IC$_{50}$ results described in Table 4.
Structure
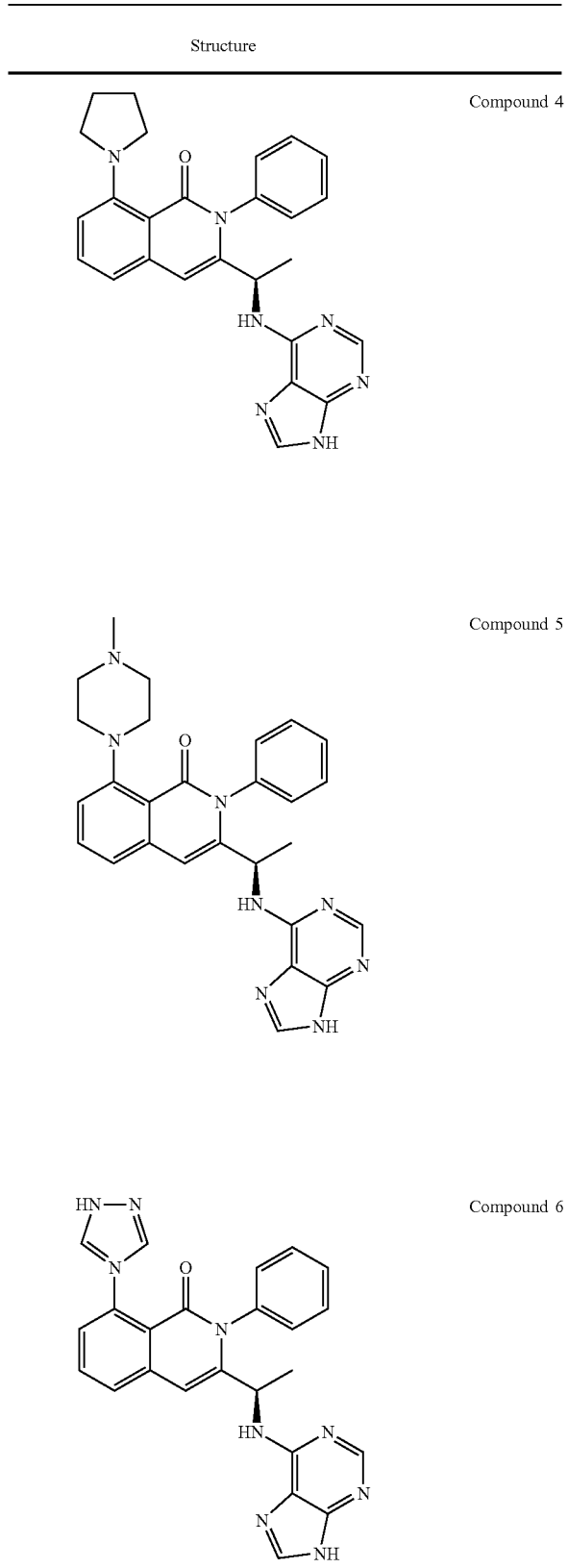
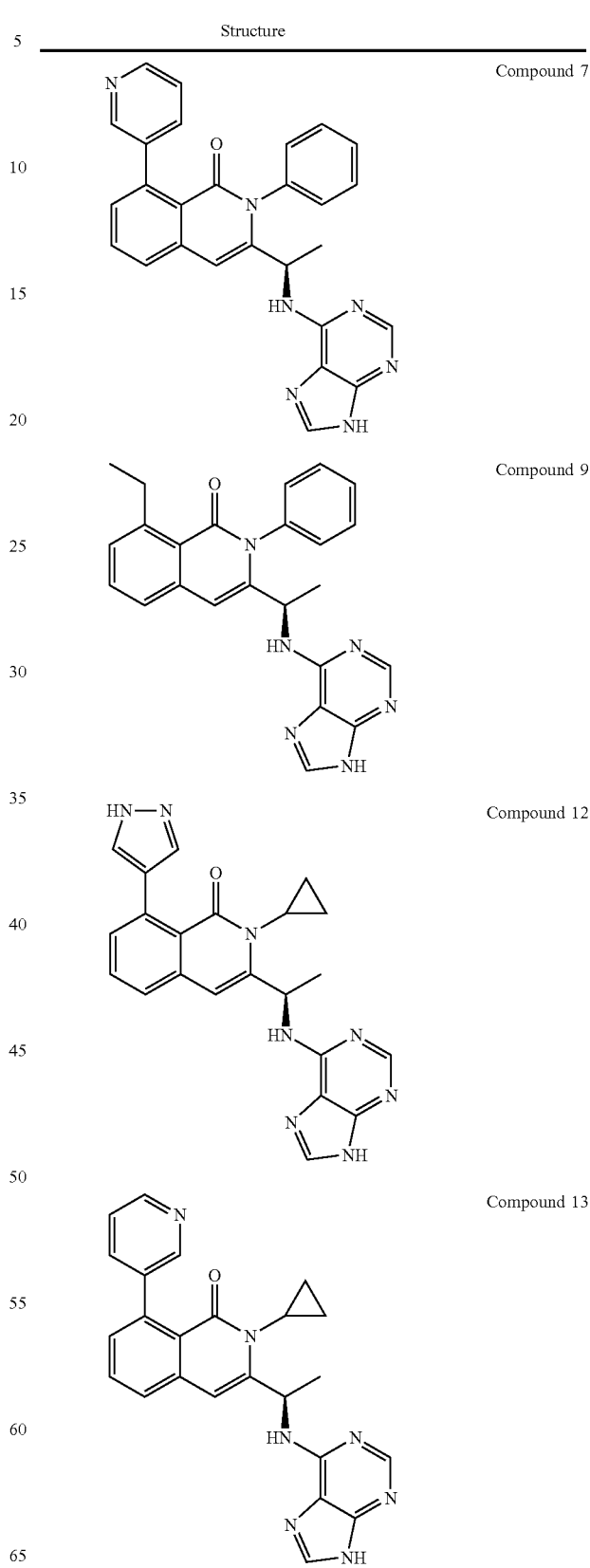

TABLE 5-continued
Structures of the Compounds for the IC$_{50}$ results described in Table 4.
Structure
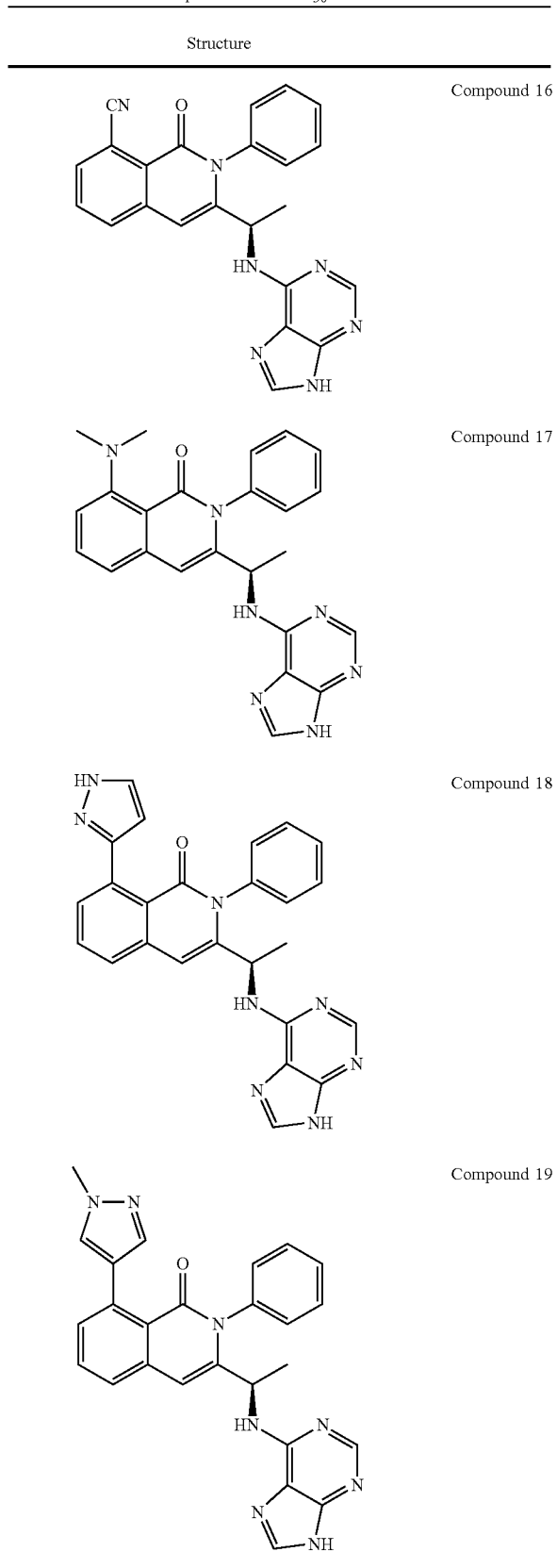
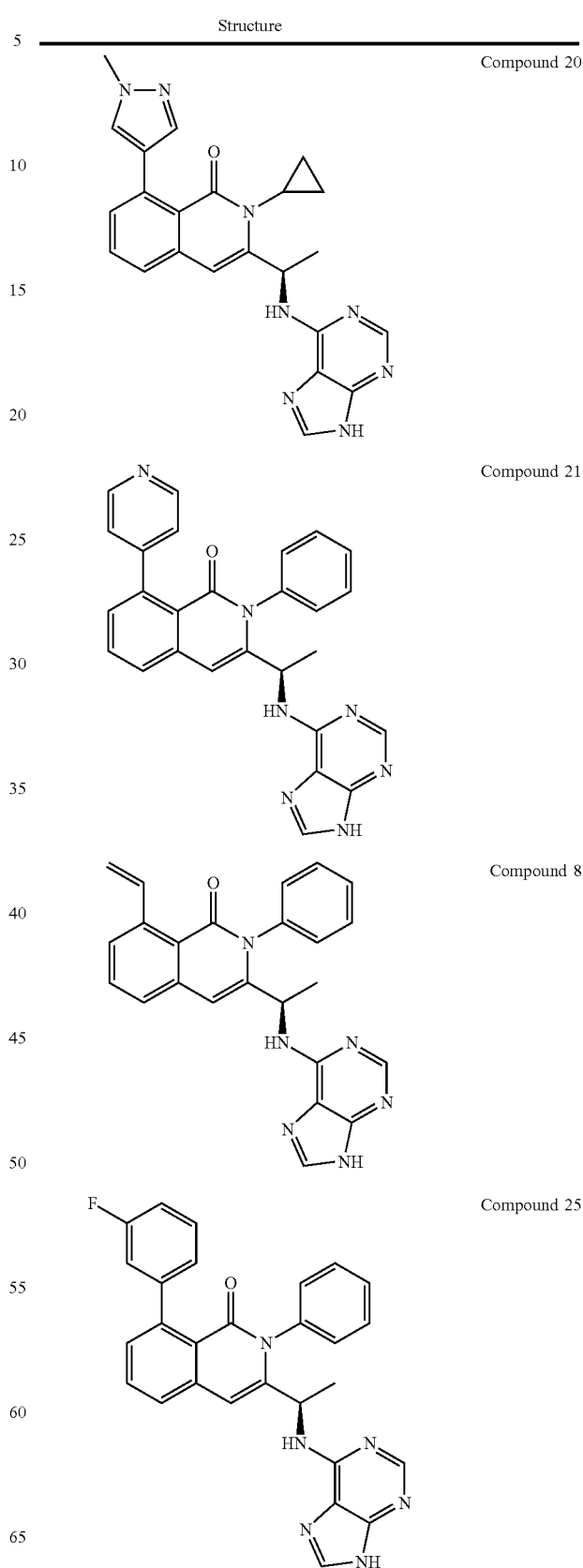

TABLE 5-continued
Structures of the Compounds for the IC$_{50}$ results described in Table 4.
Structure
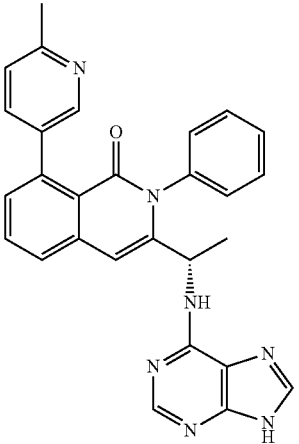 [SMILES: Cc1ccc(-c2cccc3cc([C@H](C)Nc4ncnc5[nH]cnc45)n(-c4ccccc4)c(=O)c23)cn1]
Compound 27
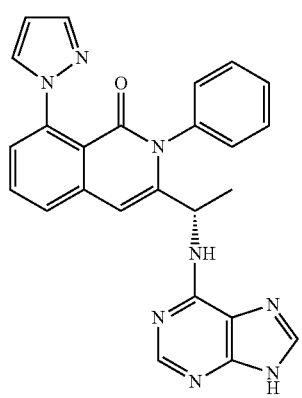 [SMILES: C[C@H](Nc1ncnc2[nH]cnc12)c1cc2cccc(-n3cccn3)c2c(=O)n1-c1ccccc1]
Compound 29
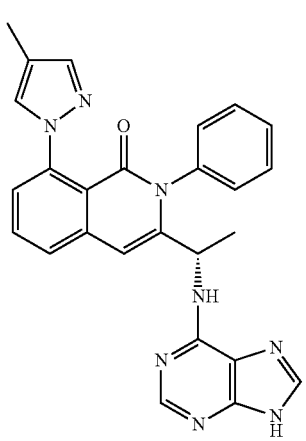 [SMILES: Cc1cnn(-c2cccc3cc([C@H](C)Nc4ncnc5[nH]cnc45)n(-c4ccccc4)c(=O)c23)c1]
Compound 30
TABLE 5-continued
Structures of the Compounds for the IC$_{50}$ results described in Table 4.
Structure
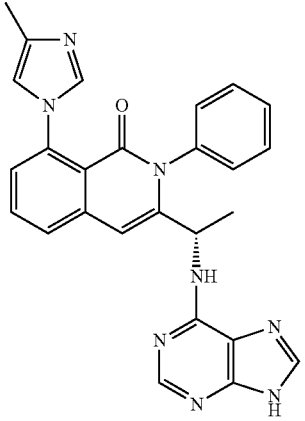
Compound 31
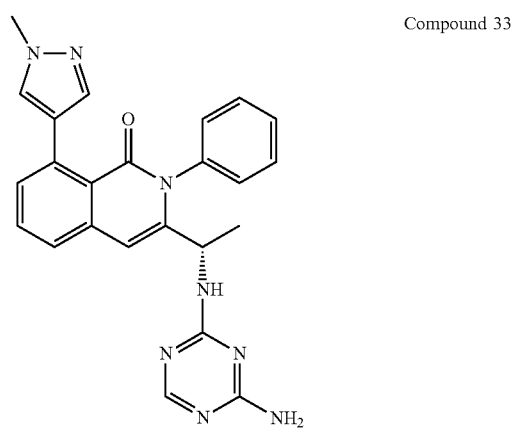
Compound 33
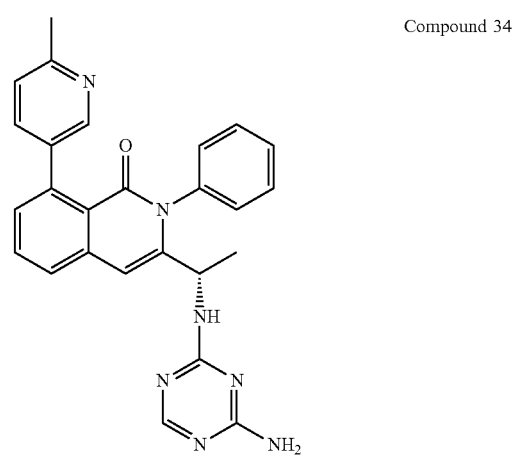
Compound 34

TABLE 5-continued
Structures of the Compounds for the IC$_{50}$ results described in Table 4.
Structure
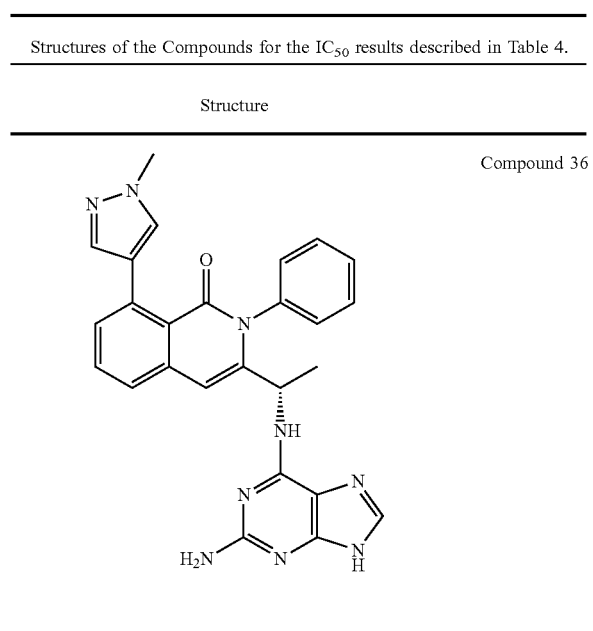
Compound 36
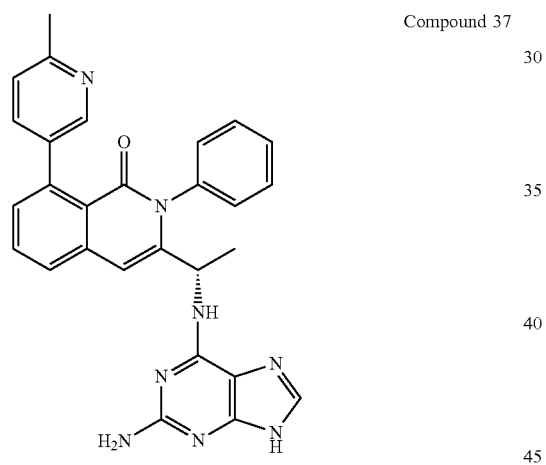
Compound 37
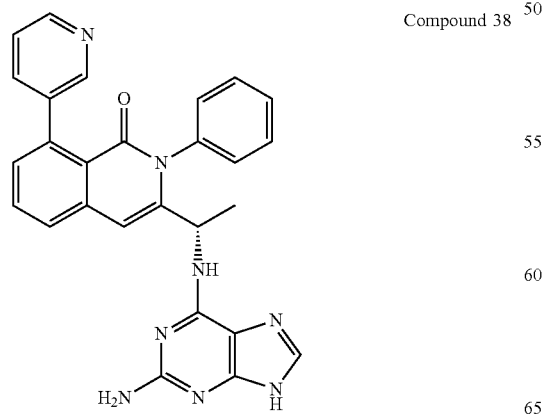
Compound 38
TABLE 5-continued
Structures of the Compounds for the IC$_{50}$ results described in Table 4.
Structure
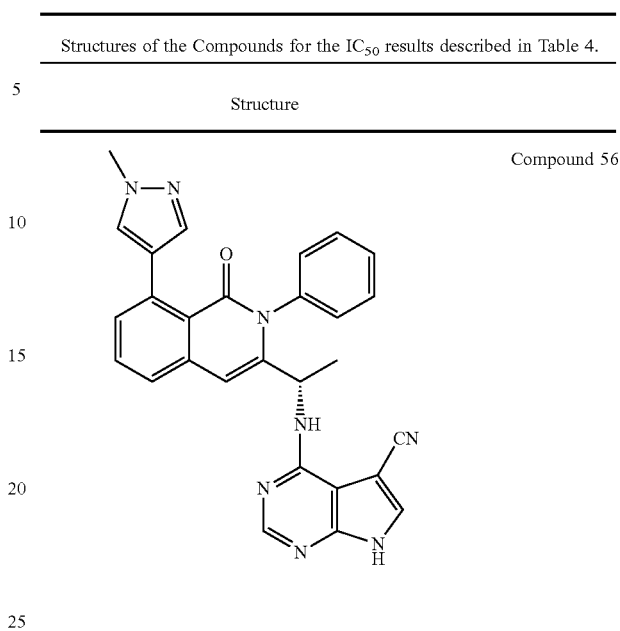
Compound 56
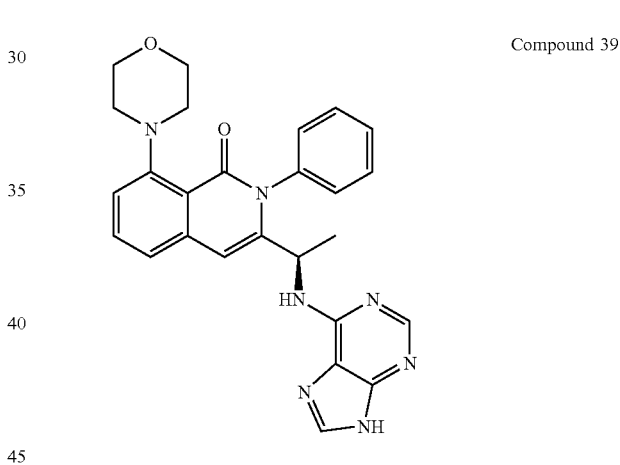
Compound 39
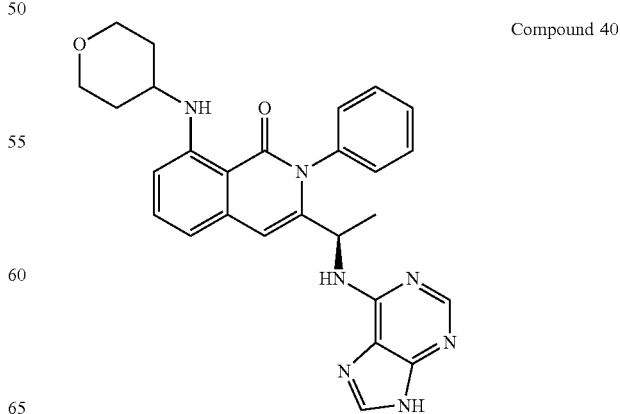
Compound 40

TABLE 5-continued
Structures of the Compounds for the IC$_{50}$ results described in Table 4.
Structure
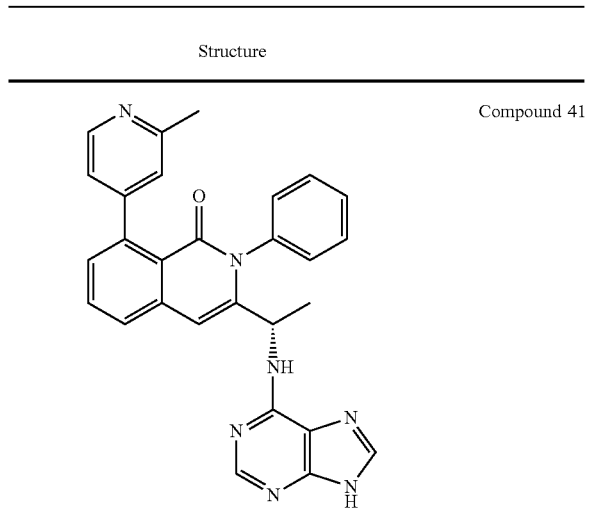
Compound 41
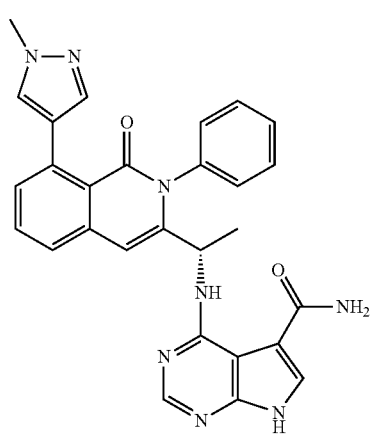 [SMILES: C[C@H](Nc1ncnc2[nH]cc(C(N)=O)c12)c1cc2cccc(-c3cnn(C)c3)c2c(=O)n1-c1ccccc1]
Compound 58
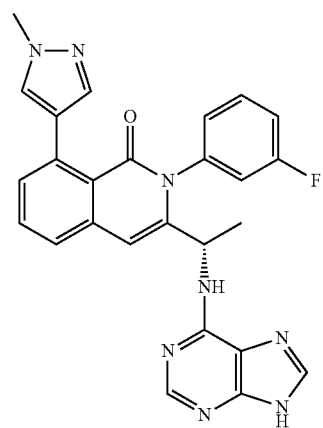 [SMILES: C[C@H](Nc1ncnc2[nH]cnc12)c1cc2cccc(-c3cnn(C)c3)c2c(=O)n1-c1cccc(F)c1]
Compound 45
TABLE 5-continued
Structures of the Compounds for the IC$_{50}$ results described in Table 4.
Structure
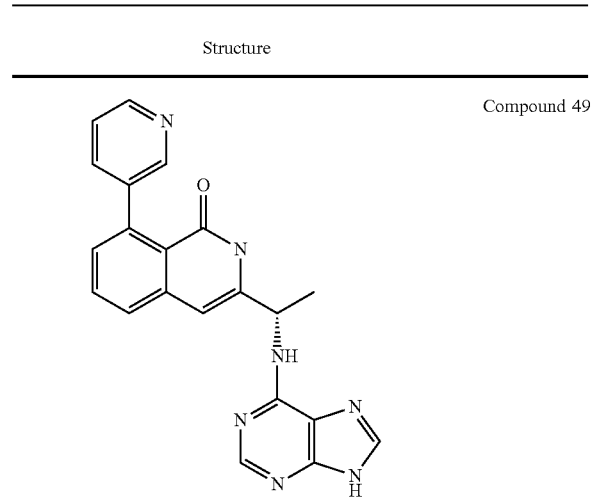
Compound 49
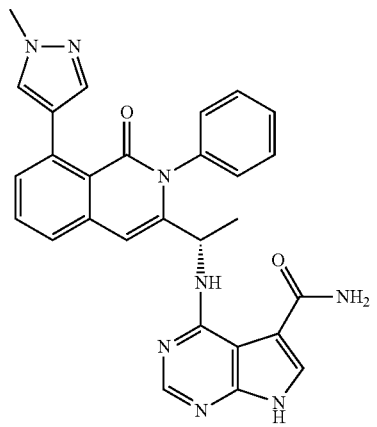
Compound 52
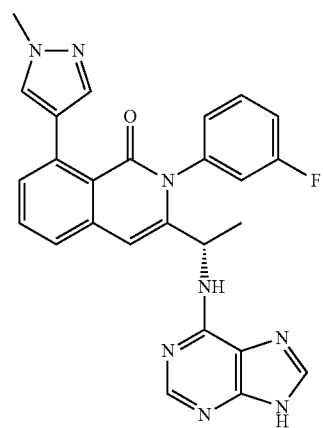
Compound 50

TABLE 5-continued
Structures of the Compounds for the IC$_{50}$ results described in Table 4.
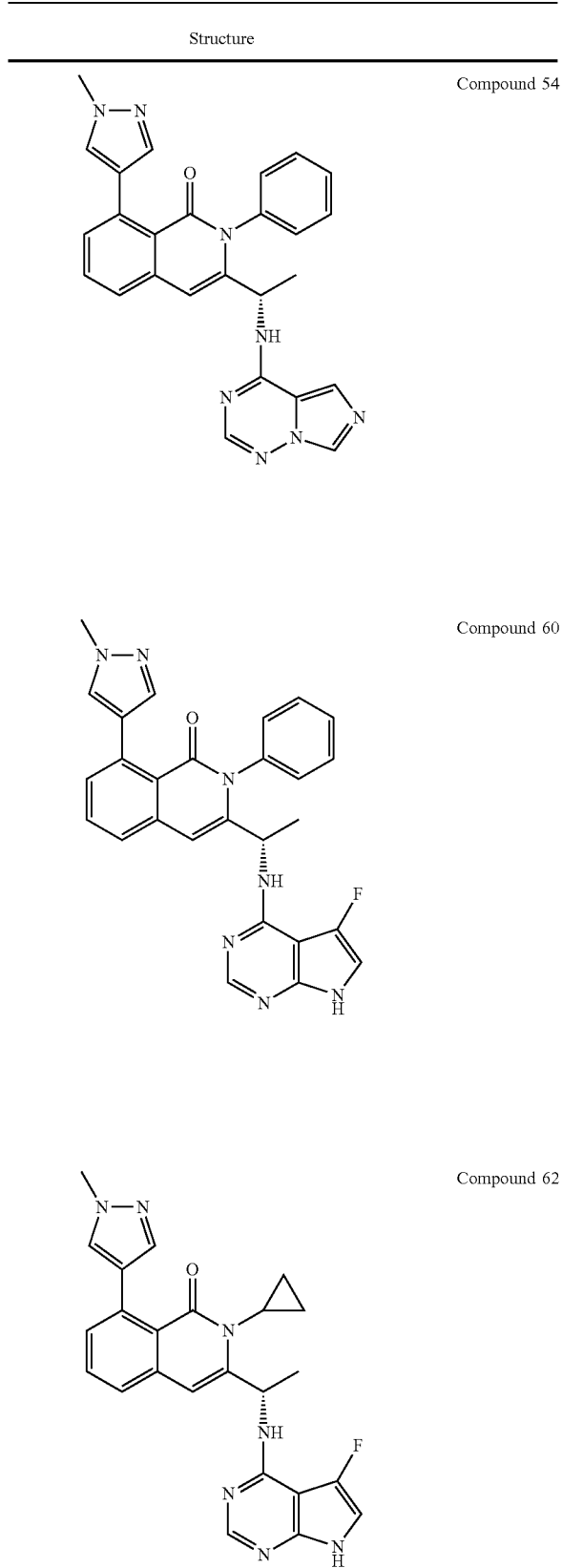
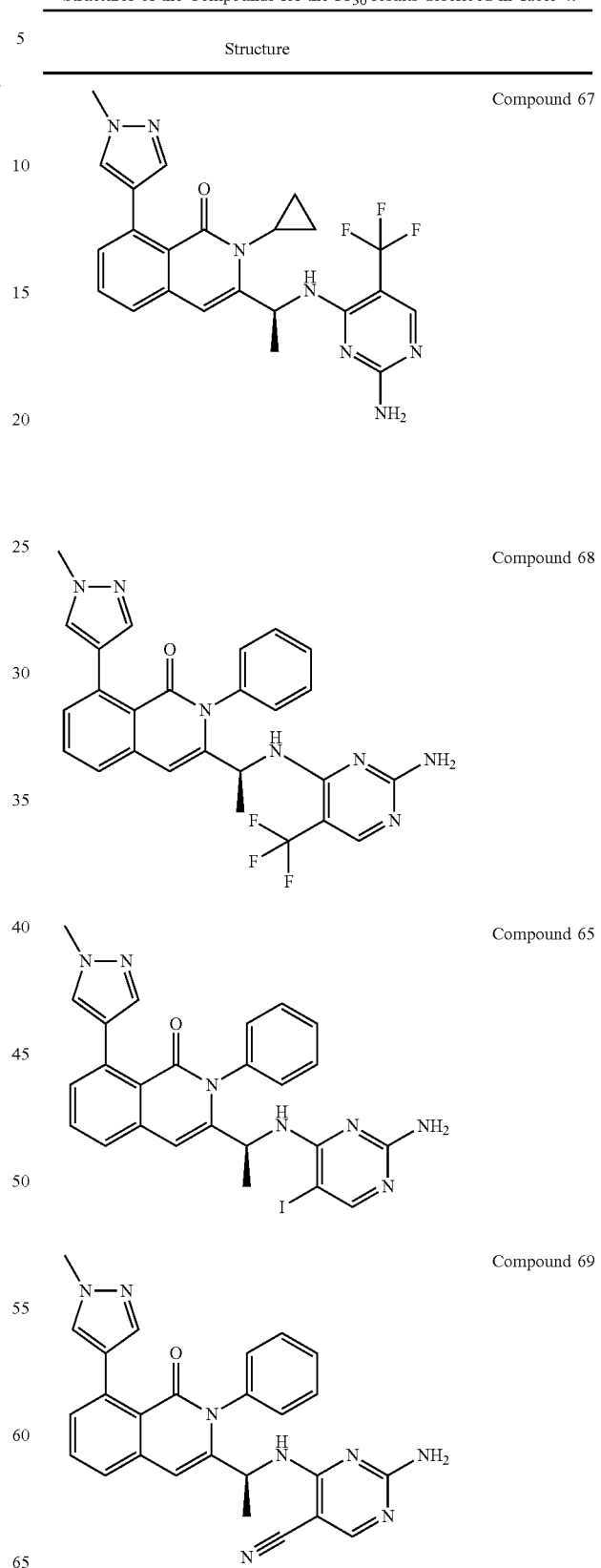

TABLE 5-continued

Structures of the Compounds for the IC$_{50}$ results described in Table 4.

| Structure | |
|---|---|
| (structure) | Compound 73 |
| (structure) | Compound 72 |
| (structure) | Compound 74 |
| (structure) | Compound 76 |

Example 48

Expression and Inhibition Assays of p110α/p85α, p110β/p85α, p110δ/p85α, and p110γ

Class I PI3-Ks can be either purchased (p110α/p85α, p110β/p85α, p110δ/p85α from Upstate, and p110γ from Sigma) or expressed as previously described (Knight et al., 2004). IC$_{50}$ values are measured using either a standard TLC assay for lipid kinase activity (described below) or a high-throughput membrane capture assay. Kinase reactions are performed by preparing a reaction mixture containing kinase, inhibitor (2% DMSO final concentration), buffer (25 mM HEPES, pH 7.4, 10 mM MgCl2), and freshly sonicated phosphatidylinositol (100 μg/ml). Reactions are initiated by the addition of ATP containing 10 μCi of γ-32P-ATP to a final concentration of 10 or 100 μM and allowed to proceed for 5 minutes at room temperature. For TLC analysis, reactions are then terminated by the addition of 105 μl 1N HCl followed by 160 μl CHCl$_3$:MeOH (1:1). The biphasic mixture is vortexed, briefly centrifuged, and the organic phase is transferred to a new tube using a gel loading pipette tip precoated with CHCl$_3$. This extract is spotted on TLC plates and developed for 3-4 hours in a 65:35 solution of n-propanol:1M acetic acid. The TLC plates are then dried, exposed to a phosphorimager screen (Storm, Amersham), and quantitated. For each compound, kinase activity is measured at 10-12 inhibitor concentrations representing two-fold dilutions from the highest concentration tested (typically, 200 μM). For compounds showing significant activity, IC$_{50}$ determinations are repeated two to four times, and the reported value is the average of these independent measurements.

Other commercial kits or systems for assaying PI3-K activities are available. The commercially available kits or systems can be used to screen for inhibitors and/or agonists of PI3-Ks including, but not limited to, PI 3-Kinase α, β, δ, and γ. An exemplary system is PI 3-Kinase (human) HTRF™ Assay from Upstate. The assay can be carried out according to the procedures suggested by the manufacturer. Briefly, the assay is a time resolved FRET assay that indirectly measures PIP3 product formed by the activity of a PI3-K. The kinase reaction is performed in a microtiter plate (e.g., a 384 well microtiter plate). The total reaction volume is approximately 20 μl per well. In the first step, each well receives 2 μl of test compound in 20% dimethylsulphoxide resulting in a 2% DMSO final concentration. Next, approximately 14.5 μl of a kinase/PIP2 mixture (diluted in 1× reaction buffer) is added per well for a final concentration of 0.25-0.3 μg/ml kinase and 10 μM PIP2. The plate is sealed and incubated for 15 minutes at room temperature. To start the reaction, 3.5 μl of ATP (diluted in 1× reaction buffer) is added per well for a final concentration of 10 μM ATP. The plate is sealed and incubated for 1 hour at room temperature. The reaction is stopped by adding 5 μl of Stop Solution per well and then 5 μl of Detection Mix is added per well. The plate is sealed, incubated for 1 hour at room temperature, and then read on an appropriate plate reader. Data is analyzed and IC$_{50}$s are generated using GraphPad Prism 5.

Example 49

Expression and Inhibition Assays of Abl

The cross-activity or lack thereof of one or more compounds as disclosed herein against Abl kinase can be measured according to any procedures known in the art or methods disclosed below. The compounds described herein can be assayed in triplicate against recombinant full-length Abl or Abl (T315I) (Upstate) in an assay containing 25 mM HEPES, pH 7.4, 10 mM MgCl$_2$, 200 µM ATP (2.5 µCi of γ-32P-ATP), and 0.5 mg/mL BSA. The optimized Abl peptide substrate EAIYAAPFAKKK is used as phosphoacceptor (200 µM). Reactions are terminated by spotting onto phosphocellulose sheets, which are washed with 0.5% phosphoric acid (approximately 6 times, 5-10 minutes each). Sheets are dried and the transferred radioactivity quantitated by phosphor imaging.

Example 50

Expression and Inhibition Assays of Hck

The cross-activity or lack thereof of one or more compounds as disclosed herein against Hck kinase can be measured according to any procedures known in the art or methods disclosed below. The compounds described herein can be assayed in triplicate against recombinant full-length Hck in an assay containing 25 mM HEPES, pH 7.4, 10 mM MgCl$_2$, 200 µM ATP (2.5 µCi of γ-32P-ATP), and 0.5 mg/mL BSA. The optimized Src family kinase peptide substrate EIYGEFKKK is used as phosphoacceptor (200 µM). Reactions are terminated by spotting onto phosphocellulose sheets, which are washed with 0.5% phosphoric acid (approximately 6 times, 5-10 minutes each). Sheets are dried and the transferred radioactivity quantitated by phosphor imaging.

Example 51

Expression and Inhibition Assays of Inulsin Receptor (IR)

The cross-activity or lack thereof of one or more compounds as disclosed herein against IR receptor kinase can be measured according to any procedures known in the art or methods disclosed below. The compounds described herein can be assayed in triplicate against recombinant insulin receptor kinase domain (Upstate) in an assay containing 25 mM HEPES, pH 7.4, 10 mM MgCl$_2$, 10 mM MnCl$_2$, 200 µM ATP (2.5 µCi of γ-32P-ATP), and 0.5 mg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphor imaging.

Example 52

Expression and Inhibition Assays of Src

The cross-activity or lack thereof of one or more compounds as disclosed herein against Src kinase can be measured according to any procedures known in the art or methods disclosed below. The compounds described herein can be assayed in triplicate against recombinant full-length Src or Src (T338I) in an assay containing 25 mM HEPES, pH 7.4, 10 mM MgCl$_2$, 200 µM ATP (2.5 µCi of γ-32P-ATP), and 0.5 mg/mL BSA. The optimized Src family kinase peptide substrate EIYGEFKKK is used as phosphoacceptor (200 µM). Reactions are terminated by spotting onto phosphocellulose sheets, which are washed with 0.5% phosphoric acid (approximately 6 times, 5-10 minutes each). Sheets were dried and the transferred radioactivity quantitated by phosphor imaging.

Example 53

Expression and Inhibition Assays of DNA-PK (DNAK)

The cross-activity or lack thereof of one or more compounds as disclosed herein against DNAK kinase can be measured according to any procedures known in the art. DNA-PK can be purchased from Promega and assayed using the DNA-PK Assay System (Promega) according to the manufacturer's instructions.

Example 54

Expression and Inhibition Assays mTOR

The cross-activity or lack thereof of one or more compounds as disclosed herein against mTor can be measured according to any procedures known in the art or methods disclosed below. The compounds described herein can be tested against recombinant mTOR (Invitrogen) in an assay containing 50 mM HEPES, pH 7.5, 1 mM EGTA, 10 mM MgCl$_2$, 2.5 mM, 0.01% Tween, 10 µM ATP (2.5 µCi of µ-32P-ATP), and 3 µg/mL BSA. Rat recombinant PHAS-1/4EBP1 (Calbiochem; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphor imaging.

Other kits or systems for assaying mTOR activity are commercially available. For instance, one can use Invitrogen's LanthaScreen™ Kinase assay to test the inhibitors of mTOR disclosed herein. This assay is a time resolved FRET platform that measures the phosphorylation of GFP labeled 4EBP1 by mTOR kinase. The kinase reaction is performed in a white 384 well microtiter plate. The total reaction volume is 20 µl per well and the reaction buffer composition is 50 mM HEPES pH 7.5, 0.01% Polysorbate 20, 1 mM EGTA, 10 mM MnCl$_2$, and 2 mM DTT. In the first step, each well receives 2 µl of test compound in 20% dimethylsulphoxide resulting in a 2% DMSO final concentration. Next, 8 µl of mTOR diluted in reaction buffer is added per well for a 60 ng/ml final concentration. To start the reaction, 10 µl of an ATP/GFP-4EBP1 mixture (diluted in reaction buffer) is added per well for a final concentration of 10 µM ATP and 0.5 µM GFP-4EBP1. The plate is sealed and incubated for 1 hour at room temperature. The reaction is stopped by adding 10 µl per well of a Tb-anti-pT46.4EBP1 antibody/EDTA mixture (diluted in TR-FRET buffer) for a final concentration of 1.3 nM antibody and 6.7 mM EDTA. The plate is sealed, incubated for 1 hour at room temperature, and then read on a plate reader set up for LanthaScreen™ TR-FRET. Data is analyzed and IC$_{50}$s are generated using GraphPad Prism 5.

Example 55

Expression and Inhibition Assays of Vascular Endothelial Growth Receptor

The cross-activity or lack thereof of one or more compounds as disclosed herein against VEGF receptor can be measured according to any procedures known in the art or methods disclosed below. The compounds described herein can be tested against recombinant KDR receptor kinase domain (Invitrogen) in an assay containing 25 mM HEPES, pH 7.4, 10 mM MgCl$_2$, 0.1% BME, 10 μM ATP (2.5 μCi of μ-32P-ATP), and 3 μg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphor imaging.

Example 56

Expression and Inhibition Assays of Ephrin receptor B4 (EphB4)

The cross-activity or lack thereof of one or more compounds as disclosed herein against EphB4 can be measured according to any procedures known in the art or methods disclosed below. The compounds described herein can be tested against recombinant Ephrin receptor B4 kinase domain (Invitrogen) in an assay containing 25 mM HEPES, pH 7.4, 10 mM MgCl$_2$, 0.1% BME, 10 μM ATP (2.5 μCi of μ-32P-ATP), and 3 μg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphor imaging.

Example 57

Expression and Inhibition Assays of Epidermal Growth Factor Receptor (EGFR)

The cross-activity or lack thereof of one or more compounds as disclosed herein against EGFR kinase can be measured according to any procedures known in the art or methods disclosed below. The compounds described herein can be tested against recombinant EGF receptor kinase domain (Invitrogen) in an assay containing 25 mM HEPES, pH 7.4, 10 mM MgCl$_2$, 0.1% BME, 10 μM ATP (2.5 μCi of μ-32P-ATP), and 3 μg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphor imaging.

Example 58

Expression and Inhibition Assays of KIT Assay

The cross-activity or lack thereof of one or more compounds as disclosed herein against KIT kinase can be measured according to any procedures known in the art or methods disclosed below. The compounds described herein can be tested against recombinant KIT kinase domain (Invitrogen) in an assay containing 25 mM HEPES, pH 7.4, 10 mM MgCl$_2$, 1 mM DTT, 10 mM MnCl$_2$, 10 μM ATP (2.5 μCi of μ-32P-ATP), and 3 μg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphor imaging.

Example 59

Expression and Inhibition Assays of RET

The cross-activity or lack thereof of one or more compounds as disclosed herein against RET kinase can be measured according to any procedures known in the art or methods disclosed below. The compounds described herein can be tested against recombinant RET kinase domain (Invitrogen) in an assay containing 25 mM HEPES, pH 7.4, 10 mM MgCl$_2$, 2.5 mM DTT, 10 μM ATP (2.5 μCi of μ-32P-ATP), and 3 μg/mL BSA. The optimized Abl peptide substrate EAIYAAPFAKKK is used as phosphoacceptor (200 μM). Reactions are terminated by spotting onto phosphocellulose sheets, which are washed with 0.5% phosphoric acid (approximately 6 times, 5-10 minutes each). Sheets are dried and the transferred radioactivity quantitated by phosphor imaging.

Example 60

Expression and Inhibition Assays of Platelet Derived Growth Factor Receptor (PDGFR)

The cross-activity or lack thereof of one or more compounds as disclosed herein against PDGFR kinase can be measured according to any procedures known in the art or methods disclosed below. The compounds described herein can be tested against recombinant PDG receptor kinase domain (Invitrogen) in an assay containing 25 mM HEPES, pH 7.4, 10 mM MgCl$_2$, 2.5 mM DTT, 10 μM ATP (2.5 μCi of μ-32P-ATP), and 3 μg/mL BSA. The optimized Abl peptide substrate EAIYAAPFAKKK is used as phosphoacceptor (200 μM). Reactions are terminated by spotting onto phosphocellulose sheets, which are washed with 0.5% phosphoric acid (approximately 6 times, 5-10 minutes each). Sheets are dried and the transferred radioactivity quantitated by phosphor imaging.

Example 61

Expression and Inhibition Assays of FMS-Related Tyrosine Kinase 3 (FLT-3)

The cross-activity or lack thereof of one or more compounds as disclosed herein against FLT-3 kinase can be measured according to any procedures known in the art or methods disclosed below. The compounds described herein can be tested against recombinant FLT-3 kinase domain (Invitrogen) in an assay containing 25 mM HEPES, pH 7.4, 10 mM MgCl$_2$, 2.5 mM DTT, 10 μM ATP (2.5 μCi of μ-32P-ATP), and 3 μg/mL BSA. The optimized Abl peptide substrate EAIYAAPFAKKK is used as phosphoacceptor (200 μM). Reactions are terminated by spotting onto phosphocellulose sheets, which are washed with 0.5% phosphoric acid (approximately 6 times, 5-10 minutes each). Sheets are dried and the transferred radioactivity quantitated by phosphor imaging.

Example 62

Expression and Inhibition Assays of TEK Receptor Tyrosine Kinase (TIE2)

The cross-activity or lack thereof of one or more compounds as disclosed herein against TIE2 kinase can be measured according to any procedures known in the art or methods disclosed below. The compounds described herein can be tested against recombinant TIE2 kinase domain (Invitrogen) in an assay containing 25 mM HEPES, pH 7.4, 10 mM MgCl$_2$, 2 mM DTT, 10 mM MnCl$_2$, 10 µM ATP (2.5 µCi of µ-32P-ATP), and 3 µg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphor imaging.

Example 63

B Cell Activation and Proliferation Assay

The ability of one or more subject compounds to inhibit B cell activation and proliferation is determined according to standard procedures known in the art. For example, an in vitro cellular proliferation assay is established that measures the metabolic activity of live cells. The assay is performed in a 96 well microtiter plate using Alamar Blue reduction. Balb/c splenic B cells are purified over a Ficoll-Paque™ PLUS gradient followed by magnetic cell separation using a MACS B cell Isolation Kit (Miletenyi). Cells are plated in 90 µl at 50,000 cells/well in B Cell Media (RPMI+10% FBS+Penn/Strep+50 µM bME+5 mM HEPES). A compound disclosed herein is diluted in B Cell Media and added in a 10 µl volume. Plates are incubated for 30 min at 37° C. and 5% CO$_2$ (0.2% DMSO final concentration). A 50 µl B cell stimulation cocktail is then added containing either 10 µg/ml LPS or 5 µg/ml F(ab')2 Donkey anti-mouse IgM plus 2 ng/ml recombinant mouse IL4 in B Cell Media. Plates are incubated for 72 hours at 37° C. and 5% CO$_2$. A volume of 15 µL of Alamar Blue reagent is added to each well and plates are incubated for 5 hours at 37° C. and 5% CO$_2$. Alamar Blue fluoresce is read at 560Ex/590Em, and IC$_{50}$ or EC$_{50}$ values are calculated using GraphPad Prism 5.

Example 64

Tumor Cell Line Proliferation Assay

The ability of one or more subject compounds to inhibit tumor cell line proliferation can be determined according to standard procedures known in the art. For instance, an in vitro cellular proliferation assay can be performed to measure the metabolic activity of live cells. The assay is performed in a 96 well microtiter plate using Alamar Blue reduction. Human tumor cell lines are obtained from ATCC (e.g., MCF7, U-87 MG, MDA-MB-468, PC-3), grown to confluency in T75 flasks, trypsinized with 0.25% trypsin, washed one time with Tumor Cell Media (DMEM+10% FBS), and plated in 90 µl at 5,000 cells/well in Tumor Cell Media. A compound disclosed herein is diluted in Tumor Cell Media and added in a 10 µl volume. Plates are incubated for 72 hours at 37° C. and 5% CO$_2$. A volume of 10 µL of Alamar Blue reagent is added to each well and plates are incubated for 3 hours at 37° C. and 5% CO$_2$. Alamar Blue fluoresce is read at 560Ex/590Em, and IC$_{50}$ values are calculated using GraphPad Prism 5.

Example 65

Antitumor Activity in Vivo

The compounds described herein can be evaluated in a panel of human and murine tumor models.

Paclitaxel-refractory Tumor Models
1. Clinically-Derived Ovarian Carcinoma Model.

This tumor model is established from a tumor biopsy of an ovarian cancer patient. Tumor biopsy is taken from the patient. The compounds described herein are administered to nude mice bearing staged tumors using an every 2 days×5 schedule.

2. A2780Tax Human Ovarian Carcinoma Xenograft (Mutated Tubulin).

A2780Tax is a paclitaxel-resistant human ovarian carcinoma model. It is derived from the sensitive parent A2780 line by co-incubation of cells with paclitaxel and verapamil, an MDR-reversal agent. Its resistance mechanism has been shown to be non-MDR related and is attributed to a mutation in the gene encoding the beta-tubulin protein. The compounds described herein can be administered to mice bearing staged tumors on an every 2 days×5 schedule.

3. HCT116/VM46 Human Colon Carcinoma Xenograft (Multi-Drug Resistant).

HCT116/VM46 is an MDR-resistant colon carcinoma developed from the sensitive HCT116 parent line. In vivo, grown in nude mice, HCT116/VM46 has consistently demonstrated high resistance to paclitaxel. The compounds described herein can be administered to mice bearing staged tumors on an every 2 days x 5 schedule.

4. M5076 Murine Sarcoma Model

M5076 is a mouse fibrosarcoma that is inherently refractory to paclitaxel in vivo. The compounds described herein can be administered to mice bearing staged tumors on an every 2 days x 5 schedule.

One or more compounds as disclosed herein can be used in combination other therapeutic agents in vivo in the multidrug resistant human colon carcinoma xenografts HCT/VM46 or any other model known in the art including those described herein.

Example 66

Microsome Stability Assay

The stability of one or more subject compounds is determined according to standard procedures known in the art. For example, stability of one or more subject compounds is established by an in vitro assay. For example, an in vitro microsome stability assay is established that measures stability of one or more subject compounds when reacting with mouse, rat or human microsomes from liver. The microsome reaction with compounds is performed in 1.5 mL Eppendorf tube. Each tube contains 0.1 µL of 10.0 mg/ml NADPH; 75 µL of 20.0 mg/ml mouse, rat or human liver microsome; 0.4 µL of 0.2 M phosphate buffer, and 425 µL of ddH$_2$O. Negative control (without NADPH) tube contains 75 µL of 20.0 mg/ml mouse, rat or human liver microsome; 0.4 µL of 0.2 M phosphate buffer, and 525 µL of ddH$_2$O. The reaction is started by adding 1.0 µL of 10.0 mM tested compound. The reaction tubes are incubated at 37° C. 100 µL sample is collected into new Eppendorf tube containing 300 µL cold methanol at 0, 5, 10, 15, 30 and 60 minutes of reaction. Samples are centrifuged at 15,000 rpm to remove protein. Supernatant of centrifuged sample is transferred to new tube. Concentration of stable compound after reaction with microsome in the supernatant is measured by Liquid Chromatography/Mass Spectrometry (LC-MS).

Example 67

Plasma Stability Assay

The stability of one or more subject compounds in plasma is determined according to standard procedures known in the art. See, e.g., *Rapid Commun. Mass Spectrom.*, 10: 1019-1026. The following procedure is an HPLC-MS/MS assay using human plasma; other species including monkey, dog, rat, and mouse are also available. Frozen, heparinized human plasma is thawed in a cold water bath and spun for 10 minutes at 2000 rpm at 4° C. prior to use. A subject compound is added from a 400 µM stock solution to an aliquot of pre-warmed plasma to give a final assay volume of 400 µL (or 800 µL for half-life determination), containing 5 µM test compound and 0.5% DMSO. Reactions are incubated, with shaking, for 0 minutes and 60 minutes at 37° C., or for 0, 15, 30, 45 and 60 minutes at 37 C for half life determination. Reactions are stopped by transferring 50 µL of the incubation mixture to 200 µL of ice-cold acetonitrile and mixed by shaking for 5 minutes. The samples are centrifuged at 6000×g for 15 minutes at 4° C. and 120 mL of supernatant removed into clean tubes. The samples are then evaporated to dryness and submitted for analysis by HPLC-MS/MS.

In one embodiment, one or more control or reference compounds (5 µM) are tested simultaneously with the test compounds: one compound, propoxycaine, with low plasma stability and another compound, propantheline, with intermediate plasma stability.

Samples are reconstituted in acetonitrile/methanol/water (1/1/2, v/v/v) and analyzed via (RP)HPLC-MS/MS using selected reaction monitoring (SRM). The HPLC conditions consist of a binary LC pump with autosampler, a mixed-mode, C12, 2×20 mm column, and a gradient program. Peak areas corresponding to the analytes are recorded by HPLC-MS/MS. The ratio of the parent compound remaining after 60 minutes relative to the amount remaining at time zero, expressed as percent, is reported as plasma stability. In case of half-life determination, the half-life is estimated from the slope of the initial linear range of the logarithmic curve of compound remaining (%) vs. time, assuming first order kinetics.

Example 68

Chemical Stability

The chemical stability of one or more subject compounds is determined according to standard procedures known in the art. The following details an exemplary procedure for ascertaining chemical stability of a subject compound. The default buffer used for the chemical stability assay is phosphate-buffered saline (PBS) at pH 7.4; other suitable buffers can be used. A subject compound is added from a 100 µM stock solution to an aliquot of PBS (in duplicate) to give a final assay volume of 400 µL, containing 5 µM test compound and 1% DMSO (for half-life determination a total sample volume of 700 µL is prepared). Reactions are incubated, with shaking, for 24 hours at 37° C.; for half-life determination samples are incubated for 0, 2, 4, 6, and 24 hours. Reactions are stopped by adding immediately 100 µL of the incubation mixture to 100 µL of acetonitrile and vortexing for 5 minutes. The samples are then stored at −20° C. until analysis by HPLC-MS/MS. Where desired, a control compound or a reference compound such as chlorambucil (5 µM) is tested simultaneously with a subject compound of interest, as this compound is largely hydrolyzed over the course of 24 hours. Samples are analyzed via (RP)HPLC-MS/MS using selected reaction monitoring (SRM). The HPLC conditions consist of a binary LC pump with autosampler, a mixed-mode, C12, 2×20 mm column, and a gradient program. Peak areas corresponding to the analytes are recorded by HPLC-MS/MS. The ratio of the parent compound remaining after 24 hours relative to the amount remaining at time zero, expressed as percent, is reported as chemical stability. In case of half-life determination, the half-life is estimated from the slope of the initial linear range of the logarithmic curve of compound remaining (%) vs. time, assuming first order kinetics.

Example 69

Akt Kinase Assay

Cells comprising components of the Akt/mTOR pathway, including but not limited to L6 myoblasts, B-ALL cells, B-cells, T-cells, leukemia cells, bone marrow cells, p190 transduced cells, phildadelphia chromosome positive cells (Ph+), and mouse embryonic fibroblasts, are typically grown in cell growth media such as DMEM supplemented with fetal bovine serum and/or antibiotics, and grown to confluency.

In order to compare the effect of one or more compounds disclosed herein on Akt activation, said cells are serum starved overnight and incubated with one or more compounds disclosed herein or about 0.1% DMSO for approximately 1 minute to about 1 hour prior to stimulation with insulin (e.g., 100 nM) for about 1 minute to about 1 hour. Cells are lysed by scraping into ice cold lysis buffer containing detergents such as sodium dodecyl sulfate and protease inhibitors (e.g., PMSF). After contacting cells with lysis buffer, the solution is briefly sonicated, cleared by centrifugation, resolved by SDS-PAGE, transferred to nitrocellulose or PVDF and immunoblotted using antibodies to phospho-Akt S473, phospho-Akt T308, Akt, and β-actin (Cell Signaling Technologies).

The results demonstrate that one or more compounds of the present disclosure inhibit insulin stimulated phosphorylation of Akt at S473. Alternatively, some compounds disclosed herein additionally inhibit insulin stimulated phosphorylation of Akt at T308. Such class of compounds can inhibit Akt more effectively than rapamycin and can be indicative of mTORC2 inhibitors or inhibitors of upstream kinases such as PI3K or Akt.

Example 70

Kinase Signaling in Blood

PI3K/Akt/mTor signaling is measured in blood cells using the phosflow method (*Methods Enzymol.* (2007) 434:131-54). This method is by nature a single cell assay so that cellular heterogeneity can be detected rather than population averages. This allows concurrent dinstinction of signaling states in different populations defined by other markers. Phosflow is also highly quantitative. To test the effects of one or more compounds disclosed herein, unfractionated splenocytes, or peripheral blood mononuclear cells are stimulated with anti-CD3 to initiate T-cell receptor signaling. The cells are then fixed and stained for surface markers and intracellular phosphoproteins Inhibitors disclosed herein inhibit anti-CD3 mediated phosphorylation of Akt-S473 and S6, whereas rapamycin inhibits S6 phosphorylation and enhances Akt phosphorylation under the conditions tested.

Similarly, aliquots of whole blood are incubated for 15 minutes with vehicle (e.g., 0.1% DMSO) or kinase inhibitors at various concentrations, before addition of stimuli to crosslink the T cell receptor (TCR) (anti-CD3 with secondary antibody) or the B cell receptor (BCR) using anti-kappa light chain antibody (Fab'2 fragments). After approximately 5 and 15 minutes, samples are fixed (e.g., with cold 4% paraformaldehyde) and used for phosflow. Surface staining is used to distinguish T and B cells using antibodies directed to cell surface markers that are known to the art. The level of phosphorylation of kinase substrates such as Akt and S6 are then measured by incubating the fixed cells with labeled antibodies specific to the phosphorylated isoforms of these proteins. The population of cells are then analyzed by flow cytometry.

Example 71

Colony Formation Assay

Murine bone marrow cells freshly transformed with a p190 BCR-Abl retrovirus (herein referred to as p190 transduced cells) are plated in the presence of various drug combinations in M3630 methylcellulose media for about 7 days with recombinant human IL-7 in about 30% serum, and the number of colonies formed is counted by visual examination under a microscope.

Alternatively, human peripheral blood mononuclear cells are obtained from Philadelphia chromosome positive (Ph+) and negative (Ph−) patients upon initial diagnosis or relapse. Live cells are isolated and enriched for CD19+CD34+B cell progenitors. After overnight liquid culture, cells are plated in methocult GF+H4435, Stem Cell Technologies) supplemented with cytokines (IL-3, IL-6, IL-7, G-CSF, GM-CSF, CF, Flt3 ligand, and erythropoietin) and various concentrations of known chemotherapeutic agents in combination with either compounds of the present disclosure. Colonies are counted by microscopy 12-14 days later. This method can be used to test for evidence of additive or synergistic activity.

Example 72

In Vivo Effect of Kinase Inhibitors on Leukemic Cells

Female recipient mice are lethally irradiated from a γ source in two doses about 4 hr apart, with approximately 5Gy each. About 1 hr after the second radiation dose, mice are injected i.v. with about $1 \times 10^6$ leukemic cells (e.g., Ph+ human or murine cells, or p190 transduced bone marrow cells). These cells are administered together with a radioprotective dose of about $5 \times 10^6$ normal bone marrow cells from 3-5 week old donor mice. Recipients are given antibiotics in the water and monitored daily. Mice who become sick after about 14 days are euthanized and lymphoid organs are harvested for analysis. Kinase inhibitor treatment begins about 10 days after leukemic cell injection and continues daily until the mice become sick or a maximum of approximately 35 days post-transplant Inhibitors are given by oral lavage.

Peripheral blood cells are collected approximately on day 10 (pre-treatment) and upon euthanization (post treatment), contacted with labeled anti-hCD4 antibodies and counted by flow cytometry. This method can be used to demonstrate that the synergistic effect of one or more compounds disclosed herein in combination with known chemotherapeutic agents can reduce leukemic blood cell counts as compared to treatment with known chemotherapeutic agents (e.g., Gleevec) alone under the conditions tested.

Example 73

Treatment of Lupus Disease Model Mice

Mice lacking the inhibitory receptor FcγRIIb that opposes PI3K signaling in B cells develop lupus with high penetrance. FcγRIIb knockout mice (R2KO, Jackson Labs) are considered a valid model of the human disease as some lupus patients show decreased expression or function of FcγRIIb (S. Bolland and J. V. Ravtech 2000. *Immunity* 12:277-285).

The R2KO mice develop lupus-like disease with antinuclear antibodies, glomerulonephritis and proteinurea within about 4-6 months of age. For these experiments, the rapamycin analogue RAD001 (available from LC Laboratories) is used as a benchmark compound, and administered orally. This compound has been shown to ameliorate lupus symptoms in the B6.Sle1z.Sle3z model (T. Wu et al. *J. Clin Invest.* 117:2186-2196).

Lupus disease model mice such as R2KO, BXSB or MLR/lpr are treated at about 2 months old, approximately for about two months. Mice are given doses of: vehicle, RAD001 at about 10 mg/kg, or compounds disclosed herein at approximately 1 mg/kg to about 500 mg/kg. Blood and urine samples are obtained at approximately throughout the testing period, and tested for antinuclear antibodies (in dilutions of serum) or protein concentration (in urine). Serum is also tested for anti-ssDNA and anti-dsDNA antibodies by ELISA. Animals are euthanized at day 60 and tissues harvested for measuring spleen weight and kidney disease. Glomerulonephritis is assessed in kidney sections stained with H&E. Other animals are studied for about two months after cessation of treatment, using the same endpoints.

This established art model can be employed to demonstrate that the kinase inhibitors disclosed herein can suppress or delay the onset of lupus symptoms in lupus disease model mice.

Example 74

Murine Bone Marrow Transplant Assay

Female recipient mice are lethally irradiated from a γ ray source. About 1 hr after the radiation dose, mice are injected with about $1 \times 106$ leukemic cells from early passage p190 transduced cultures (e.g., as described in *Cancer Genet Cytogenet.* 2005 August; 161(1):51-6). These cells are administered together with a radioprotective dose of approximately $5 \times 10^6$ normal bone marrow cells from 3-5 wk old donor mice. Recipients are given antibiotics in the water and monitored daily. Mice who become sick after about 14 days are euthanized and lymphoid organs harvested for flow cytometry and/or magnetic enrichment. Treatment begins on approximately day 10 and continues daily until mice become sick, or after a maximum of about 35 days post-transplant. Drugs are given by oral gavage (p.o.). In a pilot experiment a dose of chemotherapeutic that is not curative but delays leukemia onset by about one week or less is identified; controls are vehicle-treated or treated with chemotherapeutic agent, previously shown to delay but not cure leukemogenesis in this model (e.g., imatinib at about 70 mg/kg twice daily). For the first phase p190 cells that express eGFP are used, and postmortem analysis is limited to enumeration of the percentage of leukemic cells in bone marrow, spleen and lymph node (LN) by flow cytometry. In the second phase, p190 cells that express a tailless form of human CD4 are used and the postmortem analysis includes magnetic sorting of hCD4+ cells from spleen followed by immunoblot analysis of key signaling endpoints: p Akt-T308 and 5473; pS6 and p4EBP-1. As controls for immunoblot detection, sorted cells are incubated in the presence or absence of kinase inhibitors of the present disclosure inhibitors before lysis. Optionally, "phosflow" is used to detect p Akt-S473 and pS6-S235/236 in hCD4-gated cells without prior sorting. These signaling studies are particularly useful if, for example, drug-treated mice have not developed clinical leukemia at the 35 day time point. Kaplan-Meier plots of survival are generated and statistical analysis done according to methods known in the art. Results from p190 cells are analyzed separated as well as cumulatively.

Samples of peripheral blood (100-200 µl) are obtained weekly from all mice, starting on day 10 immediately prior to commencing treatment. Plasma is used for measuring drug concentrations, and cells are analyzed for leukemia markers (eGFP or hCD4) and signaling biomarkers as described herein.

This general assay known in the art can be used to demonstrate that effective therapeutic doses of the compounds disclosed herein can be used for inhibiting the proliferation of leukemic cells.

Example 75

Cell Culture of Epithelial Cells of Ocular Origin

Ocular epithelial cells are obtained within 5 days post-mortem post-mortem from corneas preserved under cold storage conditions in Optisol (Bausch and Lomb, Irvine, Calif.) or from corneal biopsy from living donors. The tissue is washed with phosphate-buffered saline and incubated in Dispase II (Roche Diagnostics, Basel, Switzerland) at 37° C. for 30 minutes, and the epithelial surface is gently scraped to separate the epithelium from the underlying stroma. The separated epithelium is then incubated and pipetted in trypsin-ethylenediaminetetraacetic acid to obtain a single cell suspension. The trypsin is then neutralized with corneal epithelium culture medium. Corneal epithelium culture medium is composed of Dulbecco modified Eagle medium: F12 basal media in a 2:1 ratio containing 10% irradiated fetal bovine serum, hydrocortisone 0.4 µg/mL, cholera toxin 0.1 nmol, recombinant human insulin 5 µg/mL, and epidermal growth factor 10 ng/mL, and the antimicrobials penicillin (100 IU/mL), streptomycin (100 µg/mL), and amphotericin B (0.25 µg/mL). Cells are maintained by sub-culturing at a 1:4 ratio after reaching 80% confluency. Ocular epithelial cells are screened for inhibition of proliferation or toxicity by contacting a test compound with the cells and assaying for viability using the commercially available MTT assay (Promega).

Example 76

Cell Culture of Endothelial Cells of Ocular Origin

All tissues are maintained at 4° C. in storage medium (Optisol; Chiron Vision, Irvine, Calif.) for less than 10 days before study. The tissue is rinsed three times with DMEM containing 50 mg/mL gentamicin and 1.25 mg/mL amphotericin B. The central cornea is removed by a trephine of 8-mm diameter. Afterward, the Descemet's membrane and corneal endothelial cells are stripped from the posterior surface of the peripheral corneoscleral tissue under a dissecting microscope and digested at 37° C. for 1.5 to 16 hours with 2 mg/mL collagenase A in supplemented hormonal epithelial medium (SHEM), which is made of an equal volume of HEPES-buffered DMEM and Ham's F12 supplemented with 5% FBS, 0.5% dimethyl sulfoxide, 2 ng/mL mouse EGF, 5 µg/mL insulin, 5 µg/mL transferrin, 5 ng/mL selenium, 0.5 µg/mL hydrocortisone, 1 nM cholera toxin, 50 µg/mL gentamicin, and 1.25 µg/mL amphotericin B. After digestion, HCECs formed aggregates, which are collected by centrifugation at 2000 rpm for 3 minutes to remove the digestion solution. As a control, Descemet's membrane strips are also digested in 10 mg/mL Dispase II in SHEM and trypsin/EDTA for up to 3 hours.

Preservation of Isolated HCEC Aggregates: The resultant aggregates of HCECs are preserved in KSFM with complete supplement (storage medium 1), DMEM/F12 with KSFM supplements (storage medium 2), or DMEM/F12 with SHEM supplements without FBS (storage medium 3). All these media are serum free, one of the major differences among them is the calcium concentration, which is 0.09 mM in storage medium 1, but is 1.05 mM in storage media 2 and 3. HCEC aggregates are stored in a tissue culture incubator at 37° C. for up to 3 weeks. Cell viability is determined (Live and Dead assay; Invitrogen) and also evaluated by subculturing them in SHEM.

Preservation of Isolated HCEC Aggregates: The resultant HCEC aggregates, either immediately after digestion or after a period of preservation in a storage medium, are then cultured in SHEM with or without additional growth factors such as 40 ng/mL bFGF, 0.1 mg/mL BPE, and 20 ng/mL NGF on a plastic dish under 37° C. and 5% $CO_2$. The media are changed every 2 to 3 days. Some HCEC aggregates are pretreated with trypsin/EDTA at 37° C. for 10 minutes to dissociate endothelial cells before the aforementioned cultivation.

Immunostaining: HCEC aggregates are embedded in OCT and subjected to frozen sectioning Cryosections of 4 µm are air-dried at room temperature (RT) for 30 minutes, and fixed in cold acetone for 10 minutes at −20° C. Sections used for immunostaining are rehydrated in PBS, and incubated in 0.2% Triton X-100 for 10 minutes. After three rinses with PBS for 5 minutes each and preincubation with 2% BSA to block nonspecific staining, the sections are incubated with anti-laminin 5, type IV collagen, perlecan, ZO-1, and connexin 43 (all at 1:100) antibodies for 1 hour. After three washes with PBS for 15 minutes, the sections are incubated with a FITC-conjugated secondary antibody (goat anti-rabbit or anti-mouse IgG at 1:100) for 45 minutes. After three additional PBS washes, each for 10 minutes, they are counterstained with propidium iodide (1:1000) or Hoechst 33342 (10 µg/mL), then mounted with an antifade solution and analyzed with a fluorescence microscope. HCECs cultured in 24-well plates or chamber slides are fixed in 4% paraformaldehyde for 15 minutes at RT and stained with anti-ZO-1 and connexin 43 antibodies as just described. For immunohistochemical staining of Ki67, endogenous peroxidase activity is blocked by 0.6% hydrogen peroxide for 10 minutes. Nonspecific staining is blocked by 1% normal goat serum for 30 minutes. Cells are then incubated with anti-Ki67 antibody (1:100) for 1 hour. After three washes with PBS for 15 minutes, cells are incubated with biotinylated rabbit anti-mouse IgG (1:100) for 30 minutes, followed by incubation with ABC reagent for 30 minutes. The reaction product is developed with DAB for 5 minutes and examined by light microscope.

Cell-Viability and TUNEL Assays: Cell-viability and terminal deoxyribonucleotidyl transferase-mediated FITC-linked dUTP nick-end DNA labeling (TUNEL) assays are used to determine living and apoptotic cells, respectively. HCEC aggregates are incubated with cell-viability assay reagents for 15 minutes at RT. Live cells are distinguished by green fluorescence staining of the cell cytoplasm, and dead cells are stained with red fluorescence in the nuclei. The TUNEL assay is performed according to the manufacturer's instructions. Briefly, cross-sections of HCEC aggregates are fixed in 4% paraformaldehyde for 20 minutes at RT and permeabilized with 1% Triton X-100. Samples are then incubated for 60 minutes at 37° C. with exogenous TdT and fluorescein-conjugated dUTP, for repair of nicked 3'-hydroxyl DNA ends. Cells are treated with DNase I as the positive control, whereas negative control cells are incubated with a buffer lacking the rTdT enzyme. The apoptotic nuclei are labeled with green fluorescence.

Example 77

Cell Culture of Retinal Cells

Eyes are cut in half along their equator and the neural retina is dissected from the anterior part of the eye in buffered saline solution, according to standard methods known in the art. Briefly, the retina, ciliary body, and vitreous are dissected away from the anterior half of the eye in one piece, and the retina is gently detached from the clear vitreous. Each retina is dissociated with papain (Worthington Biochemical Corporation, Lakewood, N.J.), followed by inactivation with fetal bovine serum (FBS) and addition of 134 Kunitz units/ml of DNaseI. The enzymatically dissociated cells are triturated and collected by centrifugation, resuspended in Dulbecco's modified Eagle's medium (DMEM)/F12 medium (Gibco BRL, Invitrogen Life Technologies, Carlsbad, Calif.) containing 25 µg/ml of insulin, 100 µg/ml of transferrin, 60 µM putrescine, 30 nM selenium, 20 nM progesterone, 100 U/ml of penicillin, 100 µg/ml of streptomycin, 0.05 M Hepes, and 10% FBS. Dissociated primary retina 1 cells are plated onto Poly-D-lysine- and Matrigel- (BD, Franklin Lakes, N.J.) coated glass coverslips that are placed in 24-well tissue culture plates (Falcon Tissue Culture Plates, Fisher Scientific, Pittsburgh, Pa.). Cells are maintained in culture for 5 days to one month in 0.5 ml of media (as above, except with only 1% FBS) at 37° C. and 5% $CO_2$.

Immunocytochemistry Analysis: The retinal neuronal cells are cultured for 1, 3, 6, and 8 weeks in the presence and absence of test compounds as disclosed herein, and the cells are analyzed by immunohistochemistry at each time point. Immunocytochemistry analysis is performed according to standard techniques known in the art. Rod photoreceptors are identified by labeling with a rhodopsin-specific antibody (mouse monoclonal, diluted 1:500; Chemicon, Temecula, Calif.). An antibody to mid-weight neurofilament (NFM rabbit polyclonal, diluted 1:10,000, Chemicon) is used to identify ganglion cells; an antibody to β3-tubulin (G7121 mouse monoclonal, diluted 1:1000, Promega, Madison, Wis.) is used to generally identify interneurons and ganglion cells, and antibodies to calbindin (AB1778 rabbit polyclonal, diluted 1:250, Chemicon) and calretinin (AB5054 rabbit polyclonal, diluted 1:5000, Chemicon) are used to identify subpopulations of calbindin- and calretinin-expressing interneurons in the inner nuclear layer. Briefly, the retina 1 cell cultures are fixed with 4% paraformaldehyde (Polysciences, Inc, Warrington, Pa.) and/or ethanol, rinsed in Dulbecco's phosphate buffered saline (DPBS), and incubated with primary antibody for 1 hour at 37° C. The cells are then rinsed with DPBS, incubated with a secondary antibody (Alexa 488- or Alexa 568-conjugated secondary antibodies (Molecular Probes, Eugene, Oreg.)), and rinsed with DPBS. Nuclei are stained with 4',6-diamidino-2-phenylindole (DAPI, Molecular Probes), and the cultures are rinsed with DPBS before removing the glass coverslips and mounting them with Fluoromount-G (Southern Biotech, Birmingham, Ala.) on glass slides for viewing and analysis.

Example 78

Matrigel Plug Angiogenesis Assay

Matrigel containing test compounds are injected subcutaneously or intraocularly, where it solidifies to form a plug. The plug is recovered after 7-21 days in the animal and examined histologically to determine the extent to which blood vessels have entered it. Angiogenesis is measured by quantification of the vessels in histologic sections. Alternatively, fluorescence measurement of plasma volume is performed using fluorescein isothiocyanate (FITC)-labeled dextran 150. The results are expected to indicate one or more compounds disclosed herein that inhibit angiogenesis and are thus expected to be useful in treating ocular disorders related to aberrant angiogenesis and/or vascular permeability.

Example 79

Corneal Angiogenesis Assay

A pocket is made in the cornea, and a plug containing an angiogenesis inducing formulation (e.g., VEGF, FGF, or tumor cells), when introduced into this pocket, elicits the ingrowth of new vessels from the peripheral limbal vasculature. Slow-release materials such as ELVAX (ethylene vinyl copolymer) or Hydron are used to introduce angiogenesis inducing substances into the corneal pocket. Alternatively, a sponge material is used.

The effect of putative inhibitors on the locally induced (e.g., sponge implant) angiogenic reaction in the cornea (e.g., by FGF, VEGF, or tumor cells). The test compound is administered orally, systemically, or directly to the eye. Systemic administration is by bolus injection or, more effectively, by use of a sustained-release method such as implantation of osmotic pumps loaded with the test inhibitor. Administration to the eye is by any of the methods described herein including but not limited to eye drops, topical administration of a cream, emulsion, or gel, intravitreal injection.

The vascular response is monitored by direct observation throughout the course of the experiment using a stereomicroscope in mice. Definitive visualization of the corneal vasculature is achieved by administration of fluorochrome-labeled high-molecular weight dextran. Quantification is performed by measuring the area of vessel penetration, the progress of vessels toward the angiogenic stimulus over time, or in the case of fluorescence, histogram analysis or pixel counts above a specific (background) threshold.

The results can indicate one or more compounds disclosed herein inhibit angiogenesis and thus can be useful in treating ocular disorders related to aberrant angiogenesis and/or vascular permeability.

Example 80

Microtiter-Plate Angiogenesis Assay

The assay plate is prepared by placing a collagen plug in the bottom of each well with 5-10 cell spheroids per collagen plug each spheroid containing 400-500 cells. Each collagen plug is covered with 1100 µl of storage medium per well and stored for future use (1-3 days at 37° C., 5% $CO_2$). The plate is sealed with sealing. Test compounds are dissolved in 200 µl assay medium with at least one well including a VEGF positive control and at least one well without VEGF or test compound as a negative control. The assay plate is removed from the incubator and storage medium is carefully pipetted away. Assay medium containing the test compounds are pipetted onto the collagen plug. The plug is placed in a humidified incubator for (37° C., 5% $CO_2$) 24-48 hours. Angiogenesis is quantified by counting the number of sprouts, measuring average sprout length, or determining cumulative sprout length. The assay can be preserved for later analysis by removing the assay medium, adding 1 ml of 10% paraformaldehyde in Hanks BSS per well, and storing at 4° C. The results are expected to identify compounds that inhibit angiogenesis in various cell types tested, including cells of ocular origin.

Example 81

Combination Use of P1310 Inhibitors and Agents that Inhibit IgE Production or Activity The compounds as disclosed herein can present synergistic or additive efficacy when administered in combination with agents that inhibit IgE production or activity. Agents that inhibit IgE production include, for example, one or more of TEI-9874, 2-(4-(6-cyclohexyloxy-2-naphtyloxy) phenylacetamide)benzoic acid, rapamycin, rapamycin analogs (i.e., rapalogs), TORC1 inhibitors, TORC2 inhibitors, and any other compounds that inhibit mTORC1 and mTORC2. Agents that inhibit IgE activity include, for example, anti-IgE antibodies such as Omalizumab and TNX-901.

One or more of the subject compounds capable of inhibiting PI3Kδ can be efficacious in treatment of autoimmune and inflammatory disorders (AIID), for example, rheumatoid arthritis. If any of the compounds causes an undesired level of IgE production, one can choose to administer it in combination with an agent that inhibits IgE production or IgE activity. Additionally, the administration of PI3Kδ or PI3Kδ/γ inhibitors as disclosed herein in combination with inhibitors of mTOR can also exhibit synergy through enhanced inhibition of the PI3K pathway. Various in vivo and in vitro models can be used to establish the effect of such combination treatment on AIID including but not limited to (a) in vitro B-cell antibody production assay, (b) in vivo TNP assay, and (c) rodent collagen induced arthritis model.

(a) B-Cell Assay

Mice are euthanized, and the spleens are removed and dispersed through a nylon mesh to generate a single-cell suspension. The splenocytes are washed (following removal of erythrocytes by osmotic shock) and incubated with anti-CD43 and anti-Mac-1 antibody-conjugated microbeads (Miltenyi Biotec). The bead-bound cells are separated from unbound cells using a magnetic cell sorter. The magnetized column retains the unwanted cells and the resting B cells are collected in the flow-through. Purified B-cells are stimulated with lipopolysaccharide or an anti-CD40 antibody and interleukin 4 Stimulated B-cells are treated with vehicle alone or with PI3Kδ inhibitors as disclosed herein with and without mTOR inhibitors such as rapamycin, rapalogs, or mTORC1/C2 inhibitors. The results are expected to show that in the presence of mTOR inhibitors (e.g., rapamycin) alone, there is little to no substantial effect on IgG and IgE response. However, in the presence of PI3Kδ and mTOR inhibitors, the B-cells are expected to exhibit a decreased IgG response as compared to the B-cells treated with vehicle alone, and the B-cells are expected to exhibit a decreased IgE response as compared to the response from B-cells treated with PI3Kδ inhibitors alone.

(b) TNP Assay

Mice are immunized with TNP-Ficoll or TNP-KHL and treated with: vehicle, a PI3Kδ inhibitor, an mTOR inhibitor, for example rapamycin, or a PI3Kδ inhibitor in combination with an mTOR inhibitor such as rapamycin. Antigen-specific serum IgE is measured by ELISA using TNP-BSA coated plates and isotype specific labeled antibodies. It is expected that mice treated with an mTOR inhibitor alone exhibit little or no substantial effect on antigen specific IgG3 response and no statistically significant elevation in IgE response as compared to the vehicle control. It is also expected that mice treated with both PI3Kδ inhibitor and mTOR inhibitor exhibit a reduction in antigen specific IgG3 response as compared to the mice treated with vehicle alone. Additionally, the mice treated with both PI3Kδ inhibitor and mTOR inhibitor exhibit a decrease in IgE response as compared to the mice treated with PI3Kδ inhibitor alone.

(c) Rat Collagen Induced Arthritis Model

Female Lewis rats are anesthetized and given collagen injections prepared and administered as described previously on day 0. On day 6, animals are anesthetized and given a second collagen injection. Caliper measurements of normal (pre-disease) right and left ankle joints are performed on day 9. On days 10-11, arthritis typically occurs and rats are randomized into treatment groups. Randomization is performed after ankle joint swelling is obviously established and there is good evidence of bilateral disease.

After an animal is selected for enrollment in the study, treatment is initiated. Animals are given vehicle, PI3Kδ inhibitor, or PI3Kδ inhibitor in combination with rapamycin. Dosing is administered on days 1-6. Rats are weighed on days 1-7 following establishment of arthritis and caliper measurements of ankles taken every day. Final body weights are taken on day 7 and animals are euthanized.

The combination treatment using a compound as disclosed herein and rapamycin can provide greater efficacy than treatment with PI3Kδ inhibitor alone.

Example 82

Delayed Type Hypersensitivity Model

DTH was induced by sensitizing 60 BALB/c male mice on day 0 and day 1 with a solution of 0.05% 2,4 dinitrofluorobenzene (DNFB) in a 4:1 acetone/olive oil mixture. Mice were gently restrained while 20 µL of solution was applied to the hind foot pads of each mouse. The hind foot pads of the mice were used as they represent an anatomical site that can be easily isolated and immobilized without anesthesia. On day 5, mice were administered a single dose of vehicle, IPI-145 at 10, 3, 1, or 0.3 mg/kg, or dexamethasone at a dose of 5 mg/kg by oral gavage. Thirty minutes later mice were anaesthetized, and a solution of 0.25% DNFB in a 4:1 acetone/olive oil solution was applied to the left inner and outer ear surface. This application resulted in the induction of swelling to the left ear and under these conditions, all animals responded to this treatment with ear swelling. A vehicle control solution of 4:1 acetone/olive oil was applied to the right inner and outer ear. Twenty four hours later, mice were anaesthetized, and measurements of the left and right ear were taken using a digital micrometer.

The difference between the two ears was recorded as the amount of swelling induced by the challenge of DNFB. Drug treatment groups were compared to vehicle control to generate the percent reduction in ear swelling. Dexamethasone is routinely used as a positive control as it has broad anti-inflammatory activity.

Example 83

Peptidoglycan-Polysaccharide Rat Arthritic Model (a) Systemic Arthritis Model

All injections are performed under anesthesia. 60 female Lewis rats (150-170) are anesthetized by inhalation isoflurane using a small animal anesthesia machine. The animals are placed in the induction chamber until anesthetized by delivery of 4-5% isoflurane in $O_2$ and then held in that state using a nose cone on the procedure table. Maintenance level of isoflurane is at 1-2%. Animals are injected intraperitoneally (i.p.) with a single injection of purified PG-PS 10S Group A, D58 strain (concentration 25 ug/g of bodyweight) suspended in sterile 0.85% saline. Each animal receives a total volume of 500 microliters administered in the lower left quadrant of the abdomen using a 1 milliliter syringe with a 23 gauge needle. Placement of the needle is critical to avoid injecting the PG-PS 10S into either the stomach or caecum. Animals are under continuous observation until fully recovered from anesthesia and moving about the cage. An acute response of a sharp increase in ankle measurement, typically 20% above baseline measurement can peak in 3-5 days post injection. Treatment with test compounds can be PO, SC, IV or IP. Rats are dosed no more than two times in a 24 hour time span. Treatment can begin on day 0 or any day after that through day 30. The animals are weighed on days 0, 1, 2, 3, 4, 5, 6, 7 and beginning again on day 12-30 or until the study is terminated. Paw/ankle diameter is measured with a digital caliper on the left and right side on day 0 prior to injection and again on day 1, 2, 3, 4, 5, 6 and 7. On day 12, measurements begin again and continue on through day 30. At this time, animals can be anesthetized with isoflurane, as described above, and terminal blood samples can be obtained by tail vein draws for the evaluation of the compound blood levels, clinical chemistry or hematology parameters. Animals are them euthanized with carbon dioxide overdose. A thoracotomy can be conducted as a means of death verification.

(b) Monoarticular Arthritis Model

All injections are performed under anesthesia. 60 female Lewis rats (150-170) are anesthetized by inhalation isoflurane using a small animal anesthesia machine. The animals are placed in the induction chamber until anesthetized by delivery of 4-5% isoflurane in $O_2$ and then held in that state using a nose cone on the procedure table. Maintenance level of isoflurane is at 1-2%. Animals are injected intra-articular (i.a.) with a single injection of purified PG-PS 100P Group A, D58 strain (concentration 500 ug/mL) suspended in sterile 0.85% saline. Each rat receives a total volume of 10 microliters administered into the tibiotalar joint space using a 1 milliliter syringe with a 27 gauge needle. Animals are under continuous observation until fully recovered from anesthesia and moving about the cage. Animals that respond 2-3 days later with a sharp increase in ankle measurement, typically 20% above baseline measurement on the initial i.a. injection, are included in the study. On day 14, all responders are anesthetized again using the procedure previously described. Animals receive an intravenous (I.V.) injection of PG-PS (concentration 250 uL/mL). Each rat receives a total volume of 400 microliters administered slowly into the lateral tail vein using a 1 milliliter syringe with a 27 gauge needle. Baseline ankle measurements are measured prior to IV injection and continue through the course of inflammation or out to day 10. Treatment with test compounds will be PO, SC, IV or IP. Rats are dosed no more than two times in a 24 hour time span. Treatment can begin on day 0 or any day after that through day 24. The animals are weighed on days 0, 1, 2, 3, 4, 5, and beginning again on day 14-24 or until the study is terminated. Paw/ankle diameter is measured with a digital caliper on the left and right side on day 0 prior to injection and again on day 1, 2, 3, 4, 5, and beginning again on day 14-24 or until the study is terminated. At this time, animals can be anesthetized with isoflurane, as described above, and terminal blood samples can be obtained by tail vein draws for the evaluation of the compound blood levels, clinical chemistry or hematology parameters. Animals are them euthanized with carbon dioxide overdose. A thoracotomy can be conducted as a means of death verification.

What is claimed is:

1. A method for inhibiting a phosphoinositide 3-kinase (PI3K) in a subject suffering from a disorder selected from a cancer, an inflammatory disease, and an auto-immune disease, comprising administering to the subject a therapeutically effective amount of a compound of formula (Ib):

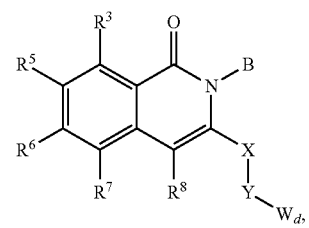

Formula (Ib)

or a pharmaceutically acceptable salt thereof, wherein B is hydrogen or a moiety of Formula II:

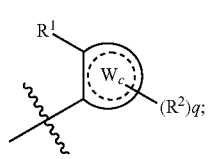

Formula II wherein $W_c$ is 6-membered aryl, or cycloalkyl;
q is an integer of 0, 1, 2, 3, or 4;
X is absent or —$(CH(R^9))_z$—;
Y is absent, —O—, —S—, —S(=O)—, —S(=O)$_2$—, —C(=O)—, —C(=O)(CHR$^9$)$_z$—, —N(R$^9$)—, —N(R$^9$)—C(=O)NH—, or —N(R$^9$)C(R$^9$)$_2$—;
z is an integer of 1, 2, 3, or 4;
$R^1$ is hydrogen, alkyl, alkenyl, alkynyl, alkoxy, amido, alkoxycarbonyl, sulfonamido, halo, cyano, or nitro;
each $R^2$ is independently alkyl, alkenyl, alkynyl, cycloalkyl, heterocycloalkyl, aryl, heteroaryl, arylalkyl, heteroarylalkyl, alkoxy, amido, amino, acyl, acyloxy, alkoxycarbonyl, sulfonamido, halo, cyano, hydroxy, nitro, phosphate, urea, or carbonate;

R³ is a 5-membered heteroaryl or a 6-membered heteroaryl, each of which comprises at least one ring nitrogen, and each of which is substituted with 0, 1, 2, or 3 R¹³;

R⁵, R⁶, R⁷, and R⁸ are independently hydrogen, halo, cyano, alkyl, or amino;

each R⁹ is independently hydrogen, alkyl, or heterocycloalkyl;

w_d is

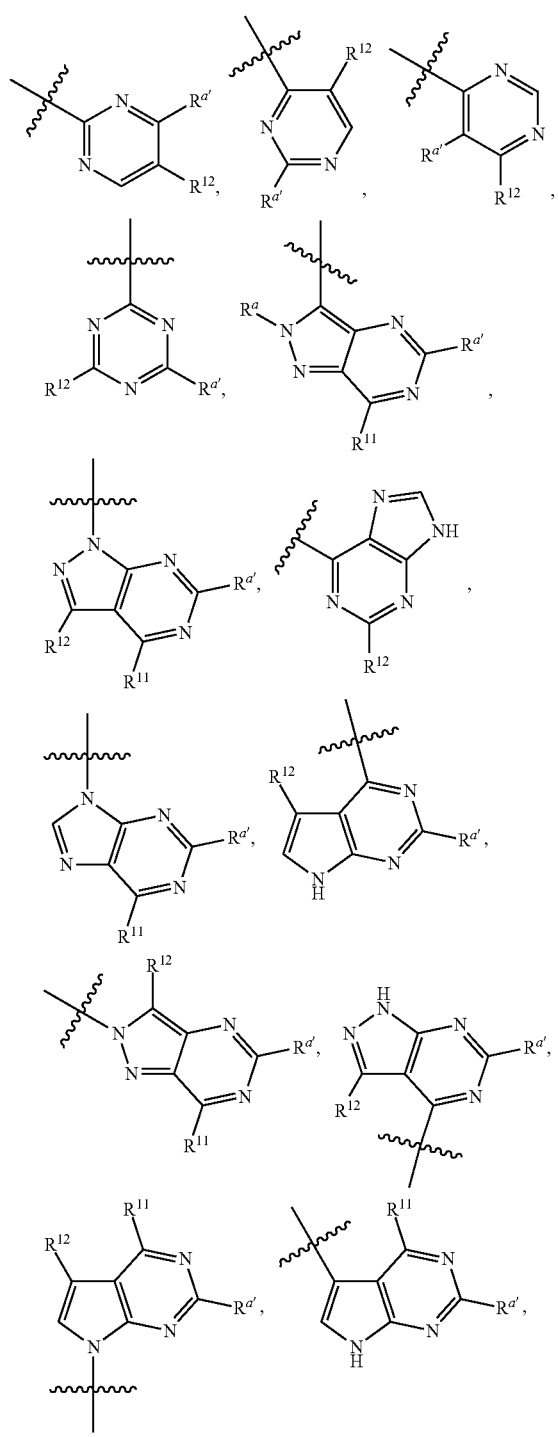

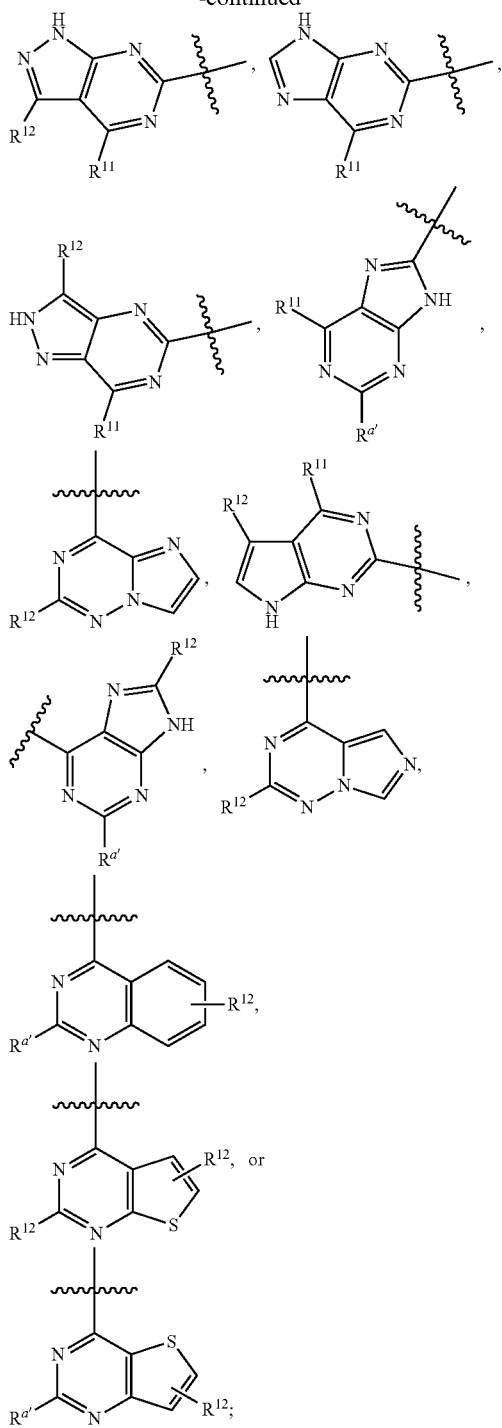

$R^{11}$ is hydrogen, alkyl, halo, amino, amido, hydroxy, alkoxy, phosphate, urea, or carbonate;

$R^{12}$ is hydrogen, alkyl, haloalkyl, alkynyl, alkenyl, halo, —C(O)NH₂, NH₂, cyano, aryl, heteroaryl, nonaromatic heterocyclyl, or cycloalkyl;

$R^a$ is methyl;

$R^{a'}$ is hydrogen, alkyl, —NH₂, cyano, or halogen; and each $R^{13}$ is independently hydrogen, C₁-C₆ alkyl, C₁-C₆ alkoxy, or halogen.

2. The method of claim 1, wherein $R^3$ is

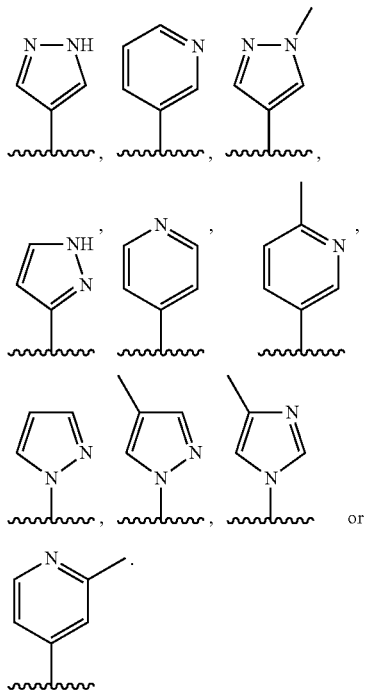

3. The method of claim 1, wherein B is:

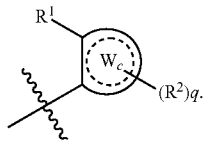

4. The method of claim 3, wherein q is 0 or 1.
5. The method of claim 4, wherein $R^1$ is hydrogen, alkyl, alkoxy, amido, halo, cyano, or nitro.
6. The method of claim 4, wherein q is 1 and $R^2$ is alkyl, cycloalkyl, aryl, heteroaryl, arylalkyl, heteroarylalkyl, alkoxy, amino, halo, cyano, hydroxy, or nitro.
7. The method of claim 1, wherein Y is —N($R^9$)—.
8. The method of claim 1, wherein X is —(CH($R^9$))$_z$—.
9. The method of claim 8, wherein z is 1.
10. The method of claim 8, wherein $R^9$ is hydrogen or alkyl.
11. The method of claim 1, wherein $W_d$ is

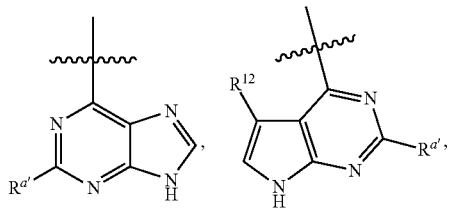

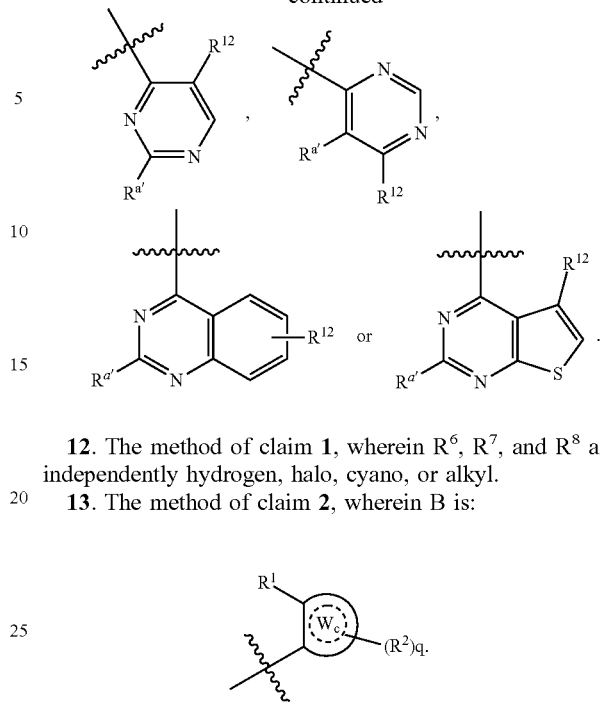

12. The method of claim 1, wherein $R^6$, $R^7$, and $R^8$ are independently hydrogen, halo, cyano, or alkyl.
13. The method of claim 2, wherein B is:

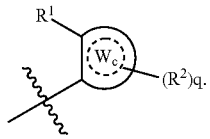

14. The method of claim 13, wherein q is 0 or 1.
15. The method of claim 14, wherein $R^1$ is hydrogen, alkyl, alkoxy, amido, halo, cyano, or nitro.
16. The method of claim 14, wherein q is 1 and $R^2$ is alkyl, cycloalkyl, aryl, heteroaryl, arylalkyl, heteroarylalkyl, alkoxy, amino, halo, cyano, hydroxy or nitro.
17. The method of claim 2, wherein Y is —N($R^9$)—.
18. The method of claim 2, wherein X is —(CH($R^9$))$_z$—.
19. The method of claim 18, wherein z is 1.
20. The method of claim 18, wherein $R^9$ is hydrogen or alkyl.
21. The method of claim 2, wherein $W_d$ is

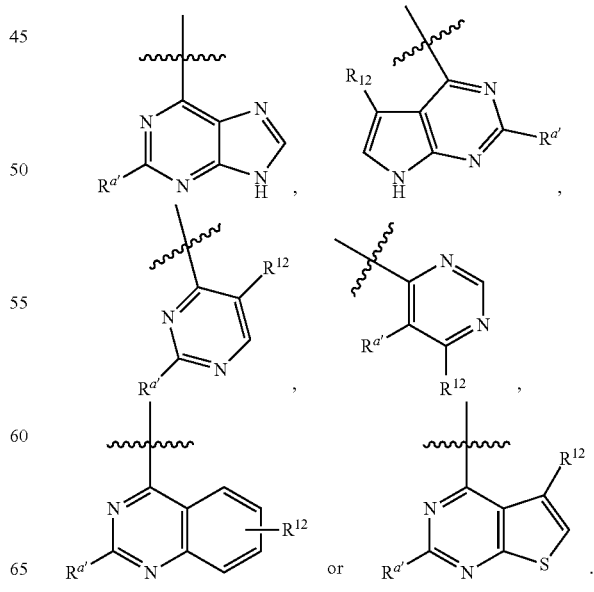

22. The method of claim 2, wherein wherein $R^6$, $R^7$, and $R^8$ are independently hydrogen, halo, cyano, or alkyl.
23. The method of claim 1, wherein the compound is:
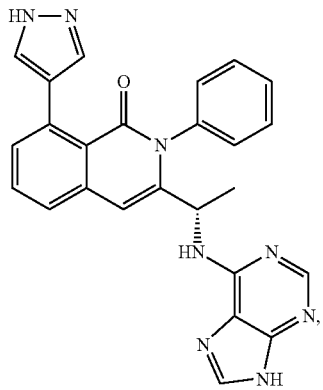
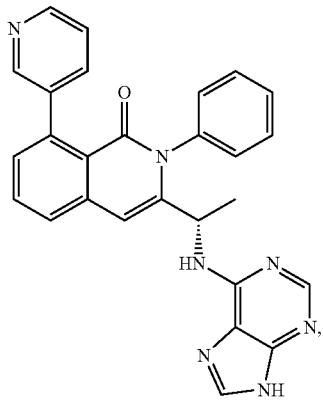
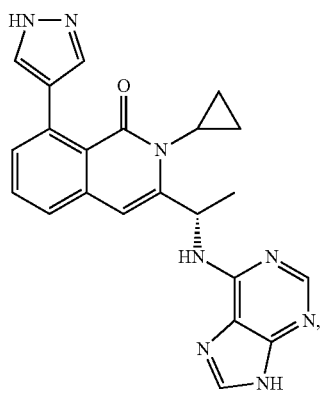
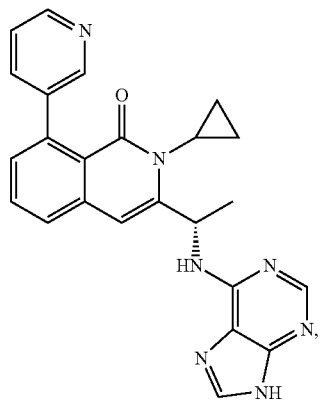
-continued
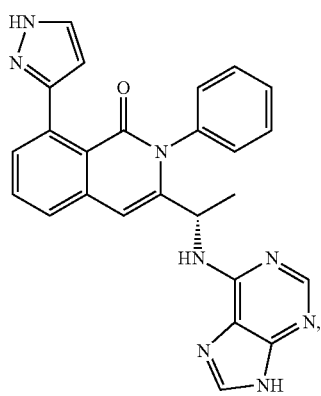
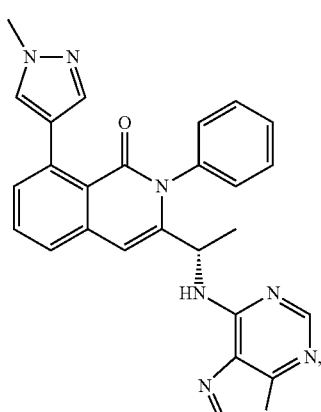
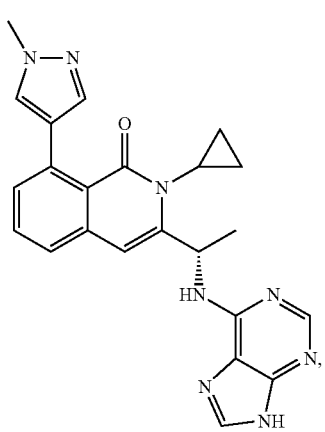
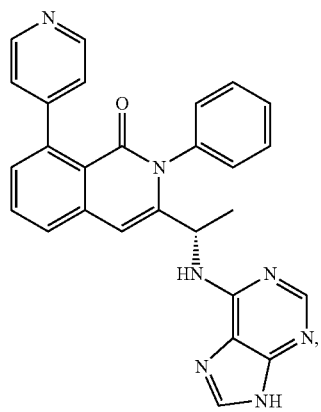

277
-continued
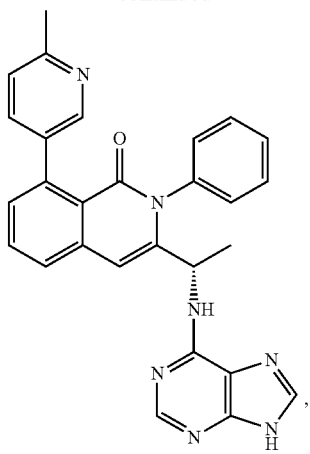
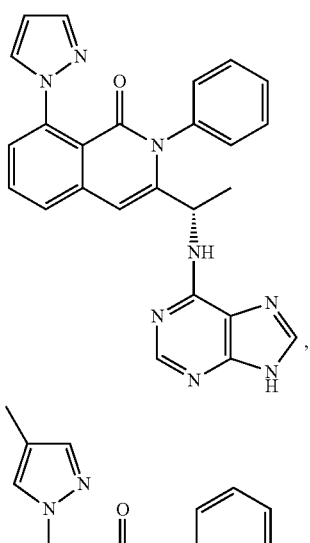
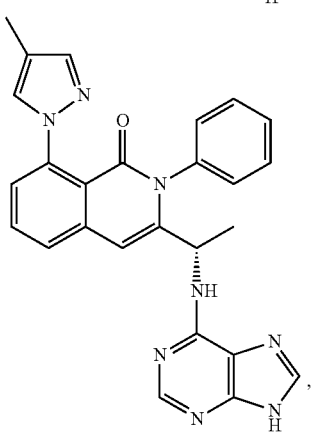
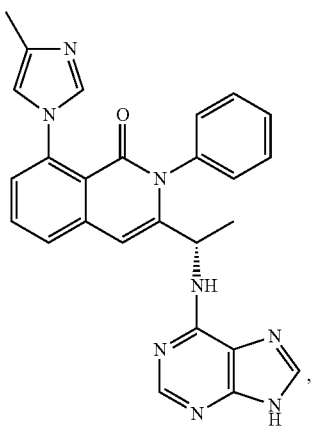
278
-continued
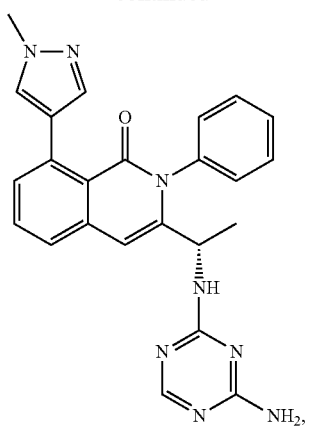 [SMILES: C[C@H](Nc1ncnc(N)n1)c1cc2cccc(-c3cnn(C)c3)c2c(=O)n1-c1ccccc1]
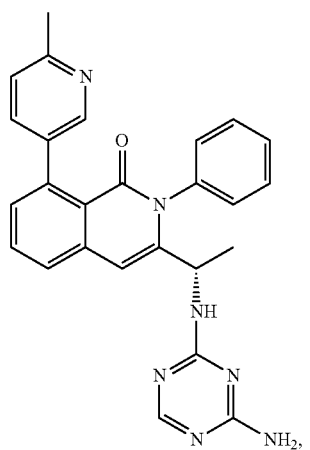
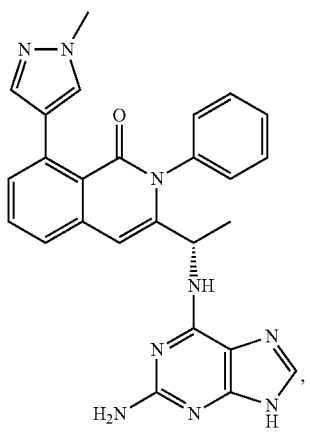

279
-continued
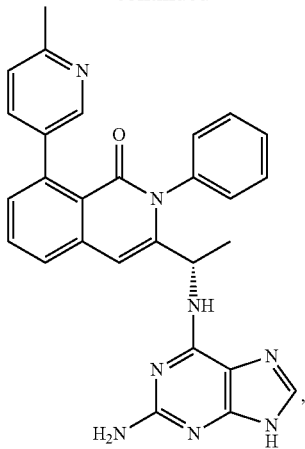
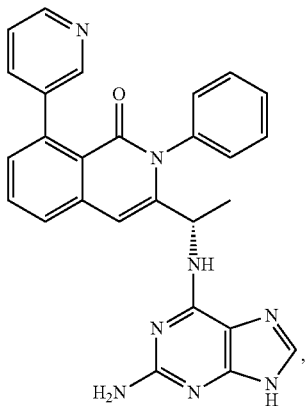
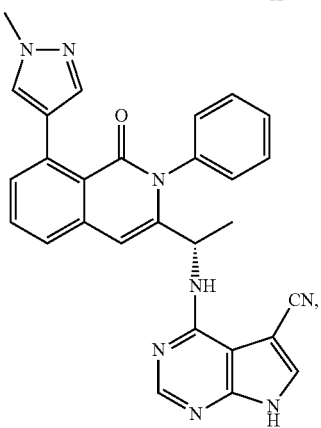
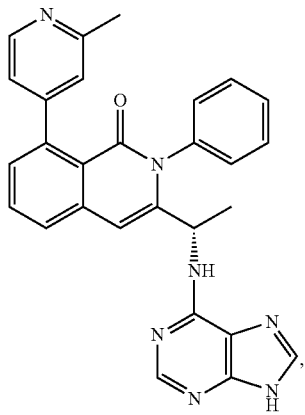
280
-continued
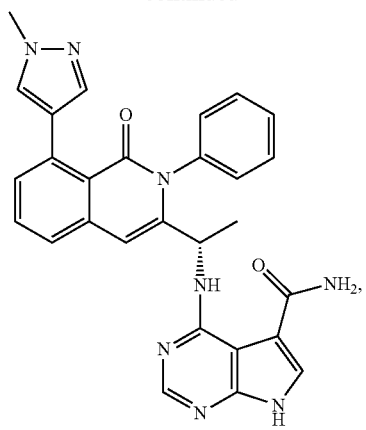
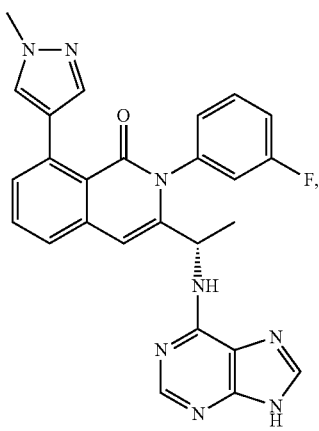
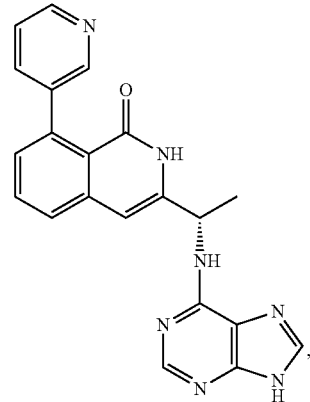
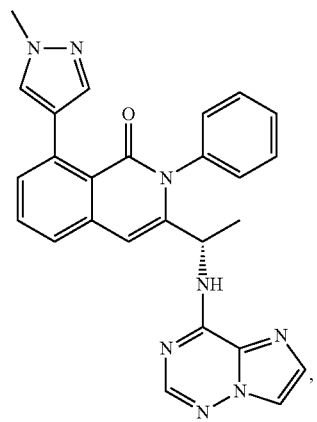

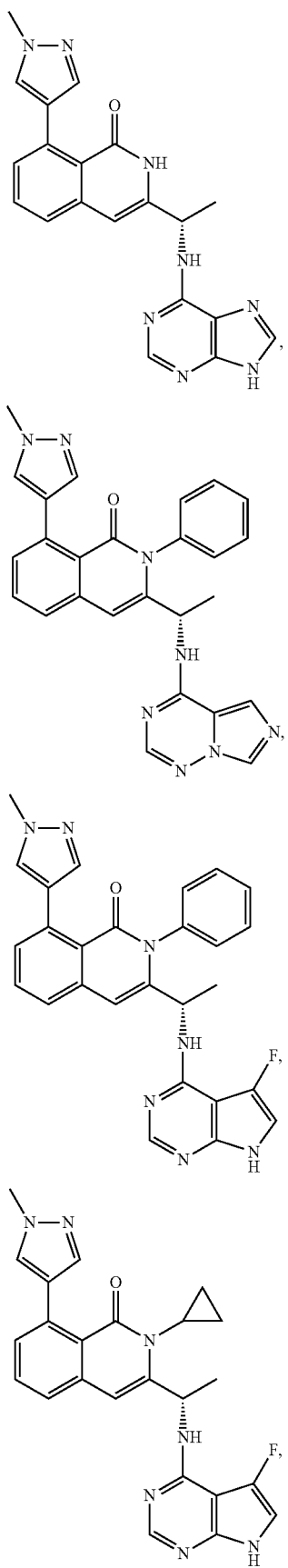
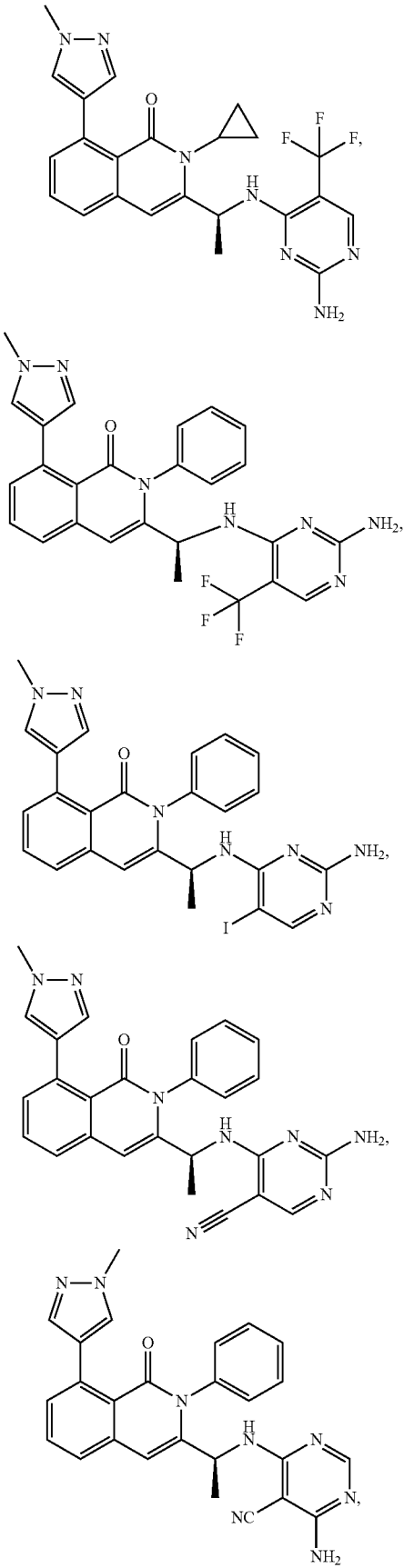

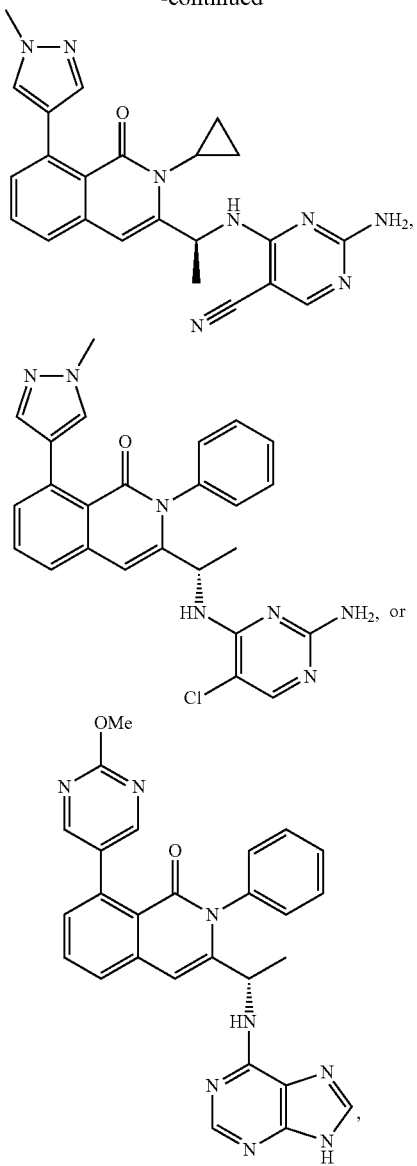

or a pharmaceutically acceptable salt thereof.

24. The method of claim 1, wherein the disorder is an inflammatory disease or an auto-immune disease.

25. The method of claim 24, wherein the inflammatory disease or auto-immune disease is acute disseminated encephalomyelitis (ADEM), Addison's disease, antiphospholipid antibody syndrome (APS), aplastic anemia, autoimmune hepatitis, coeliac disease, Crohn's disease, diabetes mellitus (type 1), Goodpasture's syndrome, Graves' disease, Guillain-Barré syndrome (GBS), Hashimoto's disease, lupus erythematosus, multiple sclerosis, myasthenia gravis, opsoclonus myoclonus syndrome (OMS), optic neuritis, Ord's thyroiditis, oemphigus, polyarthritis, primary biliary cirrhosis, psoriasis, rheumatoid arthritis, Reiter's syndrome, Takayasu's arteritis, temporal arteritis, warm autoimmune hemolytic anemia, Wegener's granulomatosis, alopecia universalis, Chagas' disease, chronic fatigue syndrome, dysautonomia, endometriosis, hidradenitis suppurativa, interstitial cystitis, neuromyotonia, sarcoidosis, scleroderma, ulcerative colitis, vitiligo, vulvodynia, asthma, emphysema, allergy, dermatitis, or graft versus host disease.

26. The method of claim 25, wherein the inflammatory disease or auto-immune disease is rheumatoid arthritis.

27. The method of claim 25, wherein the inflammatory disease or auto-immune disease is asthma.

28. The method of claim 1, wherein the disorder is a cancer.

29. The method of claim 28, wherein the cancer is breast cancer, ductal carcinoma, colloid carcinomas, tubular carcinomas, inflammatory breast cancer, ovarian cancer, epithelial ovarian tumors, adenocarcinoma, uterine cancer, cervical cancer, squamous cell carcinoma, prostate cancer, pancreatic cancer, epitheliod carcinoma, bladder cancer, transitional cell carcinoma, urothelial carcinomas, small cell cancers, acute lymphocytic leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), myelodysplastic syndrome (MDS), bone cancer, lung cancer, non-small cell lung cancer (NSCLC), large cell undifferentiated carcinomas, small cell lung cancer, skin cancer, basal cell carcinoma, melanoma, actinic keratosis, eye retinoblastoma, cutaneous melanoma, intraocular melanoma, primary liver cancer, kidney cancer, thyroid cancer, AIDS-related lymphoma, diffuse large B-cell lymphoma, B-cell immunoblastic lymphoma, small non-cleaved cell lymphoma, Kaposi's Sarcoma, viral-induced cancers, hepatitis B virus (HBV), hepatitis C virus (HCV), hepatocellular carcinoma, human lymphotropic virus-type 1 (HTLV-1), adult T-cell leukemia/lymphoma, human papilloma virus (HPV), cervical cancer, central nervous system cancers (CNS), primary brain tumor, gliomas, astrocytoma, anaplastic astrocytoma, glioblastoma multiforme, oligodendroglioma, ependymoma, meningioma, lymphoma, schwannoma, medulloblastoma, peripheral nervous system (PNS) cancers, acoustic neuromas, malignant peripheral nerve sheath tumor (MPNST), neurofibromas, malignant fibrous cytoma, malignant meningioma, malignant mesothelioma, malignant mixed Müllerian tumor, oral cavity and oropharyngeal cancer, hypopharyngeal cancer, laryngeal cancer, nasopharyngeal cancer, stomach cancer, gastric stromal tumors, carcinoid tumors, testicular cancer, germ cell tumors (GCTs), seminomas, nonseminomas, gonadal stromal tumors, Leydig cell tumors, Sertoli cell tumors, thymus cancer, thymic carcinomas, Hodgkin disease, non-Hodgkin lymphomas, rectal cancer, colon cancer, or mantle cell lymphoma.

30. The method of claim 1, further comprising administering a second therapeutic agent to the subject.

* * * * *